United States Patent
Ying et al.

(10) Patent No.: US 8,318,790 B2
(45) Date of Patent: Nov. 27, 2012

(54) TRIAZOLE COMPOUNDS THAT MODULATE HSP90 ACTIVITY

(75) Inventors: Weiwen Ying, Ayer, MA (US); David James, Cambridge, MA (US); Shijie Zhang, Nashua, NH (US); Junghyun Chae, Youngdengpo-gu (KR); Teresa Przewloka, Tewksbury, MA (US); Howard P. Ng, Belmont, MA (US); Hao Li, Brookline, MA (US); Zachary Demko, Somerville, MA (US); Dinesh U. Chimmanamada, Arlington, MA (US); Chi-wan Lee, Grafton, MA (US); Zhenjian Du, Northborough, MA (US); Kevin Foley, Waltham, MA (US); Minghu Song, Waltham, MA (US); Lijun Sun, Harvard, MA (US); Keizo Koya, Chestnut Hill, MA (US); Dan Zhou, Lexington, MA (US); Shuzhen Qin, West Roxbury, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 851 days.

(21) Appl. No.: 11/807,201

(22) Filed: May 25, 2007

(65) Prior Publication Data

US 2008/0090887 A1    Apr. 17, 2008

Related U.S. Application Data

(60) Provisional application No. 60/808,425, filed on May 25, 2006, provisional application No. 60/808,248, filed on May 25, 2006, provisional application No. 60/808,256, filed on May 25, 2006.

(51) Int. Cl.
*A61K 31/4196* (2006.01)
*A61P 35/00* (2006.01)
*C07D 249/12* (2006.01)

(52) U.S. Cl. .................................. 514/384; 548/264.6

(58) Field of Classification Search ...................... None
See application file for complete search history.

(56) References Cited

U.S. PATENT DOCUMENTS

| | | | |
|---|---|---|---|
| 3,189,614 A | 6/1965 | Pesson | |
| 4,269,846 A | 5/1981 | Huang et al. | |
| 4,624,995 A | 11/1986 | Katritzky et al. | |
| 4,740,568 A | 4/1988 | Katritzky et al. | |
| 4,931,084 A | 6/1990 | Findeisen et al. | |
| 5,006,650 A | 4/1991 | Barbachyn | |
| 5,298,520 A | 3/1994 | Baker et al. | |
| 5,371,101 A | 12/1994 | Itoh et al. | |
| 5,395,818 A | 3/1995 | Haas et al. | |
| 5,436,252 A | 7/1995 | Sorensen et al. | |
| 5,466,820 A | 11/1995 | Itoh et al. | |
| 5,476,946 A | 12/1995 | Linker et al. | |
| 5,489,598 A | 2/1996 | Connor et al. | |
| 5,510,362 A | 4/1996 | Matassa et al. | |
| 5,538,988 A | 7/1996 | Martinez et al. | |
| 5,663,362 A | 9/1997 | Haas et al. | |
| 5,869,509 A | 2/1999 | Romine et al. | |
| 5,888,694 A | 3/1999 | Yamada et al. | |
| 6,077,861 A | 6/2000 | Romine et al. | |
| 6,194,090 B1 | 2/2001 | Okada | |
| 6,258,957 B1 | 7/2001 | Linker et al. | |
| 6,271,249 B1 | 8/2001 | Romine et al. | |
| 6,492,406 B1 | 12/2002 | Karabelas et al. | |
| 6,583,090 B1 | 6/2003 | Gewehr et al. | |
| 7,825,148 B2 | 11/2010 | Ying et al. | |
| 2005/0058956 A1 | 3/2005 | Watanabe et al. | |
| 2005/0154039 A1 | 7/2005 | Glacera Contour | |
| 2005/0288347 A1 | 12/2005 | Hodge et al. | |

FOREIGN PATENT DOCUMENTS

| | | |
|---|---|---|
| EP | 1 857 446 | 11/2007 |
| FR | 2 546 887 | 12/1984 |
| JP | 59010574 | 1/1984 |
| JP | 2000284412 | 10/2000 |
| JP | 2003114488 | 4/2003 |
| WO | WO 98/04135 | 2/1998 |
| WO | WO 2007/094819 | 8/2003 |
| WO | WO 2005/000300 A1 | 1/2005 |
| WO | WO 2005/044194 | 5/2005 |
| WO | WO 2005/097758 | 10/2005 |
| WO | WO 2006/055760 | 5/2006 |
| WO | WO 2006/087077 | 8/2006 |
| WO | WO 2007/134678 | 11/2007 |

OTHER PUBLICATIONS

Newman et al., DDT vol. 8, Oct. 2003, p. 898-90.*
Chawla et al., CRIPS vol. 5, No. 1, Jan.-Mar. 2004, p. 9-12.*
Collins, Expert Opinion Investig Drugs (2007), 16(11), p. 1743-1751.*
Arbiser, The Journal of Clinical Investigation, 117, 10, 2762-2765.*
Suzuki et al., caplus an 2001:597968.*
Ciugureanu, C., et al., "Studial Activității Biologice a unor noi Tiosemicarbazide Și a Derivaților Acestora cu Nucleu Triazolic Și Tiadiazolic III. Testarea Activității Antimicrobiene," *Farmacia, XXX*(1): 57-64 (1982).
Ciugureanu, C., et al., "Studial Activității Biologice a unor noi Tiosemicarbazide Și a Derivaților Acestora cu Nucleu Triazolic Și Tiadiazolic IV. Testarea Activității Citostatice,"*Farmacia, XXX*(2): 101-110 (1982).
Yuksek, Haydar and Ikizler A. A., "Synthesis of 4-Succinimido-4,5-Dihydro-1H-1,2,4-Triazol-5-ones," *Turkish Journal of Chemistry*, 18: 57-61 (1994).

(Continued)

*Primary Examiner* — Sun Jae Loewe
(74) *Attorney, Agent, or Firm* — McCarter & English LLP; Steven G. Davis

(57) ABSTRACT

The present invention relates to substituted triazole compounds and compositions comprising substituted triazole compounds. The invention further relates to methods of inhibiting the activity of Hsp90 in a subject in need thereof and methods for preventing or treating hyperproliferative disorders, such as cancer, in a subject in need thereof comprising administering to the subject a substituted triazole compound of the invention, or a composition comprising such a compound.

68 Claims, No Drawings

OTHER PUBLICATIONS

Maliszewska, A., "The Reaction of N3-Substituted Amidrazones with Urea," *Annales Universitatis Mariae Curie-Sklodowska Lublin-Polonia*, vol. XLI, 5, Sectio AA:63-67 (1986).

Grashey, R., et al., "Zur Synthese Mesoionischer 1,2,4-Triazol-3-Thione," *Tetrahedron Letters* 29: 2939-2942 (1972).

Goswami, B.N., et al., "Synthesis and Antibacterial Activity of 1-(2,4-Dichlorobenzoyl)-4-Substituted Thiosemicarbazides, 1,2,4-Triazoles and Their Methyl Derivatives," *Journal of Heterocyclic Chemistry* 21(4): 1225-1229 (Jul.-Aug. 1984).

Goswami, B.N., et al., "Synthesis and Antifungal Activities of Some New Substituted 1,2,4-Triazoles and Related Compounds," *Journal of the Indian Chemical Society* LXI(6): 471-564 (1984).

Malbec, F., et al., "Dérivés de la Dihydro-2,4 Triazole-1,2,4 Thione-3 et de 1-amino-2 Thiadiazole-1,3,4 a Partir de Nouvelles Thiosemicarbazones d'esters," *Journal of Heterocyclic Chemistry* 21(6): 1689-1698 (Nov.-Dec. 1984).

Coburn, M.D., et al., "Picrylamino-Substituted Heterocycles III. 1,2,4,-Triazoles (1,2)," *Journal of Heterocyclic Chemistry* 5(2): 199-203 (Apr. 1968).

Eckstein, M., et al., "The Aminoxides of Physiologically Active Compounds," *Department of Pharmaceutical Chemistry, Academy of Medicine*, Cracow: 197-204.

Potts, K.T., et al., "meso Ionic Compounds. II. Derivatives of the s-Triazole Series," *The Journal of Organic Chemistry*, 32(7): 2245-2252 (1967).

El-Sharief, A.M., et al., "Utility of Cyanothioformamides in Synthesis of Some Bis(Imidazole, Oxazole, Thiazole, Oxadiazole, Triazole, Benzoxazinethione and Quinazoline) Derivatives," *J. Chem. Research* (S): 162-167 (2003).

Sawhney, et al., "Synthesis of Some 2-(5-Substituted 1,3,4-Oxadiazol-2-Y1)-, 2-(5-Substituted 1,3,4-Thiadiazol-2-Y1)- and 2-(3-Mercapto-4-Substituted-4H-1,2,4-Triazol-5-Y1)-Benzimidazoles as Potential Anti-Inflammatory Agents," *Indian J. of Chem.*, 30B: 407-412 (1991).

Tehranchian, S. et al., "Synthesis and antibacterial activity of 1-[1, 2, 4-triazol-3-yl] and 1-[1, 3, 4-thiadiazol-2-yl]-3-methylthio-6, 7-dihydrobenzo[c]thiophen-4(5H)ones," *Bioorganic & Medicinal Chemistry Letters*, 15: 1023-1025 (2005).

Soni, N., et al., "Analgesic Activity and Monoamine Oxidase Inhibitory Property of Substituted Mercapto 1,2,4-Triazoles," *Eur. J. Med. Chem.*, 20(2): 190-192 (1985).

Russo, et al., "Derivati Benzotiazolici del 1,2,4-triazolo," *Annali di Chimica*, 62: 351-372 (1972).

Romine, Jeffrey, L., et al., "4,5-Diphenyltriazol-3-ones: Openers of Large-Conductance Ca2+-Activated Potassium (Maxi-K) Channels," *J. Med. Chem.*, 45: 2942-2952 (2002).

Ramazani, A. et al., "Crystal structure of 4-[4-(dimethylamino)phenyl]-5-(2, 4-dimethyl-1, 3-thiazol-5-y1)-2, 4-dihydro-3H-1, 2, 4-triazol-3-thione, C15H17N5S2," *K. Kristallogr, NCS*, 217:149-150 (2002).

Modzelewska-Banachiewicz, B., et al., "Synthesis and Biological Activity of BIS-1, 2, 4-Triazole and BIS-1, 3, 4-Thiadiazole Derivatives," *Acta Poloniac Pharmaceutica Drug Research*, 57(3): 199-204 (2000).

Modzelewska, B., and Maliszewska, A., "The Reaction of N3-substituted Amidrazones with the Aromatic Izothiocyanates, Part III," vol. XXXIXIXL, 13: 163-170 (1985).

Modzelewska, B., "Cyclization Reaction of Thiosemicarbazone-4-Picolinamide Derivatives," Acta Poloniac Pharmaceutica-Drug Research, 52(5): 425-427 (1995).

Milcent, R., and Vicart, P., "Synthèse Et Activitè Antibactèrienne D'amino-4 Triazol-1,2,4 Ones-5 Substituèes," *Eur. J. Med. Chem.—Chim. Ther.*, 18(3): 215-220 (1983).

Ikizler, A., et al., "Synthesis of some New N,N'-Linked Biheteroaryls," *Polish Journal of Chemistry*, 69:1497-1502 (1995).

Ikizler, A., et al., "Biological Activities of Some 1,2,4-triazoles and 1,2,4-triazolin-5-ones," *Die Pharmazie*, 44(7): 506-507 (1989).

Ikizler, A., and Un, R., "Reactions of Ester Ethoxycarbonylhydrazones With Some Amine Type Compounds," *Chimica Acta Turcica*, 7: 269-290 (1979).

Husain, S., et al., "3,4-Disubstituted 5-Hydroxy-1,2,4-triazoles Derived from 4-Substituted Semicarbazones," *Indian Journal of Chemistry*, 9: 642-646 (1971).

Ciugureanu, C., and Ungureanu, M., "Synthesis of Novel 1,2,4-Triazoles and 1,3,4-Thiadiazoles Derivatives of 1,3-Benzoxazole," *Analele ÿtintifice Ale Universitaÿii*, 5:151-158 (1997).

Cansiz, A., et al., "Synthesis of Some New 4,5-Substituted-4H-1,2,4-triazole-3-thiol Derivatives," Molecules, 9: 204-212 (2004).

Ayca, E. et al., "Mass Spectra of Some 3,4-Disubstituted-ÿ2-1,2,4-Triazolin-5-Ones," *Chimica Acta Turcica*, 11: 285-289 (1983).

Ayça, E. et al., "Preparation of 3-Alkyl(aryl)-4-Aryl-ÿ2-1,2,4-Triazolin-5-Ones1," *Chimica Acta Turcica*, 9: 100-108(1981).

Cesur N., and Cesur, Z., "Synthesis of Some 4-Thiazoline and 4H-1,2,4-Triazole Derivatives of Imidazo(1,2-a) Pyridine as Possible Anticonvulsants" *Il Farmaco*, 49(10): 679-681 (1984).

El-Sharief, A.M. Sh. et al., "1, 4-Phenylenediisothiocyanate in the Synthesis of Bis-(Thiourea, Benzothiazole, Quinazoline, 1, 3-Benzoxazine and Imidazolidineiminothiones) Derivatives," *Phosphorus, Sulfur, and Silicon*, 179: 267-275 (2004).

El-Zahar, M.I., et al., "Synthesis of Some Novel 3-(N-Alkyl Carbamoyl) and 3-(1,2,4-Triazol-3-yl)-1,8-Naphthyridines of Anticipated Biological Activity," *Egypt. J. Chem.*, 45(2): 323-344 (2002).

Gawande, N.G., et al., "Synthesis of Some Thiosemicarbazides and Related Compounds," *Chemistry*, 13(2): 109-111 (1987) XP-002372384.

Ikizler, A.A. and Yüksek, H., "Acetylation of 4-Amino-4,5-Dihydro-1H-1,2,4-Triazol-5-Ones," *Organic Preparations and Procedures Int.*, 25(1): 99-139(1993).

Ciugureanu, C., et al., "Studial Activităţii biologice a unor noi Tiosemicarbazide Şi a Derivaţilor Acestora cu Nucleu Triazolic Şi Tiadiazolic II. Testarea Activităţii Antifungice," *Farmacia*, XXX(1): 49-56 (1982).

Iorga, T., et al., "Studial Activităţii Biologice a unor Noi Tiosemicarbazide Şi a Derivaţilor Acestora cu Nucleu Triazolic Şi Tiadiazolic I. Testarea Toxicităţii," *Farmacia*, XXVIII(2): 103-114 (1980).

Lixue, Z., et al., "Studies on Acylthiosemicarbazides and Related Heterocyclic Derivatives," *Chemical Journal of Chinese Universities* 11(2): 148-153 (1990).

Günay, N.S. et al., "5-Nitroimidazole derivatives as possible antibacterial and antifungal agents," *Il Farmaco*, 54: 826-831 (1999).

Ikizler, A.A. et al., "Susuz Ortamda Bazi 1,2,4-Trÿazole ve 1,2,4-Trÿazolin-5- on Türevlerÿnÿn pKa Degerlerinin Hesaplanmasi," *Doga Tu Kimya* 12(1): 57-66 (1988).

Ikizler, A.A. et al., "Synthesis and Biological Activities of Some 4,5-Dihydro-1H-1,2,4-Triazol-5-One Derivatives," *Acta Poloniae Pharmaceuticals—Drug Research*, 55(2) 117-123 (1998).

Ikizler, A.A. et al., "Ultraviolet Spectra of Some 1, 2, 4-Triazole Derivatives," *J. of Chemistry*, 16: 164-170 (1992).

Labanauskas, L., et al., "Synthesis of 5-(2-,3- and 4-Methoxyphenyl)-4H-1,2,4-Triazole-3-Thiol Derivatives Exhibiting Anti-Inflammatory Activity," *Il Farmaco*, 59: 255-259 (2004).

Milcent, R. and Redeuilh, C., "Recherche en Série du Triazole-1,2,4. II-Réactivité des Amino-4 Aryl-3 Triazp;-1,2,4 Ones-5," *Journal of Heterocyclic Chemistry*, 17(8): 1691-1696 (1980).

Ikizler, A.A and Yüksek, H., "A Study on 4,5-Dihydro-1H-1,2,4-Triazol-5-Ones," *Revue Roumaine de Chimie*, 41(7-8): 585-590 (1996).

Sawhney, et al., "Synthesis and Anti-inflammatory Activity of Some 3-Heterocycly1-1,2-Benzisothiazoles," *Bioorganic & Medicinal Chemistry Letters*, 3(8): 1551-1554 (1993).

Beilstein Registry No. 574001, 5-26-09-00436, XP-002372386.

Beilstein Registry No. 625992, 5-26-03-00436, XP-002372385.

Ikizler, A.A. and Yüksek, H., "Synthesis of 3-Alkyl-4-(2-Hydroxyethyl)-and 3-Alky1-4-(2-Chloroethyl)-4,5-Dihydro-1H-1,2,4-Triazol-5-Ones," *Turkish Journal of Chemistry*, 16(4): 284-288 (1992).

Modzelewska, B., "Studies on the Reaction of N3-Substituted Amidrazones with Metoxycarbonylethyl Isothatcyanate Part I," *Annales Universitatis Mariae Curie-Sklodowska Lublin-Polonia*, vol. XLI (3): 45-52 (1986).

Modzelewska, B., "Studies on the Reaction of N3-Substituted Amidrazones with Metoxycarbonylethyl Isothatcyanate Part II," *Annales Universitatis Mariae Curie-Sklodowska Lublin-Polonia*, vol. XLI (4): 53-61 (1986).

Modzelewska, B., "On the Reaction of Cyclization of p-Phenyleno-bis-(-N3-2-pikolinamidrazonu)," *Annales Universitatis Mariae Curie-Sklodowska Lublin-Polonia*, vol. XLVI/XLVII, 10, Sectio AA:61-66 (1991/1992).

Bahceci, S., et al., "Reactions of 4-Amino-4,5-Dihydro-1H-1,2,4-Triazol-5-ones and 4-Amino-4H-1,2,4-Triazoles with Some Carboxylic Acid Anhydrides," *Turkish Journal of Chemistry*, 22(3): 237-241 (1998).

Rostom, S., et al., "Polysubstitued Pyrazoles, Part 51. Synthesis of New 1-(4-Chlorophenyl)-4-Hydroxy-1H-Pyrazole-3-Carboxylic Acid Hydrazide Analogs and Some Derived Ring Systems. A Novel Class of Potential Antitumor and Anti-HCV Agents," *European Journal of Medicinal Chemistry* 38: 959-974 (2003).

Dymock, B.W., et al., "Inhibitors of HSP90 and Other Chaperones for the Treatment of Cancer," *Expert Opin. Ther. Patents*, 14(6): 837-847 (2004).

Mazzone, et al., "Cyclic Derivatives from Alkoxybenzohydrazides. Synthesis of Pyrazoles, Pyrroles and Triazol-5-Ones of Pharmaceutical Interest," *Eur. J. Med. Chem.—Chim. Ther.*, 21(4): 277-284 (1986).

PCT International Search Report and Written Opinion—(PCT/US2007/012524) Date of Mailing Jul. 2, 2008.

Tandon M, et al., "Synthesis & Antiinflammatory Activity of Some New 3-(0-Substituted=Pheny1-5-Alkyl/Alkenyl-Mercapto-1H-1, 2, 4-Triazoles", Indian Journal of Chemistry, Section B: Organic, Inc. Medicinal, Publications & Informations Directorate, vol. 20B, No. 11, 1981, pp. 1017-1018.

Cheung KMJ, et al., "The Identification, Synthesis, Protein Crystal Structure and in Vitro Biochemical Evaluation of a New 3,4-diarylpyrazole class of Hsp90 Inhibitors", Bioorganic & Medicinal Chemistry Letters, Oxford, GB, vol. 15, No. 14, Jul. 15, 2005, pp. 3338-3343.

\* cited by examiner

TRIAZOLE COMPOUNDS THAT MODULATE HSP90 ACTIVITY

RELATED APPLICATIONS

This application claims the benefit of U.S. Provisional Application No. 60/808,425, filed May 25, 2006, U.S. Provisional Application No. 60/808,248, filed May 25, 2006, and U.S. Provisional Application No. 60/808,256, filed May 25, 2006, the entire teachings of which are incorporated herein by reference.

BACKGROUND OF THE INVENTION

Although tremendous advances have been made in elucidating the genomic abnormalities that cause malignant cancer cells, currently available chemotherapy remains unsatisfactory, and the prognosis for the majority of patients diagnosed with cancer remains dismal. Most chemotherapeutic agents act on a specific molecular target thought to be involved in the development of the malignant phenotype. However, a complex network of signaling pathways regulate cell proliferation, and the majority of malignant cancers are facilitated by multiple genetic abnormalities in these pathways. Therefore, it is unlikely that a therapeutic agent that acts on one molecular target will be fully effective in curing a patient who has cancer.

Heat shock proteins (HSPs) are a class of chaperone proteins that are up-regulated in response to elevated temperature and other environmental stresses, such as ultraviolet light, nutrient deprivation, and oxygen deprivation. HSPs act as chaperones to other cellular proteins (called client proteins) and facilitate their proper folding and repair, and aid in the refolding of misfolded client proteins. There are several known families of HSPs, each having its own set of client proteins. The Hsp90 family is one of the most abundant HSP families, accounting for about 1-2% of proteins in a cell that is not under stress and increasing to about 4-6% in a cell under stress. Inhibition of Hsp90 results in degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer. Examples of Hsp90 client proteins that have been implicated in the progression of cancer are described below.

Her-2 is a transmembrane tyrosine kinase cell surface growth factor receptor that is expressed in normal epithelial cells. Her2 has an extracellular domain that interacts with extracellular growth factors and an internal tyrosine kinase portion that transmits the external growth signal to the nucleus of the cell. Her2 is overexpressed in a significant proportion of malignancies, such as breast cancer, ovarian cancer, prostate cancer, and gastric cancers, and is typically associated with a poor prognosis.

Akt kinase is a serine/threonine kinase which is a downstream effector molecule of phosphoinositide 3-kinase and is involved in protecting the cell from apoptosis. Akt kinase is thought to be involved in the progression of cancer because it stimulates cell proliferation and suppresses apoptosis.

Cdk4/cyclin D complexes are involved in phosphorylation of retinoblastoma protein which is an essential step in progression of a cell through the G1 phase of the cell cycle. Disruption of Hsp90 activity has been shown to decrease the half life of newly synthesized Cdk4.

The Raf family of proto-oncogenes (A-raf, B-raf and C-raf) was first identified when C-raf (raf-1) was discovered due to its homology with v-raf, the transforming gene of the mouse sarcoma virus 3611. A-raf was later discovered by screening a cDNA library under low stringency conditions using a v-raf probe, and B-raf was discovered due to its homology with C-Rmil, a transforming gene in avaian retrovirus Mill Hill No. 2. The Raf family of proteins is involved in the Ras/Raf/MEK/ERK pathway, referred to herein as the "MAP kinase pathway" (MEK stands for "MAPK/ERK kinase" and ERK stands for "extracellularly regulated kinases"), which has been implicated in the genesis and progression of many human cancers through upregulation of cell division and proliferation. All raf proteins are serine/threonine kinases which are capable of activating the MAP kinase pathway. However, B-raf is far more potent at activating this pathway than A-raf or C-raf, and mutations in the gene encoding B-raf are more common in cancer. For example, B-raf mutations have been identified in 60% to 70% of malignant melanomas, 83% of anaplastic thyroid carcinoma, 35% to 69% of papillary thyroid caricinoma, 4% to 16% of colon cancer, 63% of low-grade ovarian carcinoma, 15% of Barrett's esophageal carcinoma, 4% of acute myeloid leukemia, 3-4.8% of head and neck squamous cell carcinoma, 2%-3% of non-small-cell lung cancer, 2% of gastric carcinoma, 2% of non-Hodgkins lymphoma and has been reported in glioma, saroma, breast cancer, cholangiocarcinoma, and liver cancer. Most mutations in B-raf that have been found in human cancers are point mutations that occur in the kinase domain and are clustered in exons 11 and 15 of the gene which contains several regulatory phosphorylation sites (S446, S447, D448, D449, T599, and S602). (Beeram, et al., *Journal of Clinical Oncology* (2005), 23(27):6771-6790). The most prevalent mutation is the T1799A transversion mutation which accounts for more than 80% of mutations in the BRAF gene and results in a V600E mutation in B-raf. The V600E was formerly designated V599E (the gene mutation was designated T1796A) due to a mistake in the GenBank nucleotide sequence NM 004333. The corrected GenBank sequence is NT 007914 and designates the protein mutation as V600E and the gene mutation as T1799A. This corrected numbering will be used herein. This mutation is thought to mimic phosphorylation in the activation segment of B-raf since it inserts a negatively charged residue near two activating phosphorylation sites, T599 and S602, and thus results in constitutively active B-raf in a Ras independent manner. (Xing, M., *Endocrine-Related Cancer* (2005), 12:245-262).

Treatment of cancer cells with 17AAG, an Hsp90 inhibitor, has been shown to stimulate the degradation of B-raf, and mutant forms of B-raf have been shown to be more sensitive to degradation than the wild type. For example, when melanoma cell line A375 which contain the V600E mutation was treated with 17AAG, B-raf was degraded more rapidly than in CHL cells which contained wild type B-raf. Other B-raf mutants (e.g., V600D, G469A, G469E, G596R, G466V, and G594V) were a found to be degraded more rapidly than wild type B-raf when transvected into COS cells. However, B-raf mutants E586K and L597V were not sensitive to degradation when cells were treated with 17AAG. Therefore, it is believed that wild type B-raf in its activated form is a client protein of Hsp90 and that most mutated forms of B-raf are more dependent on Hsp90 for folding, stability and/or function than the wild type protein. (Dias, et al., *Cancer Res.* (2005), 65(23): 10686-10691).

Raf-1 is a MAP 3-kinase (MAP3K) which when activated can phosphorylate and activate the serine/threonine specific protein kinases ERK1 and ERK2. Activated ERKs play an important role in the control of gene expression involved in the cell division cycle, apoptosis, cell differentiation and cell migration.

Anaplastic large-cell lymphoma (ALCL) is a type of non-Hodgkin's lymphoma characterized by the expression of CD30/Ki-1 antigen. ALCL normally arises from T-cells, however, a subset of cases have either a null cell or B-cell phenotype. Cases that arise from B-cells are sometimes categorized as diffuse large B-cell lymphomas. About 60% of the ALCL case that express CD30/Ki-1 antigen also have the chromosomal translocation t(2;5)(p23;q35) which fuses the nucleophosmin (NPM/B23) gene to the anaplastic lymphoma kinse (ALK) gene and results in the oncogenetic fusion protein NPM-ALK with tyrosine kinase activity. Within specific subtypes of ALCL, ALK rearrangements have been observed in the following percentages: 1) 30% to 50% of pleomorphic ALCL, 2) more than 80% of monomorphic ALCL, 3) 75% to 100% of small-cell cases, and 4) 60% to 100% of lympho-histiocytic ALCL. NPM-ALK is able to transform both fibroblasts, hematopoietic, and primary bone marrow cell lines, and is thought to stimulate mitosis through the RAS pathway and the through activation of phospholipase C-gamma (PLC-gamma), and to protect against apoptosis through its activation of phosphatidylinositol 3 kinase (PI-3 kinase) survival pathway. (Duyster, et al., *Oncogene* (2001), 20:5623-5637). NPM-ALK has been shown to associate with Hsp90 and incubation of NPM-ALK expressing ALCL cells with the benzoquinone ansamycin, 17AAG, has been shown to disrupt this association resulting in increased degradation of NPM-ALK and induce cell-cycle arrest and apoptosis. (Georgakis, et al., *Exp. Hematology* (2006), 34(12):1670-1679; Bonvini, et al., Cancer Research (2002), 62:1559-1566).

The transforming protein of Rous sarcoma virus, v-src, is a prototype of an oncogene family that induces cellular transformation (i.e., tumorogenesis) by non-regulated kinase activity. Hsp90 has been shown to complex with v-scr and inhibit its degradation.

Hsp90 is required to maintain steroid hormone receptors in a conformation capable of binding hormone with high affinity. Inhibition of the action of Hsp90 therefore is expected to be useful in treating hormone-associated malignancies such as breast cancer.

p53 is a tumor suppressor protein that causes cell cycle arrest and apoptosis. Mutation of the p53 gene is found in about half of all human cancers making it one of the most common genetic alterations found in cancerous cells. In addition, p53 mutation is associated with a poor prognosis. Wild-type p53 has been shown to interact with Hsp90, but mutated p53 forms a more stable association than wild-type p53 as a result of its misfolded conformations. A stronger interaction with Hsp90 protects the mutated protein form normal proteolytic degradation and prolongs its half-life. In a cell that is heterozygous for mutated and wild-type p53, inhibition of the stabilizing effect of Hsp90 causes mutant p53 to be degraded and restores the normal transcriptional activity of wild-type p53.

Hif-1α is a hypoxia-inducible transcription factor that is up-regulated under low oxygen conditions. Under normal oxygen conditions Hif-1α associates with Von Hippel-Lindau (VHL) tumor suppressor protein and is degraded. Low oxygen conditions inhibit this association and allows Hif-1α to accumulate and complex with Hif-1β to form an active transcription complex that associates with hypoxia-response elements to activate the transcription of vascular endothelial growth factor (VEGF). Increased Hif-1α is associated with increased metastasis and a poor prognosis.

There are two classes of PKs: protein tyrosine kinases (PTKs), which catalyze the phosphorylation of tyrosine kinase residues, and the serine-threonine kinases (STKs), which catalyze the phosphorylation of serine or threonine residues. Growth factor receptors with PTK activity are known as receptor tyrosine kinases. Receptor tyrosine kinases are a family of tightly regulated enzymes, and the aberrant activation of various members of the family is one of the hallmarks of cancer. The receptor tyrosine kinase family can be divided into subgroups that have similar structural organization and sequence similarity within the kinase domain.

Epidermal Growth Factor Receptor (EGFR) is a member of the type 1 subgroup of receptor tyrosine kinase family of growth factor receptors, which play critical roles in cellular growth, differentiation, and survival. Activation of these receptors typically occurs via specific ligand binding which results in hetero- or homodimerization between receptor family members, with subsequent autophosphorylation of the tyrosine kinase domain. Specific ligands which bind to EGFR include epidermal growth factor (EGF), transforming growth factor α (TGFα, amphiregulin and some viral growth factors. Activation of EGFR triggers a cascade of intracellular signaling pathways involved in both cellular proliferation (the ras/raf/MAP kinase pathway) and survival (the PI3 kinase/Akt pathway). Members of this family, including EGFR and HER2, have been directly implicated in cellular transformation.

A number of human malignancies are associated with aberrant or overexpression of EGFR and/or overexpression of its specific ligands (Gullick, *Br. Med. Bull.* (1991), 47:87-98; Modijtahedi and Dean, *Int. J. Oncol.* (1994), 4:277-96; Salomon, et al., *Crit. Rev. Oncol. Hematol.* (1995); 19:183-232, the entire teachings of each of these references are incorporated herein by reference). Aberrant or overexpression of EGFR has been associated with an adverse prognosis in a number of human cancers, including head and neck, breast, colon, prostate, lung (e.g., NSCLC, adenocarcinoma and squamous lung cancer), ovaries, gastrointestinal cancers (gastric, colon, pancreatic), renal cell cancer, bladder cancer, glioma, gynecological carcinomas, and prostate cancer. In some instances, overexpression of tumor EGFR has been correlated with both chemoresistance and a poor prognosis (Lei, et al., *Anticancer Res.* (1999), 19:221-8; Veale, et al., *Br. J. Cancer* (1993); 68:162-5, the entire teachings of each of these references are incorporated herein by reference).

Gefitinib, a chemotherapeutic agent that inhibits the activity of EGFR, has been found to be highly efficacious in a subset of lung cancer patients that have mutations in the tyrosine kinase domain of EGFR. In the presence of EGF, these mutants displayed two to three times higher activity than wild type EGFR. In addition, wild type EGFR was internalized by the cells and down-regulated after 15 minutes, where as mutant EGFR was internalized more slowly and continued to be activated for up to three hours (Lynch, et al., *The New England Journal of Medicine* (2006), 350:2129-2139, the entire teachings of which are incorporated herein by reference).

Gliomas are another type of cancer that is characterized by amplification and/or mutation of the EGFR gene. One of the most common mutations in the EGFR gene is a deletion of exons 2-7 which results in a truncated form of EGFR in which amino acids 6-273 of the extracellular domain are replaced with a single glycine residue. This mutation is called EGFRvIII and is expressed in about half of all glioblastomas. EGFRvIII is unable to bind EGF and TGFα and has constitutive, ligand-independent tyrosine kinase activity. Hsp90 copurifies with EGFRvIII indicating that Hsp90 complexes with EGFRvIII. Moreover, Hsp90 inhibitor geldanamycin, a benzoquinone ansamycin antibiotic, was able to decrease the expression of EGFRvIII indicating that interaction with Hsp90 is essential to maintain high expression levels of EGFRvIII (Lavictoire, et al., Journal of Biological Chemistry (2003), 278(7):5292-5299, the entire teachings of which are incorporated herein by reference). These results demonstrate that inhibiting the activity of Hsp90 is an effective strategy for treating cancers that are associated with inappropriate EGFR activity.

The members of the type III group of receptor tyrosine kinases include platelet-derived growth factor (PDGF) receptors (PDGF receptors alpha and beta), colony-stimulating factor (CSF-1) receptor (CSF-1R, c-Fms), Fms-like tyrosine kinase (FLT3), and stem cell factor receptor (c-kit). FILT3 is primarily expressed on immature hematopoietic progenitors and regulates their proliferation and survival.

Hematologic cancers, also known as hematologic or hematopoietic malignancies, are cancers of the blood or bone marrow; including leukemia and lymphoma. Acute myelogenous leukemia (AML) is a clonal hematopoietic stem cell leukemia that represents about 90% of all acute leukemias in adults with an incidence of 3.9 per 100,000 (See e.g., Lowenberg et al., *N. Eng. J. Med.* 341: 1051-62 (1999) and Lopesde Menezes, et al, Clin. Cancer Res. (2005), 11(14):5281-5291, the enter teachings of both references are incorporated by reference). While chemotherapy can result in complete remissions, the long term disease-free survival rate for AML is about 14% with about 7,400 deaths from AML each year in the United States. Approximately 70% of AML blasts express wild type FLT3 and about 25% to about 35% express FLT3 kinase receptor mutations which result in constitutively active FLT3. Two types of activating mutations have been identified in AML patients: internal tandem duplications (ITDs) and point mutation in the activating loop of the kinase domain. FLT3-ITD mutations in AML patients is indicative of a poor prognosis for survival, and in patients who are in remission, FLT3-ITD mutations are the most significant factor adversely affecting relapse rate with 64% of patients having the mutation relapsing within 5 years (see *Current Pharmaceutical Design* (2005), 11:3449-3457, the entire teachings of which are incorporated herein by reference). The prognostic significance of FLT3 mutations in clinical studies suggests that FLT3 plays a driving role in AML and may be necessary for the development and maintenance of the disease.

Mixed Lineage Leukemia (MLL) involve translocations of chromosome 11 band q23 (11q23) and occur in approximately 80% of infant hematological malignancies and 10% of adult acute leukemias. Although certain 11q23 translocation have been shown to be essential to immortalization of hematopoietic progenitors in vitro, a secondary genotoxic event is required to develop leukemia. There is a strong concordance between FLT3 and MLL fusion gene expression, and the most consistently overexpressed gene in MLL is FLT3. Moreover, it has been shown that activated FLT3 together with MLL fusion gene expression induces acute leukemia with a short latency period (see Ono, et al., *J. of Clinical Investigation* (2005), 115:919-929, the entire teachings of which are incorporated by reference). Therefore, it is believed that FLT3 signally is involved in the development and maintenance of MLL (see Armstrong, et al., *Cancer Cell* (2003), 3:173-183, the entire teachings of which are incorporated herein by reference).

The FLT3-ITD mutation is also present in about 3% of cases of adult myelodysplastic syndrome and some cases of acute lymphocytic leukemia (ALL) (*Current Pharmaceutical Design* (2005), 11:3449-3457).

FLT3 has been shown to be a client protein of Hsp90, and 17MG, a benzoquinone ansamycin antibiotic that inhibits Hsp90 activity, has been shown to disrupts the association of Flt3 with Hsp90. The growth of leukemia cell that express either wild type FLT3 or FLT3-ITD mutations was found to be inhibited by treatment with 17"MG (Yao, et al., *Clinical Cancer Research* (2003), 9:4483-4493, the entire teachings of which are incorporated herein by reference).

c-Kit is a membrane type III receptor protein tyrosine kinase which binds Stem Cell Factor (SCF) to its extraellular domain. c-Kit has tyrosine kinase activity and is required for normal hematopoiesis. However, mutations in c-kit can result in ligand-independent tyrosine kinase activity, autophosphorylation, and uncontrolled cell proliferation. Aberrant expression and/or activation of c-Kit has been implicated in a variety of pathologic states. For example, evidence for a contribution of c-Kit to neoplastic pathology includes its association with leukemias and mast cell tumors, small cell lung cancer, testicular cancer, and some cancers of the gastrointestinal tract and central nervous system. In addition, c-Kit has been implicated in playing a role in carcinogenesis of the female genital tract sarcomas of neuroectodermal origin, and Schwann cell neoplasia associated with neurofibromatosis. (Yang et al., *J Clin Invest*. (2003), 112:1851-1861; Viskochil, *J Clin Invest*. (2003), 112:1791-1793, the entire teachings of each of these reference are incorporated herein by reference). c-Kit has been shown to be a client protein of Hsp90, and Hsp90 inhibitor 17AAG, a benzoquinon ansamycin, has been shown to induce apoptosis in Kasumi-1 cells, an acute myeloid leukemia cell line that harbors a mutation in c-kit.

c-Met is a receptor tyrosine kinase that is a client protein of Hsp90 and is encoded by the Met protooncogene. Hepatocyte growth factor (HGF) (also referred to as scatter factor (SF)) is the natural ligand of c-Met which binds to c-Met and leads to a variety of cellular responses such as proliferation, survival, angiogenesis, wound healin, tissue regeneration, scattering, motility, invasion and branching morphogenesis (Ma et al., *Cancer and Metastasis Reviews* (2003), 22: 309-325). c-Met and HGF are expressed in numerous tissues, although their expression is normally confined predominantly to cells of epithelial and mesenchymal origin, respectively. c-Met and HGF are required for normal mammalian development and have been shown to be important in cell migration, cell proliferation and survival, morphogenic differentiation, and organization of 3-dimensional tubular structures (e.g., renal tubular cells, gland formation, etc.). However, dysregulation of c-Met and/or HGF is believed to contribute to tumor growth, dissemination and invasion in several human cancers. c-Met and/or HGF are highly expressed in numerous cancers and their expression correlates with poor prognosis (Christensen, et al., *Cancer Research* (2003), 63:7345-7355). For example, c-Met receptor mutations have been shown to be expressed in a number of human cancers including hereditary and sporadic human papillary renal carcinomas, ovarian cancer, childhood hepatocellular carcinoma, metastatic head and neck squamous cell carcinomas, esophageal cancer and gastric cancer. Met gene amplification and over expression of c-Met has been shown to be associated with both non-small cell lung cancer (NSCLC) and small cell lung cancer (SCLC), as well as colorectal cancer, and the Tpr/Met fusion protein has been shown to be present in human osteogenic sarcoma and gastric cancer. Families with germine mutations that activate c-Met kinase are prone to multiple kidney tumors as well as tumors in other tissues. Numerous studies have correlated the expression of c-Met and/or HGF with the state of disease progression of different types of cancer (including lung, colon, breast, prostate, liver, pancreas, brain, kidney, ovarian, stomach, skin, and bone cancers).

The validity of targeting receptor tyrosine kinases (RTK) that are dysregulated in human cancers is illustrated by the successes of Gleevec targeting Bcr-Abl in chronic myelogenous leukemia and c-Kit in gastroinstinal stromal tumors, Herceptin in Her-2 overexpressing breast cancers, and Iressa in select NSCLC that have dysregulated EGFR. Compelling evidence exists for targeting c-Met in the treatment of human cancers and several small drug molecules that inhibit c-Met are currently in development. However, therapies that target specific RTK often work well initially for treating cancer but eventually fail due to additional mutations which allow RTK to maintain its activity in the presence of the drug. Moreover, the selective c-Met inhibitor SU11274, while highly affected against wild type c-Met and some mutants of c-Met, has been shown to be ineffective against other c-Met mutants (Berthou, et al., *Oncogene* (2004), 23:5387-5393). Therefore, a need exists to develop new anticancer therapeutics that reduce the expression and/or activity of c-Met via a different mechanism than therapeutics that directly inhibit c-Met.

BCR-ABL is an ocoprotein with tyrosine kinase activity and has been associated with chronic myelogenous leukemia (CML), with a subset of patients with acute lymphocytic leukemia (ALL) and with a subset of patients with acute myelogenous leukemia (AML). In fact, the BCR-ABL oncogene has been found in at least 90-95% of patients with CML, 20% of adults with ALL, 5% of children with ALL, and in about 2% of adults with AML. The BCR-ABL oncoprotein is generated by the transloction of gene sequences from the c-ABL protein tyrosine kinase on chromosome 9 into the BCR sequences on chromosome 22, producing the Philadelphia chromosome. The BCR-ABL gene has been shown to produce at least three alternative chimeric proteins, p230 Bcr-Abl, p210 Bcr-Abl, and p190 Bcr-Abl which have unregulated tyrosine kinase activity. The p210 Bcr-Abl fusion protein is most often associated with CML, while the p190 Bcr-Abl fusion protein is most often associated with ALL. Bcr-Abl has also been associated with a variety of additional hematological malignancies including granulocytic hyperplasia, myelomonocytic leukemia, lymphomas and erythroid leukemia.

Studies have shown that lowering the expression or activity of Bcr-Abl is effective in treating Bcr-Abl-positive leukemias. For example, agents such as $As_2O_3$ which lower Bcr-Abl expression have been shown to be highly effective against Bcr-Abl leukemias. In addition, inhibition of Bcr-Abl tyrosine kinase activity by Imatinib (also known as STI571 and Gleevic) induces differentiation and apoptosis and causes eradication of Bcr-Abl positive leukemia cells both in vivo and in vitro. In patients with CML in the chronic phase, as well as in a blast crisis, treatment with Imatinib typically will induce remission. However, in many cases, particularly in those patients who were in a blast crisis before remission, the remission is not durable because the Bcr-Abl fusion protein develops mutations that cause it to be resistance to Imatinib. (See Nimmanapalli, et al., *Cancer Research* (2001), 61:1799-1804; and Gorre, et al., *Blood* (2002), 100:3041-3044, the entire teachings of each of these references are incorporated herein by reference).

Bcr-Abl fusion proteins exist as complexes with Hsp90 and are rapidly degraded when the action of Hsp90 is inhibited. It has been shown that geldanamycin, a benzoquinone ansamycin antibiotic that disrupts the association of Bcr-Abl with Hsp90, results in proteasomal degradation of Bcr-Abl and induces apoptosis in Bcr-Abl leukemia cells.

Hsp90 has been shown by mutational analysis to be necessary for the survival of normal eukaryotic cells. However, Hsp90 is over expressed in many tumor types indicating that it may play a significant role in the survival of cancer cells and that cancer cells may be more sensitive to inhibition of Hsp90 than normal cells. For example, cancer cells typically have a large number of mutated and overexpressed oncoproteins that are dependent on Hsp90 for folding. In addition, because the environment of a tumor is typically hostile due to hypoxia, nutrient deprivation, acidosis, etc., tumor cells may be especially dependent on Hsp90 for survival. Moreover, inhibition of Hsp90 causes simultaneous inhibition of a number of oncoproteins, as well as hormone receptors and transcription factors making it an attractive target for an anti-cancer agent. In fact, benzoquinone ansamycins, a family of natural products that inhibit Hsp90, has shown evidence of therapeutic activity in clinical trials.

Although promising, benzoquinone ansamycins, and their derivatives, suffer from a number of limitations. For example, they have low oral bioavailability, and their limited solubility makes them difficult to formula. In addition, they are metabolized by polymorphic cytochrome P450 CYP3A4 and are a substrate for P-glycoprotein export pump involved in the development of multidrug resistance. Therefore, a need exist for new therapeutics that improve the prognosis of cancer patients and that reduces or overcomes the limitations of currently used anti-cancer agents.

SUMMARY OF THE INVENTION

The present invention provides compounds which inhibit the activity of Hsp90 and are useful in the treatment of proliferative disorders, such as cancer.

In one embodiment, the present invention provides compounds represented by structural formula (I):

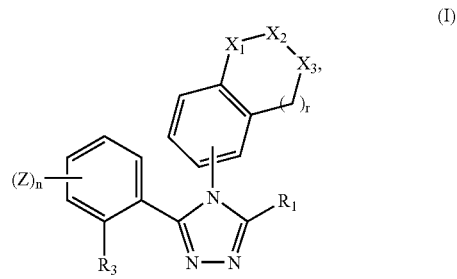

wherein:
$R_1$ and $R_3$ are, independently, —OH, —SH, —NHR$_7$, —OR$_{26}$, —SR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O) R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S) OR$_7$, —OC(S)NR$_{10}$R$_{11}$, —SC(S)NR$_{10}$R$_{11}$, —NR$_7$C(S)

NR₁₀R₁₁, —OC(NR₈)R₇, —SC(NR₈)R₇, —NR₇C(NR₈)R₇, —OC(NR₈)OR₇, —SC(NR₈)OR₇, —NR₇C(NR₈)OR₇, —OC(NR₈)NR₁₀R₁₁, —SC(NR₈)NR₁₀R₁₁, —NR₇C(NR₈)NR₁₀R₁₁, —OP(O)(OR₇)₂, or —SP(O)(OR₇)₂;

R₇ and R₈, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;

R₁₀ and R₁₁, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or R₁₀ and R₁₁, taken together with the nitrogen to which they are attached, form an optionally substituted heterocyclyl or an optionally substituted heteroaryl;

R₂₆ is a lower alkyl;

X₁, X₂, and X₃ are each independently C(R₂₇)₂, NR₇₇, C(O), S(O)ₚ, O or S;

R₂₇, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanidino, a hydroxyalkyl, alkoxyalkyl, haloalkyl, a heteroalkyl, —NR₁₀R₁₁, —OR₇, —C(O)R₇, —C(O)OR₇, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁, —S(O)ₚOR₇, —OP(O)(OR₇)₂, —SP(O)(OR₇)₂, —S(O)ₚOR₇, —OP(O)(OR₇)₂, or —SP(O)(OR₇)₂;

or two R₂₇ groups taken together with the carbon atom to which they are attached form an optionally substituted cycloalkyl or optionally substituted heterocyclyl ring;

R₇₇, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, guanidino, a hydroxyalkyl, alkoxyalkyl, haloalkyl, a heteroalkyl, —OR₇, —C(O)R₇, —C(O)OR₇, —OC(O)R₇, —C(O)NR₁₀R₁₁, —SR₇, —S(O)ₚR₇, —OS(O)ₚR₇, —S(O)ₚOR₇, —S(O)ₚNR₁₀R₁₁, —S(O)ₚOR₇, —OP(O)(OR₇)₂, —SP(O)(OR₇)₂, —S(O)ₚOR₇, —OP(O)(OR₇)₂, or —SP(O)(OR₇)₂;

Z is a substituent;

p, for each occurrence, is independently, 1 or 2;

m, for each occurrence, is independently, 1, 2, 3 or 4;

n is 0, 1, 2, or 3;

r is 0 or 1;

or a tautomer, pharmaceutically acceptable salt, solvate, clathrate or a prodrug thereof.

In one embodiment, of the compounds represented by formula (I), the compound is not 3-(2,4-Dihydroxyphenyl)-4-(1,2,3,4-tetrahydronaphthalen-5-yl)-5-mercapto-[1,2,4]triazole;

4-ethyl-6-(5-mercapto-4-(1-methylindolin-5-yl)-4H-1,2,4-triazol-3-yl)benzene-1,3-diol;

4-(4-(benzo[d][1,3]dioxol-5-yl)-5-mercapto-4H-1,2,4-triazol-3-yl)-6-isopropylbenzene-1,3-diol;

4-(4-(2,3-dihydro-1H-inden-5-yl)-5-mercapto-4H-1,2,4-triazol-3-yl)-6-isopropylbenzene-1,3-diol;

6-(3-(5-ethyl-2,4-dihydroxyphenyl)-5-mercapto-4H-1,2,4-triazol-4-yl)-3-methylbenzo[d]thiazol-2(3H)-one;

5-(3-(5-ethyl-2,4-dihydroxyphenyl)-5-mercapto-4H-1,2,4-triazol-4-yl)indolin-2-one;

5-(3-(5-ethyl-2,4-dihydroxyphenyl)-5-mercapto-4H-1,2,4-triazol-4-yl)-1H-benzo[d]imidazol-2(3H)-one; or 6-(3-(5-ethyl-2,4-dihydroxyphenyl)-5-mercapto-4H-1,2,4-triazol-4-yl)benzo[d]thiazol-2(3H)-one.

In another embodiment, the present invention provides compounds represented by structural formula (XI):

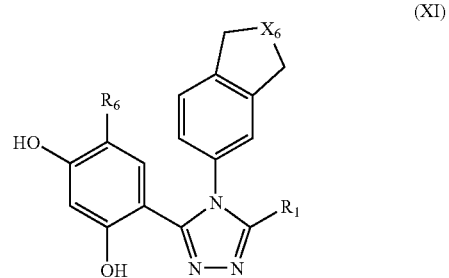

(XI)

X₆ is CHR₂₈ or NR₇₇;

R₂₈, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanidino, a hydroxyalkyl, alkoxyalkyl, haloalkyl, a heteroalkyl, —NR₁₀R₁₁, —OR₇, —C(O)R₇, —C(O)OR₇, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁, —S(O)ₚOR₇, —OP(O)(OR₇)₂, or —SP(O)(OR₇)₂, —S(O)ₚOR₇, —OP(O)(OR₇)₂, or —SP(O)(OR₇)₂;

R₇₇, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, guanidino, a hydroxyalkyl, alkoxyalkyl, haloalkyl, a heteroalkyl, —OR₇, —C(O)R₇, —C(O)OR₇, —OC(O)R₇, —C(O)NR₁₀R₁₁, —SR₇, —S(O)ₚR₇, —OS(O)ₚR₇, —S(O)ₚOR₇, —S(O)ₚNR₁₀R₁₁, —S(O)ₚOR₇, —OP(O)(OR₇)₂, —SP(O)(OR₇)₂, —S(O)ₚOR₇, —OP(O)(OR₇)₂, or —SP(O)(OR₇)₂;

or a tautomer, pharmaceutically acceptable salt, solvate, clathrate or a prodrug thereof, where R₁ is defined as for formula (I), and R₆ is defined as for formula (III).

In another embodiment, the present invention provides compounds represented by structural formula (XII):

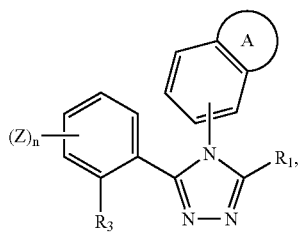

(XII)

wherein:
Ring A is an Optionally Substituted Heteroaromatic Ring, Selected from the Group consisting of furanyl, oxazolyl, thiazolyl, indazolyl, thiophenyl, triazolyl, or pyridyl;
or a tautomer, pharmaceutically acceptable salt, solvate, clathrate or a prodrug thereof, where $R_1$, $R_3$, n, and Z are defined as for formula (I).

In one embodiment of compounds of formula (XII), that the compound is not
3-(2,4-dihydroxy-5-ethyl-phenyl)-4-(2-methyl-7-methoxy-benzofuran-4-yl)-5-mercapto-[1,2,4]triazole;
3-(2,4-dihydroxy-5-ethyl-phenyl)-4-(benzofuran-5-yl)-5-mercapto-[1,2,4]triazole;
3-(2,4-dihydroxy-5-ethyl-phenyl)-4-(2-methyl-1,3-benzoxaz-5-yl)-5-mercapto-[1,2,4]triazole;
3-(2,4-dihydroxy-5-isopropyl-phenyl)-4-(1-methyl-indazol-5-yl)-5-mercapto-[1,2,4]triazole;
3-(2,4-dihydroxy-5-isopropyl-phenyl)-4-(1-methyl-2-trifluoromethyl-benzimidazol-5-yl)-5-mercapto-[1,2,4]triazole;
3-(2,4-Dihydroxyphenyl)-4-(quinolin-5-yl)-5-mercapto-[1,2,4]triazole;
3-(2,4-Dihydroxy-phenyl)-4-(isoquinolin-5-yl)-5-mercapto-[1,2,4]triazole;
3-[2,4-Di-(dimethyl-carbamoyloxy)-phenyl]-4-(quinolin-5-yl)-5-(dimethyl-carbamoylsulfanyl)-[1,2,4]triazole;
3-(2,4-Dihydroxy-5-ethyl-phenyl)-4-(quinolin-5-yl)-5-ureido-[1,2,4]triazole;
3-(2,4-Dihydroxy-5-isopropyl-phenyl)-4-(3-methyl-quinolin-5-yl)-5-carboxyamino-[1,2,4]triazole;
3-[2-Hydroxy-4-(dimethyl-carbamoyoxy)-5-chloro-phenyl]-4-(quinolin-5-yl)-5-mercapto-[1,2,4]triazole;
3-(2,4-dihydroxy-5-isopropyl-phenyl)-4-(1-methyl-indazol-6-yl)-5-mercapto-[1,2,4]triazole; or
3-(2,4-dihydroxy-5-isopropyl-phenyl)-4-(2-methyl-indazol-6-yl)-5-mercapto-[1,2,4]triazole.

In another embodiment, the present invention provides compounds represented by structural formula (XVI):

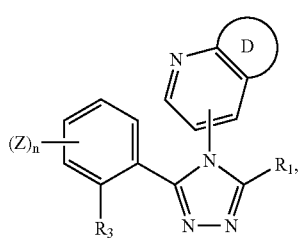

(XVI)

Ring D is an optionally substituted aryl or an optionally substituted heteroaryl;
or a tautomer, pharmaceutically acceptable salt, solvate, clathrate or a prodrug thereof, where $R_1$, $R_3$, n, and Z are defined as for formula (I).

In one embodiment, the present invention provides compounds represented by structural formula (XVIII):

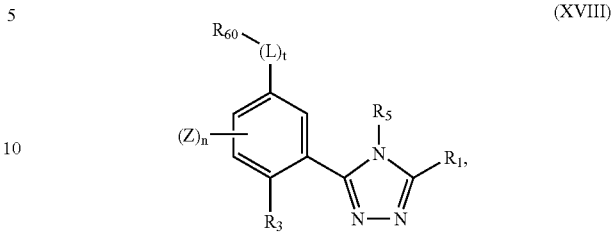

(XVIII)

or a tautomer, pharmaceutically acceptable salt, solvate, clathrate or a prodrug thereof, wherein:
$R_1$ and $R_3$ are, independently, —OH, —SH, —NHR$_7$, —OR$_{26}$, —SR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$;
$R_5$ is an optionally substituted heteroaryl or an optionally substituted aryl;
$R_{60}$ is an optionally substituted heteroaryl or an optionally substituted aryl;
$R_7$ and $R_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;
$R_{10}$ and $R_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or $R_{10}$ and $R_{11}$, taken together with the nitrogen to which they are attached, form an optionally substituted heterocyclyl or an optionally substituted heteroaryl;
$R_{26}$ is a lower alkyl;
L is an optionally substituted 1 to 6 atom linker, wherein each linker atom is independently selected from the group consisting of C, O, S or N, provided that L is not —N=N—;
Z is a substituent;
p, for each occurrence, is independently, 1 or 2;
m, for each occurrence, is independently, 1, 2, 3 or 4;
n is 0, 1, 2, or 3; and
t is 0 or 1.

In one embodiment, the present invention provides compounds represented by structural formula (XVIII):

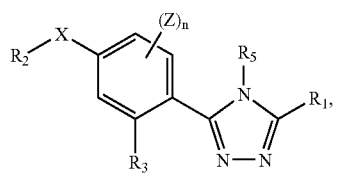

(XVIII)

wherein:
$R_1$ and $R_3$ are, independently, —OH, —SH, —NHR$_7$, —OR$_{26}$, —SR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$;
$R_2$ is —OH, —SH, —NHR$_7$;
$R_5$ is an optionally substituted heteroaryl or an optionally substituted aryl;
$R_7$ and $R_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl;
$R_{10}$ and $R_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl; or $R_{10}$ and $R_{11}$, taken together with the nitrogen to which they are attached, form an optionally substituted heterocyclyl or an optionally substituted heteroaryl;
$R_{26}$ is a lower alkyl;
X is an optionally substituted 1 to 6 atom linker, wherein each linker atom is independently selected from the group consisting of C, O, P, N, or S;
Z is a substituent;
p, for each occurrence, is independently, 1 or 2;
m, for each occurrence, is independently, 1, 2, 3 or 4; and
n is 0, 1, or 2;
or a tautomer, pharmaceutically acceptable salt, solvate, clathrate or a prodrug thereof.

In one aspect of the compounds of formula (I), the compound is not
3-(2,5-Dihydroxy-4-carboxy)-4-(naphthalen-1-yl)-5-mercapto-[1,2,4]triazole;
3-(2,5-Dihydroxy-4-hydroxymethyl-phenyl)-4-(naphthalen-1-yl)-5-mercapto-[1,2,4]triazole;
3-[2,4-Di-(dimethyl-carbamoyloxy)-phenyl]-4-(naphthalen-1-yl)-5-(dimethyl-carbamoylsulfanyl)-[1,2,4]triazole;
3-[2,4-Di-(dimethyl-carbamoyloxy)-phenyl]-4-(quinolin-5-yl)-5-(dimethyl-carbamoylsulfanyl)-[1,2,4]triazole;
3-[2-Hydroxy-4-(dimethyl-carbamoyoxy)-5-ethyl-phenyl]-4-(naphthalin-2-yl)-5-hydroxy-[1,2,4]triazole;
3-[2-Hydroxy-4-(dimethyl-carbamoyoxy)-5-chloro-phenyl]-4-(quinolin-5-yl)-5-mercapto-[1,2,4]triazole; or
3-[2-Hydroxy-4-(dimethyl-carbamoyoxy)-5-ethyl-phenyl]-4-(2,3-difluoro-phenyl)-5-mercapto-[1,2,4]triazole.

The compounds shown in Table 1, 2 or 3 or compounds of any formula herein, or tautomers, pharmaceutically acceptable salts, solvates, clathrates, hydrates, polymorphs or prodrugs thereof, inhibit the activity of Hsp90 and, thereby facilitates the degradation of Hsp90 client proteins. Hsp90 is necessary for the survival of normal eukaryotic cells. However, Hsp90 is over expressed in many tumor types indicating that it may play a significant role in the survival of cancer cells and that cancer cells may be more sensitive to inhibition of Hsp90 than normal cells. Thus, the compounds shown in Table 1, 2 or 3 or compounds of any formula herein, or tautomers, pharmaceutically acceptable salts, solvates, clathrates, hydrates, polymorphs or prodrugs thereof, are useful treating proliferative disorders such as cancer.

Although chemotherapeutic agents initially cause tumor regression, most agents that are currently used to treat cancer target only one pathway to tumor progression. Therefore, in many instances, after treatment with one or more chemotherapeutic agents, a tumor develops multidrug resistance and no longer responses positively to treatment. One of the advantages of inhibiting Hsp90 activity is that several of its client proteins, which are mostly protein kinases or transcription factors involved in signal transduction, have been shown to be involved in the progression of cancer. Thus, inhibition of Hsp90 provides a method of short circuiting several pathways for tumor progression simultaneously. Therefore, treatment of tumors with an Hsp90 inhibitor of the invention either alone, or in combination with other chemotherapeutic agents, is more likely to result in regression or elimination of the tumor, and less likely to result in the development of more aggressive multidrug resistant tumors than other currently available therapeis.

DETAILED DESCRIPTION OF THE INVENTION

A description of preferred embodiments of the invention follows.

The present invention provides compounds disclosed herein and uses of said compounds to inhibit Hsp90 activity and for the treatment of a proliferative disorder, such as cancer. In particular, the present invention encompasses the use of compounds of the invention to slow or stop the growth of cancerous cells or to reduce or eliminate cancerous cells in a subject, preferably the subject is a mammal.

In certain embodiments, the compounds of the invention can be used in combination with other chemotherapeutic agents and may help to prevent or reduce the development of multidrug resistant cancerous cells in a mammal. In this embodiment, the compounds of the invention may allow a reduced efficacious amount of a second chemotherapeutic agent given to a mammal, because compounds of the invention should inhibit the development of multidrug resistant cancerous cells.

In certain embodiments, the compounds of the invention can be used to block, occlude, or otherwise disrupt blood flow in neovasculature.

In other embodiments, the compounds of the invention can be used to treat or inhibit angiogenesis in a subject in need thereof.

The present invention also relates to compounds which inhibit the activity of topoisomerase II.

The present invention also relates to the discovery that treatment of cells, such as peripheral blood mononuclear cells (PMBCs) that have been stimulated with an inflammatory stimulus, such as INFγ/LPS or SAC, with an Hsp90 inhibitor reduces the expression of GR in the PMBCs and reduces the production of inflammatory cytokines.

The present invention also relates to compounds which inhibit the activity of Hsp90 and are useful in the treatment of or prevention of infections.

A. Terminology

Unless otherwise specified, the below terms used herein are defined as follows:

As used herein, the term "alkyl" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. The term "$(C_1-C_6)$alkyl" means a saturated straight chain or branched non-cyclic hydrocarbon having from 1 to 6 carbon atoms. Representative $(C_1-C_6)$alkyl groups are those shown above having from 1 to 6 carbon atoms. Alkyl groups included in compounds of this invention may be optionally substituted with one or more substituents.

As used herein, the term "alkenyl" means a saturated straight chain or branched non-cyclic hydrocarbon having from 2 to 10 carbon atoms and having at least one carbon-carbon double bond. Representative straight chain and branched $(C_2-C_{10})$alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups may be optionally substituted with one or more substituents.

As used herein, the term "alkynyl" means a saturated straight chain or branched non-cyclic hydrocarbon having from 2 to 10 carbon atoms and having at least one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkynyl groups may be optionally substituted with one or more substituents.

As used herein, the term "cycloalkyl" means a saturated, mono- or polycyclic alkyl radical having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, -cyclodecyl, octahydropentalenyl, and the like. Cycloalkyl groups may be optionally substituted with one or more substituents.

As used herein, the term "cycloalkenyl" means a mono- or poly-cyclic non-aromatic alkyl radical having at least one carbon-carbon double bond in the cyclic system and from 3 to 20 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl, 1,2,3,4,5,8-hexahydronaphthalenyl and the like. Cycloalkenyl groups may be optionally substituted with one or more substituents.

As used herein, the term "haloalkyl" means an alkyl group, in which one or more (including all) the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker.

As used herein, an "haloalkoxy" is an haloalkyl group which is attached to another moiety via an oxygen linker.

As used herein, the term an "aromatic ring" or "aryl" means a hydrocarbon monocyclic or polycyclic radical in which at least one ring is aromatic. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Aryl groups may be optionally substituted with one or more substituents. In one embodiment, the aryl group is a monocyclic ring, wherein the ring comprises 6 carbon atoms, referred to herein as "$(C_6)$aryl."

As used herein, the term "aralkyl" means an aryl group that is attached to another group by a $(C_1-C_6)$alkylene group. Representative aralkyl groups include benzyl, 2-phenylethyl, naphth-3-yl-methyl and the like. Aralkyl groups may be optionally substituted with one or more substituents.

As used herein, the term "alkylene" refers to an alkyl group that has two points of attachment. The term "$(C_1-C_6)$alkylene" refers to an alkylene group that has from one to six carbon atoms. Straight chain $(C_1-C_6)$alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like. Alkylene groups may be optionally substituted with one or more substituents.

As used herein, the term "heterocyclyl" means a monocyclic (typically having 3- to 10-members) or a polycyclic (typically having 7- to 20-members) heterocyclic ring system which is either a saturated ring or a unsaturated non-aromatic ring. A 3- to 10-membered heterocycle can contain up to 5 heteroatoms; and a 7- to 20-membered heterocycle can contain up to 7 heteroatoms. Typically, a heterocycle has at least one carbon atom ring member. Each heteroatom is independently selected from nitrogen, which can be oxidized (e.g., N(O)) or quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents. Only stable isomers of such substituted heterocyclic groups are contemplated in this definition.

As used herein, the term "heteroaromatic", "heteroaryl" or like terms means a monocyclic or polycyclic heteroaromatic ring comprising carbon atom ring members and one or more heteroatom ring members. Each heteroatom is independently selected from nitrogen, which can be oxidized (e.g., N(O)) or quaternized; oxygen; and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring is selected from 5-8 membered monocyclic heteroaryl rings. The point of attachment of a heteroaromatic or heteroaryl ring may be at either a carbon atom or a heteroatom of the heteroaromatic or heteroaryl rings. Heteroaryl groups may be optionally substituted with one or more substituents.

As used herein, the term "($C_5$)heteroaryl" means an aromatic heterocyclic ring of 5 members, wherein at least one carbon atom of the ring is replaced with a heteroatom such as, for example, oxygen, sulfur or nitrogen. Representative ($C_5$) heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "($C_6$)heteroaryl" means an aromatic heterocyclic ring of 6 members, wherein at least one carbon atom of the ring is replaced with a heteroatom such as, for example, oxygen, nitrogen or sulfur. Representative ($C_6$) heteroaryls include pyridyl, pyridazinyl, pyrazinyl, triazinyl, tetrazinyl and the like.

As used herein, the term "heteroaralkyl" means a heteroaryl group that is attached to another group by a ($C_1$-$C_6$) alkylene. Representative heteroaralkyls include 2-(pyridin-4-yl)-propyl, 2-(thien-3-yl)-ethyl, imidazol-4-yl-methyl and the like. Heteroaralkyl groups may be optionally substituted with one or more substituents.

As used herein, the term "halogen" or "halo" means —F, —Cl, —Br or —I.

As used herein the term "heteroalkyl" means a linear straight or branched chain alkyl group, wherein one or more of the internal carbon atoms in the chain is replaced by a heteroatom, such as, O, N or S, e.g., —[$CH_2$]$_x$—O—[$CH_2$]$_y$ [$CH_3$] wherein x is a positive integer and y is 0 or a positive integer, and wherein replacement of the carbon atom does not result in a unstable compound.

Suitable substituents for an alkyl, alkylene, alkenyl, alkynyl, cycloalkyl, cycloalkenyl, heterocyclyl, aryl, aralkyl, heteroaryl, and heteroaralkyl groups include are those substituents which form a stable compound of the invention without significantly adversely affecting the reactivity or biological activity of the compound of the invention. Examples of substituents for an alkyl, alkylene, alkenyl, alkynyl, cycloalkyl, cycloalkenyl, heterocyclyl, aryl, aralkyl, heteroaryl, and heteroarylalkyl include an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, an optionally substituted haloalkyl, an optionally substituted heteroalkyl, optionally substituted alkoxy, —C(O)$NR_{28}R_{29}$, —C(S)$NR_{28}R_{29}$, —C($NR_{32}$)$NR_{28}R_{29}$, —$NR_{33}$C(O)$R_{31}$, —$NR_{33}$C(S)$R_{31}$, —$NR_{33}$C($NR_{32}$)$R_{31}$, halo, —$OR_{33}$, cyano, nitro, haloalkoxy, —C(O)$R_{33}$, —C(S)$R_{33}$, —C($NR_{32}$)$R_{33}$, —$NR_{28}R_{29}$, —C(O)$OR_{33}$, —C(S)$OR_{33}$, —C($NR_{32}$)$OR_{33}$, —OC(O)$R_{33}$, —OC(S)$R_{33}$, —OC($NR_{32}$)$R_{33}$, —$NR_3$OC(O)$NR_{28}R_{29}$, —$NR_{33}$C(S)$NR_{28}R_{29}$, —$NR_{33}$C($NR_{32}$)$NR_{28}R_{29}$, —OC(O)$NR_{28}R_{29}$, —OC(S)$NR_{28}R_{29}$, —OC($NR_{32}$)$NR_{28}R_{29}$, —$NR_{33}$C(O)$OR_{31}$, —$NR_{33}$C(S)$OR_{31}$, —$NR_{33}$C($NR_{32}$)$OR_{31}$, —S(O)$_h$$R_{33}$, —OS(O)$_p$$R_{33}$, —$NR_{33}$S(O)$_p$$R_{33}$, —S(O)$_p$$NR_{28}R_{29}$, —OS(O)$_p$$NR_{28}R_{29}$, or —$NR_{33}$S(O)$_p$$NR_{28}R_{29}$ guanidino, —C(O)$SR_{31}$, —C(S)$SR_{31}$, —C($NR_{32}$)$SR_{31}$, —OC(O)$R_{31}$, —OC(S)$R_{31}$, —OC($NR_{32}$)$R_{31}$, —SC(O)$R_{33}$, —SC(O)$OR_{31}$, —SC($NR_{32}$)$OR_{31}$, —SC(S)$R_{33}$, —SC(S)$OR_{31}$, —SC(O)$NR_{28}R_{29}$, —SC($NR_{32}$)$NR_{28}R_{28}$, —SC(S)$NR_{28}R_{29}$, —SC($NR_{32}$)$R_{33}$, —OS(O)$_p$$OR_{31}$, —S(O)$_p$$OR_{31}$, —$NR_3$OS(O)$_p$$OR_{31}$, —SS(O)$_p$$R_{33}$, —SS(O)$_p$$OR_{31}$, —SS(O)$_p$$NR_{28}R_{29}$, —OP(O)(O$R_{31}$)$_2$, or —SP(O)(O$R_{31}$)$_2$, (preferably the alkyl, alkenyl, alkynyl, cycloalkyl, cycloalkenyl, heterocyclyl, aryl, heteroaryl, aralkyl, heteroalkyl, alkoxy, heteroaralkyl and haloalkyl are unsubstituted); wherein $R_{28}$ and $R_{29}$, for each occurrence is independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl (preferably the alkyl, alkenyl, alkynyl, cycloalkyl, cycloalkenyl, heterocyclyl, aryl, heteroaryl, aralkyl and heteroaralkyl are unsubstituted);

$R_{33}$ and $R_{31}$ for each occurrence is independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteroaralkyl (preferably the alkyl, alkenyl, alkynyl, cycloalkyl, cycloalkenyl, heterocyclyl, aryl, heteroaryl, aralkyl, and heteroaralkyl are unsubstituted); and $R_{32}$, for each occurrence is independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, —C(O)$R_{33}$, —C(O)$NR_{28}R_{29}$, —S(O)$_p$$R_{33}$, or —S(O)$_p$$NR_{28}R_{29}$ (preferably the alkyl, alkenyl, alkynyl, cycloalkyl, cycloalkenyl, heterocyclyl, aryl, heteroaryl, aralkyl and heteroaralkyl are unsubstituted);

p is 1 or 2; and h is 0, 1 or 2.

In addition, alkyl, cycloalkyl, alkylene, a heterocyclyl, and any saturated portion of a alkenyl, cycloalkenyl, alkynyl, aralkyl, and heteroaralkyl groups, may also be substituted with =O, =S, =N—$R_{32}$.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, the term "lower" refers to a group having up to four atoms. For example, a "lower alkyl" refers to an alkyl radical having from 1 to 4 carbon atoms, "lower alkoxy" refers to "—O—($C_1$-$C_4$)alkyl and a "lower alkenyl" or "lower alkynyl" refers to an alkenyl or alkynyl radical having from 2 to 4 carbon atoms, respectively.

As used herein, the term "contiguous linear connectivity" means connected together so as to form an uninterrupted linear array or series of atoms. For example, a linker of the compounds described herein having a specified number of atoms in contiguous linear connectivity has at least that number of atoms connected together so as to form an uninterrupted chain, but may also include additional atoms that are not so connected (e.g., branches or atoms contained within a ring system).

As used herein, the term "linker" means a diradical having from 1-6 atoms in contiguous linear connectivity (i.e., as defined above and excluding atoms present in any side chains and branches), that covalently connects the phenyl ring portion of a compound of this invention to the $R_{60}$ group of the compound, as illustrated in formula (XVIII).

Unless indicated otherwise, the compounds of the invention containing reactive functional groups (such as (without limitation) carboxy, hydroxy, thiol, and amino moieties) also include protected derivatives thereof. "Protected derivatives" are those compounds in which a reactive site or sites are blocked with one or more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxycarbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981.

As used herein, the term "compound(s) of this invention" and similar terms refers to a compound of formula (I)-(XXXII), or Table 1, 2 or 3, or a pharmaceutically acceptable salt, solvate, clathrate, hydrate, polymorph or prodrug thereof, and also include protected derivatives thereof.

The compounds of the invention may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

As used herein, the term "polymorph" means solid crystalline forms of a compound of the present invention or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "hydrate" means a compound of the present invention or a salt thereof, that further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of formula (I)-(XXXII), or Table 1, 2 or 3 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of formula (I)-(XXXII), or Table 1, 2 or 3 that comprise —NO, —$NO_2$, —ONO, or —$ONO_2$ moieties. Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., $5^{th}$ ed).

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as improved water solubility, improved circulating half-life in the blood (e.g., because of reduced metabolism of the prodrug), improved uptake, improved duration of action, or improved onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, "Hsp90" includes each member of the family of heat shock proteins having a mass of about 90-kiloDaltons. For example, in humans the highly conserved Hsp90 family includes cytosolic Hsp90α and Hsp90β isoforms, as well as GRP94, which is found in the endoplasmic reticulum, and HSP75/TRAP1, which is found in the mitochondrial matrix.

c-Met is a receptor tyrosine kinase that is expressed in normal and malignant cells and has been identified as a proto-oncogene. HGF/c-Met signaling triggers an invasive growth program that is thought to be essential in early embryonic development but when dysregulated can result malignant growth, motility, migration and invasion by a mechanism that is not yet completely understood. The human Met gene is located on chromosome 7 band 7q21-q31 and spans more than 120 kb (Ma, et al., Cancer and Metastasis Reviews (2003), 22:309-325). In wild type cells, c-Met is a heterodimer that consists of an extracellular α-subunit and α'-subunit with a large extracellular domain, a membrane spanning segment and an intracellular tyrosine kinase domain. Functional structures and domains of c-Met include 1) Sema domain at the N-terminus which includes a MRS cysteine-rich region; 2) PSI domain which is also found in plexins, semaphorins and integrins; 3) IPT repeats which are found in immunoglobulin, plexins and transcription factors; 4) transmembrane domain; 5) juxtamembrane domain; and 6) the intracellular tyrosine kinase domain at the C-terminus.

Activation of c-Met signaling is dependent on phosphorylation of multiple residues on c-Met. Upon binding of HGF, c-Met undergoes autophosphorylation at Y1230, Y1234, and Y1235 in the activation loop of the tyrosine kinase domain which activates the kinase activity of c-Met. Y1313 can also be phosphorylated in response to HGF binding and is important in binding PI3-K which is implicated in prosurvival signaling. Phosphorylation of Y1349 and Y1356 at the C-terminus of c-Met activates the multisubstrate signal transducer docking site which has been implicated in Met-mediated signal transduction and mediates the interactions of SHC, Src, and Gab1, while recruitment of Grb2, PI3-K, PLC-γ and SHP2 is dependent on phosphorylation of Y1356 alone. Regulation of cell morphogenesis is mediated via Y1365. Phosphorylation of the Y1003 residue in the juxtamembrane domain mediates the binding of c-Cbl. c-Cbl acts as a negative regulator protein of c-Met by promoting the polyubiquitinization of c-Met which leads to degradation.

Dysregulation of HGF/c-Met signaling can be caused by 1) increased expression of HGF; 2) activating mutations which typically occur in the tyrosine kinase domain or the juxtamembrane domain of c-Met and confer constitutive kinase activity; 3) intra-chromosomal amplification of the Met gene and over expression of c-Met; 4) chromosomal translocation such as in the Trp/Met fusion protein which results in the loss of the juxtamembrane domain and leads to constitutive activation; and 5) alternate splicing variants c-Met mRNA which lead to loss of the juxtamembrane domain and also lead to constitutive activation.

Activating mutation in the tyrosine kinase domain or in the juxtamembrane domain of c-Met which result in increased activation of the tyrosine kinase activity have been observed in hereditary and sporadic papillary renal carcinoma, ovarian cancer, hepatocellular carcinoma, metastatic head and neck squamous cell carcinomas, NSCLC, SCLC, glioma, breast cancer, and gastric cancer. In somatic papillary renal cell carcinoma activating mutations have been found at amino acid residues M1268 (e.g., M1268T), Y1248 (e.g., Y1248D, Y1248H), Y1246 (e.g., Y1246H), Y1230 (e.g., Y1230C), L1213 (e.g., L1213V), H1124 (e.g., H1124D, H1112L, and H1112Y), and V1110 (V1110I). In germline papillary renal cell carcinoma activating mutations have been found at amino acid residues Y1248 (e.g., Y1248C), Y1246 (e.g., Y1246N), V1238 (e.g., V1238I), Y1230 (e.g., Y1230C and Y1230H), V1206 (e.g., V1206L), M1149 (e.g., M1149T), and H1112 (e.g., H1112R). In hepatocellular carcinoma activating mutations have been found at amino acid residues M1268 (e.g., M1268I), K1262 (e.g., K1262R), and T1191 (e.g., T1191I). In head and neck squamous cell carcinoma activating mutations have been found at amino acid residues Y1253 (e.g., Y1253D), Y1235 (e.g., Y1235D), and Y1230 (e.g., Y1230C and Y1230D). In glioma activating mutations have been found at amino acid residue G1137 (e.g., G1137V). In NSCLC activating mutations have been found at amino acid residue T1010 (e.g., T1010I). In SCLC activating mutations have been found at amino acid residues R988 (e.g., R988C) and T1010 (e.g., T1010I). In breast cancer activating mutations have been found at amino acid residues T1010 (e.g., T1010). In gastric cancer activating mutations have been found at amino acid residue P1009 (e.g., P1009S). Amino acids listed herein for c-Met are numbered as in Schmit, et al., *Onogene* (1999), 18:2343-2350. Compounds of the invention cause the degradation of c-Met and can be used either alone or in combination with other anticancer therapies to treat patients with cancers that have activating mutations in the tyrosine kinase domain or in the juxtamembrane domain of c-Met.

The juxtamembrane of receptor tyrosine kinases has been shown to repress catalytic function and mutation in the juxtamembrane relieve this repression and can lead to oncogenesis. The Tpr/Met fusion protein results from replacement of the 5' region of the Met gene with Tpr which provides two strong dimerization motifs. Dimerization activates the Met kinase activity and results in transforming and metastatic properties. The Tpr/Met fusion protein has been found in gastric cancer and results in increased Met kinase activity. In addition, an alternative splicing form of Met mRNA has been found in small cell lung cancer which results in skipping the juxtamembrane domain. Loss of the juxtamembrane domain leads to increased Met kinase activity and oncogenesis. Compounds of the invention cause the degradation of c-Met and can be used either alone or in combination with other anticancer therapies to treat patients with cancers that have juxtamembrane mutations or deletions in c-Met.

Amplification of the Met gene and overexpression of c-Met has been found in several types of cancers including gastric cancer, esophageal cancer, small cell lung cancer, non-small cell lung cancer, breast cancer, multiple myeloma, and colorectal cancer metastases. Compounds of the invention cause the degradation of c-Met and can be used either alone or in combination with other anticancer therapies to treat patients with cancers that have Met gene amplification and/or c-Met overexpression.

Met amplification and mutation has also been implicated as a strategy by which certain cancers become resistant to therapy (e.g., chemotherapy or radiation therapy). For example, certain non-small cell lung cancers contain an activating mutation in receptor tyrosine kinase EGFR which results in oncogenesis. Most EGFR mutant NSCLCs initially respond to EGFR inhibitors such as Iressa and Tarceva but the vast majority of these tumors ultimately become resistant to the drug. A subset of these resistant cancers have been shown to have amplified Met, and it is thought that Met amplification is a mechanisms of acquired resistance, and in particular acquired resistance to kinase inhibitors such as Iressa and Tarceva (EGFR inhibitors), Gleevec (a Bcr-Abl, PDGF, and c-Kit inhibitor) (Engelman et al., Sciencexpress, www-.sciencexpress.orq/26 Apr. 2007/page 1/10.1126/science.1141478). Compounds of the invention cause the degradation of c-Met and can be used either alone or in combination with other anticancer therapies, such as treatment with kinase inhibitors, to treat patients with cancer that has become resistant to other anticancer therapies.

As used herein, "c-Met associated cancer" refers to any type of malignant growth or metastasis that is caused by or enhanced by dysregulation in HGF/c-Met signaling.

B-raf is a serine/threonine kinase that is involved in the MAP kinase pathway and is encoded by a gene located on chromosome 7q32. Ten isoforms of B-raf have been identified which are the result of splicing variants. The term "B-raf" refers to all such splicing variants. B-raf has three conserved regions (CR): 1) CR1 which contains a cysteine rich domain (CRD) and most of the Ras binding domain (RBD) and facilitates the binding of B-raf to Ras and recruitment to the cell membrane; 2) CR2 which is rich in serine and threonine and includes the S365 residue which is an inhibitory phosphorylation site; and 3) CR3 which contains the kinase domain including a G-loop GXGXXG motif, an activation segment and regulatory phosphorylation sites S446, S447, D448, D449, T599 and S602. B-raf is translocated to the cell membrane and activated by association with GTP-bound Ras. B-raf is regulated by changes in its conformation and is inactive when the activation segment is held in an inactive conformation as a result of hydrophobic interactions with the P-loop. Phosphorylation in the activation segment results in a shift to the active conformation of B-raf. Interestingly, the activation segment and P-loop that interact with one-another and restraining the activation segment in an inactive conformation, are where the majority of B-raf oncogenic mutations are clustered. This indicates that as a result of B-raf mutations the inactive B-raf conformation is destabilized thereby promoting an active B-raf conformation. (Berram, et al., *Journal of Clinical Oncology* (2005), 23(27):6771-6790).

B-raf associated cancers are cancers in which inappropriate B-raf activity is detected. In one embodiment, B-raf associated cancers have increased B-raf activity, such as B-raf with mutations in the kinase domain that confer increased activity over that of wild type B-raf and/or constitutively active B-raf (e.g., B-raf that has activity that is not dependent on interaction with Ras). Activating mutations in the kinase domain include V600E, V600D, G596R, G594V, G469A, G469E, G466V, and G464V mutations. Examples of B-raf associated cancers include malignant melanomas, anaplastic thyroid carcinoma, papillary thyroid caricinoma, follicular thyroid cancer, para-follicular C-cell-derived medullary thyroid cancer, colon cancer, ovarian carcinoma, Barrett's esophageal carcinoma, acute myeloid leukemia, head and neck squamous cell carcinoma, non-small-cell lung cancer, gastric carcinoma, non-Hodgkins lymphoma, glioma, saroma, breast cancer, cholangiocarcinoma, and liver cancer in which inappropriate B-raf activity can be detected, such as increased B-raf activity of a mutant form of B-raf over that of wild type B-raf or constitutive activity of B-raf.

As used herein, "NPM-ALK" refers to a fusion protein which is the result of a t(2;5)(p23;q35) translocation of the gene sequence for NPM/B23 nucleolar protein into the sequence which encodes for the tyrosine kinase ALK. Typically, the NPM-ALK fusion protein contains the first 117 amino acids of the amine terminal of NPM and the C-terminal residues 1058 to 1620 of ALK. For a schematic representation of NPM-ALK see FIG. 1 of Duyster, et al., *Oncogene* (2001), 20:5623-5637, the entire teachings of which are incorporated herein by reference.

The term "NPM-ALK associated cancers" refers to cancers in which the NPM-ALK fusion protein is expressed, such as ALCL and diffuse large B-cell lymphomas.

The term "c-kit" or "c-kit kinase" refers to a membrane receptor protein tyrosine kinase which is preferably activated upon binding Stem Cell Factor (SCF) to its extracellular domain (Yarden et al., 1987; Qiu et al., 1988). The full length amino acid sequence of a c-kit kinase preferably is as set forth in Yarden, et al., 1987, *EMBO J.*, 11:3341-3351; and Qiu, et al., 1988, *EMBO J.*, 7:1003-1011, which are incorporated by reference herein in their entirety, including any drawings. Mutant versions of c-kit kinase are encompassed by the term "c-kit" or "c-kit kinase" and include those that fall into two classes: (1) having a single amino acid substitution at codon 816 of the human c-kit kinase, or its equivalent position in other species (Ma et al., 1999, *J. Invest Dermatol.*, 112:165-170), and (2) those which have mutations involving the putative juxtamembrane z-helix of the protein (Ma, et al., 1999, *J. Biol. Chem.*, 274:13399-13402). Both of these publications are incorporated by reference herein in their entirety, including any drawings.

As used herein, "Bcr-Abl" is a fusion protein that results from the translocation of gene sequences from c-ABL protein tyrosine kinase on chromosome 9 into BCR sequences on chromosome 22 producing the Philadelphia chromosome. A schematic representation of human Bcr, Abl, and Bcr-Abl can be seen in FIG. 1 of U.S. patent application Ser. No. 10/193,651, filed on Jul. 9, 2002, the entire teachings of which are incorporated herein by reference. Depending on the breaking point in the Bcr gene, Bcr-Abl fusion proteins can vary in size from 185-230 kDa but they must contain at least the OLI domain from Bcr and the TK domain from Abl for transforming activity. The most common Bcr-Abl gene products found in humans are P230 Bcr-Abl, P210 Bcr-Abl, and P190 Bcr-Abl. P210 Bcr-Abl is characteristic of CML and P190 Bcr-Abl is characteristic of ALL.

FLT3 kinase is a tyrosine kinase receptor involved in the regulation and stimulation of cellular proliferation (see Gilliland et al., *Blood* (2002), 100:1532-42, the entire teachings of which are incorporated herein by reference). The FLT3 kinase has five immunoglobulin-like domains in its extracellular region as well as an insert region of 75-100 amino acids in the middle of its cytoplasmic domain. FLT3 kinase is activated upon the binding of the FLT3 ligand, which causes receptor dimerization. Dimerization of the FLT3 kinase by FLT3 ligand activates the intracellular kinase activity as well as a cascade of downstream substrates including Stat5, Ras, phosphatidylinositol-3-kinase (PI3K), PLC☐, Erk2, Akt, MAPK, SHC, SHP2, and SHIP (see Rosnet et al., *Acta Haematol.* (1996), 95:218; Hayakawa et al., *Oncogene* (2000), 19:624; Mizuki et al., *Blood* (2000), 96:3907; and Gilliand et al., *Curr. Opin. Hematol.* (2002), 9: 274-81, the entire teachings of each of these references are incorporated herein by reference). Both membrane-bound and soluble FLT3 ligand bind, dimerize, and subsequently activate the FLT3 kinase.

Normal cells that express FLT3 kinase include immature hematopoietic cells, typically CD34+ cells, placenta, gonads, and brain (see Rosnet, et al., *Blood* (1993), 82:1110-19; Small et al., *Proc. Natl. Acad. Sci. U.S.A.* (1994), 91:459-63; and Rosnet et al., *Leukemia* (1996), 10:238-48, the entire teachings of each of these references are incorporated herein by reference). However, efficient stimulation of proliferation via FLT3 kinase typically requires other hematopoietic growth factors or interleukins. FLT3 kinase also plays a critical role in immune function through its regulation of dendritic cell proliferation and differentiation (see McKenna et al., *Blood* (2000), 95:3489-97, the entire teachings of which are incorporated herein by reference).

Numerous hematologic malignancies express FLT3 kinase, the most prominent of which is AML (see Yokota et al., *Leukemia* (1997), 11:1605-09, the entire teachings of which are incorporated herein by reference). Other FLT3 expressing malignancies include B-precursor cell acute lymphoblastic leukemias, myelodysplastic leukemias, T-cell acute lymphoblastic leukemias, and chronic myelogenous leukemias (see Rasko et al., *Leukemia* (1995), 9:2058-66, the entire teachings of which are incorporated herein by reference).

FLT3 kinase mutations associated with hematologic malignancies are activating mutations. In other words, the FLT3 kinase is constitutively activated without the need for binding and dimerization by FLT3 ligand, and therefore stimulates the cell to grow continuously. Two types of activating mutations have been identified: internal tandem duplications (ITDs) and point mutation in the activating loop of the kinase domain. As used herein, the term "FLT3 kinase" refers to both wild type FLT3 kinase and mutant FLT3 kinases, such as FLT3 kinases that have activating mutations.

Compounds provided herein are useful in treating conditions characterized by inappropriate FLT3 activity such as proliferative disorders. Inappropriate FLT3 activity includes, but is not limited to, enhanced FLT3 activity resulting from increased or de novo expression of FLT3 in cells, increased FLT3 expression or activity, and FLT3 mutations resulting in constitutive activation. The existence of inappropriate or abnormal FLT3 ligand and FLT3 levels or activity can be determined using well known methods in the art. For example, abnormally high FLT3 levels can be determined using commercially available ELISA kits. FLT3 levels can be determined using flow cytometric analysis, immunohistochemical analysis, and in situ hybridization techniques.

By "epidermal growth factor receptor" or "EGFR" as used herein is meant, any epidermal growth factor receptor (EGFR) protein, peptide, or polypeptide having EGFR or EGFR family (e.g., HER1, HER2, HER3, and/or HER4) activity (such as encoded by EGFR Genbank Accession Nos. shown in Table I of U.S. patent application Ser. No. 10/923, 354, filed on Aug. 20, 2004, the entire teachings of which are incorporated herein by reference), or any other EGFR transcript derived from a EGFR gene and/or generated by EGFR translocation. The term "EGFR" is also meant to include other EGFR protein, peptide, or polypeptide derived from EGFR isoforms (e.g., HER1, HER2, HER3, and/or HER4), mutant EGFR genes, splice variants of EGFR genes, and EGFR gene polymorphisms.

As used herein, a "proliferative disorder" or a "hyperproliferative disorder," and other equivalent terms, means a disease or medical condition involving pathological growth of cells. Proliferative disorders include cancer, smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors, Smooth muscle cell proliferation includes hyperproliferation of cells in the vasculature, for example, intimal smooth muscle cell hyperplasia, restenosis and vascular occlusion, particularly stenosis following biologically- or mechanically-mediated vascular injury, e.g., vascular injury associated with angioplasty. Moreover, intimal smooth muscle cell hyperplasia can include hyperplasia in smooth muscle other than the vasculature, e.g., bile duct blockage, bronchial airways of the lung in patients with asthma, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

In a preferred embodiment, the proliferative disorder is cancer. Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562

(chronic) cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Frie Cancer Medicine* 5th Ed., Bast et al. Eds., B.C. Decker Inc. (2000). The entire teachings of the preceding references are incorporated herein by reference.

In one embodiment, the disclosed method is believed to be particularly effective in treating subject with non-solid tumors such as multiple myeloma. In another embodiment, the disclosed method is believed to be particularly effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1 (acute) cell line); and lymphoma (e.g., as exemplified by the U937 cell line).

In one embodiment, the disclosed method is believed to be particularly effective in treating subject with non-Hodgkin's lymphoma (NHL). Lymphomas are generally classified as either Hodgkin's disease (HD) or non-Hodgkin's lymphomas (NHL). NHL differs from HD by the absence of Reed-Sternberg cells. The course of NHL is less predictable than HD and is more likely to spread to areas beyond the lymph nodes. NHL can be further divided into B-cell NHL and T-cell NHL each of which can be further categorized into a variety of different subtypes. For example, B-cell NHL includes Burkitt's lymphoma, follicular lymphoma, diffuse large B-cell lymphoma, nodal marginal zone B-cell lymphoma, plasma cell neoplasms, small lymphocytic lymphoma/chronic lymphocytic leukemia, mantle cell lymphoma, extranodal marginal zone B-cell lymphoma, and lymphoplamacytic lymphoma/Waldenstrom macroglobulinemia. T-cell NHL include anaplastic large-cell lymphoma, precursor-T-cell lymphoblastic leukemia/lymphoma, unspecified peripheral T-cell lymphoma, acute lymphoblastic leukemia/lymphoma, angioimmunoblastic T-cell lymphoma, and mycosis fungoides.

Without wishing to be bound by any theory, it is believed that the compounds of the invention are useful for treating NHLs, including B-cell and T-cell NHLs, since Hsp90 is upregulated in many NHLs. In particular, in a survey of 412 cases of NHL in B-cell NHL, Hsp90 was found to be moderately to strongly over expressed in all cases of Burkitt's lymphoma (5/5, 100%), and in a subset of follicular lymphoma (17/28, 61%), diffuse large B-cell lymphoma (27/46, 59%), nodal marginal zone B-cell lymphoma (6/16, 38%), plasma cell neoplasms (14/39, 36%), small lymphocytic lymphoma/chronic lymphocytic leukemia (3/9, 33%), mantle cell lymphoma (12/38, 32%), and lymphoplamacytic lymphoma/Waldenstrom macroglobulinemia (3/10, 30%). In addition, in T-cell NHL, Hsp90 was found to be moderately to strongly over expressed in a subset of anaplastic large-cell lymphoma (14/24, 58%), precursor-T-cell lymphoblastic leukemia/lymphoma (20/65, 31%), unspecified peripheral T-cell lymphoma (8/43, 23%), and angioimmunoblastic T-cell lymphoma (2/17, 12%). (See Valbuena, et al., *Modern Pathology* (2005), 18:1343-1349, the entire teachings of which are incorporated herein by reference.)

Some of the disclosed methods can be particularly effective at treating subjects whose cancer has become "multi-drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

As used herein, the term "c-kit associated cancer" refers to a cancer which has aberrant expression and/or activation of c-kit. c-Kit associated cancers include leukemias, mast cell tumors, small cell lung cancer, testicular cancer, some cancers of the gastrointestinal tract and some central nervous system. In addition, c-kit has been implicated in playing a role in carcinogenesis of the female genital tract (Inoue, et al., 1994, *Cancer Res.*, 54(11):3049-3053), sarcomas of neuro-ectodermal origin (Ricotti, et al., 1998, *Blood*, 91:2397-2405), and Schwann cell neoplasia associated with neurofibromatosis (Ryan, et al., 1994, *J. Neuro. Res.*, 37:415-432).

In one embodiment, compounds of the invention are vascular targeting agents. In one aspect, compounds of the invention are effective for blocking, occluding, or otherwise disrupting blood flow in "neovasculature." In one aspect, the invention provides a novel treatment for diseases involving the growth of new blood vessels ("neovasculature"), including, but not limited to: cancer; infectious diseases; autoimmune disorders; benign tumors, e.g. hemangiomas, acoustic neuromas, neurofibromas, trachomas, and pyogenic granulomas; artheroscleric plaques; ocular angiogenic diseases, e.g., diabetic retinopathy, retinopathy of prematurity, macular degeneration, corneal graft rejection, neovascular glaucoma, retrolental fibroplasia, rubeosis, retinoblastoma, persistent hyperplastic vitreous syndrome, choroidal neovascularization, uvietis and Pterygia (abnormal blood vessel growth) of the eye; rheumatoid arthritis; psoriasis; warts; allergic dermatitis; blistering disease; Karposi sarcoma; delayed wound healing; endometriosis; uterine bleeding; ovarian cysts; ovarian hyperstimulation; vasculogenesis; granulations; hypertrophic scars (keloids); nonunion fractures; scleroderma; trachoma; vascular adhesions; vascular malformations; DiGeorge syndrome; HHT; transplant arteriopathy; restinosis; obesity; myocardial angiogenesis; coronary collaterals; cerebral collaterals; arteriovenous malformations; ischemic limb angiogenesis; primary pulmonary hypertension; asthma; nasal polyps; inflammatory bowel disease; periodontal disease; ascites; peritoneal adhesions; Osler-Webber Syndrome; plaque neovascularization; telangiectasia; hemophiliac joints; synovitis; osteomyelitis; osteophyte formation; angiofibroma; fibromuscular dysplasia; wound granulation; Crohn's disease; and atherosclerosis.

Vascular targeting can be demonstrated by any method known to those skilled in the art, such as the method described herein in Examples E and F.

As used herein, the term "angiogenesis" refers to a fundamental process of generating new blood vessels in tissues or organs. Angiogenesis is involved with or associated with many diseases or conditions, including, but not limited to: cancer; ocular neovascular disease; age-related macular degeneration; diabetic retinopathy, retinopathy of prematurity; corneal graft rejection; neovascular glaucoma; retrolental fibroplasias; epidemic keratoconjunctivitis; Vitamin A deficiency; contact lens overwear; atopic keratitis; superior limbic keratitis; pterygium keratitis sicca; sjogrens; acne rosacea; warts; eczema; phylectenulosis; syphilis; *Mycobacteria* infections; lipid degeneration; chemical burns; bacterial ulcers; fungal ulcers; Herpes simplex infections; Herpes zoster infections; protozoan infections; Kaposi's sarcoma; Mooren's ulcer; Terrien's marginal degeneration; mariginal keratolysis; rheumatoid arthritis; systemic lupus; polyarteritis; trauma; Wegener's sarcoidosis; scleritis; Stevens-Johnson disease; pemphigoid; radial keratotomy; corneal graph rejection; diabetic retinopathy; macular degeneration; sickle cell anemia; sarcoid; syphilis; pseudoxanthoma elasticum; Paget's disease; vein occlusion; artery occlusion; carotid obstructive disease; chronic uveitis/vitritis; mycobacterial infections; Lyme's disease; systemic lupus erythematosis; retinopathy of prematurity; Eales' disease; Behcet's disease; infections causing a retinitis or choroiditis; presumed ocular histoplasmosis; Best's disease; myopia; optic pits; Stargardt's disease; pars planitis; chronic retinal detachment; hyperviscosity syndromes; toxoplasmosis; trauma and post-laser complications; diseases associated with rubeosis (neovasculariation of the angle); diseases caused by the abnormal proliferation of fibrovascular or fibrous tissue including all forms of proliferative vitreoretinopathy; rheumatoid arthritis; osteoarthritis; ulcerative colitis; Crohn's disease; Bartonellosis; atherosclerosis; Osler-Weber-Rendu disease; hereditary hemorrhagic telangiectasia; pulmonary hemangiomatosis; pre-eclampsia; endometriosis; fibrosis of the liver and of the kidney; developmental abnormalities (organogenesis); skin discolorations (e.g., hemangioma, nevus flammeus, or nevus simplex); wound healing; hypertrophic scars, i.e., keloids; wound granulation; vascular adhesions; cat scratch disease (*Rochele ninalia quintosa*); ulcers (*Helicobacter pylori*); keratoconjunctivitis; gingivitis; periodontal disease; epulis; hepatitis; tonsillitis; obesity; rhinitis; laryngitis; tracheitis; bronchitis; bronchiolitis; pneumonia; interstitial pulmonary fibrosis; neurodermitis; thyroiditis; thyroid enlargement; endometriosis; glomerulonephritis; gastritis; inflammatory bone and cartilage destruction; thromboembolic disease; and Buerger's disease.

The term "infection" is used herein in its broadest sense and refers to any infection e.g. a viral infection or one caused by a microorganism: bacterial infection, fungal infection, or parasitic infection (e.g. protozoal, amoebic, or helminth). Examples of such infections may be found in a number of well known texts such as "Medical Microbiology" (Greenwood, D., Slack, R., Peutherer, J., Churchill Livingstone Press, 2002); "Mims' Pathogenesis of Infectious Disease" (Mims, C., Nash, A., Stephen, J., Academic Press, 2000); "Fields" Virology. (Fields, B. N., Knipe, D. M., Howley, P. M., Lippincott Williams and Wilkins, 2001); and "The Sanford Guide To Antimicrobial Therapy," 26th Edition, J. P. Sanford et al., (Antimicrobial Therapy, Inc., 1996), all of which are incorporated by reference herein in their entirety.

"Bacterial infections" include, but are not limited to, infections caused by Gram Positive Bacteria including *Bacillus cereus, Bacillus anthracis, Clostridium botulinum, Clostridium difficile, Clostridium tetani, Clostridium perfringens, Corynebacteria diphtheriae, Enterococcus* (*Streptococcus* D), *Listeria monocytogenes, Pneumoccoccal* infections (*Streptococcus pneumoniae*), Staphylococcal infections and Streptococcal infections; Gram Negative Bacteria including *Bacteroides, Bordetella pertussis, Brucella, Campylobacter* infections, enterohaemorrhagic *Escherichia coli* (EHEC/*E. coli* 0157: H7) enteroinvasive *Escherichia coli* (EIEC), enterotoxigenic *Escherichia coli* (ETEC), *Haemophilus influenzae, Helicobacter pylori, Klebsiella pneumoniae, Legionella* spp., *Moraxella catarrhalis, Neisseria gonorrhoeae, Neisseria meningitidis, Proteus* spp., *Pseudomonas aeruginosa, Salmonella* spp., *Shigella* spp., *Vibrio cholera* and *Yersinia*; acid fast bacteria including *Mycobacterium tuberculosis, Mycobacterium avium-intracellulare, Myobacterium johnei, Mycobacterium leprae*, atypical bacteria, *Chlamydia, Mycoplasma, Rickettsia, Spirochetes, Treponema pallidum, Borrelia recurrentis, Borrelia burgdorfii* and *Leptospira icterohemorrhagiae*; or other miscellaneous bacteria, including *Actinomyces* and *Nocardia*.

The term "fungus" or "fungal" refers to a distinct group of eukaryotic, spore-forming organisms with absorptive nutrition and lacking chlorophyll. It includes mushrooms, molds, and yeasts.

"Fungal infections" include, but are not limited to, infections caused by *Alternaria alternata, Aspergillus flavus, Aspergillus fumigatus, Aspergillus nidulans, Aspergillus niger, Aspergillus versicolor, Blastomyces dermatiditis, Candida albicans, Candida dubliensis, Candida krusei, Candida parapsilosis, Candida tropicalis, Candida glabrata, Coccidioides immitis, Cryptococcus neoformans, Epidermophyton floccosum, Histoplasma capsulatum, Malassezia furfur, Microsporum canis, Mucor* spp., *Paracoccidioides brasiliensis, Penicillium marneffei, Pityrosporum ovale, Pneumocystis carinii, Sporothrix schenkii, Trichophyton rubrum, Trichophyton interdigitale, Trichosporon beigelii, Rhodotorula* spp., *Brettanomyces clausenii, Brettanomyces custerii, Brettanomyces anomalous, Brettanomyces naardenensis, Candida himilis, Candida intermedia, Candida saki, Candida solani, Candida tropicalis, Candida versatilis, Candida bechii, Candida famata, Candida lipolytica, Candida stellata, Candida vini, Debaromyces hansenii, Dekkera intermedia, Dekkera bruxellensis, Geotrichium sandidum, Hansenula fabiani, Hanseniaspora uvarum, Hansenula anomala, Hanseniaspora guillermondii Hanseniaspora vinae, Kluyveromyces lactis, Kloekera apiculata, Kluveromyces marxianus, Kluyveromyces fragilis, Metschikowia pulcherrima, Pichia guilliermodii, Pichia orientalis, Pichia fermentans, Pichia memranefaciens, Rhodotorula Saccharomyces bayanus, Saccharomyces cerevisiae, Saccharomyces dairiensis Saccharomyces exigus, Saccharomyces uinsporus, Saccharomyces uvarum, Saccharomyces oleaginosus, Saccharomyces boulardii, Saccharomycodies ludwigii, Schizosaccharomyces pombe, Torulaspora delbruekii, Torulopsis stellata, Zygoaccharomyces bailli* and *Zygosaccharomyces rouxii*.

"Parasitic infections" include, but are not limited to, infections caused by *Leishmania, Toxoplasma, Plasmodia, Theileria, Acanthamoeba, Anaplasma, Giardia, Trichomonas, Trypanosoma, Coccidia*, and *Babesia*.

For example, parasitic infections include those caused by *Trypanosoma cruzi, Eimeria tenella, Plasmodium falciparum, Plasmodium vivax, Plasmodium ovale, Cryptosporidium parvum, Naegleria fowleri, Entamoeba histolytica, Balamuthia mandrillaris, Entameoba histolytica, Schistostoma mansoni, Plasmodium falciparum, P. vivax, P. ovale P. malariae, P. berghei, Leishmania donovani, L. infantum, L. chagasi, L. mexicana, L. amazonensis, L. venezuelensis, L. tropics, L. major, L. minor, L. aethiopica, L. Biana braziliensis, L.* (V.) *guyanensis, L.* (V.) *panamensis, L.* (V.) *peruviana, Trypanosoma brucei rhodesiense, T brucei gambiense, Giardia intestinalis, G. lambda, Toxoplasma gondii, Trichomonas vaginalis, Pneumocystis carinii, Acanthamoeba castellani A. culbertsoni, A. polyphaga, A. healyi,* (*A. astronyxis*), *A. hatchetti, A. rhysodes,* and *Trichinella spiralis*.

As used herein, the term "viral infection" refers to any stage of a viral infection, including incubation phase, latent or dormant phase, acute phase, and development and maintenance of immunity towards a virus. Consequently, the term "treatment" is meant to include aspects of generating or restoring immunity of the patient's immune system, as well as aspects of suppressing or inhibiting viral replication.

Viral infections include, but are not limited to those caused by Adenovirus, Lassa fever virus (Arenavirus), Astrovirus, Hantavirus, Rift Valley Fever virus (Phlebovirus), Calicivirus, Ebola virus, Marburg Virus, Japanese encephalitis virus, Dengue virus, Yellow fever virus, Hepatitis C virus, Hepatitis G virus, Hepatitis B virus, Hepatitis D virus, Herpes simplex virus 1, Herpes simplex virus 2), Cytomegalovirus, Epstein Barr virus, Varicella Zoster Virus, Human Herpesvirus 7, Human Herpesvirus 8, Influenza virus, Parainfluenza virus, Rubella virus, Mumps virus, Morbillivirus, Measles virus, Respiratory Syncytial virus, Papillomaviruses, JC virus (Polyomavirus), BK virus (Polyomavirus), Parvovirus, Coxsackie virus (A and B), Hepatitis A virus, Polioviruses, Rhinoviruses, Reovirus, Rabies Virus (Lyssavirus), Human Immunodeficiency virus 1 and 2, Human T-cell Leukemia virus.

Examples of viral infections include Adenovirus acute respiratory disease, Lassa fever, Astrovirus enteritis, Hantavirus pulmonary syndrome, Rift valley fever, Hepatitis E, diarrhoea, Ebola hemorrhagic fever, Marburg hemorrhagic fever, Japanese encephalitis, Dengue fever, Yellow fever, Hepatitis C, Hepatitis G, Hepatitis B, Hepatitis D, Cold sores, Genital sores, Cytomegalovirus infection, Mononucleosis, Chicken Pox, Shingles, Human Herpesvirus infection 7, Kaposi Sarcoma, Influenza, Brochiolitis, German measles, Mumps, Measles (rubeola), Measles, Brochiolitis, Papillomas (Warts), cervical cancer, Progressive multifocal leukoencephalopathy, Kidney disease, Erythema infectiosum, Viral myocarditis, meninigitis, entertitis, Hepatitis, Poliomyelitis, Cold, Diarrhoea, Rabies, AIDS and Leukemia.

DNA topoisomerases are enzymes present in all cells that catalyze topological changes in DNA. Topoisomerase II ("topo II") plays important roles in DNA replication, chromosome segregation and the maintenance of the nuclear scaffold in eukaryotic cells. The enzyme acts by creating breaks in DNA, thereby allowing the DNA strands to unravel and separate. Due to the important roles of the enzyme in dividing cells, the enzyme is a highly attractive target for chemotherapeutic agents, especially in human cancers. The ability of compounds to inhibit topo II can be determined by any method known in the art such as in Example K.

The glucocorticoid receptor is a member of the steroid hormone nuclear receptor family which includes glucocorticoid receptors (GR), androgen receptors (AR), mineralocorticoid receptors (MR), estrogen receptors (ER), and progesterone receptors (PR). Glucocorticoid receptors bind glucocorticoids such as cortisol, corticosterone, and cortisone.

"Immunosuppression" refers to impairment of any component of the immune system resulting in decreased immune function. This impairment may be measured by any conventional means including whole blood assays of lymphocyte function, detection of lymphocyte proliferation and assessment of the expression of T cell surface antigens. The antisheep red blood cell (SRBC) primary (IgM) antibody response assay (usually referred to as the plaque assay) is one specific method. This and other methods are described in Luster, M. I., Portier, C., Pait, D. G., White, K. L., Jr., Gennings, C., Munson, A. E., and Rosenthal, G. J. (1992). "Risk Assessment in Immunotoxicology I: Sensitivity and Predictability of Immune Tests." Fundam. Appl. Toxicol., 18, 200-210. Measuring the immune response to a T-cell dependent immunogen is another particularly useful assay (Dean, J. H., House, R. V., and Luster, M. I. (2001). "Immunotoxicology: Effects of, and Responses to, Drugs and Chemicals." In Principles and Methods of Toxicology: Fourth Edition (A. W. Hayes, Ed.), pp. 1415-1450, Taylor & Francis, Philadelphia, Pa.). In one embodiment, a decrease in the expression of glucocorticoid receptors in PBMCs indicates impairment of immune function. A patient in need of immunosuppression is within the judgement of a physician, and can include patients with immune or inflammatory disorders. In one embodiment, patients that have undergone or will be undergoing an organ, tissue, bone marrow, or stem cell transplantation are in need of immunosuppression to prevent inflammation and/or rejection of the transplanted organ or tissue.

The compounds of this invention can be used to treat subjects with immune disorders. As used herein, the term "immune disorder" and like terms means a disease, disorder or condition caused by the immune system of an animal, including autoimmune disorders. Immune disorders include those diseases, disorders or conditions that have an immune component and those that are substantially or entirely immune system-mediated. Autoimmune disorders are those wherein the animal's own immune system mistakenly attacks itself, thereby targeting the cells, tissues, and/or organs of the animal's own body. For example, the autoimmune reaction is directed against the nervous system in multiple sclerosis and the gut in Crohn's disease. In other autoimmune disorders such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus. Specific autoimmune disorders that may be ameliorated using the compounds and methods of this invention include without limitation, autoimmune disorders of the nervous system (e.g., multiple sclerosis, myasthenia gravis, autoimmune neuropathies such as Guillain-Barré, and autoimmune uveitis), autoimmune disorders of the blood (e.g., autoimmune hemolytic anemia, pernicious anemia, and autoimmune thrombocytopenia), autoimmune disorders of the blood vessels (e.g., temporal arteritis, anti-phospholipid syndrome, vasculitides such as Wegener's granulomatosis, and Behcet's disease), autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland); and autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome). In addition, other immune system mediated diseases, such as graft-versus-host disease and allergic disorders, are also included in the definition of immune disorders herein. Because a number of immune disorders are caused by inflammation, there is some overlap between disorders that are considered immune disorders and inflammatory disorders. For the purpose of this invention, in the case of such an overlapping disorder, it may be considered either an immune disorder or an inflammatory disorder. "Treatment of an immune disorder" herein refers to administering a compound represented by any of the formulas disclosed herein to a subject, who has an immune disorder, a symptom of such a disease or a predisposition towards such a disease, with the purpose to cure, relieve, alter, affect, or prevent the autoimmune disorder, the symptom of it, or the predisposition towards it.

As used herein, the term "allergic disorder" means a disease, condition or disorder associated with an allergic response against normally innocuous substances. These substances may be found in the environment (such as indoor air pollutants and aeroallergens) or they may be non-environmental (such as those causing dermatological or food allergies). Allergens can enter the body through a number of routes, including by inhalation, ingestion, contact with the skin or injection (including by insect sting). Many allergic disorders are linked to atopy, a predisposition to generate the allergic antibody IgE. Because IgE is able to sensitize mast cells anywhere in the body, atopic individuals often express disease in more than one organ. For the purpose of this invention, allergic disorders include any hypersensitivity that occurs upon re-exposure to the sensitizing allergen, which in turn causes the release of inflammatory mediators. Allergic disorders include without limitation, allergic rhinitis (e.g., hay fever), sinusitis, rhinosinusitis, chronic or recurrent otitis media, drug reactions, insect sting reactions, latex reactions, conjunctivitis, urticaria, anaphylaxis and anaphylactoid reactions, atopic dermatitis, asthma and food allergies.

As used herein, the term "asthma" means a pulmonary disease, disorder or condition characterized by reversible airway obstruction, airway inflammation, and increased airway responsiveness to a variety of stimuli.

Compounds represented by any of the formulas disclosed herein can be used to prevent or to treat subjects with inflammatory disorders. As used herein, an "inflammatory disorder" means a disease, disorder or condition characterized by inflammation of body tissue or having an inflammatory component. These include local inflammatory responses and systemic inflammation. Examples of such inflammatory disorders include: transplant rejection, including skin graft rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis; as well as various other diseases with significant inflammatory components, including preeclampsia; chronic liver failure, brain and spinal cord trauma.

There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy. "Treatment of an inflammatory disorder" herein refers to administering a compound or a composition of the invention to a subject, who has an inflammatory disorder, a symptom of such a disorder or a predisposition towards such a disorder, with the purpose to cure, relieve, alter, affect, or prevent the inflammatory disorder, the symptom of it, or the predisposition towards it.

As used herein, the term "pharmaceutically acceptable salt," is a salt formed from, for example, an acid and a basic group of one of the compounds of formula (I)-(XXXII), or Table 1, 2 or 3. Illustrative salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also refers to a salt prepared from a compound of formula (I)-(XXXII), or Table 1, 2 or 3 having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of formula (I)-(XXXII), or Table 1, 2 or 3 having a basic functional group, such as an amine functional group, and a pharmaceutically acceptable inorganic or organic acid. Suitable acids include, but are not limited to, hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "pharmaceutically acceptable solvate," is a solvate formed from the association of one or more pharmaceutically acceptable solvent molecules to one of the compounds of formula (I)-(XXXII), or Table 1, 2 or 3. The term solvate includes hydrates (e.g., hemihydrate, monohydrate, dihydrate, trihydrate, tetrahydrate, and the like).

A pharmaceutically acceptable carrier may contain inert ingredients which do not unduly inhibit the biological activity of the compounds. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986).

As used herein, the term "effective amount" refers to an amount of a compound of this invention which is sufficient to reduce or ameliorate the severity, duration, progression, or onset of a disease or disorder, e.g. a proliferative disorder, prevent the advancement of a a disease or disorder, e.g. a proliferative disorder, cause the regression of a a disease or disorder, e.g. a proliferative disorder, prevent the recurrence, development, onset or progression of a symptom associated with a a disease or disorder, e.g. a proliferative disorder, or enhance or improve the prophylactic or therapeutic effect(s) of another therapy. The precise amount of compound administered to a subject will depend on the mode of administration, the type and severity of the disease or condition and on the characteristics of the subject, such as general health, age, sex, body weight and tolerance to drugs. It will also depend on the degree, severity and type of cell proliferation, and the mode of administration. The skilled artisan will be able to determine appropriate dosages depending on these and other factors. When co-administered with other agents, e.g., when co-administered with an anti-cancer agent, an "effective amount" of the second agent will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

Non-limiting examples of an effective amount of a compound of the invention are provided herein below. In a specific embodiment, the invention provides a method of preventing, treating, managing, or ameliorating a proliferative disorder or one or more symptoms thereof, said methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every day, preferably, once every 2 days, once every 3 days, once every 4 days, once every 5 days, once every 6 days, once every 7 days, once every 8 days, once every 10 days, once every two weeks, once every three weeks, or once a month.

The dosages of a chemotherapeutic agents other than compounds of the invention, which have been or are currently being used to prevent, treat, manage, or ameliorate a proliferative disorder, or one or more symptoms thereof, can be used in the combination therapies of the invention. Preferably, dosages lower than those which have been or are currently being used to prevent, treat, manage, or ameliorate a proliferative disorder, or one or more symptoms thereof, are used in the combination therapies of the invention. The recommended dosages of agents currently used for the prevention, treatment, management, or amelioration of a proliferative disorder, or one or more symptoms thereof, can obtained from any reference in the art including, but not limited to, Hardman et al., eds., 1996, Goodman & Gilman's The Pharmacological Basis Of Basis Of Therapeutics $9^{th}$ Ed, Mc-Graw-Hill, New York; Physician's Desk Reference $(PDR)_{57}$th Ed., 2003, Medical Economics Co., Inc., Montvale, N.J., which are incorporated herein by reference in its entirety.

As used herein, the terms "treat", "treatment" and "treating" refer to the reduction or amelioration of the progression, severity and/or duration of a a disease or disorder, e.g. a proliferative disorder, or the amelioration of one or more symptoms (preferably, one or more discernible symptoms) of a a disease or disorder, e.g. a proliferative disorder resulting from the administration of one or more therapies (e.g., one or more therapeutic agents such as a compound of the invention). In specific embodiments, the terms "treat", "treatment" and "treating" refer to the amelioration of at least one measurable physical parameter of a a disease or disorder, e.g. a proliferative disorder, such as growth of a tumor, not necessarily discernible by the patient. In other embodiments the terms "treat", "treatment" and "treating" refer to the inhibition of the progression of a a disease or disorder, e.g. a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

As used herein, the terms "prevent", "prevention" and "preventing" refer to the reduction in the risk of acquiring or developing a given a disease or disorder, e.g. a proliferative disorder, or the reduction or inhibition of the recurrence or a a disease or disorder, e.g. a proliferative disorder. In one embodiment, a compound of the invention is administered as a preventative measure to a patient, preferably a human, having a genetic predisposition to any of the disorders described herein.

As used herein, the terms "therapeutic agent" and "therapeutic agents" refer to any agent(s) which can be used in the treatment, management, or amelioration of a a disease or disorder, e.g. a proliferative disorder or one or more symptoms thereof. In certain embodiments, the term "therapeutic agent" refers to a compound of the invention. In certain other embodiments, the term "therapeutic agent" refers does not refer to a compound of the invention. Preferably, a therapeutic agent is an agent which is known to be useful for, or has been or is currently being used for the treatment, management, prevention, or amelioration of a disease or disorder, e.g. a proliferative disorder or one or more symptoms thereof.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject with a disease or disorder, e.g. a proliferative disorder. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a disease or disorder, e.g. a proliferative disorder. In addition, a synergistic effect can result in improved efficacy of agents in the prevention, management or treatment of a disease or disorder, e.g. a proliferative disorder. Finally, a synergistic effect of a combination of therapies (e.g., a combination of prophylactic or therapeutic agents) may avoid or reduce adverse or unwanted side effects associated with the use of either therapy alone.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

As used herein, the term "in combination" refers to the use of more than one therapies (e.g., one or more prophylactic and/or therapeutic agents). The use of the term "in combination" does not restrict the order in which therapies (e.g., prophylactic and/or therapeutic agents) are administered to a subject with a proliferative disorder. A first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject with a proliferative disorder, such as cancer.

As used herein, the terms "therapies" and "therapy" can refer to any protocol(s), method(s), and/or agent(s) that can be used in the prevention, treatment, management, or amelioration of a a disease or disorder, e.g. a proliferative disorder or one or more symptoms thereof.

A used herein, a "protocol" includes dosing schedules and dosing regimens. The protocols herein are methods of use and include prophylactic and therapeutic protocols.

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., one or more prophylactic or therapeutic agents) to "manage" a disease so as to prevent the progression or worsening of the disease.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

As used herein, a racemic mixture means about 50% of one enantiomer and about 50% of is corresponding enantiomer relative to a chiral center in the molecule. The invention encompasses all enantiomerically-pure, enantiomerically-enriched, diastereomerically pure, diastereomerically enriched, and racemic mixtures of the compounds of the invention.

Enantiomeric and diastereomeric mixtures can be resolved into their component enantiomers or diastereomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

The compounds of the invention are defined herein by their chemical structures and/or chemical names. Where a compound is referred to by both a chemical structure and a chemical name, and the chemical structure and chemical name conflict, the chemical structure is determinative of the compound's identity.

When administered to a patient, e.g., to a non-human animal for veterinary use or for improvement of livestock, or to a human for clinical use, the compounds of the invention are administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, the compounds of the invention are purified via conventional techniques. As used herein, "purified" means that when isolated, the isolate contains at least 95%, preferably at least 98%, of a compound of the invention by weight of the isolate either as a mixture of stereoisomers or as a diastereomeric or enantiomeric pure isolate.

As used herein, a composition that is "substantially free" of a compound means that the composition contains less than about 20% by weight, more preferably less than about 10% by weight, even more preferably less than about 5% by weight, and most preferably less than about 3% by weight of the compound.

Only those choices and combinations of substituents that result in a stable structure are contemplated. Such choices and combinations will be apparent to those of ordinary skill in the art and may be determined without undue experimentation.

The invention can be understood more fully by reference to the following detailed description and illustrative examples, which are intended to exemplify non-limiting embodiments of the invention.

B. The Compounds of the Invention

The present invention encompasses compounds having formulas (I)-(XXXII), and those set forth in Table 1, 2 or 3 and tautomers, pharmaceutically acceptable salts, solvates, clathrates, hydrates, polymorphs and prodrugs thereof.

Compounds of formulas (I)-(XXXII), inhibit the activity of Hsp90 and are particularly useful for treating or preventing proliferative disorders, such as cancer. In addition, compounds of formula (I)-(XXXII), are particularly useful in treating cancer when given in combination with another anti-cancer agent.

In one embodiment, the invention provides compounds of formula (I) as set forth below:

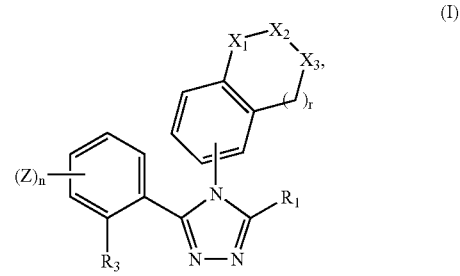

or a tautomer, pharmaceutically acceptable salt, solvate, clathrate or a prodrug thereof, where $R_1$, $R_3$, Z, n, r, $X_1$, $X_2$, and $X_3$ are defined as above.

In one embodiment, of the compounds represented by formula (I), the compound is not 3-(2,4-Dihydroxyphenyl)-4-(1,2,3,4-tetrahydronaphthalen-5-yl)-5-mercapto-[1,2,4]triazole;
4-ethyl-6-(5-mercapto-4-(1-methylindolin-5-yl)-4H-1,2,4-triazol-3-yl)benzene-1,3-diol;
4-(4-(benzo[d][1,3]dioxol-5-yl)-5-mercapto-4H-1,2,4-triazol-3-yl)-6-isopropylbenzene-1,3-diol;
4-(4-(2,3-dihydro-1H-inden-5-yl)-5-mercapto-4H-1,2,4-triazol-3-yl)-6-isopropylbenzene-1,3-diol;
6-(3-(5-ethyl-2,4-dihydroxyphenyl)-5-mercapto-4H-1,2,4-triazol-4-yl)-3-methylbenzo[d]thiazol-2(3H)-one;
5-(3-(5-ethyl-2,4-dihydroxyphenyl)-5-mercapto-4H-1,2,4-triazol-4-yl)indolin-2-one;
5-(3-(5-ethyl-2,4-dihydroxyphenyl)-5-mercapto-4H-1,2,4-triazol-4-yl)-1H-benzo[d]imidazol-2(3H)-one; or
6-(3-(5-ethyl-2,4-dihydroxyphenyl)-5-mercapto-4H-1,2,4-triazol-4-yl)benzo[d]thiazol-2(3H)-one.

In one embodiment, the invention provides compounds of formula (II) as set forth below:

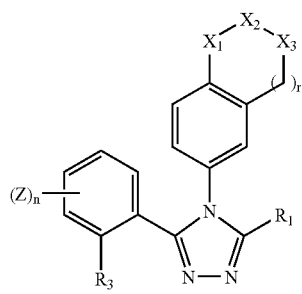

(II)

or a tautomer, pharmaceutically acceptable salt, solvate, clathrate or a prodrug thereof, where $R_1$, $R_3$, Z, n, r, $X_1$, $X_2$, and $X_3$ are defined as above.

In one embodiment, the invention provides compounds of formula (III) as set forth below:

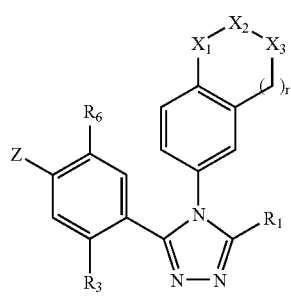

(III)

or a tautomer, pharmaceutically acceptable salt, solvate, clathrate or a prodrug thereof, wherein
$R_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$; and
$R_1$, $R_3$, Z, r, $X_1$, $X_2$, and $X_3$ are defined as above.

In one embodiment, the invention provides compounds of formula (IV) as set forth below:

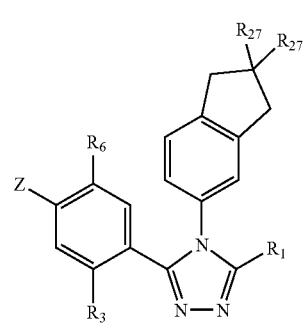

(IV)

or a tautomer, pharmaceutically acceptable salt, solvate, clathrate or a prodrug thereof, where $R_1$, $R_3$, Z, $R_{27}$, and $R_6$ are defined as above.

In one embodiment, the invention provides compounds of formula (V) as set forth below:

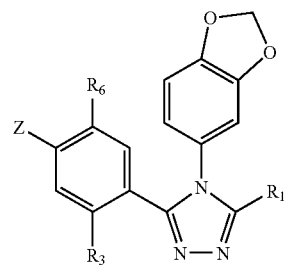

(V)

or a tautomer, pharmaceutically acceptable salt, solvate, clathrate or a prodrug thereof, where $R_1$, $R_3$, Z, and $R_6$ are defined as above.

In one embodiment, the invention provides compounds of formula (VI) as set forth below:

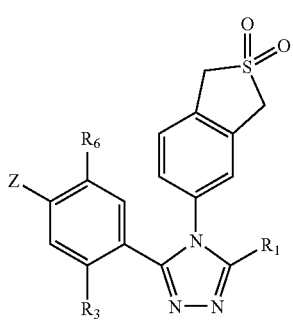

(VI)

or a tautomer, pharmaceutically acceptable salt, solvate, clathrate or a prodrug thereof, where $R_1$, $R_3$, Z, and $R_6$ are defined as above.

In one embodiment, the invention provides compounds of formula (VII) as set forth below:

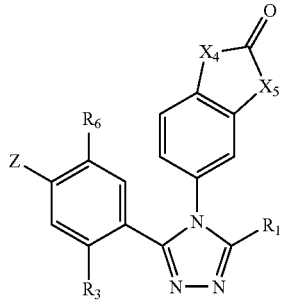
(VII)

wherein each of $X_4$ and $X_5$ is, independently, $C(R_7)_2$, $NR_7$, or S; or a tautomer, pharmaceutically acceptable salt, solvate, clathrate or a prodrug thereof, where $R_1$, $R_3$, $X_4$, $X_5$, Z, and $R_6$ are defined as above.

In one embodiment, the invention provides compounds of formula (VII) as set forth below:

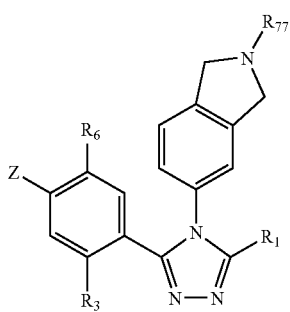
(VIII)

or a tautomer, pharmaceutically acceptable salt, solvate, clathrate or a prodrug thereof, where $R_1$, $R_3$, $R_{77}$, Z, and $R_6$ are defined as above.

In one embodiment, the invention provides compounds of formula (IX) as set forth below:

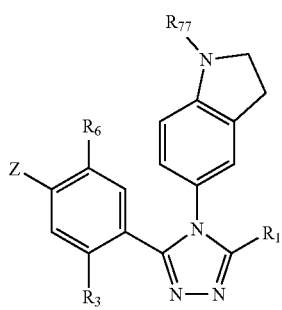
(IX)

or a tautomer, pharmaceutically acceptable salt, solvate, clathrate or a prodrug thereof, where $R_1$, $R_3$, $R_{77}$, Z, $R_6$ are defined as above.

In one embodiment, the invention provides compounds of formula (X) as set forth below:

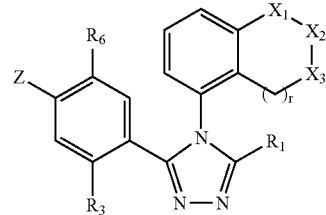
(X)

or a tautomer, pharmaceutically acceptable salt, solvate, clathrate or a prodrug thereof, where $R_1$, $R_3$, $R_7$, $X_1$, $X_2$, $X_3$, r, Z, and $R_6$ are defined as above.

In one embodiment, the invention provides compounds of formula ($X_1$) as set forth below:

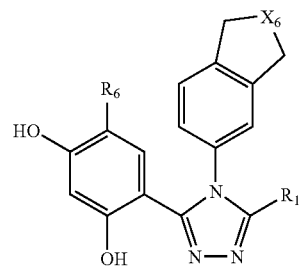
(XI)

or a tautomer, pharmaceutically acceptable salt, solvate, clathrate or a prodrug thereof, where $R_1$, $R_6$, and $X_6$ are defined as above.

In one embodiment, the invention provides compounds of formula (XII) as set forth below:

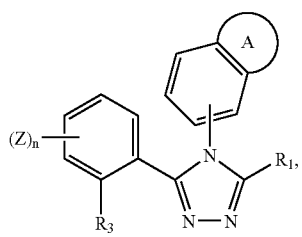
(XII)

or a tautomer, pharmaceutically acceptable salt, solvate, clathrate or a prodrug thereof, where $R_1$, $R_3$, n, and Z, and Ring A are Defined as Above.

In one embodiment of compounds of formula (XII), that the compound is not
3-(2,4-dihydroxy-5-ethyl-phenyl)-4-(2-methyl-7-methoxy-benzofuran-4-yl)-5-mercapto-[1,2,4]triazole;
3-(2,4-dihydroxy-5-ethyl-phenyl)-4-(benzofuran-5-yl)-5-mercapto-[1,2,4]triazole;
3-(2,4-dihydroxy-5-ethyl-phenyl)-4-(2-methyl-1,3-benzoxaz-5-yl)-5-mercapto-[1,2,4]triazole;
3-(2,4-dihydroxy-5-isopropyl-phenyl)-4-(1-methyl-indazol-5-yl)-5-mercapto-[1,2,4]triazole;
3-(2,4-dihydroxy-5-isopropyl-phenyl)-4-(1-methyl-2-trifluoromethyl-benzimidazol-5-yl)-5-mercapto-[1,2,4]triazole;
3-(2,4-Dihydroxyphenyl)-4-(quinolin-5-yl)-5-mercapto-[1,2,4]triazole;

3-(2,4-Dihydroxy-phenyl)-4-(isoquinolin-5-yl)-5-mercapto-[1,2,4]triazole;
3-[2,4-Di-(dimethyl-carbamoyloxy)-phenyl]-4-(quinolin-5-yl)-5-(dimethyl-carbamoylsulfanyl)-[1,2,4]triazole;
3-(2,4-Dihydroxy-5-ethyl-phenyl)-4-(quinolin-5-yl)-5-ureido-[1,2,4]triazole;
3-(2,4-Dihydroxy-5-isopropyl-phenyl)-4-(3-methyl-quinolin-5-yl)-5-carboxyamino-[1,2,4]triazole;
3-[2-Hydroxy-4-(dimethyl-carbamoyoxy)-5-chloro-phenyl]-4-(quinolin-5-yl)-5-mercapto-[1,2,4]triazole;
3-(2,4-dihydroxy-5-isopropyl-phenyl)-4-(1-methyl-indazol-6-yl)-5-mercapto-[1,2,4]triazole; or
3-(2,4-dihydroxy-5-isopropyl-phenyl)-4-(2-methyl-indazol-6-yl)-5-mercapto-[1,2,4]triazole.

In one embodiment, the invention provides compounds of formula (XIII) as set forth below:

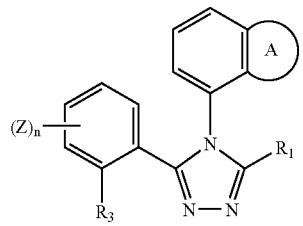

(XIII)

or a tautomer, pharmaceutically acceptable salt, solvate, clathrate or a prodrug thereof, where $R_1$, $R_3$, n, Z, and Ring A is defined as above.

In one embodiment, the invention provides compounds of formula (XIV) as set forth below:

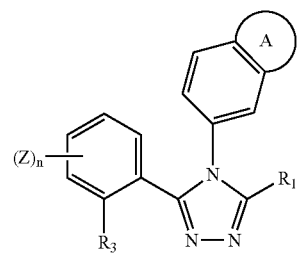

(XIV)

or a tautomer, pharmaceutically acceptable salt, solvate, clathrate or a prodrug thereof, where $R_1$, $R_3$, n, Z, and Ring A is defined as above.

In one embodiment, the invention provides compounds of formula (XV) as set forth below:

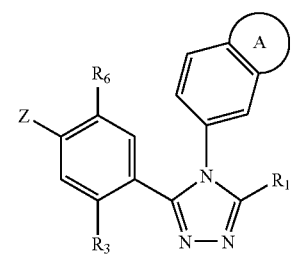

(XV)

or a tautomer, pharmaceutically acceptable salt, solvate, clathrate or a prodrug thereof, where $R_1$, $R_3$, n, Z, $R_6$, and Ring A is defined as above.

In one embodiment, the invention provides compounds of formula (XVI) as set forth below:

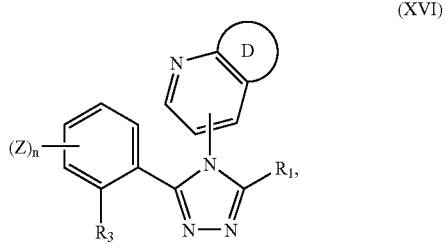

(XVI)

or a tautomer, pharmaceutically acceptable salt, solvate, clathrate or a prodrug thereof, where $R_1$, $R_3$, n, Z, and Ring D are defined as above.

In one embodiment, the invention provides compounds of formula (XVII) as set forth below:

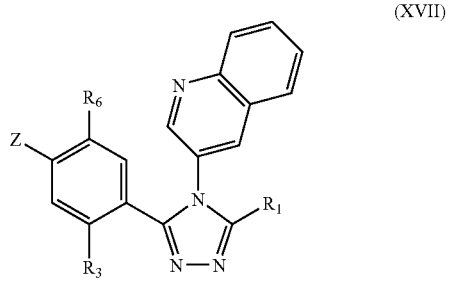

(XVII)

or a tautomer, pharmaceutically acceptable salt, solvate, clathrate or a prodrug thereof, wherein $R_1$, $R_3$, Z, and $R_6$ are defined above.

In one embodiment, the invention provides compounds of formula (XVIII) as set forth below:

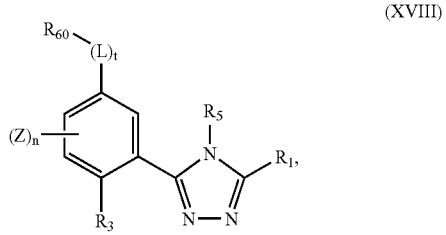

(XVIII)

or a tautomer, pharmaceutically acceptable salt, solvate, clathrate or a prodrug thereof, wherein: $R_1$, $R_3$, $R_5$, $R_{60}$, L, Z, n, and t are defined as above.

In one embodiment, the invention provides compounds of formula (XIX) as set forth below:

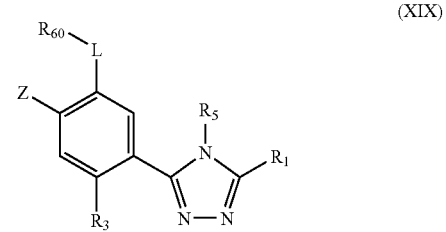

(XIX)

or a tautomer, pharmaceutically acceptable salt, solvate, clathrate or a prodrug thereof, wherein Z, L, $R_1$, $R_3$, $R_5$, and $R_{60}$ are defined as above.

In one embodiment, the invention provides compounds of formula (XX) as set forth below:

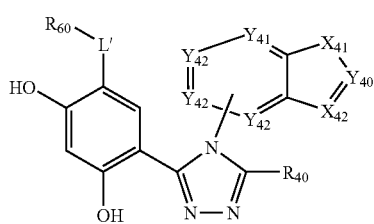

(XX)

or a tautomer, pharmaceutically acceptable salt, solvate, clathrate or a prodrug thereof, and wherein
L' is a $C_1$-$C_4$ alkylene;
$X_{41}$ is O, S, or $NR_{42}$;
$X_{42}$ is $CR_{44}$ or N;
$Y_{40}$ is N or $CR_{43}$;
$Y_{41}$ is N or $CR_{45}$;
$Y_{42}$, for each occurrence, is independently N, C or $CR_{46}$;
$R_{40}$ is OH, SH, or $NHR_7$;
$R_{42}$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, hydroxyalkyl, alkoxyalkyl, a haloalkyl, a heteroalkyl, —C(O)$R_7$, $(CH_2)_mC(O)OR_7$, —C(O)O$R_7$, —OC(O)$R_7$, —C(O)$NR_{10}R_{11}$, —S(O)$_pR_7$, —S(O)$_pOR_7$, or —S(O)$_pNR_{10}R_{11}$;
$R_{43}$ and $R_{44}$ are, independently, —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, hydroxyalkyl, alkoxyalkyl, halo, cyano, nitro, guanidino, a haloalkyl, a heteroalkyl, —C(O)$R_7$, —C(O)O$R_7$, —OC(O)$R_7$, —C(O)$NR_{10}R_{11}$, —$NR_8$C(O)$R_7$, —S$R_7$, —S(O)$_pR_7$, —OS(O)$_pR_7$, —S(O)$_pOR_7$, —$NR_8$S(O)$_pR_7$, —S(O)$_pNR_{10}R_{11}$, or $R_{43}$ and $R_{44}$ taken together with the carbon atoms to which they are attached form an optionally substituted cycloalkenyl, an optionally substituted aryl, an optionally substituted heterocyclyl, or an optionally substituted heteroaryl;
$R_{45}$ is —H, —OH, —SH, —$NR_7$H, —O$R_{26}$, —S$R_{26}$, —$NHR_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)$NR_{10}R_{11}$, —SC(O)$NR_{10}R_{11}$, —$NR_7$C(O)$NR_{10}R_{11}$, —OC(O)$R_7$, —SC(O)$R_7$, —$NR_7$C(O)$R_7$, —OC(O)O$R_7$, —SC(O)O$R_7$, —$NR_7$C(O)O$R_7$, —OCH$_2$C(O)$R_7$, —SCH$_2$C(O)$R_7$, —$NR_7$CH$_2$C(O)$R_7$, —OCH$_2$C(O)O$R_7$, —SCH$_2$C(O)O$R_7$, —$NR_7$CH$_2$C(O)O$R_7$, —OCH$_2$C(O)$NR_{10}R_{11}$, —SCH$_2$C(O)$NR_{10}R_{11}$, —$NR_7$CH$_2$C(O)$NR_{10}R_{11}$, —OS(O)$_pR_7$, —SS(O)$_pR_7$, —$NR_7$S(O)$_pR_7$, —OS(O)$_pNR_{10}R_{11}$, —SS(O)$_pNR_{10}R_{11}$, —$NR_7$S(O)$_pNR_{10}R_{11}$, —OS(O)$_pOR_7$, —SS(O)$_pOR_7$, —$NR_7$S(O)$_pOR_7$, —OC(S)$R_7$, —SC(S)$R_7$, —$NR_7$C(S)$R_7$, —OC(S)O$R_7$, —SC(S)O$R_7$, —$NR_7$C(S)O$R_7$, —OC(S)$NR_{10}R_{11}$, —SC(S)$NR_{10}R_{11}$, —$NR_7$C(S)$NR_{10}R_{11}$, —OC($NR_8$)$R_7$, —SC($NR_8$)$R_7$, —$NR_7$C($NR_8$)$R_7$, —OC($NR_8$)O$R_7$, —SC($NR_8$)O$R_7$, —$NR_7$C($NR_8$)O$R_7$, —OC($NR_8$)$NR_{10}R_{11}$, —SC($NR_8$)$NR_{10}R_{11}$, or —$NR_7$C($NR_8$)$NR_{10}R_{11}$; and $R_{46}$, for each occurrence, is independently, selected from the group consisting of H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanidino, a haloalkyl, a heteroalkyl, —$NR_{10}R_{11}$, —O$R_7$, —C(O)$R_7$, —C(O)O$R_7$, —OC(O)$R_7$, —C(O)$NR_{10}R_{11}$, —$NR_8$C(O)$R_7$, —S$R_7$, —S(O)$_pR_7$, —OS(O)$_pR_7$, —S(O)$_pOR_7$, —$NR_8$S(O)$_pR_7$, or —S(O)$_pNR_{10}R_{11}$.

In one embodiment, the invention provides compounds of formula (XXI) as set forth below:

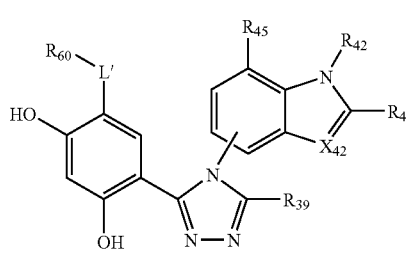

(XXI)

or a tautomer, pharmaceutically acceptable salt, solvate, clathrate, or prodrug thereof, wherein
$R_{39}$ is —OH or —SH; and
$R_{60}$, L', $R_{42}$, $R_{43}$, $R_{45}$, and $X_{42}$ are defined as above.

In one embodiment, the invention provides compounds of formula (XXII) as set forth below:

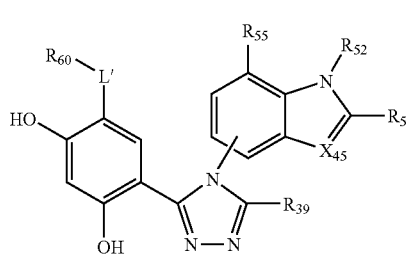

(XXII)

or a tautomer, pharmaceutically acceptable salt, solvate, clathrate, or prodrug thereof,
$X_{45}$ is $CR_{54}$ or N;
$R_{39}$ is —OH or —SH;
$R_{52}$ is selected from the group consisting of —H, methyl, ethyl, n-propyl, isopropyl, n-butyl, n-pentyl, n-hexyl, —(CH$_2$)$_2$OCH$_3$, —CH$_2$C(O)OH, and —C(O)N(CH$_3$)$_2$;
$R_{53}$ and $R_{54}$ are each, independently, —H, methyl, ethyl, or isopropyl; or $R_{53}$ and
$R_{54}$ taken together with the carbon atoms to which they are attached form a phenyl, cyclohexenyl, or cyclooctenyl ring;
$R_{55}$ is selected from the group consisting of —H, —OH, —OCH$_3$, and —OCH$_2$CH$_3$; and $R_{60}$ and L' are defined as above.

In one embodiment, the invention provides compounds of formula (XXIII) as set forth below:

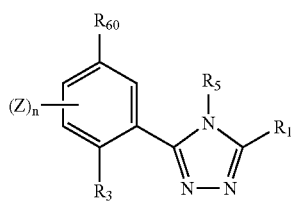
(XXIII)

or a tautomer, pharmaceutically acceptable salt, solvate, clathrate or a prodrug thereof, wherein Z, n, $R_1$, $R_3$, $R_5$, and $R_{60}$ are defined as above.

In one embodiment, the invention provides compounds of formula (XXIV) as set forth below:

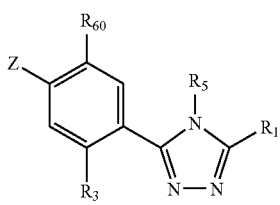
(XXIV)

or a tautomer, pharmaceutically acceptable salt, solvate, clathrate or a prodrug thereof, wherein Z, n, $R_1$, $R_3$, $R_5$, and $R_{60}$ are defined as above.

In one embodiment, the invention provides compounds of formula (XXV) as set forth below:

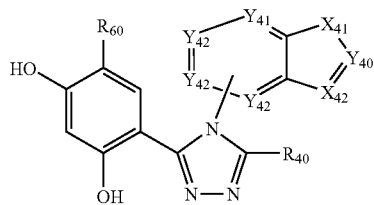
(XXV)

or a tautomer, pharmaceutically acceptable salt, solvate, clathrate, or prodrug thereof, wherein $R_{60}$, $R_{40}$, $X_{40}$, $X_{41}$, $X_{42}$, $Y_{41}$, $Y_{42}$ are defined as above.

In one embodiment, the invention provides compounds of formula (XXVI) as set forth below:

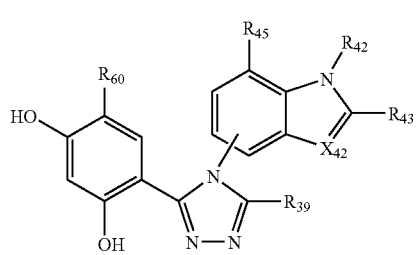
(XXVI)

or a tautomer, pharmaceutically acceptable salt, solvate, clathrate, or prodrug thereof, wherein $R_{39}$, $R_{60}$, $R_{42}$, $R_{43}$, $R_{45}$, and $X_{42}$ are defined as above.

In one embodiment, the invention provides compounds of formula (XXVII) as set forth below:

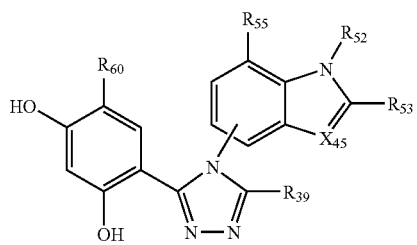
(XXVII)

or a tautomer, pharmaceutically acceptable salt, solvate, clathrate, or prodrug thereof, and wherein $R_{60}$, $R_{39}$, $R_{52}$, $R_{53}$, $R_{55}$, and $X_{45}$ are defined as above In one embodiment, the invention provides compounds of formula (XXVIII) as set forth below:

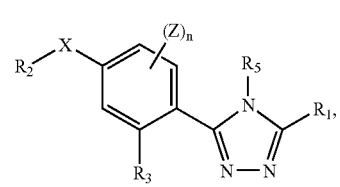
(XXVIII)

or a tautomer, pharmaceutically acceptable salt, solvate, clathrate or a prodrug thereof, and $R_1$, $R_2$, $R_3$, $R_5$, X, Z, and n are defined above.

In one aspect of the compounds of formula (I), the compound is not
3-(2,5-Dihydroxy-4-carboxy)-4-(naphthalen-1-yl)-5-mercapto-[1,2,4]triazole;
3-(2,5-Dihydroxy-4-hydroxymethyl-phenyl)-4-(naphthalen-1-yl)-5-mercapto-[1,2,4]triazole;
3-[2,4-Di-(dimethyl-carbamoyloxy)-phenyl]-4-(naphthalen-1-yl)-5-(dimethyl-carbamoylsulfanyl)-[1,2,4]triazole;
3-[2,4-Di-(dimethyl-carbamoyloxy)-phenyl]-4-(quinolin-5-yl)-5-(dimethyl-carbamoylsulfanyl)-[1,2,4]triazole;
3-[2-Hydroxy-4-(dimethyl-carbamoyoxy)-5-ethyl-phenyl]-4-(naphthalin-2-yl)-5-hydroxy-[1,2,4]triazole;
3-[2-Hydroxy-4-(dimethyl-carbamoyoxy)-5-chloro-phenyl]-4-(quinolin-5-yl)-5-mercapto-[1,2,4]triazole; or
3-[2-Hydroxy-4-(dimethyl-carbamoyoxy)-5-ethyl-phenyl]-4-(2,3-difluoro-phenyl)-5-mercapto-[1,2,4]triazole.

In another embodiment, the invention provides compounds of formula (XXIX) as set forth below:

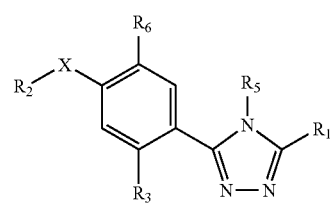
(XXIX)

or a tautomer, pharmaceutically acceptable salt, solvate, clathrate or a prodrug thereof, and $R_1$, $R_2$, $R_3$, $R_5$, $R_6$, and X are defined as for formula (XVIII).

In another embodiment, the invention provides compounds of formula (XXX) as set forth below:

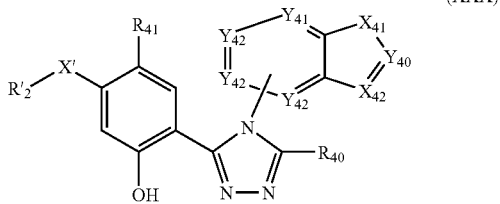
(XXX)

or a tautomer, pharmaceutically acceptable salt, solvate, clathrate or a prodrug thereof, and $R_{12}$, $R_{40}$, $R_{41}$, X', $X_{41}$, $X_{42}$, $Y_{40}$, $Y_{41}$, and $Y_{42}$ are defined above.

In another embodiment, the invention provides compounds of formula (XXXI) as set forth below:

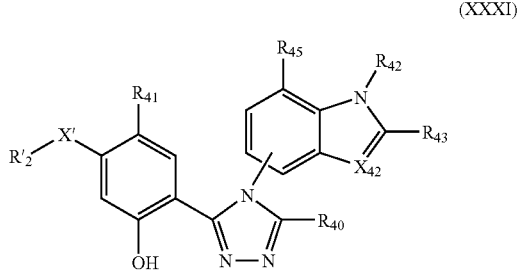
(XXXI)

or a tautomer, pharmaceutically acceptable salt, solvate, clathrate or a prodrug thereof, and $R_{12}$, $R_{40}$, $R_{41}$, $R_{42}$, $R_{43}$, $R_{45}$, X', and $X_{42}$ are defined as above.

In another embodiment, the invention provides compounds of formula (XXXII) as set forth below:

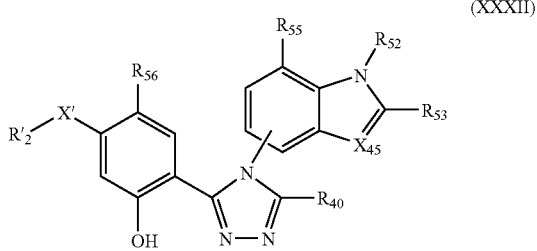
(XXXII)

or a tautomer, pharmaceutically acceptable salt, solvate, clathrate or a prodrug thereof, and $R_{12}$, $R_{40}$, $R_{52}$, $R_{53}$, $R_{55}$, $R_{56}$, $X_{45}$, and X' are defined above.

In one embodiment, of the compounds represented by formula (I), (II), (XII), (XIII), (XIV), and (XVI), Z, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanidino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)R_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$.

In another embodiment, of the compounds represented by formula (I), (II), (XII), (XIII), (XIV), and (XVI), Z is —OH, —SH, —$NHR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$, —$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$.

In another embodiment, of the compounds represented by formula (I), (II), (XII), (XIII), (XIV), and (XVI), Z is —OH, —SH, or —$NHR_7$.

In one embodiment, of the compounds represented by formula (I)-(X) and (XIII)-(XVII), $R_1$ and $R_3$ are each, independently, —OH, —SH, or —$NHR_7$.

In one embodiment, of the compounds represented by formula (III), (IV), (V), (VI), (VII), (VIII), (IX), (X), (XV), and (XVII), Z is an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanidino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$.

In another embodiment, of the compounds represented by formula (III), (IV), (V), (VI), (VII), (VII), (IX), (X), (XV), and (XVII), Z is —OH, —SH, —$NHR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$, —$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$.

In another embodiment, of the compounds represented by formula (III), (IV), (V), (VI), (VII), (VII), (IX), (X), (XV), and (XVII), Z is —OH, —SH, or —$NHR_7$.

In one embodiment, of the compounds represented by formula (III), (IV), (V), (VI), (VII), (VII), (IX), (X), (XV), and (XVII), $R_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl.

In one embodiment, of the compounds represented by formula (III), (IV), (V), (VI), (VII), (VII), (IX), (X), (XV), and (XVII), Z and $R_3$ are each —OH.

In one embodiment, of the compounds represented by formula (I), (II), (III), and (X), r is 1.

In one embodiment, of the compounds represented by formula (I), (II), (III), and (X), r is 0.

In one embodiment, of the compounds represented by formula (III), (IV), (V), (VI), (VII), (VII), and (IX), Z and $R_3$ are each —OH; $R_1$ is —OH, —SH, or —NHR$_7$; and $R_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl.

In one embodiment, of the compounds represented by formula (I), (II), (III), or (X), $X_1$, $X_2$, and $X_3$ are each independently $C(R_{27})_2$, $NR_7$, C(O), $S(O)_p$, O or S.

In one embodiment, of the compounds represented by formula (I), (II), (III), or (X), $X_1$, $X_2$, and $X_3$ are each independently $C(R_{27})_2$, $NR_{77}$, C(O), $S(O)_p$, O or S.

In one embodiment, of the compounds represented by formula (X), $X_1$, $X_2$, and $X_3$ is $CH_2$. In one aspect, r is 1. In another aspect, r is 0.

In one embodiment, of the compounds represented by formula (XI), $X_6$ is $CHR_{28}$. In one aspect, $R_{28}$ is selected from the group consisting of —OR$_7$ or —NR$_{10}$R$_{11}$.

In one embodiment, of the compounds represented by formula (XI), $X_6$ is $NR_{77}$. In one aspect, $R_{77}$ is an optionally substituted lower alkyl.

In one embodiment, of the compounds represented by formula (XVII), the compound is 4-isopropyl-6-(5-mercapto-4-(quinolin-3-yl)-4H-1,2,4-triazol-3-yl)benzene-1,3-diol.

In another embodiment, the compound is selected from the group consisting of
4-[4-(2,2-dioxo-2,3-dihydro-1H-2λ$^6$-benzo[c]thiophen-5-yl)-5-mercapto-4H-[1,2,4]triazol-3-yl]-6-ethyl-benzene-1,3-diol;
5-(3-(5-ethyl-2,4-dihydroxyphenyl)-5-mercapto-4H-1,2,4-triazol-4-yl)-1-methylindolin-2-one;
4-isopropyl-6-(5-mercapto-4-(5,6,7,8-tetrahydronaphthalen-1-yl)-4H-1,2,4-triazol-3-yl)benzene-1,3-diol;
4-(5-hydroxy-4-(2-hydroxy-2,3-dihydro-1H-inden-5-yl)-4H-1,2,4-triazol-3-yl)-6-isopropylbenzene-1,3-diol;
4-(4-(2-ethylisoindolin-5-yl)-5-mercapto-4H-1,2,4-triazol-3-yl)-6-isopropylbenzene-1,3-diol;
4-isopropyl-6-(5-mercapto-4-(2-methoxy-2,3-dihydro-1H-inden-5-yl)-4H-1,2,4-triazol-3-yl)benzene-1,3-diol;
4-isopropyl-6-(5-mercapto-4-(2-methylisoindoline-5-yl)-4H-1,2,4-triazol-3-yl)benzene-1,3-diol;
4-(4-(2-ethoxy-2,3-dihydro-1H-inden-5-yl)-5-mercapto-4H-1,2,4-triazol-3-yl)-6-isopropylbenzene-1,3-diol;
4-isopropyl-6-(5-mercapto-4-(2-propoxy-2,3-dihydro-1H-inden-5-yl)-4H-1,2,4-triazol-3-yl)benzene-1,3-diol;
4-(4-(1',3'-dihydrospiro[[1,3]dioxolane-2,2'-indene]-5'-yl)-5-mercapto-4H-1,2,4-triazol-3-yl)-6-isopropylbenzene-1,3-diol;
5-(3-(2,4-dihydroxy-5-isopropylphenyl)-5-mercapto-4H-1,2,4-triazol-4-yl)-1H-inden-2(3H)-one;
4-(4-(2,3-dihydro-1H-inden-4-yl)-5-mercapto-4H-1,2,4-triazol-3-yl)-6-isopropylbenzene-1,3-diol;
4-(4-(2-(dimethylamino)-2,3-dihydro-1H-inden-5-yl)-5-mercapto-4H-1,2,4-triazol-3-yl)-6-isopropylbenzene-1,3-diol;
4-cyclopropyl-2-(5-mercapto-4-(2-methoxy-2,3-dihydro-1H-inden-5-yl)-4H-1,2,4-triazol-3-yl)phenol;
4-isopropyl-6-(5-mercapto-4-(2-morpholino-2,3-dihydro-1H-inden-5-yl)-4H-1,2,4-triazol-3-yl)benzene-1,3-diol;
4-isopropyl-6-(5-mercapto-4-(2-(pyrrolidin-1-yl)-2,3-dihydro-1H-inden-5-yl)-4H-1,2,4-triazol-3-yl)benzene-1,3-diol;
4-(5-hydroxy-4-(2-methoxy-2,3-dihydro-1H-inden-5-yl)-4H-1,2,4-triazol-3-yl)-6-isopropylbenzene-1,3-diol;
4-isopropyl-6-(5-mercapto-4-(2-(methoxymethoxy)-2,3-dihydro-1H-inden-5-yl)-4H-1,2,4-triazol-3-yl)benzene-1,3-diol;
4-(4-(1',3'-dihydrospiro[[1,3]dioxolane-2,2'-indene]-5'-yl)-5-hydroxy-4H-1,2,4-triazol-3-yl)-6-isopropylbenzene-1,3-diol;
5-(3-(2,4-dihydroxy-5-isopropylphenyl)-5-mercapto-4H-1,2,4-triazol-4-yl)indolin-2-one;
4-(5-hydroxy-4-(2-(methoxymethoxy)-2,3-dihydro-1H-inden-5-yl)-4H-1,2,4-triazol-3-yl)-6-isopropylbenzene-1,3-diol;
4-(4-(2-(ethoxymethoxy)-2,3-dihydro-1H-inden-5-yl)-5-hydroxy-4H-1,2,4-triazol-3-yl)-6-isopropylbenzene-1,3-diol;
1-(5-(3-(2,4-dihydroxy-5-isopropylphenyl)-5-hydroxy-4H-1,2,4-triazol-4-yl)isoindolin-2-yl)ethanone;
4-(4-(2-(dimethylamino)-2,3-dihydro-1H-inden-5-yl)-5-hydroxy-4H-1,2,4-triazol-3-yl)-6-isopropylbenzene-1,3-diol;
5-(3-hydroxy-5,6,7,8-tetrahydronaphthalen-2-yl)-4-(1-methylindolin-5-yl)-4H-1,2,4-triazol-3-ol;
4-(5-hydroxy-4-(2-(2-methoxyethyl)isoindolin-5-yl)-4H-1,2,4-triazol-3-yl)-6-isopropylbenzene-1,3-diol;
4-(5-hydroxy-4-(2-(pyrrolidin-1-yl)-2,3-dihydro-1H-inden-5-yl)-4H-1,2,4-triazol-3-yl)-6-isopropylbenzene-1,3-diol;
4-(5-hydroxy-4-(1-methylindolin-5-yl)-4H-1,2,4-triazol-3-yl)-6-isopropylbenzene-1,3-diol; or
4-(5-hydroxy-4-(2-((2-methoxyethyl)(methyl)amino)-2,3-dihydro-1H-inden-5-yl)-4H-1,2,4-triazol-3-yl)-6-isopropylbenzene-1,3-diol;
or a tautomer, pharmaceutically acceptable salt, solvate, clathrate, or a prodrug thereof.

In another embodiment, the compound is selected from the group consisting of
4-(4-(benzo[d]thiazol-5-yl)-5-mercapto-4H-1,2,4-triazol-3-yl)-6-ethylbenzene-1,3-diol;
4-(4-(benzo[d]thiazol-6-yl)-5-mercapto-4H-1,2,4-triazol-3-yl)-6-ethylbenzene-1,3-diol;
4-isopropyl-6-(5-mercapto-4-(1-methyl-1H-benzo[d]imidazol-6-yl)-4H-1,2,4-triazol-3-yl)benzene-1,3-diol;
4-isopropyl-6-(5-mercapto-4-(1-methyl-1H-benzo[d]imidazol-5-yl)-4H-1,2,4-triazol-3-yl)benzene-1,3-diol;
4-ethyl-6-(5-mercapto-4-(2-methyl-1H-benzo[d]imidazol-5-yl)-4H-1,2,4-triazol-3-yl)benzene-1,3-diol; or
4-(4-(1H-benzo[d][1,2,3]triazol-6-yl)-5-mercapto-4H-1,2,4-triazol-3-yl)-6-ethylbenzene-1,3-diol;
or a tautomer, pharmaceutically acceptable salt, solvate, clathrate, or a prodrug thereof.

In another embodiment, the compound is selected from the group consisting of
4-(4-(2,3-dihydro-1H-inden-5-yl)-5-hydroxy-4H-1,2,4-triazol-3-yl)-6-isopropylbenzene-1,3-diol;
(4-aminocyclohexyl)(5-(3-(2,4-dihydroxy-5-isopropylphenyl)-5-hydroxy-4H-1,2,4-triazol-4-yl)indolin-1-yl)methanone hydrochloride;
2-(4-(benzo[d][1,3]dioxol-5-yl)-5-mercapto-4H-1,2,4-triazol-3-yl)-4-methoxyphenol;

4-(1-(4-fluorophenyl)propan-2-yl)-6-(5-hydroxy-4-(2-(methoxymethoxy)-2,3-dihydro-1H-inden-5-yl)-4H-1,2,4-triazol-3-yl)benzene-1,3-diol;

4-(1-(4-fluorophenyl)propan-2-yl)-6-(5-hydroxy-4-(2-(pyrrolidin-1-yl)-2,3-dihydro-1H-inden-5-yl)-4H-1,2,4-triazol-3-yl)benzene-1,3-diol;

4-(4-fluorophenethyl)-6-(5-mercapto-4-(2-methoxy-2,3-dihydro-1H-inden-5-yl)-4H-1,2,4-triazol-3-yl)benzene-1,3-diol;

4-(5-hydroxy-4-(1-(methylsulfonyl)indolin-5-yl)-4H-1,2,4-triazol-3-yl)-6-isopropylbenzene-1,3-diol; or 4-(5-hydroxy-4-(2-morpholino-2,3-dihydro-1H-inden-5-yl)-4H-1,2,4-triazol-3-yl)-6-isopropylbenzene-1,3-diol;

or a tautomer, pharmaceutically acceptable salt, solvate, clathrate, or a prodrug thereof.

In one embodiment, in the compounds represented by formula (XVIII), (XIX), (XXIII), or (XXIV), $R_5$ is represented by the following formula:

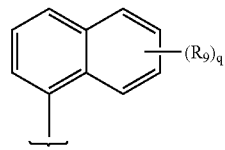

wherein:

$R_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, hydroxyalkyl, alkoxyalkyl, halo, cyano, nitro, guanidino, a haloalkyl, a heteroalkyl, $-NR_{10}R_{11}$, $-OR_7$, $-C(O)R_7$, $-C(O)OR_7$, $-OC(O)R_7$, $-C(O)NR_{10}R_{11}$, $-NR_8C(O)R_7$, $-SR_7$, $-S(O)_pR_7$, $-OS(O)_pR_7$, $-S(O)_pOR_7$, $-NR_8S(O)_pR_7$, or $-S(O)_pNR_{10}R_{11}$, $-S(O)_pOR_7$, $-OP(O)(OR_7)_2$, or $-SP(O)(OR_7)_2$;

or two $R_9$ groups taken together with the carbon atoms to which they are attached form a fused ring; and q is zero or an integer from 1 to 7.

In one embodiment, in the compounds represented by formula (XVIII), (XIX), (XXIII), or (XXIV), $R_5$ is represented by the following formula:

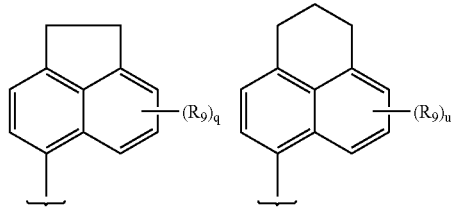

wherein: q is zero or an integer from 1 to 5; and u is zero or an integer from 1 to 5.

In one embodiment, in the compounds represented by formula (XVIII), (XIX), (XXIII), or (XXIV), $R_5$ is represented by the following formula:

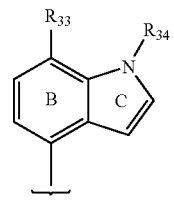

wherein:

$R_{33}$ is a halo, lower alkyl, a lower alkoxy, a lower haloalkyl, a lower haloalkoxy, and lower alkyl sulfanyl;

$R_{34}$ is H, a lower alkyl, or a lower alkylcarbonyl; and

Ring B and Ring C are optionally substituted with one or more substituents.

In one embodiment, in the compounds represented by formula (XVIII), (XIX), (XXIII), or (XXIV), $R_5$ is selected from the group consisting of:

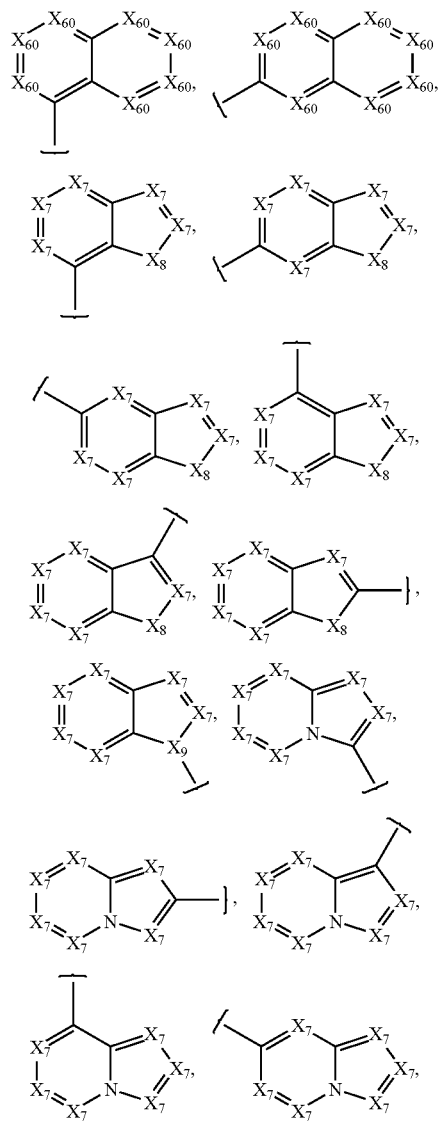

-continued

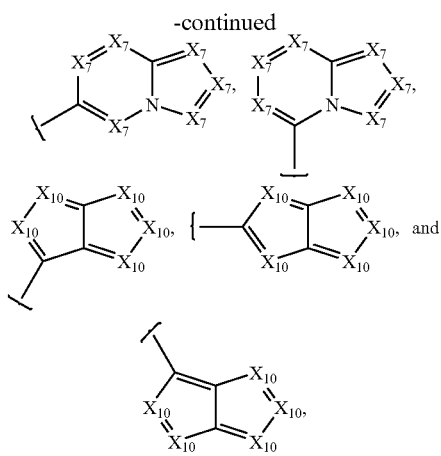

wherein:
$X_{60}$, for each occurrence, is independently CH, $CR_9$, N, N(O), $N^+(R_{17})$, provided that at least three $X_{60}$ groups are independently selected from CH and $CR_9$;
$X_7$, for each occurrence, is independently CH, $CR_9$, N, N(O), $N^+(R_{17})$, provided that at least three $X_7$ groups are independently selected from CH and $CR_9$;
$X_8$, for each occurrence, is independently $CH_2$, $CHR_9$, $C(R_9)_2$, S, $S(O)_p$, $NR_7$, or $NR_{17}$;
$X_9$, for each occurrence, is independently N or CH;
$X_{10}$, for each occurrence, is independently CH, $CR_9$, N, N(O), $N^+(R_{17})$, provided that at least one $X_{10}$ is selected from CH and $CR_9$;
$R_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, hydroxyalkyl, alkoxyalkyl, halo, cyano, nitro, guanidino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$, —$S(O)_pOR_7$, —$OP(O)(OR_7)_2$, or —$SP(O)(OR_7)_2$, —$S(O)_pOR_7$, —$OP(O)(OR_7)_2$, or —$SP(O)(OR_7)_2$;
or two $R_9$ groups taken together with the carbon atoms to which they are attached form a fused ring; and
$R_{17}$, for each occurrence, is independently —H, an alkyl, an aralkyl, —$C(O)R_7$, —$C(O)OR_7$, or —$C(O)NR_{10}R_{11}$.

In one embodiment, in the compounds represented by formula (XVIII), (XIX), (XXIII), or (XXIV), $R_5$ is an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, and optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo(b)thienyl.

In one embodiment, in the compounds represented by formula (XVIII), (XIX), (XXIII), or (XXIV), $R_5$ is selected from the group consisting of:

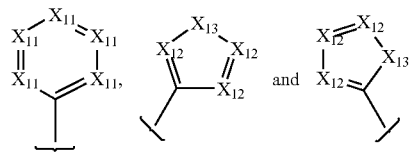

wherein:
$X_{11}$, for each occurrence, is independently CH, $CR_9$, N, N(O), or $N^+(R_{17})$, provided that at least two $X_{11}$ groups are independently selected from CH and $CR_9$;
$X_{12}$, for each occurrence, is independently CH, $CR_9$, N, N(O), $N^+(R_{17})$, provided that at least one $X_{12}$ group is independently selected from CH and $CR_9$;
$X_{13}$, for each occurrence, is independently O, S, $S(O)_p$, $NR_7$, or $NR_{17}$;
$R_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanidino, a hydroxyalkyl, alkoxyalkyl, haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$, —$S(O)_pOR_7$, —$OP(O)(OR_7)_2$, or —$SP(O)(OR_7)_2$, —$S(O)_pOR_7$, —$OP(O)(OR_7)_2$, or —$SP(O)(OR_7)_2$;
or two $R_9$ groups taken together with the carbon atoms to which they are attached form a fused ring; and
$R_{17}$, for each occurrence, is independently an alkyl or an aralkyl.

In one embodiment, in the compounds represented by formula (XVIII) or (XXIII), Z, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanidino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$.

In one aspect, in the compounds represented by formula (XVIII) or (XXIII), Z is —OH, —SH, —$NHR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$, —$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$.

In one aspect, in the compounds represented by formula (XVIII) or (XXIII), Z is —OH, —SH, or —$NHR_7$.

In one embodiment, in the compounds represented by formula (XIX) or (XXIV), $Z_1$ is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanidino, a haloalkyl, a heteroalkyl, alkoxy, haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$.

In one aspect, in the compounds represented by formula (XIX) or (XXIV), Z is —OH, —SH, —$NHR_7$, —$OC(O)NR_{10}R_{11}$, —$SC(O)NR_{10}R_{11}$, —$OC(O)R_7$, —$SC(O)R_7$, —$OC(O)OR_7$, —$SC(O)OR_7$, —$OS(O)_pR_7$, —$S(O)_pOR_7$, —$SS(O)_pR_7$, —$OS(O)_pOR_7$, —$SS(O)_pOR_7$, —$OC(S)R_7$, —$SC(S)R_7$, —$OC(S)OR_7$, —$SC(S)OR_7$, —$OC(S)NR_{10}R_{11}$, —$SC(S)NR_{10}R_{11}$, —$OC(NR_8)R_7$, —$SC(NR_8)R_7$, —$OC(NR_8)OR_7$, —$SC(NR_8)OR_7$, —$OP(O)(OR_7)_2$ or —$SP(O)(OR_7)_2$.

In one aspect, in the compounds represented by formula (XIX) or (XXIV), Z is —OH, —SH, or —$NHR_7$.

In one embodiment, in the compounds represented by formula (XVIII), (XIX), (XXIII), or (XXIV), $R_{60}$ is an optionally substituted phenyl, an optionally substituted furanyl, an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, an optionally substituted pyrimidinyl, an optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo(b)thienyl.

In one aspect, in the compounds represented by formula (XVIII), (XIX), (XXIII), or (XXIV) $R_{60}$ is an optionally substituted phenyl. In one aspect, $R_{60}$ is substituted with 1 to 4 substituents independently selected from the group consisting of halo, lower alkoxy, cyano, amino, dialkyl amino, alkyl amino, —$C(O)N(R_y)_2$, —$C(O)R_x$, or —$C(OH)R_x$.

In another aspect, in the compounds represented by formula (XVIII), (XIX), (XXIII), or (XXIV) $R_{60}$ is an unsubstituted phenyl.

In one embodiment, in the compounds represented by formula (XXIII) or (XXIV), $R_{60}$ is an optionally substituted furanyl.

In one embodiment, in the compounds represented by formula (XVIII) or (XIX), L is a $C_1$-$C_6$ alkylene. In one aspect, L is $C_2$-$C_3$ alkylene.

In one embodiment, in the compounds represented by formula (XVIII), (XIX), (XXIIII), or (XXIV), $R_1$ and $R_3$ are each, independently, —OH, —SH, or —$NHR_7$.

In one embodiment, in the compounds represented by formula (XIX) or (XXIV), $R_1$, $R_3$, and Z are each, independently, —OH, —SH, or —$NHR_7$. In one aspect, $R_3$ and Z are each —OH.

In one embodiment, in the compounds represented by formula (XIX), $R_{60}$ is an optionally substituted phenyl; $R_1$, $R_3$, and Z are each, independently, —OH, —SH, or —$NHR_7$; and L is a $C_1$-$C_6$ alkylene. In one aspect, $R_1$, $R_3$, and Z are each, independently, —OH, —SH, or —$NHR_7$. In another aspect, $R_3$ and Z are each —OH. In another aspect, L is $C_2$-$C_3$ alkylene.

In one embodiment, in the compounds represented by formula (XXIV), $R_{60}$ is an optionally substituted phenyl; $R_1$, $R_3$, and Z are each, independently, —OH, —SH, or —NHR$_7$. In one aspect, R$_1$, R$_3$, and Z are each, independently, —OH, —SH, or —NHR$_7$. In another aspect, R$_3$ and Z are each —OH.

In one embodiment, in the compounds represented by formula (XX) or (XXV), X$_{41}$ is NR$_{42}$ and X$_{42}$ is CR$_{44}$.

In one embodiment, in the compounds represented by formula (XX) or (XXV), X$_{41}$ is NR$_{42}$ and X$_{42}$ is N.

In one embodiment, in the compounds represented by formula (XX) or (XXV), X$_{41}$ is NR$_{42}$, and R$_{42}$ is selected from the group consisting of —H, a lower alkyl, a lower cycloalkyl, —C(O)N(R$_{27}$)$_2$, and —C(O)OH, wherein each R$_{27}$ is independently —H or a lower alkyl.

In one embodiment, in the compounds represented by formula (XX) or (XXV), X$_{41}$ is NR$_{42}$, and R$_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$.

In one embodiment, in the compounds represented by formula (XX) or (XXV), R$_{43}$ and R$_{44}$ are, independently, selected from the group consisting of —H, methyl, ethyl, propyl, isopropyl, cyclopropyl, methoxy, ethoxy, propoxy, and cyclopropoxy.

In one embodiment, in the compounds represented by formula (XX) or (XXV), X$_{42}$ is CR$_{44}$; Y$_{40}$ is CR$_{43}$; and R$_{43}$ and R$_{44}$ together with the carbon atoms to which they are attached form a cycloalkenyl, an aryl, heterocyclyl, or heteroaryl ring.

In one embodiment, in the compounds represented by formula (XX) or (XXV), R$_{43}$ and R$_{44}$ together with the carbon atoms to which they are attached form a C$_5$-C$_8$ cycloalkenyl or a C$_5$-C$_8$ aryl.

In one embodiment, in the compounds represented by formula (XX) or (XXV), R$_{45}$ or CR$_{45}$ is selected from the group consisting of —H, —OH, —SH, —NH$_2$, a lower alkoxy, a lower alkyl amino, and a lower dialkyl amino.

In one embodiment, in the compounds represented by formula (XX) or (XXV), R$_{45}$ is selected from the group consisting of —H, —OH, methoxy and ethoxy.

In one embodiment, in the compounds represented by formula (XX) or (XXV), X$_{41}$ is O.

In one embodiment, in the compounds represented by formula (XX) or (XXV), R$_{40}$ is —OH or —SH.

In one embodiment, in the compounds represented by formula (XX), (XXI), (XXII), (XXV), (XXVI), or (XXVII), R$_{60}$ is an optionally substituted phenyl.

In one embodiment, in the compounds represented by formula (XXI) or (XXVI), X$_{42}$ is CR$_{44}$, and R$_{43}$ and R$_{44}$ are, independently, selected from the group consisting of —H, methyl, ethyl, propyl, isopropyl, cyclopropyl, methoxy, ethoxy, propoxy, and cyclopropoxy.

In one embodiment, in the compounds represented by formula (XXI) or (XXVI), X$_{42}$ is CR$_{44}$, and R$_{43}$ and R$_{44}$, taken together with the carbon atoms to which they are attached, form a cycloalkenyl, aryl, heterocyclyl, or heteroaryl ring.

In one embodiment, in the compounds represented by formula (XXI) or (XXVI), R$_{43}$ and R$_{44}$, taken together with the carbon atoms to which they are attached, form a C$_5$-C$_8$ cycloalkenyl or a C$_5$-C$_8$ aryl.

In one embodiment, in the compounds represented by formula (XXI) or (XXVI), X$_{42}$ is CR$_{44}$.

In one embodiment, in the compounds represented by formula (XXI) or (XXVI), X$_{42}$ is N.

In another embodiment, the compound is selected from the group consisting of
4-[2-(3,4-Dimethoxy-phenyl)-ethyl]-6-[5-hydroxy-4-(1-methyl-1H-indol-5-yl)-4H-[1,2,4]triazol-3-yl]-benzene-1,3-diol;
4-[5-hydroxy-4-(1-methyl-1H-indol-5-yl)-4H-[1,2,4]triazol-3-yl]-6-phenethyl-benzene-1,3-diol;
4-[2-(2,6-Difluoro-phenyl)-ethyl]-6-[5-hydroxy-4-(1-methyl-1H-indol-5-yl)-4H-[1,2,4]triazol-3-yl]-benzene-1,3-diol;
4-(2-{2,4-Dihydroxy-5-[5-hydroxy-4-(1-methyl-1H-indol-5-yl)-4H-[1,2,4]triazol-3-yl]-phenyl}-ethyl)-benzonitrile;
4-[5-Hydroxy-4-(1-methyl-1H-indol-5-yl)-4H-[1,2,4]triazol-3-yl]-6-[2-(3,4,5-trimethoxy-phenyl)-ethyl]-benzene-1,3-diol;
4-[5-Hydroxy-4-(1-methyl-1H-indol-5-yl)-4H-[1,2,4]triazol-3-yl]-6-(2-pentafluorophenyl-ethyl)-benzene-1,3-diol;
4-(2-Benzo[1,3]dioxol-5-yl-1-methyl-ethyl)-6-[5-hydroxy-4-(1-methyl-1H-indol-5-yl)-4H-[1,2,4]triazol-3-yl]-benzene-1,3-diol;
4-[5-Hydroxy-4-(1-methyl-1H-indol-5-yl)-4H-[1,2,4]triazol-3-yl]-6-[2-(4-methoxy-phenyl)-ethyl]-benzene-1,3-diol;
4-[5-Hydroxy-4-(1-methyl-1H-indol-5-yl)-4H-[1,2,4]triazol-3-yl]-6-[2-(3-methoxy-phenyl)-ethyl]-benzene-1,3-diol;
4-[5-Hydroxy-4-(1-methyl-1H-indol-5-yl)-4H-[1,2,4]triazol-3-yl]-6-(1-methyl-2-phenyl-ethyl)-benzene-1,3-diol;
4-(1-(3,4-dimethoxyphenyl)propan-2-yl)-6-(5-hydroxy-4-(1-methyl-1H-indol-5-yl)-4H-1,2,4-triazol-3-yl)benzene-1,3-diol;
4-(5-hydroxy-4-(1-methyl-1H-indol-5-yl)-4H-1,2,4-triazol-3-yl)-6-(2-(pyrimidin-2-yl)ethyl)benzene-1,3-diol;
1-(3-(2,4-dihydroxy-5-(5-hydroxy-4-(1-methyl-1H-indol-5-yl)-4H-1,2,4-triazol-3-yl)phenethyl)phenyl)ethanone;
4-(2-fluorophenethyl)-6-(5-hydroxy-4-(1-methyl-1H-indol-5-yl)-4H-1,2,4-triazol-3-yl)benzene-1,3-diol;
4-(3-fluorophenethyl)-6-(5-hydroxy-4-(1-methyl-1H-indol-5-yl)-4H-1,2,4-triazol-3-yl)benzene-1,3-diol;
4-(4-fluorophenethyl)-6-(5-hydroxy-4-(1-methyl-1H-indol-5-yl)-4H-1,2,4-triazol-3-yl)benzene-1,3-diol;
4-(2-chlorophenethyl)-6-(5-hydroxy-4-(1-methyl-1H-indol-5-yl)-4H-1,2,4-triazol-3-yl)benzene-1,3-diol;
4-(3-chlorophenethyl)-6-(5-hydroxy-4-(1-methyl-1H-indol-5-yl)-4H-1,2,4-triazol-3-yl)benzene-1,3-diol;
4-(4-chlorophenethyl)-6-(5-hydroxy-4-(1-methyl-1H-indol-5-yl)-4H-1,2,4-triazol-3-yl)benzene-1,3-diol;
4-(5-hydroxy-4-(1-methyl-1H-indol-5-yl)-4H-1,2,4-triazol-3-yl)-6-(3-(1-hydroxyethyl)phenethyl)benzene-1,3-diol;
4-(4-((dimethylamino)methyl)phenethyl)-6-(5-hydroxy-4-(1-methyl-1H-indol-5-yl)-4H-1,2,4-triazol-3-yl)benzene-1,3-diol
4-(5-hydroxy-4-(1-methyl-1H-indol-5-yl)-4H-1,2,4-triazol-3-yl)-6-(4-(hydroxymethyl)phenethyl)benzene-1,3-diol;
(R)-4-(1-(2,6-difluorophenyl)propan-2-yl)-6-(5-hydroxy-4-(1-methyl-1H-indol-5-yl)-4H-1,2,4-triazol-3-yl)benzene-1,3-diol;
(S)-4-(1-(2,6-difluorophenyl)propan-2-yl)-6-(5-hydroxy-4-(1-methyl-1H-indol-5-yl)-4H-1,2,4-triazol-3-yl)benzene-1,3-diol;
4-((R)-1-(2,6-difluorophenyl)propan-2-yl)-6-(5-hydroxy-4-(2-methoxy-2,3-dihydro-1H-inden-5-yl)-4H-1,2,4-triazol-3-yl)benzene-1,3-diol;
4-(2,3-difluorophenethyl)-6-(5-hydroxy-4-(1-methyl-1H-indol-5-yl)-4H-1,2,4-triazol-3-yl)benzene-1,3-diol;

4-(2,5-difluorophenethyl)-6-(5-hydroxy-4-(1-methyl-1H-indol-5-yl)-4H-1,2,4-triazol-3-yl)benzene-1,3-diol;

4-(2,6-difluorophenethyl)-6-(4-(4-(dimethylamino)phenyl)-5-hydroxy-4H-1,2,4-triazol-3-yl)benzene-1,3-diol;

1-(4-(2-(2,4-dihydroxy-5-(5-hydroxy-4-(2-methoxy-2,3-dihydro-1H-inden-5-yl)-4H-1,2,4-triazol-3-yl)phenyl)propyl)-3,5-difluorophenyl)ethanone;

4-(2,6-difluorophenethyl)-6-(4-(4-((2-(dimethylamino)ethyl)(methyl)amino)-3-fluorophenyl)-5-hydroxy-4H-1,2,4-triazol-3-yl)benzene-1,3-diol;

4-(4-(4-((dimethylamino)methyl)phenyl)-5-hydroxy-4H-1,2,4-triazol-3-yl)-6-(1-phenylpropan-2-yl)benzene-1,3-diol;

1-(3-(2-(2,4-dihydroxy-5-(5-hydroxy-4-(1-methyl-1H-indol-5-yl)-4H-1,2,4-triazol-3-yl)phenyl)propyl)phenyl)ethanone;

4-(2,4-dihydroxy-5-(5-hydroxy-4-(1-methyl-1H-indol-5-yl)-4H-1,2,4-triazol-3-yl)phenethyl)benzamide;

4-(5-hydroxy-4-(1-methyl-1H-indol-5-yl)-4H-1,2,4-triazol-3-yl)-6-(4-(methoxymethyl)phenethyl)benzene-1,3-diol;

5-(5-mercapto-4-(naphthalen-1-yl)-4H-1,2,4-triazol-3-yl)biphenyl-2,4-diol;

4-(furan-2-yl)-6-(5-mercapto-4-(naphthalen-1-yl)-4H-1,2,4-triazol-3-yl)benzene-1,3-diol;

4-(5-hydroxy-4-(1-methyl-1H-indol-5-yl)-4H-1,2,4-triazol-3-yl)-6-(1H-pyrazol-1-yl)benzene-1,3-diol; or 4-(5-hydroxy-4-(1-methyl-1H-indol-5-yl)-4H-1,2,4-triazol-3-yl)-6-(1H-pyrazol-1-yl)benzene-1,3-diol;

or a tautomer, pharmaceutically acceptable salt, solvate, clathrate, or a prodrug thereof.

In one embodiment in the compounds represented by formula (XXVIII), Z, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanidino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$OR$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$.

In one embodiment in the compounds represented by formula (XXVIII), n is 1.

In another embodiment in the compounds represented by formula (XXVIII), n is 0.

In one embodiment in the compounds represented by formula (XXVIII) or (XXIX), R$_5$ is represented by the following formula:

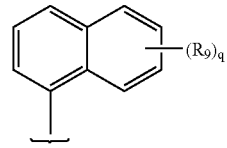

wherein:
R$_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, hydroxyalkyl, alkoxyalkyl, halo, cyano, nitro, guanidino, a haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$, —S(O)$_p$OR$_7$, —OP(O)(OR$_7$)$_2$, or —SP(O)(OR$_7$)$_2$;

or two R$_9$ groups taken together with the carbon atoms to which they are attached form a fused ring; and q is zero or an integer from 1 to 7.

In another embodiment in the compounds represented by formula (XXVIII) or (XXIX), R$_5$ is represented by the following formula:

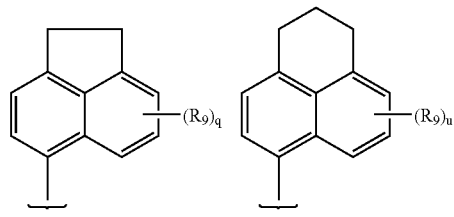

wherein: q is zero or an integer from 1 to 5; and u is zero or an integer from 1 to 5.

In another embodiment in the compounds represented by formula (XXVIII) or (XXIX), R$_5$ is represented by the following formula:

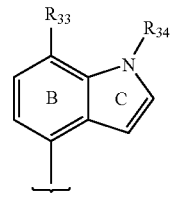

wherein:
R$_{33}$ is a halo, lower alkyl, a lower alkoxy, a lower haloalkyl, a lower haloalkoxy, and lower alkyl sulfanyl;
R$_{34}$ is H, a lower alkyl, or a lower alkylcarbonyl; and
Ring B and Ring C are optionally substituted with one or more substituents.

In another embodiment in the compounds represented by formula (XXVIII) or (XXIX), R$_5$ is selected from the group consisting of:

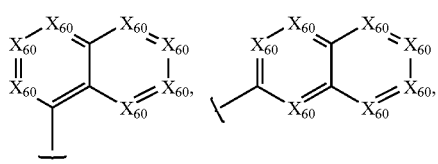
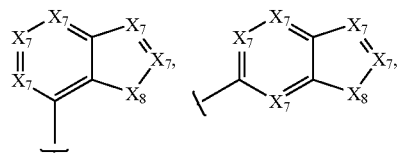
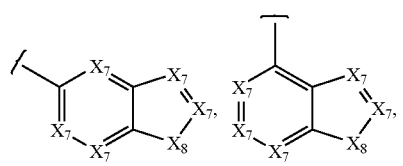
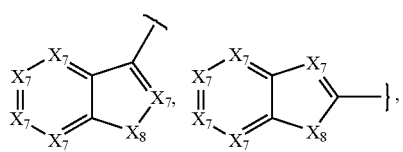
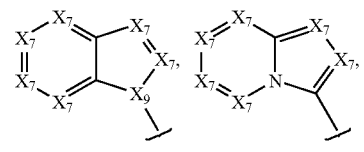
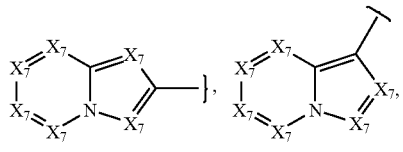
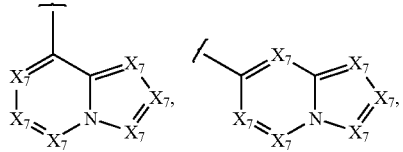
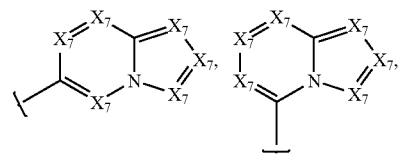

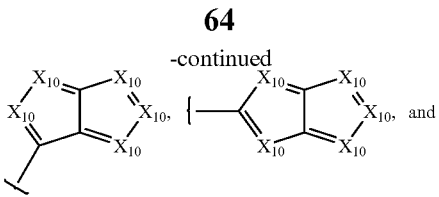

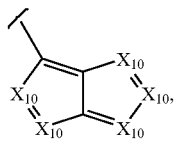

wherein:

$X_{60}$, for each occurrence, is independently CH, $CR_9$, N, N(O), $N^+(R_{17})$, provided that at least three $X_{60}$ groups are independently selected from CH and $CR_9$;

$X_7$, for each occurrence, is independently CH, $CR_9$, N, N(O), $N^+(R_{17})$, provided that at least three $X_7$ groups are independently selected from CH and $CR_9$;

$X_8$, for each occurrence, is independently $CH_2$, $CHR_9$, $C(R_9)_2$, S, $S(O)_p$, $NR_7$, or $NR_{17}$;

$X_9$, for each occurrence, is independently N or CH;

$X_{10}$, for each occurrence, is independently CH, $CR_9$, N, N(O), $N^+(R_{17})$, provided that at least one $X_{10}$ is selected from CH and $CR_9$;

$R_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, hydroxyalkyl, alkoxyalkyl, halo, cyano, nitro, guanidino, a haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$, —$S(O)_pOR_7$, —$OP(O)(OR_7)_2$, or —$SP(O)(OR_7)_2$, —$S(O)_pOR_7$, —$OP(O)(OR_7)_2$, or —$SP(O)(OR_7)_2$;

or two $R_9$ groups taken together with the carbon atoms to which they are attached form a fused ring; and $R_{17}$, for each occurrence, is independently —H, an alkyl, an aralkyl, —$C(O)R_7$, —$C(O)OR_7$, or —$C(O)NR_{10}R_{11}$.

In another embodiment in the compounds represented by formula (XXVIII) or (XXIX), $R_5$ is an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo

[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, and optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo(b)thienyl.

In another embodiment in the compounds represented by formula (XXVIII) or (XXIX), $R_5$ is selected from the group consisting of:

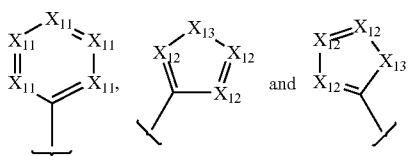

wherein:

$X_{11}$, for each occurrence, is independently CH, $CR_9$, N, N(O), or $N^+(R_{17})$, provided that at least one $X_{11}$ is N, N(O), or $N^+(R_{17})$ and at least two $X_{11}$ groups are independently selected from CH and $CR_9$;

$X_{12}$, for each occurrence, is independently CH, $CR_9$, N, N(O), $N^+(R_{17})$, provided that at least one $X_{12}$ group is independently selected from CH and $CR_9$;

$X_{13}$, for each occurrence, is independently O, S, $S(O)_p$, $NR_7$, or $NR_{17}$;

$R_9$, for each occurrence, is independently a substituent selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanidino, a hydroxyalkyl, alkoxyalkyl, haloalkyl, a heteroalkyl, —$NR_{10}R_{11}$, —$OR_7$, —$C(O)R_7$, —$C(O)OR_7$, —OC(O)$R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_p NR_{10}R_{11}$, —$S(O)_pOR_7$, —$OP(O)(OR_7)_2$, or —$SP(O)(OR_7)_2$, —$S(O)_pOR_7$, —$OP(O)(OR_7)_2$, or —$SP(O)(OR_7)_2$;

or two $R_9$ groups taken together with the carbon atoms to which they are attached form a fused ring; and $R_{17}$, for each occurrence, is independently an alkyl or an aralkyl.

In one embodiment in the compounds represented by formula (XXVIII) or (XXIX), $R_1$ and $R_3$ are each, independently, —OH, —SH, or —$NHR_7$. In one aspect, $R_1$ and $R_3$ are each, independently, —OH or —SH.

In one embodiment in the compounds represented by formula (XXVIII) or (XXIX), $R_2$ is —$NH_2$.

In another embodiment in the compounds represented by formula (XXVIII) or (XXIX), $R_2$ is —OH.

In another embodiment in the compounds represented by formula (XXVIII) or (XXIX), $R_2$ is —SH.

In one embodiment in the compounds represented by formula (XXVIII) or (XXIX), X is an optionally substituted 1 to 4 atom linker, wherein each linker atom is independently selected from the group consisting of C or O.

In another embodiment in the compounds represented by formula (XXVIII) or (XXIX), X is —$(CH_2)_s$—, —$(CH_2)_tC(O)$—, —$O(CH_2)_t$—, or —OC(O)—; s is 1, 2, or 3; and t is 0, 1, or 2. In one aspect, X is —$(CH_2)_s$—. In one aspect, X is —$(CH_2)_tC(O)$—. In one aspect, X is —$O(CH_2)_t$—. In one aspect, X is —OC(O)—.

In one embodiment in the compounds represented by formula (XXIX), $R_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl.

In one embodiment in the compounds represented by formula (XXIX), $R_1$ and $R_3$ are each, independently, —OH or —SH; $R_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl; X is —$(CH_2)_s$—, —$(CH_2)_tC(O)$—, —$O(CH_2)_t$—, or —OC(O)—; s is 1, 2, or 3; and t is 0, 1, or 2. In one aspect, $R_2$ is —$NH_2$.

In one embodiment in the compounds represented by formula (XXX), $X_{41}$ is $NR_{42}$ and $X_{42}$ is $CR_{44}$.

In another embodiment in the compounds represented by formula (XXX), $X_{41}$ is $NR_{42}$ and $X_{42}$ is N.

In another embodiment in the compounds represented by formula (XXX), $R_{41}$ is selected from the group consisting of —H, lower alkyl, lower alkoxy, lower cycloalkyl, and lower cycloalkoxy.

In another embodiment in the compounds represented by formula (XXX), $R_{41}$ is selected from the group consisting of —H, methyl, ethyl, propyl, isopropyl, cyclopropyl, methoxy, ethoxy, propoxy, and cyclopropoxy.

In another embodiment in the compounds represented by formula (XXX), $X_{41}$ is $NR_{42}$, and $R_{42}$ is selected from the group consisting of —H, a lower alkyl, a lower cycloalkyl, —$C(O)N(R_{27})_2$, and —C(O)OH, wherein each $R_{27}$ is independently —H or a lower alkyl.

In another embodiment in the compounds represented by formula (XXX), $X_{41}$ is $NR_{42}$, and $R_{42}$ is selected from the group consisting of —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$.

In another embodiment in the compounds represented by formula (XXX), $R_{43}$ and $R_{44}$ are, independently, selected from the group consisting of —H, methyl, ethyl, propyl, isopropyl, cyclopropyl, methoxy, ethoxy, propoxy, and cyclopropoxy.

In another embodiment in the compounds represented by formula (XXX), $X_{42}$ is $CR_{44}$; $Y_{40}$ is $CR_{43}$; and $R_{43}$ and $R_{44}$ together with the carbon atoms to which they are attached form a cycloalkenyl, an aryl, heterocyclyl, or heteroaryl ring.

In another embodiment in the compounds represented by formula (XXX), $R_{43}$ and $R_{44}$ together with the carbon atoms to which they are attached form a $C_5$-$C_8$ cycloalkenyl or a $C_5$-$C_8$ aryl.

In another embodiment in the compounds represented by formula (XXX), $R_{45}$ or $CR_{45}$ is selected from the group consisting of —H, —OH, —SH, —NH$_2$, a lower alkoxy, a lower alkyl amino, and a lower dialkyl amino.

In another embodiment in the compounds represented by formula (XXX), $R_{45}$ is selected from the group consisting of —H, —OH, methoxy and ethoxy.

In another embodiment in the compounds represented by formula (XXX), $X_{41}$ is O.

In another embodiment in the compounds represented by formula (XXX), $R_{40}$ is —OH or —SH.

In another embodiment in the compounds represented by formula (XXX), R'$_2$ is —NH$_2$.

In another embodiment in the compounds represented by formula (XXX), R'$_2$ is —OH.

In another embodiment in the compounds represented by formula (XXX), R'$_2$ is —SH.

In another embodiment in the compounds represented by formula (XXX), X' is —(CH$_2$)$_s$—, —(CH$_2$)$_t$C(O)—, —O(CH$_2$)$_t$—, or —OC(O)—; s is 1, 2, or 3; and t is 0, 1, or 2. In one aspect, X' is —(CH$_2$)$_s$—. In one aspect, X' is —(CH$_2$)$_t$C(O)—. In one aspect, X' is —O(CH$_2$)$_t$—. In one aspect, X' is —OC(O)—.

In one embodiment in the compounds represented by formula (XXXI), $X_{42}$ is $CR_{44}$, and $R_{43}$ and $R_{44}$ are, independently, selected from the group consisting of —H, methyl, ethyl, propyl, isopropyl, cyclopropyl, methoxy, ethoxy, propoxy, and cyclopropoxy.

In another embodiment in the compounds represented by formula (XXXI), $X_{42}$ is $CR_{44}$, and $R_{43}$ and $R_{44}$, taken together with the carbon atoms to which they are attached, form a cycloalkenyl, aryl, heterocyclyl, or heteroaryl ring.

In another embodiment in the compounds represented by formula (XXXI), $R_{43}$ and $R_{44}$, taken together with the carbon atoms to which they are attached, form a $C_5$-$C_8$ cycloalkenyl or a $C_5$-$C_8$ aryl.

In another embodiment in the compounds represented by formula (XXXI), $X_{42}$ is $CR_{44}$.

In another embodiment in the compounds represented by formula (XXXI), $X_{42}$ is N.

In another embodiment in the compounds represented by formula (XXXI), R'$_2$ is —NH$_2$.

In another embodiment in the compounds represented by formula (XXXI), R'$_2$ is —OH.

In another embodiment in the compounds represented by formula (XXXI), R'$_2$ is —SH.

In another embodiment in the compounds represented by formula (XXXI), X' is —(CH$_2$)$_s$—, —(CH$_2$)$_t$C(O)—, —O(CH$_2$)$_t$—, or —OC(O)—; s is 1, 2, or 3; and t is 0, 1, or 2. In one aspect, X' is —(CH$_2$)$_s$—. In one aspect, X' is —(CH$_2$)$_t$C(O)—. In one aspect, X' is —O(CH$_2$)$_t$—. In one aspect, X' is —OC(O)—.

In one embodiment in the compounds represented by formula (XXXII), R'$_2$ is NH$_2$.

In another embodiment in the compounds represented by formula (XXXII), R'$_2$ is —OH.

In another embodiment in the compounds represented by formula (XXXII), R'$_2$ is —SH.

In another embodiment in the compounds represented by formula (XXXII), X' is —(CH$_2$)$_s$—, —(CH$_2$)$_t$C(O)—, —O(CH$_2$)$_t$—, or —OC(O)—; s is 1, 2, or 3; and t is 0, 1, or 2. In one aspect, X' is —(CH$_2$)$_s$—. In one aspect, X' is —(CH$_2$)$_t$C(O)—. In one aspect, X' is —O(CH$_2$)$_t$—. In one aspect, X' is —OC(O)—.

In another embodiment, the compound is selected from the group consisting of 5-(4-(2-aminoethoxy)-2-hydroxy-5-isopropylphenyl)-4-(1-methyl-1H-indol-5-yl)-4H-1,2,4-triazol-3-ol;

5-(4-(aminomethyl)-2-hydroxy-5-isopropylphenyl)-4-(1-methyl-1H-indol-5-yl)-4H-1,2,4-triazol-3-ol;

5-(4-(aminooxy)-2-hydroxy-5-isopropylphenyl)-4-(1-methyl-1H-indol-5-yl)-4H-1,2,4-triazol-3-ol;

5-(4-(2-aminoethyl)-2-hydroxy-5-isopropylphenyl)-4-(1-methyl-1H-indol-5-yl)-4H-1,2,4-triazol-3-ol;

2-(5-hydroxy-4-(5-hydroxy-4-(1-methyl-1H-indol-5-yl)-4H-1,2,4-triazol-3-yl)-2-isopropylphenyl)acetamide;

5-hydroxy-4-(5-hydroxy-4-(1-methyl-1H-indol-5-yl)-4H-1,2,4-triazol-3-yl)-2-isopropylphenyl carbamate;

5-(4-(3-aminopropyl)-2-hydroxy-5-isopropylphenyl)-4-(1-methyl-1H-indol-5-yl)-4H-1,2,4-triazol-3-ol; or 3-hydroxy-4-(5-hydroxy-4-(1-methyl-1H-indol-5-yl)-4H-1,2,4-triazol-3-yl)benzoic acid;

or a tautomer, pharmaceutically acceptable salt, solvate, clathrate, or a prodrug thereof.

In one embodiment, the compounds of the invention do not include the compounds disclosed in U.S. patent application Ser. No. 11/282,119, filed Nov. 17, 2005.

Exemplary compounds of the invention are depicted in Table 1 below, including tautomers, pharmaceutically acceptable salts, solvates, clathrates, hydrates, polymorphs or prodrugs thereof.

| NO. | Structure | Tautomeric structure | Name |
|---|---|---|---|
| 1 | 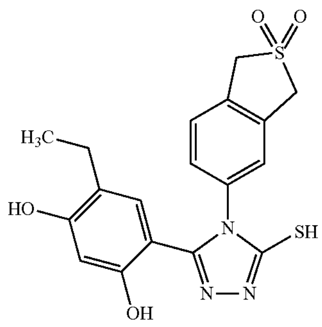 | | 4-[4-(2,2-dioxo-2,3-dihydro-1H-2λ⁶-benzo[c]thiophen-5-yl)-5-mercapto-4H-[1,2,4]triazol-3-yl]-6-ethyl-benzene-1,3-diol |
| 2 | 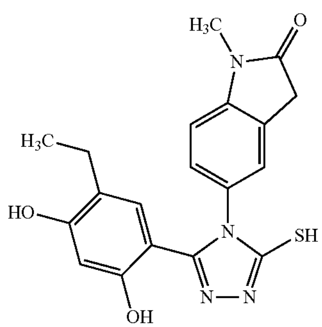 | | 5-(3-(5-ethyl-2,4-dihydroxyphenyl)-5-mercapto-4H-1,2,4-triazol-4-yl)-1-methylindolin-2-one |
| 3 | 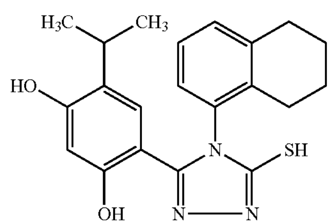 | | 4-isopropyl-6-(5-mercapto-4-(5,6,7,8-tetrahydronaphthalen-1-yl)-4H-1,2,4-triazol-3-yl)benzene-1,3-diol |

| NO. | Structure | Tautomeric structure | Name |
|---|---|---|---|
| 4 | 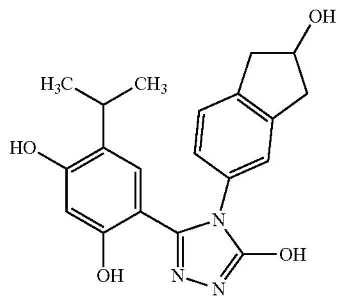 | | 4-(5-hydroxy-4-(2-hydroxy-2,3-dihydro-1H-inden-5-yl)-4H-1,2,4-triazol-3-yl)-6-isopropylbenzene-1,3-diol |
| 5 | 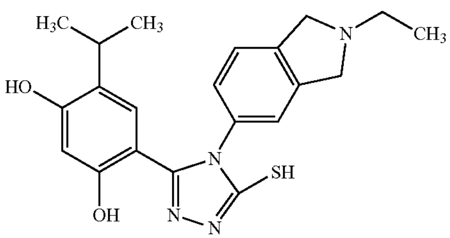 | | 4-(4-(2-ethylisoindolin-5-yl)-5-mercapto-4H-1,2,4-triazol-3-yl)-6-isopropylbenzene-1,3-diol |
| 6 | 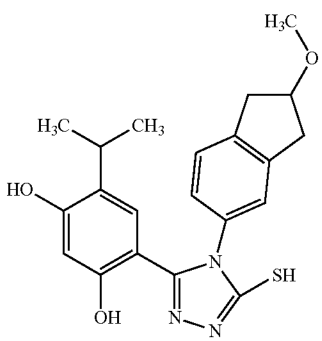 | | 4-isopropyl-6-(5-mercapto-4-(2-methoxy-2,3-dihydro-1H-inden-5-yl)-4H-1,2,4-triazol-3-yl)benzene-1,3-diol |

-continued

| NO. | Structure | Tautomeric structure | Name |
|---|---|---|---|
| 7 | 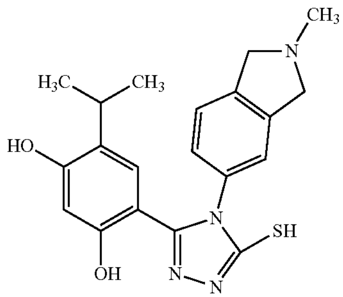 | | 4-isopropyl-6-(5-mercapto-4-(2-methylisoindolin-5-yl)-4H-1,2,4-triazol-3-yl)benzene-1,3-diol |
| 8 | 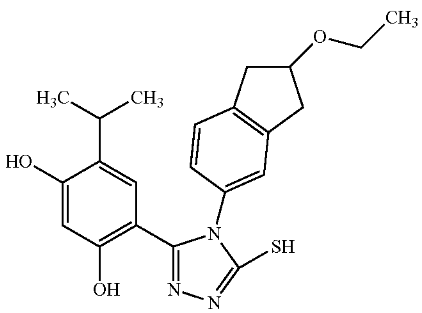 | | 4-(4-(2-ethoxy-2,3-dihydro-1H-inden-5-yl)-5-mercapto-4H-1,2,4-triazol-3-yl)-6-isopropylbenzene-1,3-diol |
| 9 | 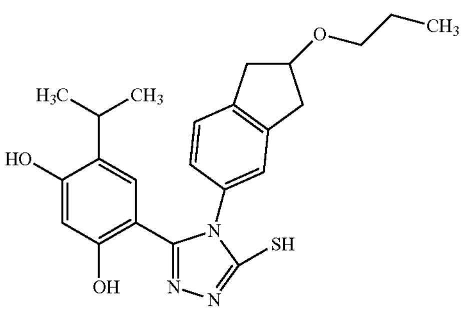 | | 4-isopropyl-6-(5-mercapto-4-(2-propoxy-2,3-dihydro-1H-inden-5-yl)-4H-1,2,4-triazol-3-yl)benzene-1,3-diol |

| NO. | Structure | Tautomeric structure | Name |
|---|---|---|---|
| 10 | 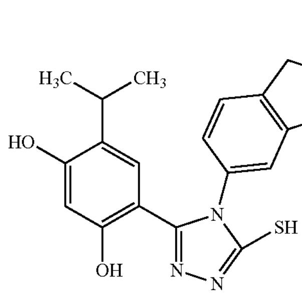 | | 4-(4-(1',3'-dihydrospiro[[1,3]dioxolane-2,2'-indene]-5'-yl)-5-mercapto-4H-1,2,4-triazol-3-yl)-6-isopropylbenzene-1,3-diol |
| 11 | 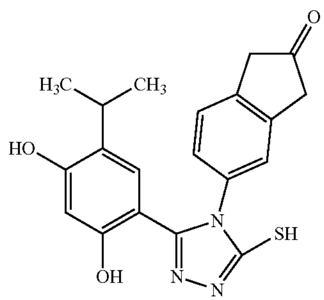 | | 5-(3-(2,4-dihydroxy-5-isopropylphenyl)-5-mercapto-4H-1,2,4-triazol-4-yl)-1H-inden-2(3H)-one |
| 12 | 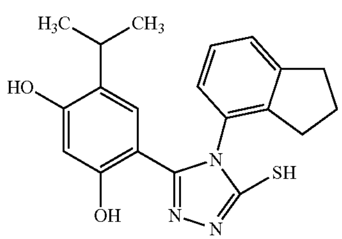 | | 4-(4-(2,3-dihydro-1H-inden-4-yl)-5-mercapto-4H-1,2,4-triazol-3-yl)-6-isopropylbenzene-1,3-diol |

-continued

| NO. | Structure | Tautomeric structure | Name |
|---|---|---|---|
| 13 | 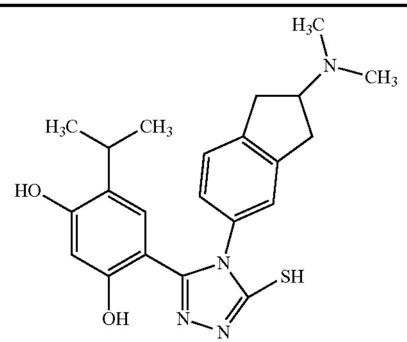 | | 4-(4-(2-(dimethyl)amino)-2,3-dihydro-1H-inden-5-yl)-5-mercapto-4H-1,2,4-triazol-3-yl)-6-isopropylbenzene-1,3-diol |
| 14 | 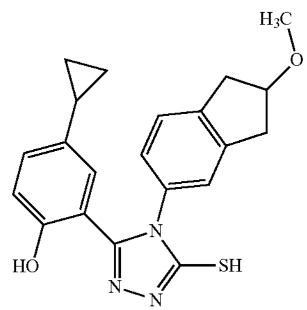 | | 4-cyclopropyl-2-(5-mercapto-4-(2-methoxy-2,3-dihydro-1H-inden-5-yl)-4H-1,2,4-triazol-3-yl)phenol |
| 15 | 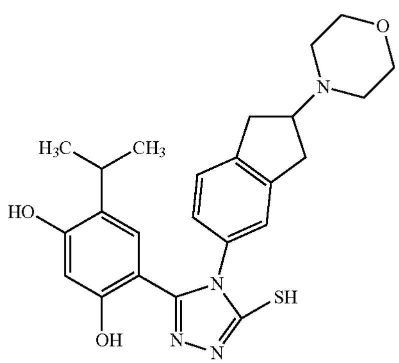 | | 4-isopropyl-6-(5-mercapto-4-(2-morpholino-2,3-dihydro-1H-inden-5-yl)-4H-1,2,4-triazol-3-yl)benzene-1,3-diol |

| NO. | Structure | Tautomeric structure | Name |
|---|---|---|---|
| 16 | 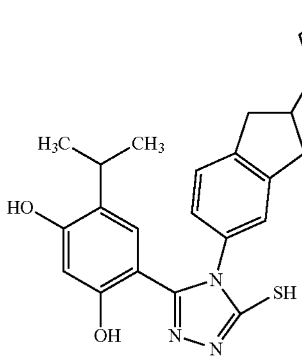 | | 4-isopropyl-6-(5-mercapto-4-(2-(pyrrolidin-1-yl)-2,3-dihydro-1H-inden-5-yl)-4H-1,2,4-triazol-3-yl)benzene-1,3-diol |
| 17 | 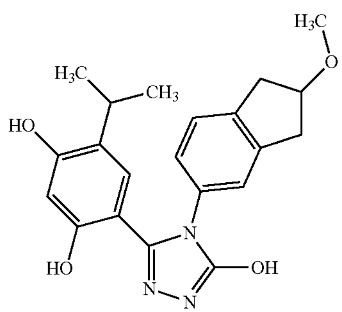 | | 4-(5-hydroxy-4-(2-methoxy-2,3-dihydro-1H-inden-5-yl)-4H-1,2,4-triazol-3-yl)-6-isopropylbenzene-1,3-diol |
| 18 | 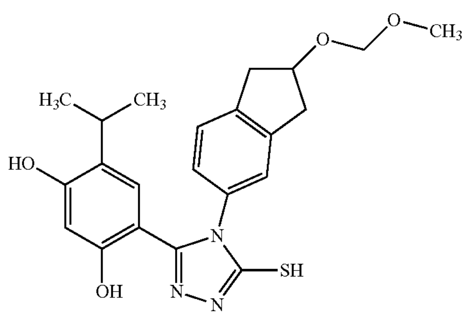 | | 4-isopropyl-6-(5-mercapto-4-(2-(methoxymethoxy)-2,3-dihydro-1H-inden-5-yl)-4H-1,2,4-triazol-3-yl)benzene-1,3-diol |

-continued

| NO. | Structure | Tautomeric structure | Name |
|---|---|---|---|
| 19 | 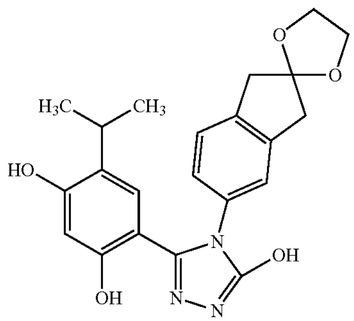 | | 4-(4-(1',3'-dihydrospiro[[1,3]dioxolane-2,2'-indene]-5'-yl)-5-hydroxy-4H-1,2,4-triazol-3-yl)-6-isopropylbenzene-1,3-diol |
| 20 | 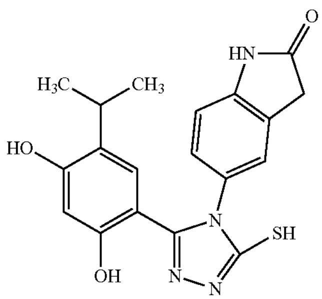 | | 5-(3-(2,4-dihydroxy-5-isopropylphenyl)-5-mercapto-4H-1,2,4-triazol-4-yl)indolin-2-one |
| 21 | 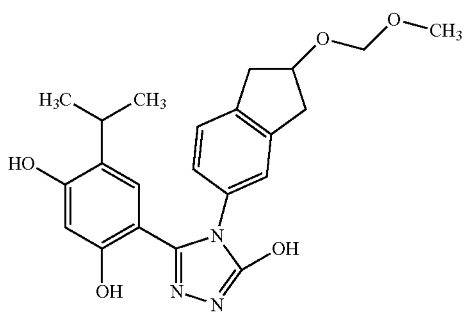 | | 4-(5-hydroxy-4-(2-(methoxymethoxy)-2,3-dihydro-1H-inden-5-yl)-1,2,4-triazol-3-yl)-6-isopropylbenzene-1,3-diol |

-continued

| NO. | Structure | Tautomeric structure | Name |
|---|---|---|---|
| 22 | 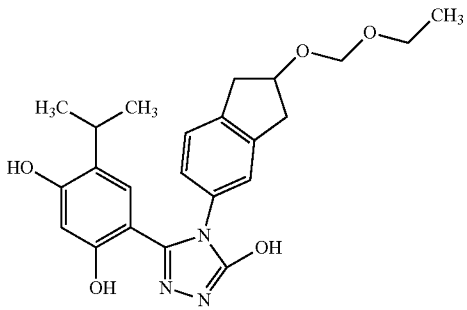 | | 4-(4-(2-(ethoxymethoxy)-2,3-dihydro-1H-inden-5-yl)-5-hydroxy-4H-1,2,4-triazol-3-yl)-6-isopropylbenzene-1,3-diol |
| 23 | 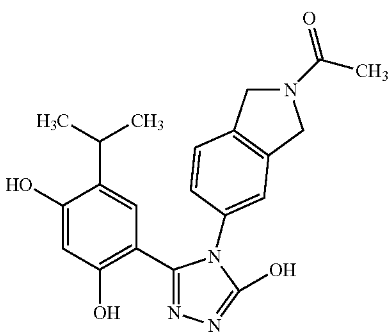 | | 1-(5-(3-(2,4-dihydroxy-5-isopropylphenyl)-5-hydroxy-4H-1,2,4-triazol-4-yl)isoindolin-2-yl)ethanone |
| 24 | 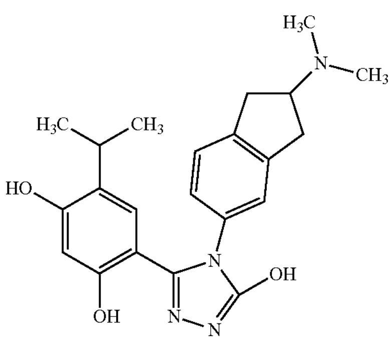 | | 4-(4-(2-(dimethylamino)-2,3-dihydro-1H-inden-5-yl)-5-hydroxy-4H-1,2,4-triazol-3-yl)-6-isopropylbenzene-1,3-diol |

-continued

| NO. | Structure | Tautomeric structure | Name |
|---|---|---|---|
| 25 | 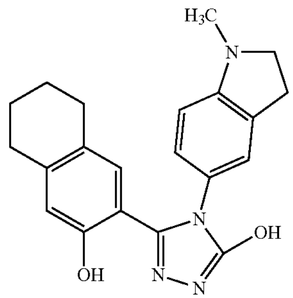 | | 5-(3-hydroxy-5,6,7,8-tetrahydronaphthalen-2-yl)-4-(1-methylindolin-5-yl)-4H-1,2,4-triazol-3-ol |
| 26 | 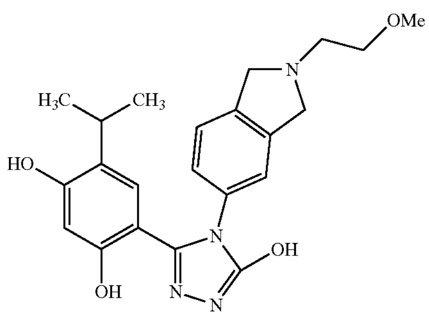 | | 4-(5-hydroxy-4-(2-(2-methoxyethyl)isoindolin-5-yl)-4H-1,2,4-triazol-3-yl)-6-isopropylbenzene-1,3-diol |
| 27 | 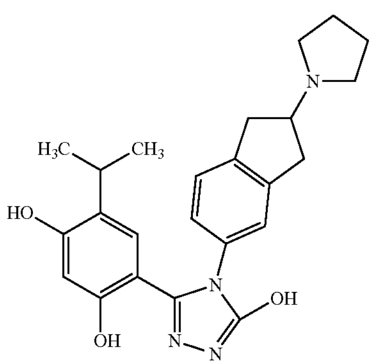 | | 4-(5-hydroxy-4-(2-(pyrrolidin-1-yl)-2,3-dihydro-1H-inden-5-yl)-4H-1,2,4-triazol-3-yl)-6-isopropylbenzene-1,3-diol |

| NO. | Structure | Tautomeric structure | Name |
|---|---|---|---|
| 28 | 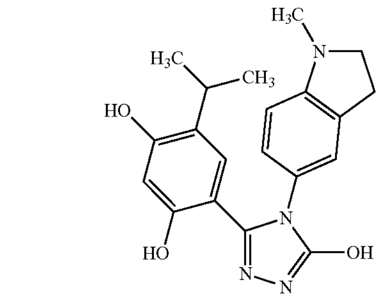 | | 4-(5-hydroxy-4-(1-methylindolin-5-yl)-4H-1,2,4-triazol-3-yl)-6-isopropylbenzene-1,3-diol |
| 29 | 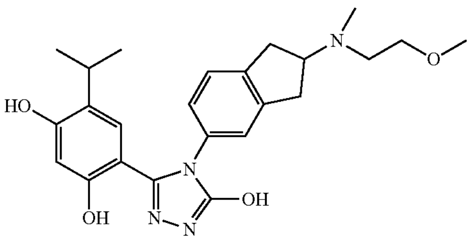 | | 4-(5-hydroxy-4-(2-((2-methoxyethyl)(methyl)amino)-2,3-dihydro-1H-inden-5-yl)-4H-1,2,4-triazol-3-yl)-6-isopropylbenzene-1,3-diol |
| 30 | 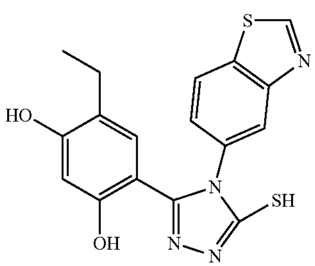 | | 4-(4-(benzo[d]thiazol-5-yl)-5-mercapto-4H-1,2,4-triazol-3-yl)-6-ethylbenzene-1,3-diol |

-continued

| NO. | Structure | Tautomeric structure | Name |
|---|---|---|---|
| 31 | 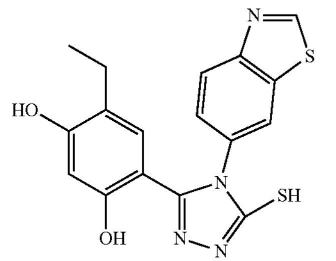 | | 4-(4-(benzo[d]thiazol-6-yl)-5-mercapto-4H-1,2,4-triazol-3-yl)-6-ethylbenzene-1,3-diol |
| 32 | 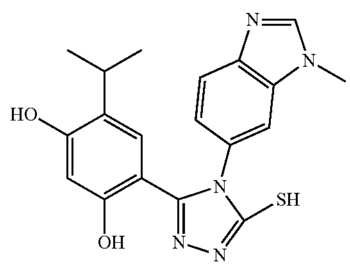 | | 4-isopropyl-6-(5-mercapto-4-(1-methyl-1H-benzo[d]imidazol-6-yl)-4H-1,2,4-triazol-3-yl)benzene-1,3-diol |
| 33 | 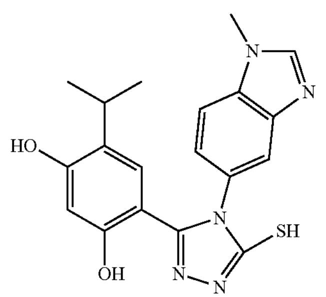 | | 4-isopropyl-6-(5-mercapto-4-(1-methyl-1H-benzo[d]imidazol-5-yl)-4H-1,2,4-triazol-3-yl)benzene-1,3-diol |

| NO. | Structure | Tautomeric structure | Name |
|---|---|---|---|
| 34 | 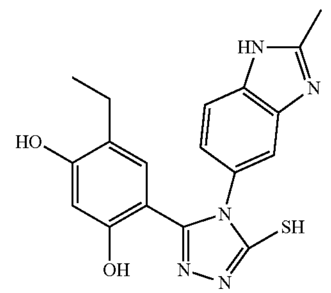 | | 4-ethyl-6-(5-mercapto-4-(2-methyl-1H-benzo[d]imidazol-5-yl)-4H-1,2,4-triazol-3-yl)benzene-1,3-diol |
| 35 | 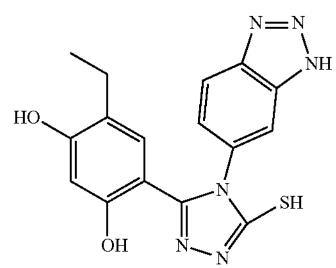 | | 4-(4-(1H-benzo[d][1,2,3]triazol-6-yl)-5-mercapto-4H-1,2,4-triazol-3-yl)-6-ethylbenzene-1,3-diol |
| 36 | 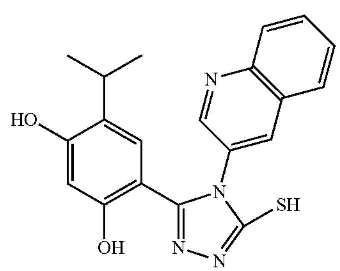 | | 4-isopropyl-6-(5-mercapto-4-(quinolin-3-yl)-4H-1,2,4-triazol-3-yl)benzene-1,3-diol |

-continued

| NO. | Structure | Tautomeric structure | Name |
|---|---|---|---|
| 37 | 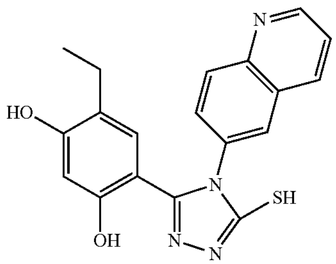 | | 4-ethyl-6-(5-mercapto-4-(quinolin-6-yl)-4H-1,2,4-triazol-3-yl)benzene-1,3-diol |
| 38 | 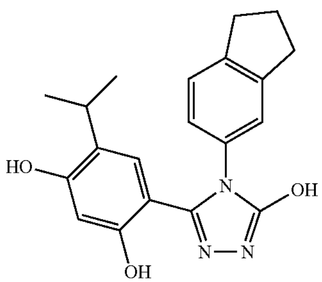 | | 4-(4-(2,3-dihydro-1H-inden-5-yl)-5-hydroxy-4H-1,2,4-triazol-3-yl)-6-isopropylbenzene-1,3-diol |
| 39 | 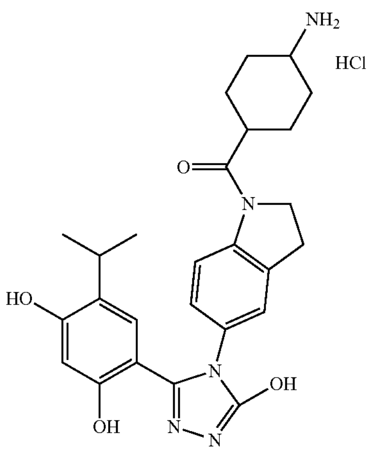 | | (4-aminocyclohexyl)(5-(3-(2,4-dihydroxy-5-isopropylphenyl)-5-hydroxy-4H-1,2,4-triazol-4-yl)indolin-1-yl)methanone hydrochloride |

| NO. | Structure | Tautomeric structure | Name |
|---|---|---|---|
| 40 | 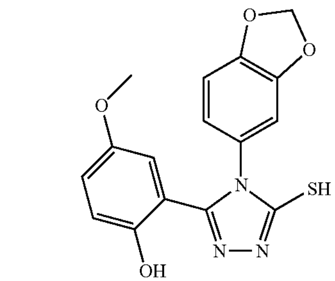 | | 2-(4-(benzo[d][1,3]dioxol-5-yl)-5-mercapto-4H-1,2,4-triazol-3-yl)-4-methoxyphenol |
| 41 | 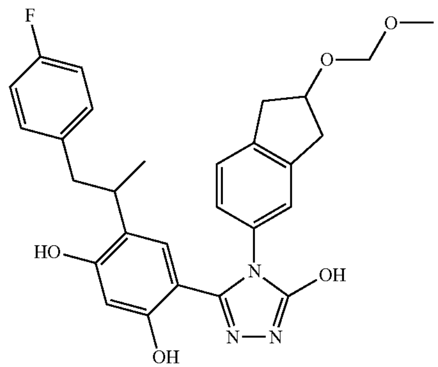 | | 4-(1-(4-fluorophenyl)propan-2-yl)-6-(5-hydroxy-4-(2-(methoxymethoxy)-2,3-dihydro-1H-inden-5-yl)-4H-1,2,4-triazol-3-yl)benzene-1,3-diol |
| 42 | 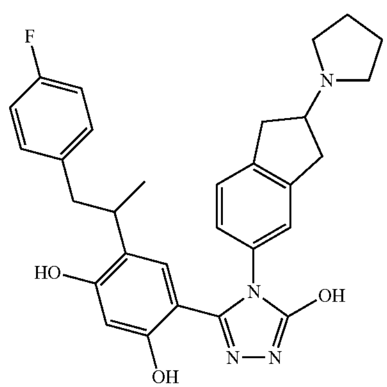 | | 4-(1-(4-fluorophenyl)propan-2-yl)-6-(5-hydroxy-4-(2-(pyrrolidin-1-yl)-2,3-dihydro-1H-inden-5-yl)-4H-1,2,4-triazol-3-yl)benzene-1,3-diol |

| NO. | Structure | Tautomeric structure | Name |
|---|---|---|---|
| 43 | 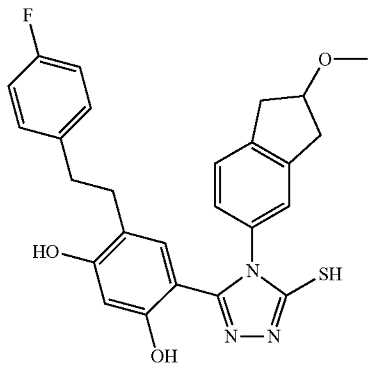 | | 4-(4-fluorophenethyl)-6-(5-mercapto-4-(2-methoxy-2,3-dihydro-1H-inden-5-yl)-4H-1,2,4-triazol-3-yl)benzene-1,3-diol |
| 44 | 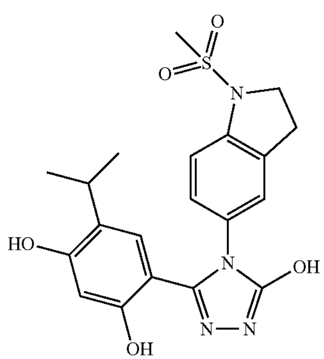 | | 4-(5-hydroxy-4-(1-(methylsulfonyl)indolin-5-yl)-4H-1,2,4-triazol-3-yl)-6-isopropylbenzene-1,3-diol |

| NO. | Structure | Tautomeric structure | Name |
|---|---|---|---|
| 45 | 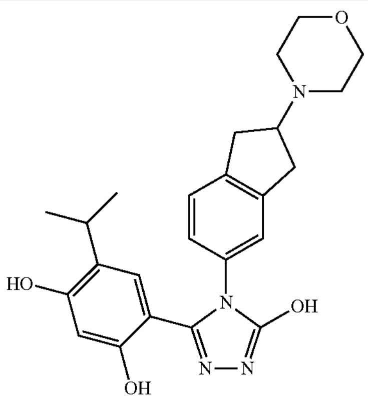 | | 4-(5-hydroxy-4-(2-morpholino-2,3-dihydro-1H-inden-5-yl)-4H-1,2,4-triazol-3-yl)-6-isopropylbenzene-1,3-diol |

Exemplary compounds of the invention are depicted in Table 2 below, including tautomers, pharmaceutically acceptable salts, solvates, clathrates, hydrates, polymorphs or prodrugs thereof.

| NO. | Structure | Tautomeric structure | Name |
|---|---|---|---|
| 1a | 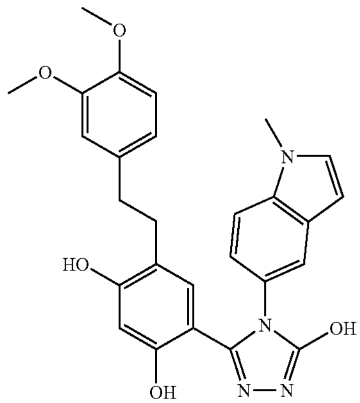 | | 4-[2-(3,4-Dimethoxy-phenyl)-ethyl]-6-[5-hydroxy-4-(1-methyl-1H-indol-5-yl)-4H-[1,2,4]triazol-3-yl]-benzene-1,3-diol |
| 2a | 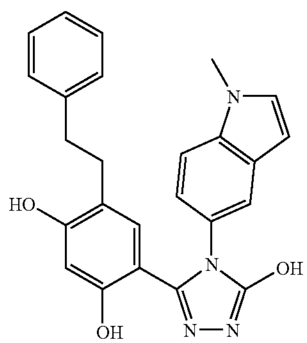 | | 4-[5-hydroxy-4-(1-methyl-1H-indol-5-yl)-4H-[1,2,4]triazol-3-yl]-6-phenethyl-benzene-1,3-diol |
| 3a | 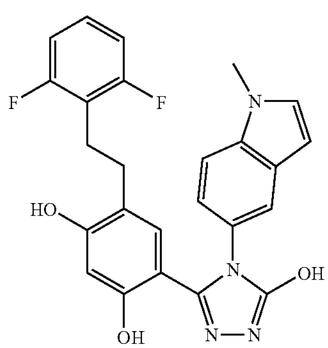 | | 4-[2-(2,6-Difluoro-phenyl)-ethyl]-6-{5-hydroxy-4-(1-methyl-1H-indol-5-yl)-4H-[1,2,4]triazol-3-yl]-benzene-1,3-diol |
| 4a | 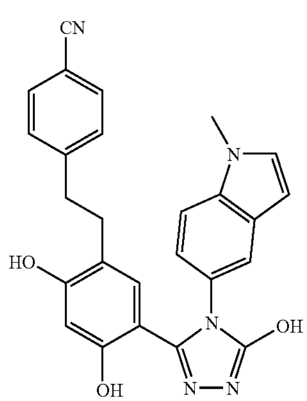 | | 4-(2-{2,4-Dihydroxy-5-[5-hydroxy-4-(1-methyl-1H-indol-5-yl)-4H-[1,2,4]triazol-3-yl]-phenyl}-ethyl)-benzonitrile |

| NO. | Structure | Tautomeric structure | Name |
|---|---|---|---|
| 5a | 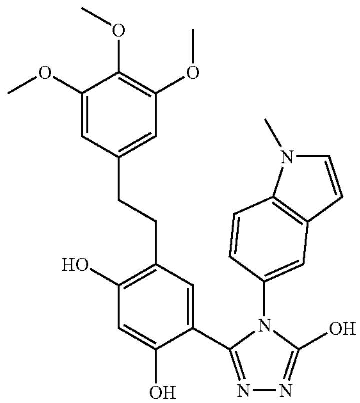 | | 4-[5-Hydroxy-4-(1-methyl-1H-indol-5-yl)-4H-[1,2,4]triazol-3-yl]-6-[2-(3,4,5-trimethoxy-phenyl)-ethyl]-benzene-1,3-diol |
| 6a | 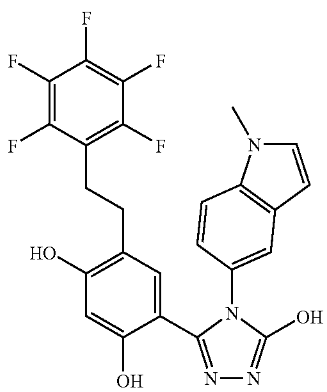 | | 4-[5-Hydroxy-4-(1-methyl-1H-indol-5-yl)-4H-[1,2,4]triazol-3-yl]-6-(2-pentafluorophenyl-ethyl)-benzene-1,3-diol |
| 7a | 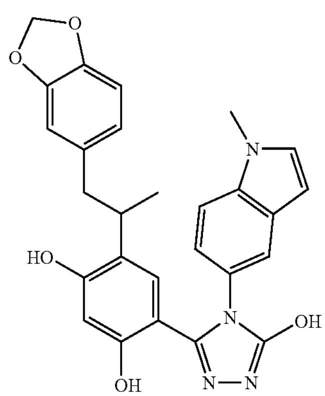 | | 4-(2-Benzo[1,3]dioxol-5-yl-1-methyl-ethyl)-6-[5-hydroxy-4-(1-methyl-1H-indol-5-yl)-4H-[1,2,4]triazol-3-yl]-benzene-1,3-diol |
| 8a | 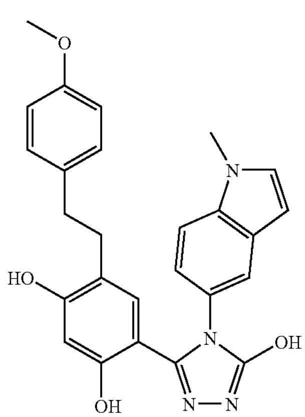 | | 4-[5-Hydroxy-4-(1-methyl-1H-indol-5-yl)-4H-[1,2,4]triazol-3-yl]-6-[2-(4-methoxy-phenyl)-ethyl]-benzene-1,3-diol |

-continued

| NO. | Structure | Tautomeric structure | Name |
|---|---|---|---|
| 9a | 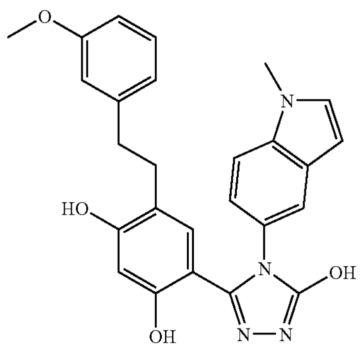 | | 4-[5-Hydroxy-4-(1-methyl-1H-indol-5-yl)-4H-[1,2,4]triazol-3-yl]-6-[2-(3-methoxy-phenyl)-ethyl]-benzene-1,3-diol |
| 10a | 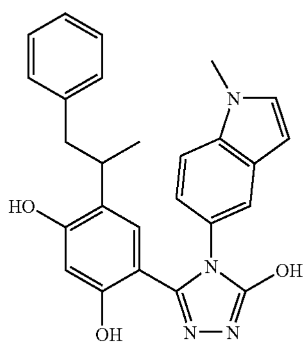 | | 4-[5-Hydroxy-4-(1-methyl-1H-indol-5-yl)-4H-[1,2,4]triazol-3-yl]-6-(1-methyl-2-phenyl-ethyl)-benzene-1,3-diol |
| 11a | 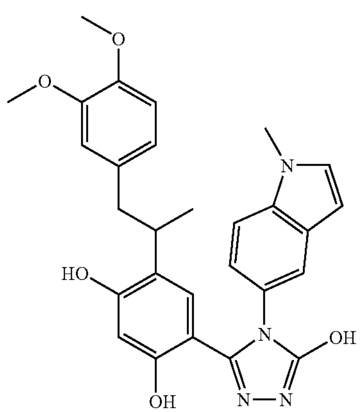 | | 4-(1-(3,4-dimethoxyphenyl)propan-2-yl)-6-(5-hydroxy-4-(1-methyl-1H-indol-5-yl)-4H-1,2,4-triazol-3-yl)benzene-1,3-diol |
| 12a | 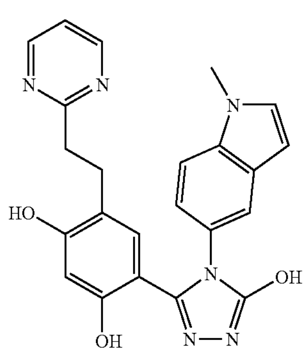 | | 4-(5-hydroxy-4-(1-methyl-1H-indol-5-yl)-4H-1,2,4-triazol-3-yl)-6-(2-(pyrimidin-2-yl)ethyl)benzene-1,3-diol |

-continued

| NO. | Structure | Tautomeric structure | Name |
|---|---|---|---|
| 13a | 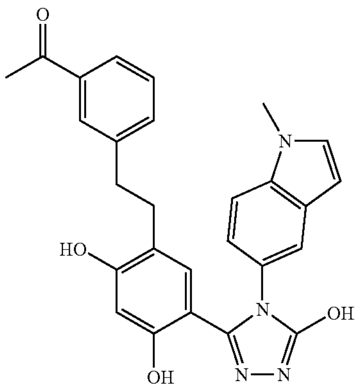 | | 1-(3-(2,4-dihydroxy-5-(5-hydroxy-4-(1-methyl-1H-indol-5-yl)-4H-1,2,4-triazol-3-yl)phenethyl)phenyl)ethanone |
| 14a | 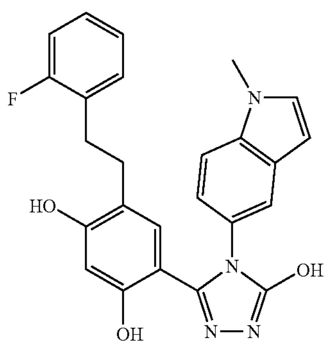 | | 4-(2-fluorophenethyl)-6-(5-hydroxy-4-(1-methyl-1H-indol-5-yl)-4H-1,2,4-triazol-3-yl)benzene-1,3-diol |
| 15a | 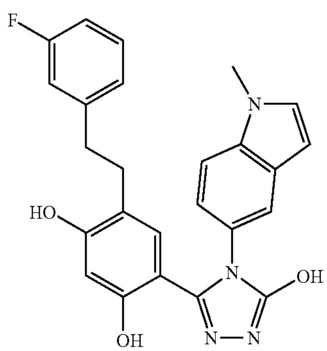 | | 4-(3-fluorophenethyl)-6-(5-hydroxy-4-(1-methyl-1H-indol-5-yl)-4H-1,2,4-triazol-3-yl)benzene-1,3-diol |
| 16a | 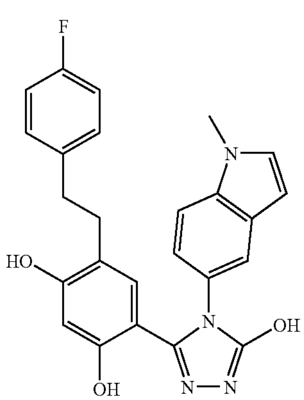 | | 4-(4-fluorophenethyl)-6-(5-hydroxy-4-(1-methyl-1H-indol-5-yl)-4H-1,2,4-triazol-3-yl)benzene-1,3-diol |

-continued

| NO. | Structure | Tautomeric structure | Name |
|---|---|---|---|
| 17a | 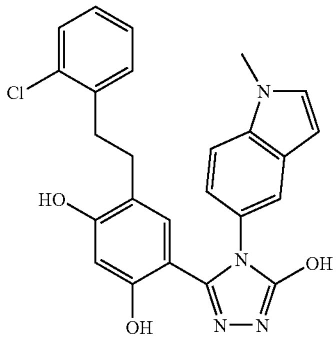 | | 4-(2-chlorophenethyl)-6-(5-hydroxy-4-(1-methyl-1H-indol-5-yl)-4H-1,2,4-triazol-3-yl)benzene-1,3-diol |
| 18a | 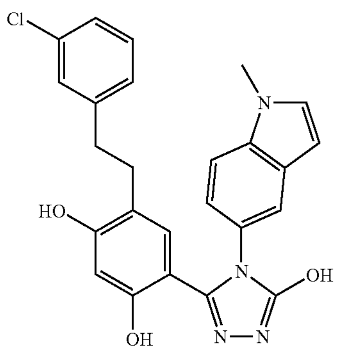 | | 4-(3-chlorophenethyl)-6-(5-hydroxy-4-(1-methyl-1H-indol-5-yl)-4H-1,2,4-triazol-3-yl)benzene-1,3-diol |
| 19a | 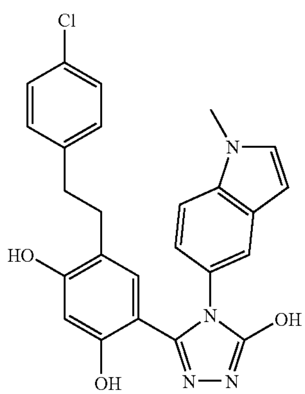 | | 4-(4-chlorophenethyl)-6-(5-hydroxy-4-(1-methyl-1H-indol-5-yl)-4H-1,2,4-triazol-3-yl)benzene-1,3-diol |
| 20a | 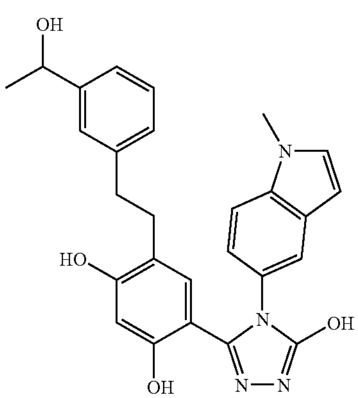 | | 4-(5-hydroxy-4-(1-methyl-1H-indol-5-yl)-4H-1,2,4-triazol-3-yl)-6-(3-(1-hydroxyethyl)phenethyl)benzene-1,3-diol |

| NO. | Structure | Tautomeric structure | Name |
|---|---|---|---|
| 21a | 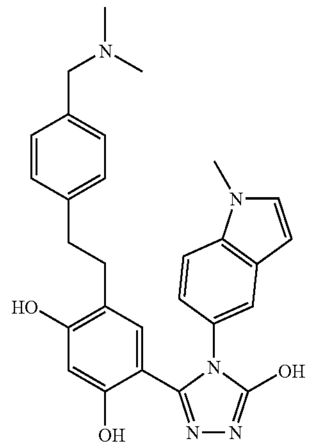 | | 4-(4-((dimethylamino)methyl)phenethyl)-6-(5-hydroxy-4-(1-methyl-1H-indol-5-yl)-4H-1,2,4-triazol-3-yl)benzene-1,3-diol |
| 22a | 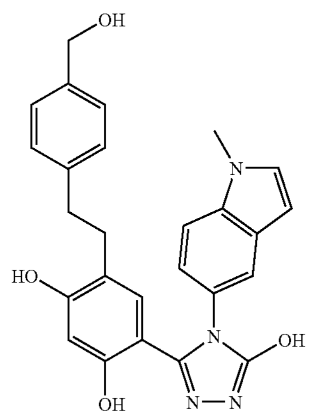 | | 4-(5-hydroxy-4-(1-methyl-1H-indol-5-yl)-4H-1,2,4-triazol-3-yl)-6-(4-(hydroxymethyl)phenethyl)benzene-1,3-diol |
| 23a | 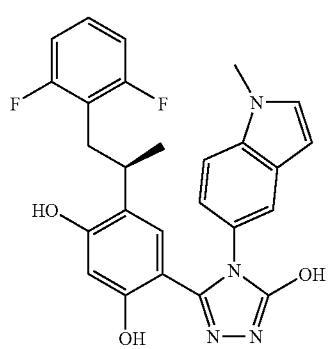 | | (R)-4-(1-(2,6-difluorophenyl)propan-2-yl)-6-(5-hydroxy-4-(1-methyl-1H-indol-5-yl)-4H-1,2,4-triazol-3-yl)benzene-1,3-diol |
| 24a | 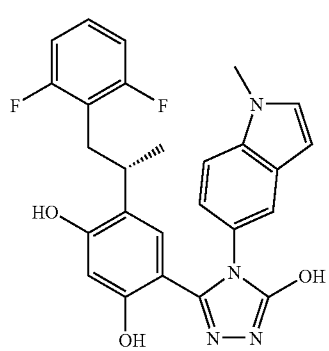 | | (S)-4-(1-(2,6-difluorophenyl)propan-2-yl)-6-(5-hydroxy-4-(1-methyl-1H-indol-5-yl)-4H-1,2,4-triazol-3-yl)benzene-1,3-diol |

-continued

| NO. | Structure | Tautomeric structure | Name |
|---|---|---|---|
| 25a | 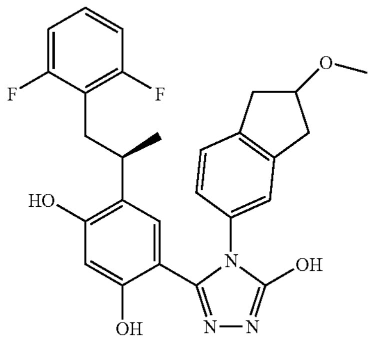 | | 4-((R)-1-(2,6-difluorophenyl)propan-2-yl)-6-(5-hydroxy-4-(2-methoxy-2,3-dihydro-1H-inden-5-yl)-4H-1,2,4-triazol-3-yl)benzene-1,3-diol |
| 26a | 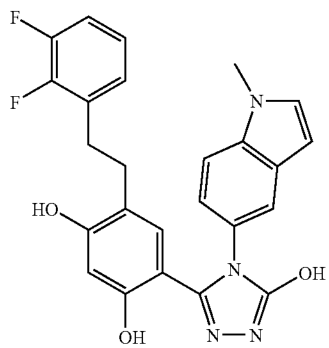 | | 4-(2,3-difluorophenethyl)-6-(5-hydroxy-4-(1-methyl-1H-indol-5-yl)-4H-1,2,4-triazol-3-yl)benzene-1,3-diol |
| 27a | 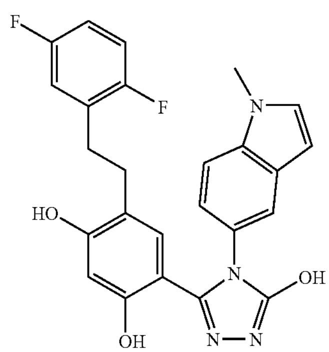 | | 4-(2,5-difluorophenethyl)-6-(5-hydroxy-4-(1-methyl-1H-indol-5-yl)-4H-1,2,4-triazol-3-yl)benzene-1,3-diol |
| 28a | 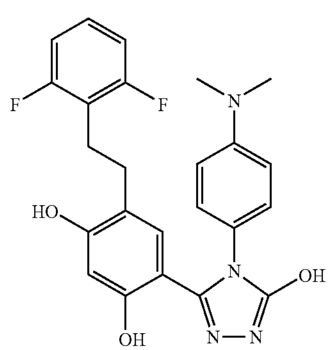 | | 4-(2,6-difluorophenethyl)-6-(4-(4-(dimethylamino)phenyl)-5-hydroxy-4H-1,2,4-triazol-3-yl)benzene-1,3-diol |

-continued

| NO. | Structure | Tautomeric structure | Name |
|---|---|---|---|
| 29a | 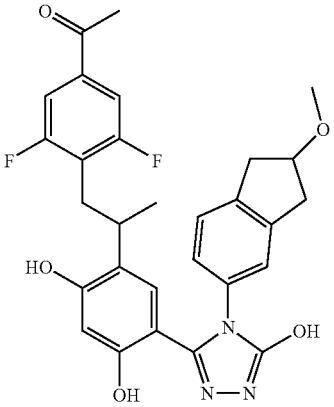 | 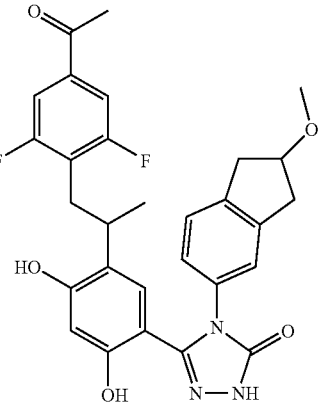 | 1-(4-(2-(2,4-dihydroxy-5-(5-hydroxy-4-(2-methoxy-2,3-dihydro-1H-inden-5-yl)-4H-1,2,4-triazol-3-yl)phenyl)propyl)-3,5-difluorophenyl)ethanone |
| 30a | 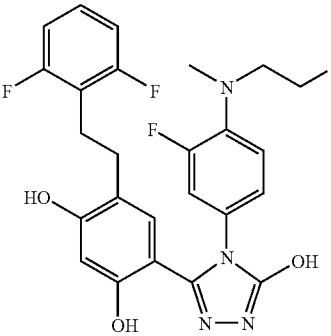 | 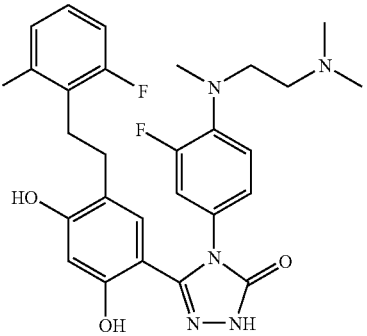 | 4-(2,6-difluorophenethyl)-6-(4-(4-((2-(dimethylamino)ethyl)(methyl)amino)-3-fluorophenyl)-5-hydroxy-4H-1,2,4-triazol-3-yl)benzene-1,3-diol |
| 31a | 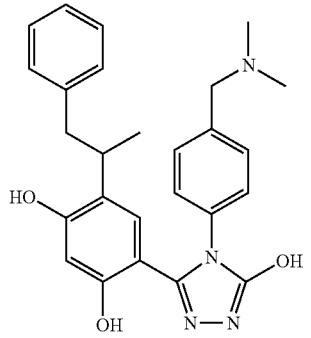 | 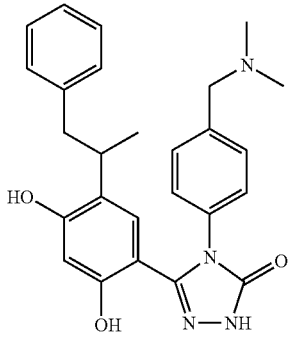 | 4-(4-(4-((dimethylamino)methyl)phenyl)-5-hydroxy-4H-1,2,4-triazol-3-yl)-6-(1-phenylpropan-2-yl)benzene-1,3-diol |
| 32a | 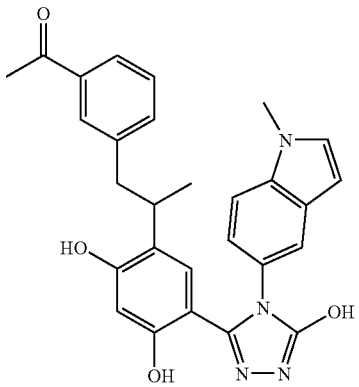 | 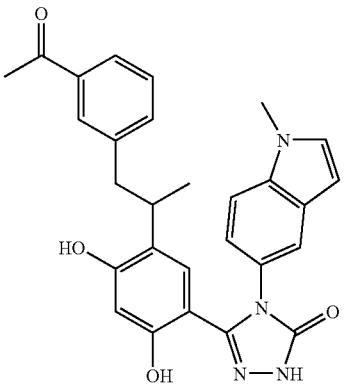 | 1-(3-(2-(2,4-dihydroxy-5-(5-hydroxy-4-(1-methyl-1H-indol-5-yl)-4H-1,2,4-triazol-3-yl)phenyl)propyl)phenyl)ethanone |

| NO. | Structure | Tautomeric structure | Name |
|---|---|---|---|
| 33a | 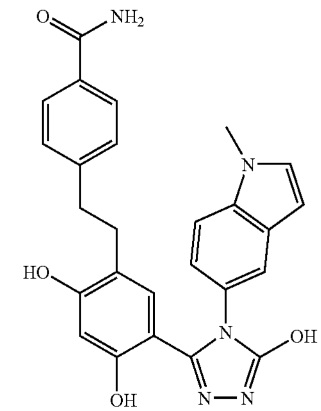 | | 4-(2,4-dihydroxy-5-(5-hydroxy-4-(1-methyl-1H-indol-5-yl)-4H-1,2,4-triazol-3-yl)phenethyl)benzamide |
| 34a | 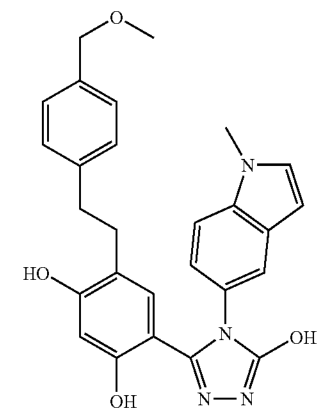 | | 4-(5-hydroxy-4-(1-methyl-1H-indol-5-yl)-4H-1,2,4-triazol-3-yl)-6-(4-(methoxymethyl)phenethyl)benzene-1,3-diol |
| 35a | 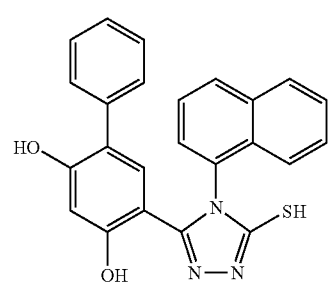 | | 5-(5-mercapto-4-(naphthalen-1-yl)-4H-1,2,4-triazol-3-yl)biphenyl-2,4-diol |
| 36a | 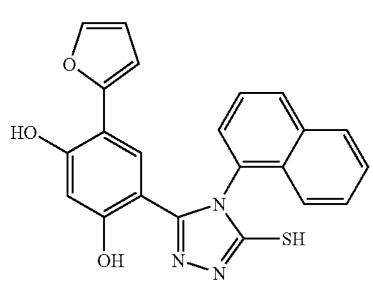 | | 4-(furan-2-yl)-6-(5-mercapto-4-(naphthalen-1-yl)-4H-1,2,4-triazol-3-yl)benzene-1,3-diol |

| NO. | Structure | Tautomeric structure | Name |
|---|---|---|---|
| 37a | 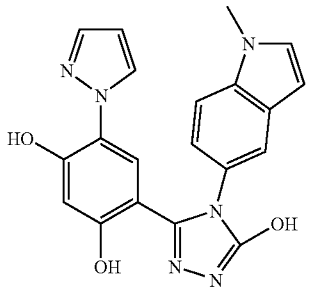 | | 4-(5-hydroxy-4-(1-methyl-1H-indol-5-yl)-4H-1,2,4-triazol-3-yl)-6-(1H-pyrazol-1-yl)benzene-1,3-diol |
| 38a | 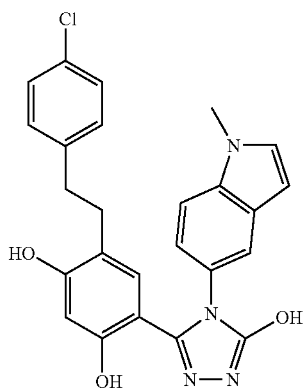 | | 4-(4-chlorophenethyl)-6-(5-hydroxy-4-(1-methyl-1H-indol-5-yl)-4H-1,2,4-triazol-3-yl)benzene-1,3-diol |
| 39a | 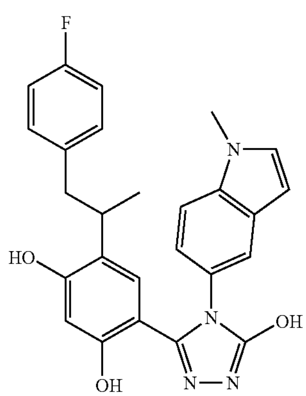 | | 4-(1-(4-fluorophenyl)propan-2-yl)-6-(5-hydroxy-4-(1-methyl-1H-indol-5-yl)-4H-1,2,4-triazol-3-yl)benzene-1,3-diol |
| 40a | 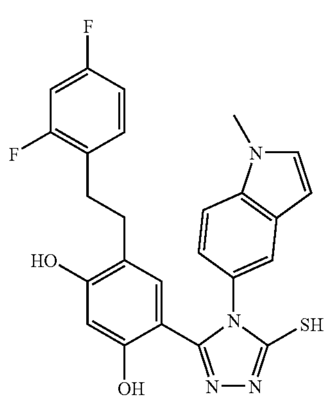 | | 4-(2,4-difluorophenethyl)-6-(5-mercapto-4-(1-methyl-1H-indol-5-yl)-4H-1,2,4-triazol-3-yl)benzene-1,3-diol |

-continued

| NO. | Structure | Tautomeric structure | Name |
|---|---|---|---|
| 41a | 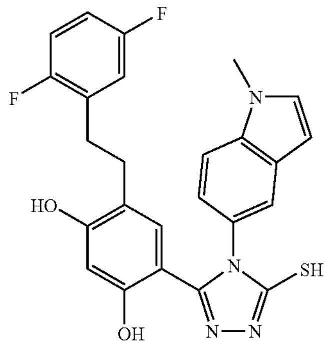 | | 4-(2,5-difluorophenethyl)-6-(5-mercapto-4-(1-methyl-1H-indol-5-3-yl)benzene-1,3-diol |
| 42a | 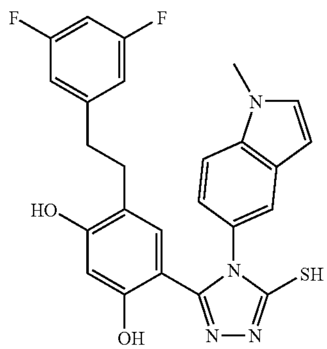 | | 4-(3,5-difluorophenethyl)-6-(5-mercapto-4-(1-methyl-1H-indol-5-yl)-4H-1,2,4-triazol-3-yl)benzene-1,3-diol |

Exemplary compounds of the invention are depicted in Table 3 below, including tautomers, pharmaceutically acceptable salts, solvates, clathrates, hydrates, polymorphs or prodrugs thereof.

| NO. | Structure | Tautomeric structure | Name |
|---|---|---|---|
| 1b | 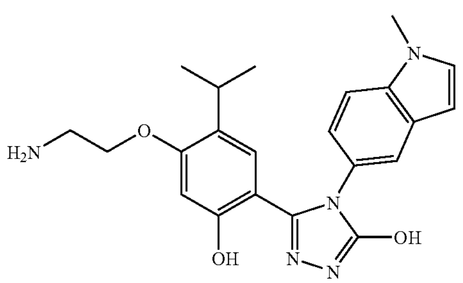 | | 5-(4-(2-aminoethoxy)-2-hydroxy-5-isopropylphenyl)-4-(1-methyl-1H-indol-5-yl)-4H-1,2,4-triazol-3-ol |
| 2b | 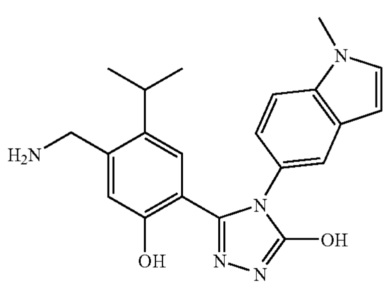 | | 5-(4-(aminomethyl)-2-hydroxy-5-isopropylphenyl)-4-(1-methyl-1H-indol-5-yl)-4H-1,2,4-triazol-3-ol |

| NO. | Structure | Tautomeric structure | Name |
|---|---|---|---|
| 3b | 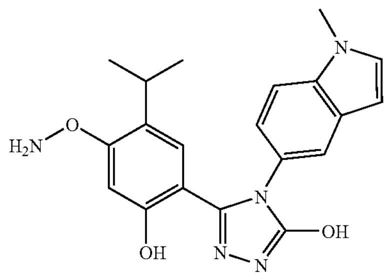 | | 5-(4-(aminooxy)-2-hydroxy-5-isopropylphenyl)-4-(1-methyl-1H-indol-5-yl)-4H-1,2,4-triazol-3-ol |
| 4b | 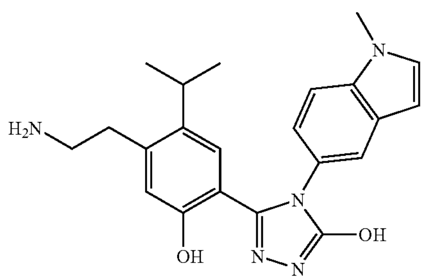 | | 5-(4-(2-aminoethyl)-2-hydroxy-5-isopropylphenyl)-4-(1-methyl-1H-indol-5-yl)-4H-1,2,4-triazol-3-ol |
| 5b | 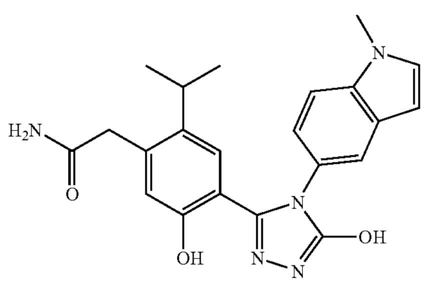 | | 2-(5-hydroxy-4-(5-hydroxy-4-(1-methyl-1H-indol-5-yl)-4H-1,2,4-triazol-3-yl)-2-isopropylphenyl)acetamide |
| 6b | 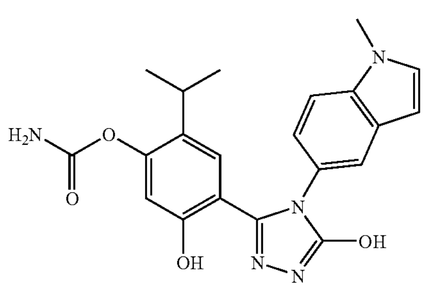 | | 5-hydroxy-4-(5-hydroxy-4-(1-methyl-1H-indol-5-yl)-4H-1,2,4-triazol-3-yl)-2-isopropylphenyl carbamate |
| 7b | 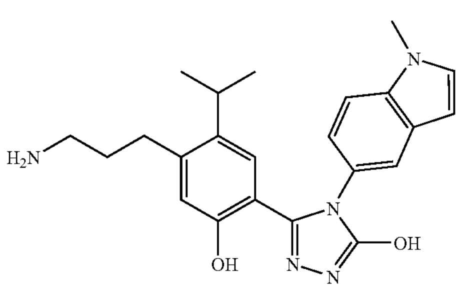 | | 5-(4-(3-aminopropyl)-2-hydroxy-5-isopropylphenyl)-4-methyl-1H-indol-5-yl)-4H-1,2,4-triazol-3-ol |

-continued

| NO. | Structure | Tautomeric structure | Name |
|---|---|---|---|
| 8b | 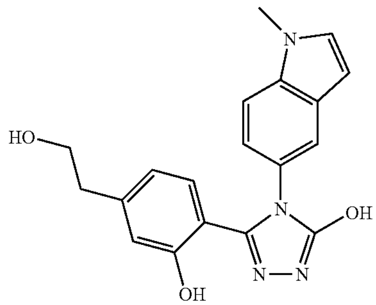 | | 5-(2-hydroxy-4-(2-hydroxyethyl)phenyl)-4-(1-methyl-1H-indol-5-yl)-4H-1,2,4-triazol-3-ol |
| 9b | 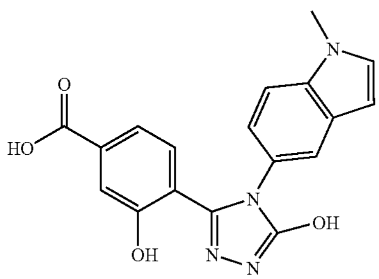 | | 3-hydroxy-4-(5-hydroxy-4-(1-methyl-1H-indol-5-yl)-4H-1,2,4-triazol-3-yl)benzoic acid |

In certain instances tautomeric forms of the disclosed compound exist, such as the tautomeric structures shown below:

$X_{15}$ = O, S or $NR_7$

It is to be understood that when a compound is represented by a structural formula herein, all other tautomeric forms which may exist for the compound are encompassed the structural formula. Compounds represented by formulas disclosed herein that can form analogous tautomeric structures to the one shown above are also preferred.

Similarly, prodrugs, i.e. compounds which can be metabolized or hydrolyzed in vivo to a compound of the present invention are encompassed by the present description. For example, the following embodiments of a compound of the present invention can be produced in vivo in the following reaction:

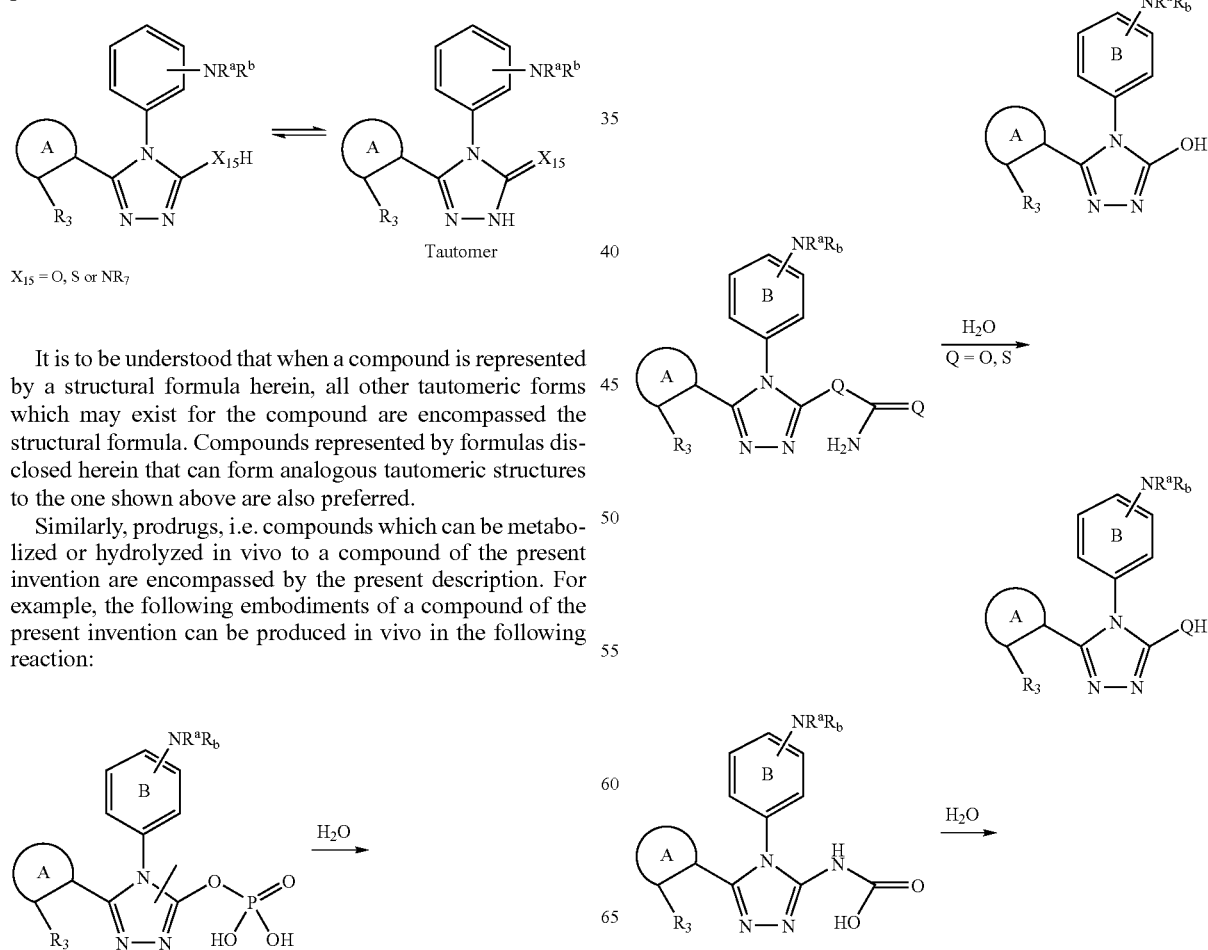

-continued

-continued

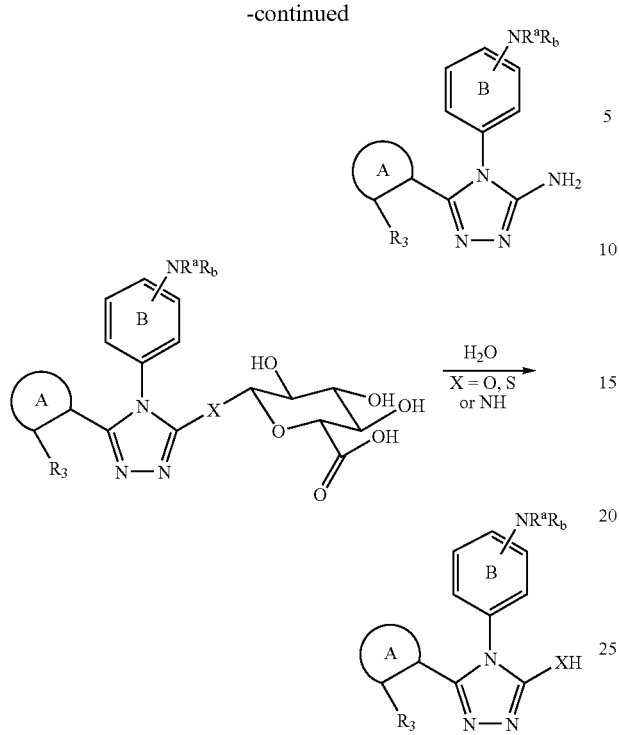

One skilled in the art will understand that other hydrolyzable protecting groups can be employed with the compounds of the present invention to obtain prodrugs encompassed by the present description.

Without wishing to be bound by any theory, it is believed that the compounds of the invention preferentially bind to Hsp90 in the tautomeric form shown above, and thereby inhibit the activity of Hsp90.

C. Methods for Making Compounds of the Invention

Compounds of the invention can be obtained via standard, well-known synthetic methodology, see e.g., March, J. Advanced Organic Chemistry; Reactions Mechanisms, and Structure, 4th ed., 1992. In particular, compounds of the invention can be obtained by heating a benzoic acid (1) with an aminophenyl (2) to give a phenyl benzamide (3) which can then be reacted with hydrazine to give a triazole (4) (see Scheme I below). Starting materials useful for preparing compounds of the invention and intermediates therefore, are commercially available or can be prepared from commercially available materials using known synthetic methods and reagents.

Additional methods of preparing the compounds of the invention can be found in U.S. Provisional Patent Application Ser. No. 60/808,376, filed on May 25, 2006; U.S. Provisional Patent Application Ser. No. 60/808,342, filed on May 25, 2006; U.S. Provisional Patent Application Ser. No. 60/808,375, filed on May 25, 2006; and U.S. Provisional Patent Application Ser. No. 60/902,031, filed on Feb. 16, 2007, the entire teachings of each of these applications are incorporated herein by reference.

Reactive functional groups can be protected during one or more reaction step, then deprotected to restore the original functionality. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. Greene, Protecting Groups in Organic Synthesis, John Wiley & Sons, Inc. 1981.

Scheme I:

Scheme I: Synthesis of triazole compounds of the invention

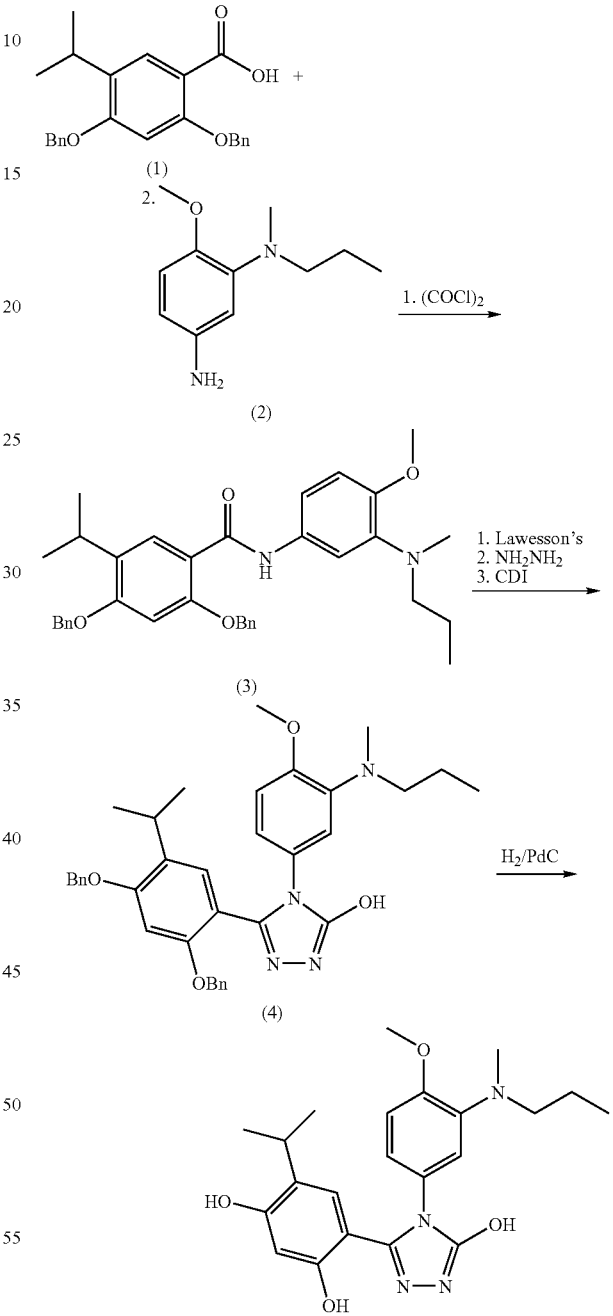

In addition, compounds of the invention can also be prepared as shown below in the Schemes and Examples below.

In one embodiment, the compounds can be prepared as shown in Scheme II. A dihydroxy benzoic acid methyl ester is reacted with benzyl chloride, to produce 5a Bis-benzyloxy benzoic acid methyl ester (1). The Bis-benzyloxy benzoic acid methyl ester can then be heated with LiOH to give a Bis-benzyloxy benzoic acid (2). The Bis-benzyloxy benzoic acid (2) is then reacted with an aminophenyl to produce a phenyl-benzamide (3). The phenyl-benzamide (3) is then reacted with hydrazine to give a triazol (4). The hydroxy groups can then be unprotected in the presence of palladium on charcoal to give the final product.

Scheme II

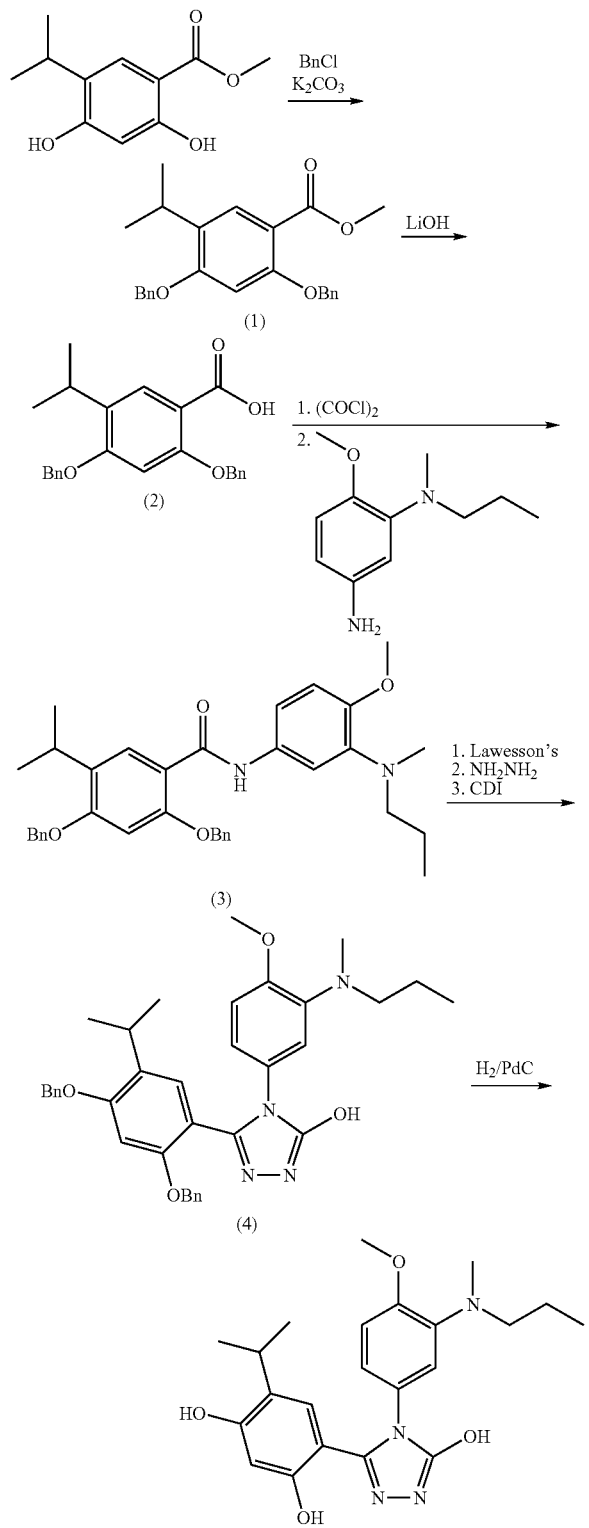

NaH can then be added to a solution of (2) in anhydrous THF followed by iodomethane to give pure product nitro-phenyl-N-methyl-propionamide (3).

The nitro-phenyl-N-methyl-propionamide (3) and borane-methyl sulfide complex are heated to give the nitro-phenyl-methyl-propyl-amine (4). A solution of (4) in MeOH/EtOAc containing Pd—C can be subjected to hydrogenation to give the N-methyl-N-propyl-benzene-1,3-diamine (5).

To a stirred solution of (5) in $CH_2Cl_2$ can be added 1,1'-thiocarbonyldiimidazole to give the (5-Isothiocyanato-2-methoxy-phenyl)-methyl-propyl-amine (6).

The isothiocyanate (6) can be reacted with the hydrazide (7) to give the intermediate (8). A solution of NaOH in water can be added to the intermediate (8), which can then be flushed with nitrogen and heated. The reaction mixture can then be cooled and acidified. The mixture can then be filtered and purified to give 4-isopropyl-6-{5-mercapto-4-[4-methoxy-3-(methyl-propyl-amino)-phenyl]-4H-[1,2,4]triazol-3-yl}-benzene-1,3-diol.

Scheme III

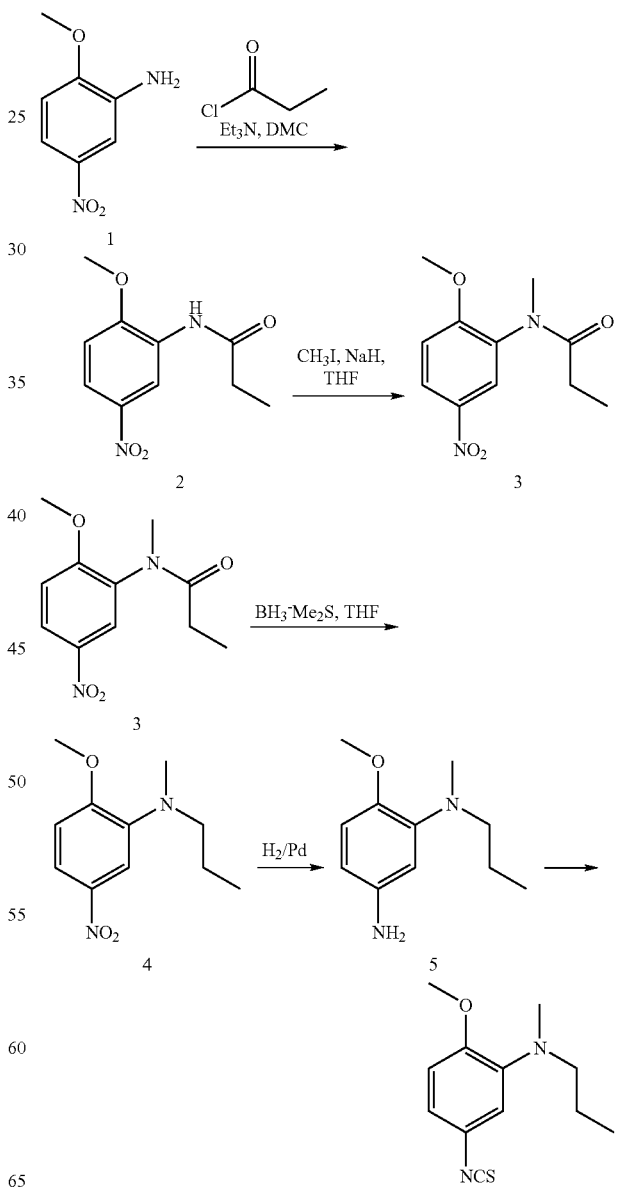

In another embodiment the compounds can be prepared as shown in Scheme III. A nitroaniline (1) can be reacted with propionyl chloride to yield nitro-phenyl-propionamide (2).

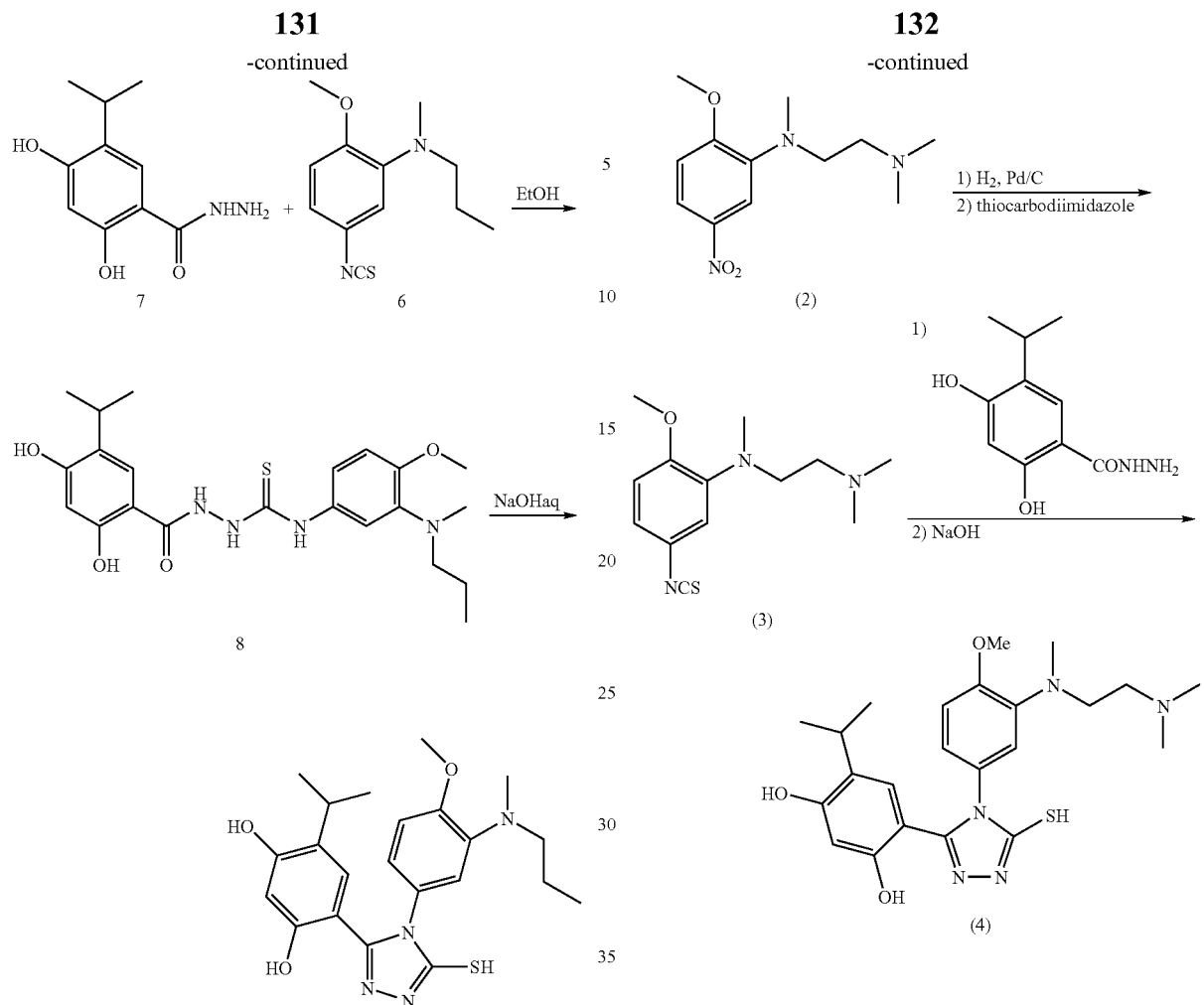

In another embodiment the compounds can be prepared as shown in Scheme IV. A bromo-nitrobenzene (1) can be reacted with $N^1$, $N^2$, $N^2$-trimethylethane-1,2-diamine to give $N^1$-(nitrophenyl)-$N^1$, $N^2$, $N^2$-trimethylethane-1,2-diamine (2). A solution of (2) in can be subjected to hydrogenation, passed through a short pad of celite, washed with MeOH and evaporated under reduced pressure. Thiocarbodiimidazole can then be added to (2) to give the $N^1$-(isothiocyanatophenyl)-)-$N^1$, $N^2$, $N^2$-trimethylethane-1,2-diamine (3).

The isothiocyanate (3) can then be reacted with a benzoic acid hydrazide to give the final product 4-(4-(3-((2-(dimethylamino)ethyl)(methyl)amino)-4-methoxyphenyl)-5-mercapto-4H-1,2,4-triazol-3-yl)-6-isopropylbenzene-1,3-diol (4).

Scheme IV

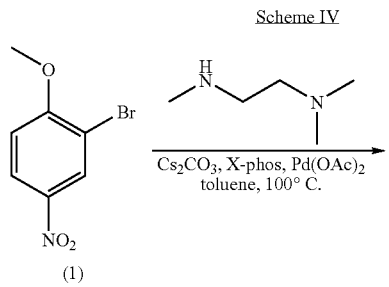

D. Uses of Compounds of the Invention

The present invention is directed to therapies which involve administering one of more compounds of the invention, and compositions comprising said compounds to a subject, preferably a human subject, to inhibit the activity of Hsp90 or to prevent, treat, manage, or ameliorate a proliferative disorder, such as cancer, or one or more symptoms thereof.

In one embodiment, the present invention is directed to treating cancers in which aberrant expression and/or activation of c-kit has been implicated as a contributing factor. The method comprises administering to a patient an effective amount of a compound represented by formula (I)-(XXXII), or any embodiment thereof, or a compound shown in Table 1, 2 or 3.

In one embodiment, the present invention is directed to treating cancers in which expression of Bcr-Abl has been implicated as a contributing factor. The method comprises administering to a patient an effective amount of a compound represented by formula (I)-(XXXII), or any embodiment thereof, or a compound shown in Table 1, 2 or 3.

In one embodiment, the present invention is directed to treating cancers in which aberrant expression and/or activation of flt-3 has been implicated as a contributing factor. The method comprises administering to a patient an effective amount of a compound represented by formula (I)-(XXXII), or any embodiment thereof, or a compound shown in Table 1, 2 or 3.

In one embodiment, the present invention is directed to treating cancers in which aberrant expression and/or activation of EGFR has been implicated as a contributing factor. The method comprises administering to a patient an effective amount of a compound represented by formula (I)-(XXXII), or any embodiment thereof, or a compound shown in Table 1, 2 or 3.

In one embodiment, the present invention is directed to treating cancers in which Hsp90 is over expressed compared with normal cells. The method comprises administering to a patient an effective amount of a compound represented by formula (I)-(XXXII), or any embodiment thereof, or a compound shown in Table 1, 2 or 3. Examples of cancers in which Hsp90 is over expressed include diffuse large B-cell lymphomas (DLBCL).

In one aspect, the invention provides a method of inhibiting the activity of Hsp90 in a cell, comprising administering to the cell an effective amount of a compound represented by formula (I)-(XXXII), or any embodiment thereof, or a compound shown in Table 1, 2 or 3. In one embodiment, the compound is administered to a cell in a subject, preferably a mammal, and more preferably a human.

In another aspect, the invention provides a method of treating or preventing a proliferation disorder in a mammal, comprising administering to the mammal an effective amount of a compound represented by formula (I)-(XXXII), or any embodiment thereof, or a compound shown in Table 1, 2 or 3. In one embodiment, the compound is administered to a human to treat or prevent a proliferative disorder. In another embodiment, the proliferation disorder is cancer. In another embodiment, the compound is administered with one or more additional therapeutic agents. In a preferred embodiment, the additional therapeutic agent is an anticancer agent.

In another aspect, the invention provides a method for treating cancer in a mammal, comprising administering to the mammal an effective amount of a compound represented by formula (I)-(XXXII), or any embodiment thereof, or a compound shown in Table 1, 2 or 3. In one embodiment, the compound is administered to a human to treat or prevent cancer. In another embodiment, the compound is administered with one or more additional therapeutic agents. In a preferred embodiment, the one or more additional therapeutic agents are anticancer agents.

In another aspect, the invention provides a method for treating a c-kit associated cancer in a mammal, comprising administering to the mammal an effective amount of a compound represented by formula (I)-(XXXII), or any embodiment thereof, or a compound shown in Table 1, 2 or 3. In one embodiment, the compound is administered to a human to treat or prevent the c-kit associated cancer. In another embodiment, the compound is administered with one or more additional therapeutic agents. In a preferred embodiment, the one or more additional therapeutic agents are anticancer agents.

In another aspect, the invention provides a method for treating a Bcr-Abl associated cancer in a mammal, comprising administering to the mammal an effective amount of a compound represented by formula (I)-(XXXII), or any embodiment thereof, or a compound shown in Table 1, 2 or 3. In one embodiment, the compound is administered to a human to treat or prevent the Bcr-Abl associated cancer. In another embodiment, the compound is administered with one or more additional therapeutic agents. In a preferred embodiment, the one or more additional therapeutic agents are anticancer agents.

In another aspect, the invention provides a method for treating a flt3 associated cancer in a mammal, comprising administering to the mammal an effective amount of a compound represented by formula (I)-(XXXII), or any embodiment thereof, or a compound shown in Table 1, 2 or 3. In one embodiment, the compound is administered to a human to treat or prevent the flt3 associated cancer. In another embodiment, the compound is administered with one or more additional therapeutic agents. In a preferred embodiment, the one or more additional therapeutic agents are anticancer agents.

In another aspect, the invention provides a method for treating an EGFR associated cancer in a mammal, comprising administering to the mammal an effective amount of a compound represented by formula (I)-(XXXII), or any embodiment thereof, or a compound shown in Table 1, 2 or 3. In one embodiment, the compound is administered to a human to treat or prevent the EGFR associated cancer. In another embodiment, the compound is administered with one or more additional therapeutic agents. In a preferred embodiment, the one or more additional therapeutic agents are anticancer agents.

In another aspect, the invention provides a method for treating a cancer in a mammal which is characterized by the upregulation of Hsp90 compared to normal cells of the same type, comprising administering to the mammal an effective amount of a compound represented by formula (I)-(XXXII), or any embodiment thereof, or a compound shown in Table 1, 2 or 3. In one embodiment, the compound is administered to a human to treat or prevent the cancer associated with the upregulation of Hsp90. In another embodiment, the cancer associated with the upregulation of Hsp90 is DLBCL. In another embodiment, the compound is administered with one or more additional therapeutic agents. In a preferred embodiment, the one or more additional therapeutic agents are anticancer agents.

In another aspect, the invention provides a method for treating or inhibiting angiogenesis in a subject in need thereof, comprising administering to the subject an effective amount of a compound represented by formula (I)-(XXXII), or any embodiment thereof, or a compound shown in Table 1, 2 or 3.

In another aspect, the invention provides a method of blocking, occluding, or otherwise disrupting blood flow in neovasculature, comprising contacting the neovasculature with an effective amount of a compound represented by formula (I)-(XXXII), or any embodiment thereof, or a compound shown in Table 1, 2 or 3. In one aspect, the neovasculature is in a subject and blood flow in the neovasculature is blocked, occluded, or otherwise disrupted in the subject by administering to the subject an effective amount of a compound represented by formula (I)-(XXXII), or any embodiment thereof, or a compound shown in Table 1, 2 or 3. In one aspect, the subject is human.

The present invention provides a method for preventing, treating, managing, or ameliorating an infection in a subject in need thereof, comprising administering an effective amount of a compound represented by formula (I)-(XXXII), or any embodiment thereof, or a compound shown in Table 1, 2 or 3.

In one aspect, the invention is directed to a method of treating or preventing a fungal infection.

In one aspect, the invention is directed to a method of treating or preventing a yeast infection.

In one aspect, the invention is directed to a method of treating or preventing a yeast infection caused by a *Candida* yeast.

In one aspect, the invention is directed to a method of treating or preventing a bacterial infection.

In one aspect, the invention is directed to a method of treating or preventing a bacterial infection caused by a Gram Positive Bacteria.

In one aspect, the invention is directed to a method of treating or preventing a bacterial infection caused by a Gram Negative Bacteria.

In one aspect, the invention is directed to a method of treating or preventing a viral infection.

In one aspect, the invention is directed to a method of treating or preventing a viral infection caused by an influenza virus, a herpes virus, a hepatitis virus, or an HIV virus.

In one aspect, the invention is directed to a method of treating or preventing a viral infection caused by influenza A virus, herpes simplex virus type 1, hepatitis C virus, hepatitis B virus, HIV-1 virus, or Epstein-Barr Virus.

In one aspect, the invention is directed to a method of treating or preventing a parasitic infection.

In one aspect, the invention is directed to a method of treating or preventing a protozoal infection.

In one aspect, the invention is directed to a method of treating or preventing an infection caused by *plasmodium falciparum* or *trypsanosoma cruzi*.

In one aspect, the invention is directed to a method of treating or preventing an infection caused by a *Leishmania* protozoa.

In one aspect, the invention is directed to a method of treating or preventing an amoebic infection.

In one aspect, the invention is directed to a method of treating or preventing a helminth infection.

In one aspect, the invention is directed to a method of treating or preventing an infection caused by *Schistostoma mansoni*.

In one aspect, compounds of the invention are administered in combination with one or more additional anti-infective therapeutic agents.

The present invention provides a method for inhibiting topoisomerase II, comprising administering an effective amount of a compound represented by formula (I)-(XXXII), or any embodiment thereof, or a compound shown in Table 1, 2 or 3.

In another embodiment, topoisomerase II is associated with a disease and administering the compound will treat or prevent the disease.

In one aspect, the disease is a proliferative disease.
In another aspect, the proliferative disease is cancer.
In one aspect, the disease is an infection.

The present invention provides a method of treating an inflammatory disorder in a subject in need thereof, comprising administering an effective amount of a compound represented by formula (I)-(XXXII), or any embodiment thereof, or a compound shown in Table 1, 2 or 3. In one embodiment, the inflammatory disorder is selected from the group consisting of transplant rejection, skin graft rejection, arthritis, rheumatoid arthritis, osteoarthritis and bone diseases associated with increased bone resorption; inflammatory bowel disease, ileitis, ulcerative colitis, Barrett's syndrome, Crohn's disease; asthma, adult respiratory distress syndrome, chronic obstructive airway disease; corneal dystrophy, trachoma, onchocerciasis, uveitis, sympathetic ophthalmitis, endophthalmitis; gingivitis, periodontitis; tuberculosis; leprosy; uremic complications, glomerulonephritis, nephrosis; sclerodermatitis, psoriasis, eczema; chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis viral or autoimmune encephalitis; autoimmune disorders, immune-complex vasculitis, systemic lupus and erythematodes; systemic lupus erythematosus (SLE); cardiomyopathy, ischemic heart disease hypercholesterolemia, atherosclerosis, preeclampsia; chronic liver failure, brain and spinal cord trauma.

The present invention provides a method of treating an immune disorder in a subject in need thereof, comprising administering an effective amount of a compound represented by formula (I)-(XXXII), or any embodiment thereof, or a compound shown in Table 1, 2 or 3. In one embodiment, the immune disorder is selected from the group consisting of multiple sclerosis, myasthenia gravis, Guillain-Barré, autoimmune uveitis, autoimmune hemolytic anemia, pernicious anemia, autoimmune thrombocytopenia, temporal arteritis, anti-phospholipid syndrome, vasculitides such as Wegener's granulomatosis, Behcet's disease, psoriasis, dermatitis herpetiformis, pemphigus vulgaris, vitiligo, Crohn's disease, ulcerative colitis, primary biliary cirrhosis, autoimmune hepatitis, Type 1 or immune-mediated diabetes mellitus, Grave's disease. Hashimoto's thyroiditis, autoimmune oophoritis and orchitis, autoimmune disorder of the adrenal gland, rheumatoid arthritis, systemic lupus erythematosus, scleroderma, polymyositis, dermatomyositis, ankylosing spondylitis, and Sjogren's syndrome.

The present invention provides a method of suppressing an immune response in a subject in need thereof, comprising administering an effective amount of a compound represented by formula (I)-(XXXII), or any embodiment thereof, or a compound shown in Table 1, 2 or 3. In one embodiment, the subject in need of immunosuppression is a subject that has received an organ or tissue transplant, such as a skin graft, heart, kidney, lung, liver, pancreas, cornea, bowel, stomach, and the like. In another embodiment, the subject in need of immunosuppression is a subject that has received stem cell transplantation. The transplant may be a syngeneic transplant (i.e., from a donor that has the same genetic make up), an allographic transplant (i.e., from a donor of the same species) or a xenographic transplant (i.e., from a donor that is a different species).

The present invention provides a method of inhibiting the production of inflammatory cytokines, such as G-CSF, GM-CSF, IL-12, IL-1β, IL-23, IL-6, IL-8, and TNF-α, in a subject in need of such treatment. The method comprises administering to the subject an effective amount of a compound represented by formula (I)-(XXXII), or any embodiment thereof, or a compound shown in Table 1, 2 or 3.

1. c-Kit Associated Cancers

SCF binding to the c-kit protects hematopoietic stem and progenitor cells from apoptosis (Lee, et al., 1997, *J. Immunol.*, 159:3211-3219), thereby contributing to colony formation and hematopoiesis. Expression of c-kit is frequently observed in acute myelocytic leukemia (AML) and sometimes observed in acute lymphocytic leukemia (ALL) (for reviews, see Sperling, et al., 1997, *Haemat.*, 82:617-621; Escribano, et al., 1998, *Leuk. Lymph.*, 30:459-466). Although c-kit is expressed in the majority of AML cells, its expression does not appear to be prognostic of disease progression (Sperling, et al, 1997, *Haemat.* 82:617-621). However, SCF protected AML cells from apoptosis induced by chemotherapeutic agents (Hassan, et al., 1996, *Acta. Hem.*, 95:257-262). Therefore, degradation of c-kit caused by the inhibition of Hsp90 by the compounds of the invention will enhance the efficacy of these agents and may induce apoptosis of AML cells.

The clonal growth of cells from patients with myelodysplastic syndrome (Sawada, et al., 1996, *Blood*, 88:319-327) or chronic myelogenous leukemia (CML) (Sawai, et al., 1996, *Exp. Hem.*, 2:116-122) was found to be significantly enhanced by SCF in combination with other cytokines. CML is characterized by expansion of Philadelphia chromosome positive cells of the marrow (Verfullie, et al., 1998, *Leuk.*, 12:136-138), which appears to primarily result from inhibition of apoptotic death (Jones, 1997, *Curr. Opin. One.*, 9:3-7). The product of the Philadelphia chromosome, p210.sup.BCR-ABL, has been reported to mediate inhibition of apoptosis (Bedi, et al., 1995, *Blood*, 86:1148-1158). Since p210.sup.BCR-ABL and the c-kit RTK both inhibit apoptosis and p62.sup.dok has been suggested as a substrate (Carpino, et al., 1997, *Cell*, 88:197-204), it is possible that clonal expansion mediated by these kinases occurs through a common signaling pathway. However, c-kit has also been reported to interact directly with p210.sup.BCR-ABL (Hallek, et al., 1996, *Brit. J Haem.*, 94:5-16), which suggests that c-kit may have a more causative role in CML pathology. Therefore, degradation of c-kit caused by the inhibition of Hsp90 by the compounds of the invention will prove useful in the treatment of CML.

Normal colorectal mucosa does not express c-kit (Bellone, et al., 1997, *J. Cell Physiol.*, 172:1-11). However, c-kit is frequently expressed in colorectal carcinoma (Bellone, et al., 1997, *J. Cell Physiol.*, 172: 1-11), and autocrine loops of SCF and c-kit have been observed in several colon carcinoma cell lines (Toyota, et al., 1993, *Turn. Biol.*, 14:295-302; Lahm, et al., 1995, *Cell Growth & Differ.*, 6:1111-1118; Bellone, et al., 1997, *J. Cell Physiol.*, 172:1-11). Furthermore, disruption of the autocrine loop by the use of neutralizing antibodies (Lahm, et al., 1995, *Cell Growth & Differ.*, 6:1111-1118) and downregulation of c-kit and/or SCF significantly inhibits cell proliferation (Lahm, et al., 1995, *Cell Growth & Differl.*, 6:1111-1118; Bellone, et al., 1997, *J. Cell Physiol.*, 172:1-11).

SCF/c-kit autocrine loops have been observed in gastric carcinoma cell lines (Turner, et al., 1992, *Blood*, 80:374-381; Hassan, et al., 1998, *Digest Dis. Science*, 43:8-14), and constitutive c-kit activation also appears to be important for gastrointestinal stromal tumors (GISTs). GISTs are the most common mesenchymal tumor of the digestive system. More than 90% of GISTs express c-kit, which is consistent with the putative origin of these tumor cells from interstitial cells of Cajal (ICCs) (Hirota, et al., 1998, *Science*, 279:577-580). The c-kit expressed in GISTs from several different patients was observed to have mutations in the intracellular juxtamembrane domain leading to constitutive activation (Hirota, et al., 1998, *Science* 279:577-580). Therefore, degradation of c-kit caused by the inhibition of Hsp90 by the compounds of the invention will be an efficacious means for the treatment of these cancers.

Male germ cell tumors have been histologically categorized into seminomas, which retain germ cell characteristics, and nonseminomas which can display characteristics of embryonal differentiation. Both seminomas and nonseminomas are thought to initiate from a preinvasive stage designated carcinoma in situ (CIS) (Murty, et al., 1998, *Sem. Oncol.*, 25:133-144). Both c-kit and SCF have been reported to be essential for normal gonadal development during embryogenesis (Loveland, et al., 1997, *J. Endocrinol.*, 153: 337-344). Loss of either the receptor or the ligand resulted in animals devoid of germ cells. In postnatal testes, c-kit has been found to be expressed in Leydig cells and spermatogonia, while SCF was expressed in Sertoli cells (Loveland, et al., 1997, *J. Endocrinol.*, 153:337-344). Testicular tumors develop from Leydig cells with high frequency in transgenic mice expressing human papilloma virus 16 (HPV16) E6 and E7 oncogenes (Kondoh, et al., 1991, *J. Virol.*, 65:3335-3339; Kondoh, et al., 1994, *J. Urol.*, 152:2151-2154). These tumors express both c-kit and SCF, and an autocrine loop may contribute to the tumorigenesis (Kondoh, et al., 1995, *Oncogene*, 10:341-347) associated with cellular loss of functional p53 and the retinoblastoma gene product by association with E6 and E7 (Dyson, et al., 1989, *Science*, 243:934-937; Werness, et al., 1990, *Science*, 248:76-79; Scheffner, et al., 1990, *Cell*, 63:1129-1136). Defective signaling mutants of SCF (Kondoh, et al., 1995, *Oncogene*, 10:341-347) or c-kit (Li, et al., 1996, *Canc. Res.*, 56:4343-4346) inhibited formation of testicular tumors in mice expressing HPV16 E6 and E7. Since c-kit kinase activation is pivotal to tumorigenesis in these animals, the compounds of the invention which inhibit Hsp90 and thereby cause the degradation of c-kit will be useful for preventing or treating testicular tumors associated with human papilloma virus.

Expression of c-kit on germ cell tumors shows that the receptor is expressed by the majority of carcinomas in situ and seminomas, but c-kit is expressed in only a minority of nonseminomas (Strohmeyer, et al., 1991, *Canc. Res.*, 51:1811-1816; Rajpert-de Meyts, et al., 1994, *Int J. Androl.*, 17:85-92; Izquierdo, et al., 1995, *J. Pathol.*, 177:253-258; Strohmeyer, et al., 1995, *J. Urol.*, 153:511-515; Bokenmeyer, et al., 1996, *J. Cance. Res., Clin. Oncol.*, 122:301-306; Sandlow, et al., 1996, *J. Androl.*, 17:403-408). Therefore, degradation of c-kit caused by the inhibition of Hsp90 by the compounds of the invention will be an efficacious means for the treatment of these cancers.

SCF and c-kit are expressed throughout the central nervous system of developing rodents, and the pattern of expression suggests a role in growth, migration and differentiation of neuroectodermal cells. Expression of SCF and c-kit have also been reported in the adult brain (Hamel, et al., 1997, *J. Neuro-One.*, 35:327-333). Expression of c-kit has also been observed in normal human brain tissue (Tada, et al. 1994, *J. Neuro.*, 80:1063-1073). Glioblastoma and astrocytoma, which define the majority of intracranial tumors, arise from neoplastic transformation of astrocytes (Levin, et al., 1997, *Principles & Practice of Oncology*, 2022-2082). Expression of c-kit has been observed in glioblastoma cell lines and tissues (Berdel, et al., 1992, *Canc. Res.*, 52:3498-3502; Tada, et al., 1994, *J. Neuro.*, 80:1063-1073; Stanulla, et al., 1995, *Act. Neuropath.*, 89:158-165).

The association of c-kit with astrocytoma pathology is less clear. Reports of expression of c-kit in normal astrocytes have been made (Natali, et al., 1992, *Int. J. Canc.*, 52:197-201), (Tada, et al. 1994, *J. Neuro.*, 80:1063-1073), while others report it is not expressed (Kristt, et al., 1993, *Neuro.*, 33:106-115). In the former case, high levels of c-kit expression in high grade tumors were observed (Kristt, et al., 1993, *Neuro.*, 33:106-115), whereas in the latter case researchers were unable to detect any expression in astrocytomas. In addition, contradictory reports of c-kit and SCF expression in neuroblastomas also exist.

One study found that neuroblastoma cell lines often express SCF, but rarely express c-kit. In primary tumors, c-kit was detected in about 8% of neuroblastomas, while SCF was found in 18% of tumors (Beck, et al., 1995, *Blood*, 86:3132-3138). In contrast, other studies (Cohen, et al., 1994, *Blood*, 84:3465-3472) have reported that all 14 neuroblastoma cell lines examined contained c-kit/SCF autocrine loops, and expression of both the receptor and ligand were observed in 45% of tumor samples examined. In two cell lines, anti-c-kit antibodies inhibited cell proliferation, suggesting that the SCF/c-kit autocrine loop contributed to growth (Cohen, et al., 1994, *Blood*, 84:3465-3472). Therefore, degradation of c-kit caused by the inhibition of Hsp90 by the compounds of the invention will be an efficacious means for treating some cancers of the central nervous system.

2. Bcr-Abl Associated Cancers

The Philadelphia chromosome which generates the fusion protein Bcr-Abl is associated with the bulk of chronic myelogenous leukemia (CML) patients (more than 95%), 10-25% of acute lymphocytic leukemia (ALL) patients, and about 2-3% of acute myelogenous leukemias (AML). In addition, Bcr-Abl is a factor in a variety of other hematological malignancies, including granulocytic hyperplasia resembling CML, myelomonocytic leukemia, lymphomas, and erythroid leukemia (see Lugo, et al., MCB (1989), 9:1263-1270; Daley, et al., Science (1990), 247:824-830; and Honda, Blood (1998), 91:2067-2075, the entire teachings of each of these references are incorporated herein by reference).

A number of different kinds of evidence support the contention that Bcr-Abl oncoproteins, such as p210 and p185 BCR-ABL, are causative factors in these leukemias (Campbell and Arlinghaus, "Current Status of Bcr Gene Involvement with Human Leukemia", In: Advances in Cancer Research, Eds. Klein, VandeWoude, Orlando, Fla. Academic Press, Inc., 57:227-256, 1991, the entire teachings of which are incorporated herein by reference). The malignant activity is due in large part to the Bcr-Abl protein's highly activated protein tyrosine kinase activity and its abnormal interaction with protein substrates (Arlinghaus et al., In: UCLA Symposia on Molecular and Cellular Biology New Series, Acute Lymphoblastic Leukemia, Eds. R. P. Gale, D. Hoelzer, New York, N.Y., Alan R. Liss, Inc., 108:81-90, 1990, the entire teachings of which are incorporated herein by reference). The Bcr-Abl oncoprotein p210 Bcr-Abl is associated with both CML and ALL, whereas the smaller oncoprotein, p185 BCR-ABL, is associated with ALL patients, although some CML patients also express p185 (Campbell et al., 1991).

3. FLT3 Associated Cancers

FLT3 associated cancers are cancers in which inappropriate FLT3 activity is detected. FLT3 associated cancers include hematologic malignancies such as leukemia and lymphoma. In some embodiments FLT3 associated cancers include acute myelogenous leukemia (AML), B-precursor cell acute lymphoblastic leukemia, myelodysplastic leukemia, T-cell acute lymphoblastic leukemia, mixed lineage leukemia (MLL), or chronic myelogenous leukemia (CML).

4. EGFR Associated Cancers

EGFR associated cancers are cancers in which inappropriate EGFR activity (e.g., overexpression of EGFR or mutation of EGFR which causes constitutive tyrosine kinase activity) has been implicated as a contributing factor. Inappropriate EGFR activity has been associated with an adverse prognosis in a number of human cancers, such as neuroblastoma, intestine carcinoma such as rectum carcinoma, colon carcinoma, familiary adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroidea carcinoma, papillary thyroidea carcinoma, renal carcinoma, kidney parenchym carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, hepatocellular carcinoma, gall bladder carcinoma, bronchial carcinoma, small cell lung carcinoma, non-small cell lung carcinoma, multiple myeloma, basalioma, teratoma, retinoblastoma, choroidea melanoma, seminoma, rhabdomyo sarcoma, craniopharyngeoma, osteosarcoma, chondrosarcoma, myosarcoma, liposarcoma, fibrosarcoma, Ewing sarcoma and plasmocytoma.

In particular, EGFR appears to have an important role in the development of human brain tumors. A high incidence of overexpression, amplification, deletion and structural rearrangement of the gene coding for EGFR has been found in biopsies of brain tumors. In fact, the amplification of the EGFR gene in glioblastoma multiforme tumors is one of the most consistent genetic alterations known, with EGFR being overexpressed in approximately 40% of malignant gliomas and EGFRvIII mutation being found in about 50% of all glioblastomas.

In addition to gliomas, abnormal EGFR expression has also been reported in a number of squamous epidermoid cancers and breast cancers. Interestingly, evidence also suggests that many patients with tumors that over-express EGFR have a poorer prognosis than those having tumors that do not over-express EGFR.

Non-small cell lung cancer (NSCLC) includes squamous cell carcinomas, adenocarcinoma, bronchioloalveolar carcinoma (BAC), and large cell undifferentiated carcinoma. A subset of patients with NSCLC have been shown to have mutations in the tyrosine kinase domain of EGFR which is thought to be necessary for the maintenance of the disease. Treatment of this subset of patients with NSCLC with gefitinib, a tyrosine kinase inhibitor which targets EGFR, has shown rapid and dramatic clinical response.

Consequently, therapeutic strategies that can potentially inhibit or reduce the aberrant expression of EGFR are of great interest as potential anti-cancer agents.

5. Combination Therapies and Treatment of Refractory Cancers

The prophylactic or therapeutic agents of the combination therapies of the invention can be administered sequentially or concurrently. In a specific embodiment, the combination therapies of the invention comprise one or more compounds and at least one other therapy (e.g., another prophylactic or therapeutic agent) which has the same mechanism of action as said compounds. In another specific embodiment, the combination therapies of the invention comprise one or more compounds of the invention and at least one other therapy (e.g., another prophylactic or therapeutic agent) which has a different mechanism of action than said compounds. In certain embodiments, the combination therapies of the present invention improve the prophylactic or therapeutic effect of one or more compounds of the invention by functioning together with the compounds to have an additive or synergistic effect. In certain embodiments, the combination therapies of the present invention reduce the side effects associated with the therapies (e.g., prophylactic or therapeutic agents). In certain embodiments, the combination therapies of the present invention reduce the effective dosage of one or more of the therapies.

The prophylactic or therapeutic agents of the combination therapies can be administered to a subject, preferably a human subject, in the same pharmaceutical composition. In alternative embodiments, the prophylactic or therapeutic agents of the combination therapies can be administered concurrently to a subject in separate pharmaceutical compositions. The prophylactic or therapeutic agents may be administered to a subject by the same or different routes of administration.

In a specific embodiment, a pharmaceutical composition comprising one or more compounds of the invention is administered to a subject, preferably a human, to prevent, treat, manage, or ameliorate a proliferative disorder, such as cancer, or one or more symptom thereof. In accordance with the invention, pharmaceutical compositions of the invention may also comprise one or more other agents (e.g., prophylactic or therapeutic agents which are currently being used, have been used, or are known to be useful in the prevention, treatment or amelioration of a proliferative disorder or a symptom thereof.

The pharmaceutical compositions can be used in therapy, e.g., to treat a mammal with an infection. In one embodiment, the pharmaceutical composition includes one or more additional therapeutic agents, such as one or more additional anti-infective agents.

In another embodiment, the present invention is the use of a compound of anyone of the formulas disclosed herein for the manufacture of a medicament for treating a mammal with an infection.

In another embodiment of the present invention is a pharmaceutical composition comprising a compound represented by any one of the formulas disclosed herein and a pharmaceutically acceptable carrier. The pharmaceutical compositions can be used in therapy, e.g., to treat a mammal with an inflammatory or immune disorder. In one embodiment, the pharmaceutical composition includes one or more additional therapeutic agent, such as one or more additional anti-inflammatory agent or one or more immunosuppressant.

In another embodiment, the present invention is the use of a compound of anyone of the formulas disclosed herein for the manufacture of a medicament for treating a mammal with an inflammatory or autoimmune disorder or for treatment of a mammal in need of immunosuppression.

The invention provides methods for preventing, managing, treating or ameliorating a proliferative disorder, such as cancer, or one or more symptoms thereof in a subject refractory (either completely or partially) to existing agent therapies for such a proliferative disorder, said methods comprising administering to said subject a dose of an effective amount of one or more compounds of the invention and a dose of an effective amount of one or more therapies (e.g., one or more prophylactic or therapeutic agents useful for the prevention, treatment, management, or amelioration of a proliferative disorder or a symptom thereof). The invention also provides methods for preventing, treating, managing, or ameliorating a proliferative disorder or a symptom thereof by administering one or more compounds of the invention in combination with any other therapy(ies) to patients who have proven refractory to other therapies but are no longer on these therapies.

The compounds of the invention and/or other therapies can be administered to a subject by any route known to one of skill in the art. Examples of routes of administration include, but are not limited to, parenteral, e.g., intravenous, intradermal, subcutaneous, oral (e.g., inhalation), intranasal, transdermal (topical), transmucosal, and rectal administration.

6) Agents Useful in Combination with the Compounds of the Invention

Without wishing to be bound by theory, it is believed that the compounds of the invention can be particularly effective at treating subjects whose cancer has become multi-drug resistant. Although chemotherapeutic agents initially cause tumor regression, most agents that are currently used to treat cancer target only one pathway to tumor progression. Therefore, in many instances, after treatment with one or more chemotherapeutic agents, a tumor develops multidrug resistance and no longer responds positively to treatment. One of the advantages of inhibiting Hsp90 activity is that several of its client proteins, which are mostly protein kinases or transcription factors involved in signal transduction, have been shown to be involved in the progression of cancer. Thus, inhibition of Hsp90 provides a method of short circuiting several pathways for tumor progression simultaneously. Therefore, it is believed that treatment of cancer with an Hsp90 inhibitor of the invention either alone, or in combination with other chemotherapeutic agents, is more likely to result in regression or elimination of the tumor, and less likely to result in the development of more aggressive multidrug resistant tumors than other currently available therapies.

In one embodiment, the compounds of the invention can be administered with agents that are tyrosine kinase inhibitors (e.g., gefitinib or erlotinib which inhibit EGFR tyrosine kinase activity). In another embodiment, the compounds of the invention can be administered to patients whose cancer has become resistant to a tyrosine kinase inhibitor (e.g., gefitinib or erlotinib). In this embodiment, the compounds of the invention can be administered either alone or in combination with the tyrosine kinase inhibitor.

In another embodiment, the compounds of the invention are useful for treating patients with hematological cancers that have become resistant to Imatinib, a chemotherapeutic agent that acts by inhibiting tyrosine kinase activity of Bcr-Abl. In patients with CML in the chronic phase, as well as in a blast crisis, treatment with Imatinib typically will induce remission. However, in many cases, particularly in those patients who were in a blast crisis before remission, the remission is not durable because the Bcr-Abl fusion protein develops mutations in the tyrosine kinase domain that cause it to be resistance to Imatinib. (See Nimmanapalli, et al., *Cancer Research* (2001), 61:1799-1804; and Gorre, et al., *Blood* (2002), 100:3041-3044, the entire teachings of each of these references are incorporated herein by reference). Compounds of the invention act by inhibiting the activity of Hsp90 which disrupt Bcr-Abl/Hsp90 complexes. When Bcr-Abl is not complex to Hsp90 it is rapidly degraded. Therefore, compounds of the invention are effective in treating Imatinib resistant leukemias since they act through a different mechanism than Imatinib. Compounds of the invention can be administered alone or with Imatinib in patients who have a Bcr-Abl associated cancer that is not resistant to Imatinib or to patients whose cancer has become resistant to Imatinib.

Anticancer agents that can be co-administered with the compounds of the invention include Taxol™, also referred to as "paclitaxel", is a well-known anti-cancer drug which acts by enhancing and stabilizing microtubule formation, and analogs of Taxol™, such as Taxotere™. Compounds that have the basic taxane skeleton as a common structure feature, have also been shown to have the ability to arrest cells in the G2-M phases due to stabilization or inhibition of microtubules.

Other anti-cancer agents that can be employed in combination with the compounds of the invention include Avastin, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anti-cancer drugs that can be employed in combination with the compounds of the invention include: 20-epi-1.25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred anticancer drugs are 5-fluorouracil and leucovorin.

Other chemotherapeutic agents that can be employed in combination with the compounds of the invention include but are not limited to alkylating agents, antimetabolites, natural products, or hormones. Examples of alkylating agents useful for the treatment or prevention of T-cell malignancies in the methods and compositions of the invention include but are not limited to, nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites useful for the treatment or prevention of T-cell malignancies in the methods and compositions of the invention include but are not limited to folic acid analog (e.g., methotrexate), or pyrimidine analogs (e.g., Cytarabine), purine analogs (e.g., mercaptopurine, thioguanine, pentostatin). Examples of natural products useful for the treatment or prevention of T-cell malignancies in the methods and compositions of the invention include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that can be employed in combination with the compounds of the invention include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites useful for the treatment or prevention of cancer in the methods and compositions of the invention include but are not limited to folic acid analog (e.g., methotrexate), or pyrimidine analogs (e.g., fluorouracil, floxouridine, Cytarabine), purine analogs (e.g., mercaptopurine, thioguanine, pentostatin). Examples of natural products useful for the treatment or prevention of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase), or biological response modifiers (e.g., interferon alpha). Examples of hormones and antagonists useful for the treatment or prevention of cancer in the methods and compositions of the invention include but are not limited to adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions of the invention for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilization or inhibition of microtubules and which can be used in combination with the compounds of the invention include without limitation the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser-.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCl), Resverastatin phosphate sodium, BPR-0Y-007 (National Health Research Institutes), and SSR-250411 (Sanofi).

7) Anti-Infective Agents Useful in Combination with the Compounds of the Invention Other anti-fungal agents that can be co-administered with the compounds of the invention include, but are not limited to, polyene antifungals (e.g., amphotericin and nystatin), azole antifungals (e.g., ketoconazole, miconazole, fluconazole, itraconazole, posaconazole, ravuconazole, voriconazole, clotrimazole, econazole, oxiconazole, sulconazole, terconazole, butoconazole, and tioconazole), amorolfine, butenafine, naftifine, terbinafine, flucytosine, nikkomycin Z, caspofungin, micafungin (FK463), anidulafungin (LY303366), griseofulvin, ciclopiroxolamine, tolnaftate, intrathecal, haloprogrin, and undecylenate.

Other anti-bacterial agents that can be co-administered with the compounds of the invention include, but are not limited to, sulfa drugs (e.g., sulfanilamide), folic acid analogs (e.g., trimethoprim), beta-lactams (e.g., penacillin, cephalosporins), aminoglycosides (e.g., stretomycin, kanamycin, neomycin, gentamycin), tetracyclines (e.g., chlorotetracycline, oxytetracycline, and doxycycline), macrolides (e.g., erythromycin, azithromycin, and clarithromycin), lincosamides (e.g., clindamycin), streptogramins (e.g., quinupristin and dalfopristin), fluoroquinolones (e.g., ciprofloxacin, levofloxacin, and moxifloxacin), polypeptides (e.g., polymixins), rifampin, mupirocin, cycloserine, aminocyclitol (e.g., spectinomycin), glycopeptides (e.g., vancomycin), oxazolidinones (e.g., linezolid), ribosomes, chloramphenicol, fusidic acid, and metronidazole.

Other anti-viral agents that can be co-administered with the compounds of the invention include, but are not limited to, Emtricitabine (FTC); Lamivudine (3TC); Carbovir; Acyclovir; Interferon; Famciclovir; Penciclovir; Zidovudine (AZT); Didanosine (ddI); Zalcitabine (ddC); Stavudine (d4T); Tenofovir DF (Viread); Abacavir (ABC); L-(–)-FMAU; L-DDA phosphate prodrugs; β-D-dioxolane nucleosides such as β-D-dioxolanyl-guanine (DG), β-D-dioxolanyl-2,6-diaminopurine (DAPD), and β-D-dioxolanyl-6-chloropurine (ACP); non-nucleoside RT inhibitors such as Nevirapine (Viramune), MKC-442, Efavirenz (Sustiva), Delavirdine (Rescriptor); protease inhibitors such as Amprenavir, Atazanavir, Fosamprenavir, Indinavir, Kaletra, Nelfinavir, Ritonavir, Saquinavir, AZT, DMP-450; combination treatments such as Epzicom (ABC+3TC), Trizivir (ABC+3TC+AZT), Truvada (FTC+Viread); Omega IFN (BioMedicines Inc.); BILN-2061 (Boehringer Ingelheim); Summetrel (Endo Pharmaceuticals Holdings Inc.); Roferon A (F. Hoffman-La Roche); Pegasys (F. Hoffman-La Roche); Pegasys/Ribaravin (F. Hoffman-La Roche); CellCept (F. Hoffman-La Roche); Wellferon (GlaxoSmithKline); Albuferon-α (Human Genome Sciences Inc.); Levovirin (ICN Pharmaceuticals); IDN-6556 (Idun Pharmaceuticals); IP-501 (Indevus Pharmaceuticals); Actimmune (InterMune Inc.); Infergen A (InterMune Inc.); ISIS 14803 (ISIS Pharmaceuticals Inc.); JTK-003 (Japan Tobacco Inc.); Pegasys/Ceplene (Maxim Pharmaceuticals); Ceplene (Maxim Pharmaceuticals); Civacir (Nabi Biopharmaceuticals Inc.); Intron A/Zadaxin (RegeneRx); Levovirin (Ribapharm Inc.); Viramidine (Ribapharm Inc.); Heptazyme (Ribozyme Pharmaceuticals); Intron A (Schering-Plough); PEG-Intron (Schering-Plough); Rebetron (Schering-Plough); Ribavirin (Schering-Plough); PEG-Intron/Ribavirin (Schering-Plough); Zadazim (SciClone); Rebif (Serono); IFN-β/EMZ701 (Transition Therapeutics); T67 (Tularik Inc.); VX-497 (Vertex Pharmaceuticals Inc.); VX-950/LY-570310 (Vertex Pharmaceuticals Inc.); Omniferon (Viragen Inc.); XTL-002 (XTL Biopharmaceuticals); SCH 503034 (Schering-Plough); isatoribine and its prodrugs ANA971 and ANA975 (Anadys); R1479 (Roche Biosciences); Valopicitabine (Idenix); NIM811 (Novartis); Actilon (Coley Pharmaceuticals); Pradefovir (Metabasis Therapeutics); zanamivir; adefovir, adefovir dipivoxil, oseltamivir; vidarabine; gancyclovir; valganciclovir; amantadine; rimantadine; relenza; tamiflu; amantadine; entecavir; and pleconaril.

Other anti-parasitic agents that can be co-administered with the compounds of the invention include, but are not limited to, avermectins, milbemycins, lufenuron, imidacloprid, organophosphates, pyrethroids, sufanamides, iodquinol, diloxanide furoate, metronidazole, paromycin, azithromycin, quinacrine, furazolidone, tinidazole, ornidazole, bovine, colostrum, bovine dialyzable leukocyte extract, chloroquine, chloroquine phosphate, diclazuril, eflornithine, paromomycin, pentamidine, pyrimethamine, spiramycin, trimethoprim-sulfamethoxazole, albendazole, quinine, quinidine, tetracycline, pyrimethamine-sulfadoxine, mefloquine, doxycycline, proguanil, clindamycin, suramin, melarsoprol, diminazene, nifurtimox, spiroarsoranes, ketoconazole, terbinafine, lovastatin, sodium stibobgluconate, N-methylglucamine antimonate, amphotericin B, allopurinol, itraconazole, sulfadiazine, dapsone, trimetrexate, clarithromycin, roxithromycin, atovaquone, aprinocid, tinidazole, mepacrine hydrochloride, emetine, polyaminopropyl biguanide, paromomycin, benzimidazole, praziquantel, or albendazole.

8) Steroid or Non-Steroidal Anti-Inflammatory Agents Useful in Combination with the Compounds of the Invention In one embodiment relating to autoimmune, allergic and inflammatory conditions, the other therapeutic agent may be a steroid or a non-steroidal anti-inflammatory agent. Particularly useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see *Paul A. Insel, Analgesic-Antipyretic and Antiinflammatory Agents and Drugs Employed in the Treatment of Gout, in Goodman & Gilman's The Pharmacological Basis of Therapeutics* 617-57 (Perry B. Molinhoff and Raymond W. Ruddon eds., $9^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

Of particular relevance to allergic disorders, the other therapeutic agent may be an antihistamine. Useful antihistamines include, but are not limited to, loratadine, cetirizine, fexofenadine, desloratadine, diphenhydramine, chlorpheniramine, chlorcyclizine, pyrilamine, promethazine, terfenadine, doxepin, carbinoxamine, clemastine, tripelennamine, brompheniramine, hydroxyzine, cyclizine, meclizine, cyproheptadine, phenindamine, acrivastine, azelastine, levocabastine, and mixtures thereof. For a more detailed description of antihistamines, see *Goodman & Gilman's The Pharmacological Basis of* Therapeutics (2001) 651-57, $10^{th}$ ed).

Immunosuppressive agents include glucocorticoids, corticosteroids (such as Prednisone or Solumedrol), T cell blockers (such as cyclosporin A and FK506), purine analogs (such as azathioprine (Imuran)), pyrimidine analogs (such as cytosine arabinoside), alkylating agents (such as nitrogen mustard, phenylalanine mustard, buslfan, and cyclophosphamide), folic acid antagonsists (such as aminopterin and methotrexate), antibiotics (such as rapamycin, actinomycin D, mitomycin C, puramycin, and chloramphenicol), human IgG, antilymphocyte globulin (ALG), and antibodies (such as anti-CD3 (OKT3), anti-CD4 (OKT4), anti-CD5, anti-CD7, anti-IL-2 receptor, anti-alpha/beta TCR, anti-ICAM-1, anti-CD20 (Rituxan), anti-IL-12 and antibodies to immunotoxins).

E. Compositions and Methods for Administering Therapies

The present invention provides compositions for the treatment, prophylaxis, and amelioration of proliferative disorders, such as cancer. In a specific embodiment, a composition comprises one or more compounds of the invention, or a pharmaceutically acceptable salt, solvate, clathrate, hydrate or prodrug thereof. In another embodiment, a composition of the invention comprises one or more prophylactic or therapeutic agents other than a compound of the invention, or a pharmaceutically acceptable salt, solvate, clathrate, hydrate, prodrug thereof. In another embodiment, a composition of the invention comprises one or more compounds of the invention, or a pharmaceutically acceptable salt, solvate, clathrate, hydrate or prodrug thereof, and one or more other prophylactic or therapeutic agents. In another embodiment, the composition comprises a compound of the invention, or a pharmaceutically acceptable salt, solvate, clathrate, hydrate, or prodrug thereof, and a pharmaceutically acceptable carrier, diluent or excipient.

In a preferred embodiment, a composition of the invention is a pharmaceutical composition or a single unit dosage form. Pharmaceutical compositions and dosage forms of the invention comprise one or more active ingredients in relative amounts and formulated in such a way that a given pharmaceutical composition or dosage form can be used to treat or prevent proliferative disorders, such as cancer. Preferred pharmaceutical compositions and dosage forms comprise a compound of formula (I)-(XXXII), or a pharmaceutically acceptable prodrug, salt, solvate, clathrate, hydrate, or prodrug thereof, optionally in combination with one or more additional active agents.

The pharmaceutical compositions can be used in therapy, e.g., to treat a mammal with an infection. In one embodiment, the pharmaceutical composition includes one or more additional therapeutic agents, such as one or more additional anti-infective agents.

In another embodiment, the present invention is the use of a compound of anyone of the formulas disclosed herein for the manufacture of a medicament for treating a mammal with an infection.

In another embodiment of the present invention is a pharmaceutical composition comprising a compound represented by any one of the formulas disclosed herein and a pharmaceutically acceptable carrier. The pharmaceutical compositions can be used in therapy, e.g., to treat a mammal with an inflammatory or immune disorder. In one embodiment, the pharmaceutical composition includes one or more additional therapeutic agent, such as one or more additional anti-inflammatory agent or one or more immunosuppressant.

In another embodiment, the present invention is the use of a compound of anyone of the formulas disclosed herein for the manufacture of a medicament for treating a mammal with an inflammatory or autoimmune disorder or for treatment of a mammal in need of immunosuppression.

A pharmaceutical composition of the invention is formulated to be compatible with its intended route of administration. Examples of routes of administration include, but are not limited to, parenteral, e.g., intravenous, intradermal, subcutaneous, oral (e.g., inhalation), intranasal, transdermal (topical), transmucosal, and rectal administration. In a specific embodiment, the composition is formulated in accordance with routine procedures as a pharmaceutical composition adapted for intravenous, subcutaneous, intramuscular, oral, intranasal or topical administration to human beings. In a preferred embodiment, a pharmaceutical composition is formulated in accordance with routine procedures for subcutaneous administration to human beings.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., Remington's Pharmaceutical Sciences (1990) 18th ed., Mack Publishing, Easton Pa.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms.

The suitability of a particular excipient may also depend on the specific active ingredients in the dosage form. For example, the decomposition of some active ingredients can be accelerated by some excipients such as lactose, or when exposed to water. Active ingredients that comprise primary or secondary amines (e.g., N-desmethylvenlafaxine and N,N-didesmethylvenlafaxine) are particularly susceptible to such accelerated decomposition. Consequently, this invention encompasses pharmaceutical compositions and dosage forms that contain little, if any, lactose. As used herein, the term "lactose-free" means that the amount of lactose present, if any, is insufficient to substantially increase the degradation rate of an active ingredient. Lactose-free compositions of the invention can comprise excipients that are well known in the art and are listed, for example, in the U.S. Pharmocopia (USP)SP(XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen (1995) Drug Stability: Principles & Practice, 2d. Ed., Marcel Dekker, NY, N.Y., 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizer" include, but are not limited to, antioxidants such as ascorbic acid, pH buffers, or salt buffers.

1) Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences (1990) 18th ed., Mack Publishing, Easton Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

2) Controlled Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

A particular extended release formulation of this invention comprises a therapeutically or prophylactically effective amount of a compound of formula (I)-(XXXII), or a pharmaceutically acceptable salt, solvate, hydrate, clathrate, or prodrug thereof, in spheroids which further comprise microcrystalline cellulose and, optionally, hydroxypropylmethylcellulose coated with a mixture of ethyl cellulose and hydroxypropylmethylcellulose. Such extended release formulations can be prepared according to U.S. Pat. No. 6,274,171, the entirely of which is incorporated herein by reference.

A specific controlled-release formulation of this invention comprises from about 6% to about 40% a compound of formula (I)-(XXXII), or a pharmaceutically acceptable salt, solvate, hydrate, clathrate, or prodrug thereof, by weight, about 50% to about 94% microcrystalline cellulose, NF, by weight, and optionally from about 0.25% to about 1% by weight of hydroxypropyl-methylcellulose, USP, wherein the spheroids are coated with a film coating composition comprised of ethyl cellulose and hydroxypropylmethylcellulose.

3) Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

4) Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences (1980 & 1990) 16th and 18th eds., Mack Publishing, Easton Pa., and Introduction to Pharmaceutical Dosage Forms (1985) 4th ed., Lea & Febiger, Philadelphia. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences (1980 & 1990) 16th and 18th eds., Mack Publishing, Easton Pa.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5) Dosage & Frequency of Administration

The amount of the compound or composition of the invention which will be effective in the prevention, treatment, management, or amelioration of a proliferative disorders, such as cancer, or one or more symptoms thereof, will vary with the nature and severity of the disease or condition, and the route by which the active ingredient is administered. The frequency and dosage will also vary according to factors specific for each patient depending on the specific therapy (e.g., therapeutic or prophylactic agents) administered, the severity of the disorder, disease, or condition, the route of administration, as well as age, body, weight, response, and the past medical history of the patient. Effective doses may be extrapolated from dose-response curves derived from in vitro or animal model test systems. Suitable regiments can be selected by one skilled in the art by considering such factors and by following, for example, dosages reported in the literature and recommended in the Physician's Desk Reference (57th ed., 2003).

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

In general, the recommended daily dose range of a compound of the invention for the conditions described herein lie within the range of from about 0.01 mg to about 1000 mg per day, given as a single once-a-day dose preferably as divided doses throughout a day. In one embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different proliferative disorders, as will be readily known by those of ordinary skill in the art. Similarly, amounts sufficient to prevent, manage, treat or ameliorate such proliferative disorders, but insufficient to cause, or sufficient to reduce, adverse effects associated with the compounds of the invention are also encompassed by the above described dosage amounts and dose frequency schedules. Further, when a patient is administered multiple dosages of a compound of the invention, not all of the dosages need be the same. For example, the dosage administered to the patient may be increased to improve the prophylactic or therapeutic effect of the compound or it may be decreased to reduce one or more side effects that a particular patient is experiencing.

In a specific embodiment, the dosage of the composition of the invention or a compound of the invention administered to prevent, treat, manage, or ameliorate a proliferative disorders, such as cancer, or one or more symptoms thereof in a patient is 150 µg/kg, preferably 250 µg/kg, 500 µg/kg, 1 mg/kg, 5 mg/kg, 10 mg/kg, 25 mg/kg, 50 mg/kg, 75 mg/kg, 100 mg/kg, 125 mg/kg, 150 mg/kg, or 200 mg/kg or more of a patient's body weight. In another embodiment, the dosage of the composition of the invention or a compound of the invention administered to prevent, treat, manage, or ameliorate a proliferative disorders, such as cancer, or one or more symptoms thereof in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosages of prophylactic or therapeutic agents other than compounds of the invention, which have been or are currently being used to prevent, treat, manage, or proliferative disorders, such as cancer, or one or more symptoms thereof can be used in the combination therapies of the invention. Preferably, dosages lower than those which have been or are currently being used to prevent, treat, manage, or ameliorate a proliferative disorders, or one or more symptoms thereof, are used in the combination therapies of the invention. The recommended dosages of agents currently used for the prevention, treatment, management, or amelioration of a proliferative disorders, such as cancer, or one or more symptoms thereof, can obtained from any reference in the art including, but not limited to, Hardman et al., eds., 1996, Goodman & Gilman's The Pharmacological Basis Of Basis Of Therapeutics 9$^{th}$ Ed, Mc-Graw-Hill, New York; Physician's Desk Reference (PDR)$_{57}$th Ed., 2003, Medical Economics Co., Inc., Montvale, N.J., which are incorporated herein by reference in its entirety.

In certain embodiments, when the compounds of the invention are administered in combination with another therapy, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one embodiment, two or more therapies (e.g., prophylactic or therapeutic agents) are administered within the same patent visit.

In certain embodiments, one or more compounds of the invention and one or more other the therapies (e.g., prophylactic or therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound of the invention may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, the invention provides a method of preventing, treating, managing, or ameliorating a proliferative disorders, such as cancer, or one or more symptoms thereof, said methods comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds of the invention once every day, preferably, once every 2 days, once every 3 days, once every 4 days, once every 5 days, once every 6 days, once every 7 days, once every 8 days, once every 10 days, once every two weeks, once every three weeks, or once a month.

F. Other Embodiments

The compounds of the invention may be used as research tools (for example, to evaluate the mechanism of action of new drug agents, to isolate new drug discovery targets using affinity chromatography, as antigens in an ELISA or ELISA-like assay, or as standards in in vitro or in vivo assays). These and other uses and embodiments of the compounds and compositions of this invention will be apparent to those of ordinary skill in the art.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1

4-[4-(2-Hydroxy-indan-5-yl)-5-mercapto-4H-[1,2,4] triazol-3-yl]-6-isopropyl-benzene-1,3-diol (Compound 4)

Scheme 1

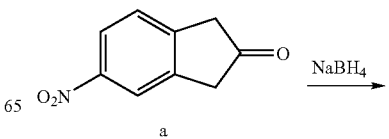

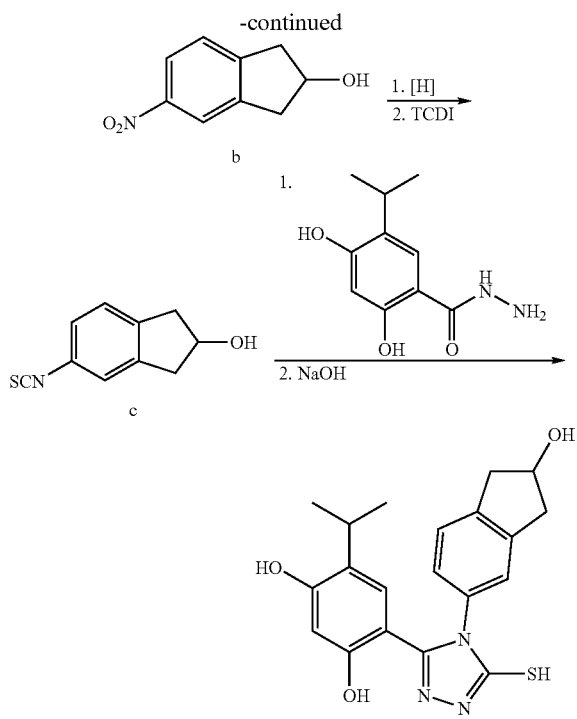

5-nitro-indan-2-ol (b, Scheme 1)

5-nitro-2-indanone (5.3 g, 30 mmol) was dissolved in EtOH: i-PrOH (1:1, 150 mL). NaBH$_4$ (1.7 g, 45 mmol) was added portion by portion at room temperature. The reaction mixture was stirred at r.t for additional 30 min and water was added at 0° C. (ice-water bath). The reaction mixture was extracted with EtOAc (100 mL×3) and the combined organic layers were washed with water and brine and dried over Na$_2$SO$_4$. Purification of the concentrated crude product by column chromatography (EtOAc:Hexane=4:6) afforded the title product as a pale yellow oil (4.47 g, 83%).

5-Isothiocyanato-indan-2-ol (c, Scheme 1)

5-nitro-indan-2-ol (450 mg, 2.5 mmol) was hydrogenated using Pd/C (10%, dry, 100 mg) and H$_2$ balloon at 1 atm at room temperature. Pd/C was filtered off through a pad of celite and the mother liquid was concentrated to give the crude product, 5-Amino-indan-2-ol.

5-Amino-indan-2-ol (149 mg, 1 mmol) was dissolved in CH$_2$Cl$_2$ (10 mL) and TCDI (thiocarbodiimidazole, 178 mg, 1 mmol) was added to the solution. The reaction mixture was stirred at room temperature for 30 min. Silica gel was added to the reaction mixture and dried. Purification of silica gel coated crude product by column chromatography (EtOAc:Hexane=3:7) afforded the title product as a white solid (132 mg).

4-[4-(2-Hydroxy-indan-5-yl)-5-mercapto-4H-[1,2,4]triazol-3-yl]-6-isopropyl-benzene-1,3-diol (Compound 4)

5-Isothiocyanato-indan-2-ol (126 mg, 0.6 mmol) and 2,4-Dihydroxy-5-isopropyl-benzoic acid hydrazide (115 mg, 1.6 mmol) was stirred in EtOH (10 mL) at 70° C. for 30 min and the reaction mixture was cooled to room temperature. Silica gel was added to the reaction mixture and dried. Purification of silica gel coated crude intermediate by column chromatography (EtOAc:Hexane=7:3) afforded the condensed intermediate as a white solid (148 mg, 61%).

To the intermediate (148 mg, 0.37 mmol) was added degassed 2N—NaOH (0.28 mL, 0.56 mmol) and the reaction mixture was stirred at 110° C. for 2 h. After cooled down to room temperature, the reaction mixture was acidified with 1N—HCl. The white precipitate was filtered and dried to give the title compound as a white solid (115 mg, 81%).

$^1$H NMR (300 MHz, DMSO-d6), δ (ppm): 9.59 (s, 1H), 9.42 (s, 1H), 7.16 (d, J=8.1 Hz, 1H), 7.10 (s, 1H), 6.91 (dd, J=8.1, 1.5 Hz, 1H), 6.83 (s, 1H), 6.22 (s, 1H), 4.90 (d, J=3.3 Hz, 1H), 4.52-4.42 (m, 1H), 3.05-2.89 (m, 3H), 2.73-2.64 (m, 2H), 0.95 (d, J=6.9 Hz, 6H). ESMS calcd. for C$_{20}$H$_{21}$N$_3$O$_3$S, 383.5. Found: 384.6 (M+1)$^+$.

Example 2

4-Isopropyl-6-[5-mercapto-4-(2-methoxy-indan-5-yl)-4H-[1,2,4]triazol-3-yl]-benzene-1,3-diol (Compound 6)

Scheme 2

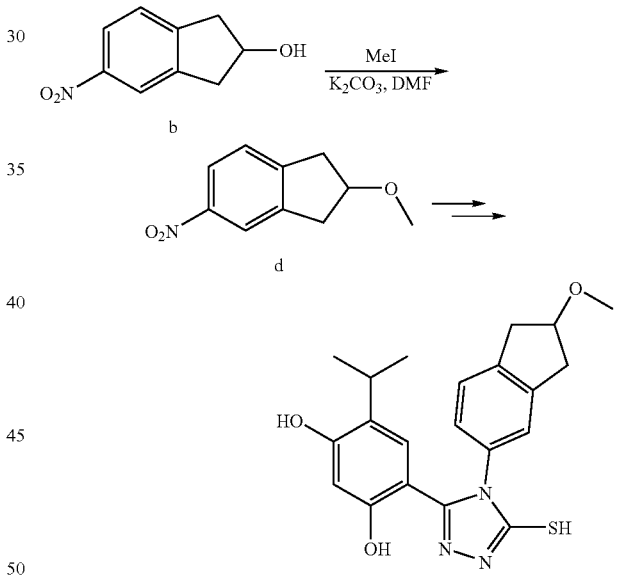

2-Methoxy-5-nitro-indan (d, Scheme 2)

5-nitro-indan-2-ol (1.55 g, 8.65 mmol) and K$_2$CO$_3$ (2.8 g, 20 mmol) was charged into a schlenk flask. The flask was evacuated and back filled with N$_2$. DMF (10 mL) was added and stirred at r.t. for 30 min. MeI (excess, 10 mL) was added and the reaction mixture was stirred at 100° C. overnight. The reaction mixture was allowed to cool to room temperature. Water was added and the reaction mixture was extracted with EtOAc. The combined organic layers were washed with water and brine and dried over Na$_2$SO$_4$. Purification of the concentrated crude product by column chromatography (EtOAc:Hexane=1:9) afforded the title product as a pale yellow oil (520 mg, 74% based on recovered starting material).

4-Isopropyl-6-[5-mercapto-4-(2-methoxy-indan-5-yl)-4H-[1,2,4]triazol-3-yl]-benzene-1,3-diol (Compound 6)

2-Methoxy-5-nitro-indan (d, Scheme 2) was further utilized in the synthesis of Compound 6 in a similar way to that of Compound 4.

$^1$H NMR (300 MHz, DMSO-d6), δ (ppm): 9.56 (s, 1H); 9.41 (s, 1H); 7.18 (d, J=7.8 Hz, 1H); 7.11 (s, 1H); 6.93 (dd, J=7.8, 2.1 Hz, 1H); 6.83 (s, 1H); 6.22 (s, 1H); 4.19-4.13 (m, 1H); 3.21 (s, 3H); 3.10-2.89 (m, 3H); 2.87-2.77 (m, 2H); 0.95 (d, J=6.9 Hz, 6H). ESMS calcd. for $C_2$,$H_{23}N_3O_3S$, 397.5. Found: 398.1 (M+1)$^+$.

Example 3

4-[4-(2-Ethoxy-indan-5-yl)-5-mercapto-4H-[1,2,4]triazol-3-yl]-6-isopropyl-benzene-1,3-diol (Compound 8)

Compound 8 was synthesized in a similar way to Compound 6.

ESMS calcd. for $C_{22}H_{25}N_3O_3S_1$ 411.5. Found: 412.1 (M+1)$^+$.

Example 4

4-Isopropyl-6-[5-mercapto-4-(2-propoxy-indan-5-yl)-4H-[1,2,4]triazol-3-yl]-benzene-1,3-diol (Compound 9)

Compound 9 was synthesized in a similar way to Compound 6.

ESMS calcd. for $C_{23}H_{27}N_3O_3S_1$ 425.5. Found: 426.2 (M+1)$^+$.

Example 5

4-Isopropyl-6-[5-mercapto-4-(2-methoxymethoxy-indan-5-yl)-4H-[1,2,4]triazol-3-yl]-benzene-1,3-diol (Compound 18)

Compound 18 was synthesized in a similar way to Compound 6.

ESMS calcd. for $C_{22}H_{25}N_3O_4S_1$ 427.5. Found: 428.1M+ 1)$^+$.

Example 6

4-Cyclopropyl-2-[5-mercapto-4-(2-methoxy-indan-5-yl)-4H-[1,2,4]triazol-3-yl]-phenol (Compound 14)

Compound 14 was synthesized in a similar way to Compound 6.

ESMS calcd. for $C_{21}H_{21}N_3O_2S_1$ 379.1. Found: 380.3M+ 1)$^+$.

Example 7

[4-(1',3'-Dihydro-spiro[[1,3]dioxolane-2,2'-inden]-5'-yl)-5-mercapto-4H-[1,2,4]triazol-3-yl]-6-isopropyl-benzene-1,3-diol (Compound 10)

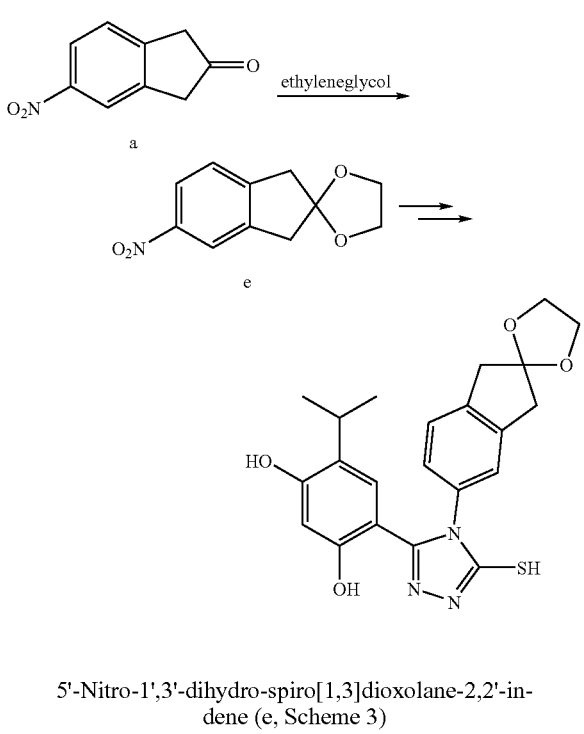

Scheme 3

5'-Nitro-1',3'-dihydro-spiro[1,3]dioxolane-2,2'-indene (e, Scheme 3)

5-nitro-2-indanone (620 mg, 3.5 mmol) and p-TsOH (67 mg, cat. amount) was charged into two-neck 100 mL r.b.f. Benzene (30 mL) was added followed by ethylene glycol (0.29 mL, 5.25 mmol). The reaction mixture was refluxed at 95° C. over night with dean stark equipped. After cooled to room temperature, water was added and the reaction mixture was extracted with EtOAc. Combined organic layers were washed with water and brine and dried over Na$_2$SO$_4$. Purification of the concentrated crude product by column chromatography (EtOAc:Hexane=2:8) afforded the title product as a pale yellow solid (660 mg, 85%).

[4-(1',3'-Dihydro-spiro[[1,3]dioxolane-2,2'-inden]-5'-yl)-5-mercapto-4H-[1,2,4]triazol-3-yl]-6-isopropyl-benzene-1,3-diol (Compound 10)

5'-Nitro-1',3'-dihydro-spiro[1,3]dioxolane-2,2'-indene (e, Scheme 3) was further utilized in the synthesis of Compound 10 in a similar way to that of Compound 4.

ESMS calcd. for $C_{22}H_{23}N_3O_4S_1$ 425.5. Found: 426.1 (M+1)$^+$.

Example 8

5-[3-(2,4-Dihydroxy-5-isopropyl-phenyl)-5-mercapto-[1,2,4]triazol-4-yl]-indan-2-one (Compound 11)

Compound 10 (160 mg, 0.38 mmol) was stirred in acetone (7 mL) and water (2 mL) at 63° C. in the presence of p-TsOH (5 mg, cat. amount) for 2 h. After cooled to room temperature, water was added and the reaction mixture was extracted with EtOAc. Combined organic layers were washed with water and brine and dried over $Na_2SO_4$. Purification of the concentrated crude product by column chromatography (EtOAc: Hexane=1:1) afforded the title product as a white solid (100 mg, 69%).

ESMS calcd. for $C_{20}H_{19}N_3O_3S_1$ 381.5. Found: 382.1 $(M+1)^+$.

Example 9

5-(2,4-Dihydroxy-5-isopropyl-phenyl)-4-(2-dimethylamino-indan-5-yl)-2,4-dihydro-[1,2,4]triazol-3-one (Compound 13)

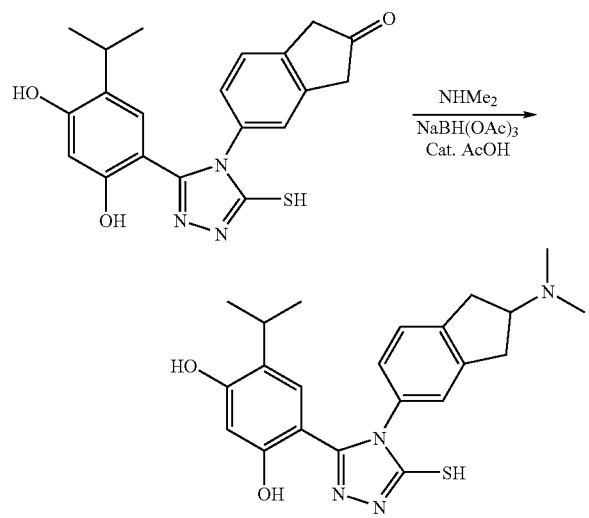

Compound 11 (340 mg, 0.9 mmol) was dissolved in THF (4 mL). AcOH (2 drops, cat. amount) was added followed by dimethylamine in THF (1N solution, 0.7 mL, 1.35 mmol). $NaBH(OAc)_3$ (286 mg, 1.35 mmol) was added to the reaction mixture and the reaction mixture was stirred at room temperature for 30 min. Water was added and the reaction mixture was extracted with EtOAc. Combined organic layers were washed with water and brine and dried over $Na_2SO_4$. Purification of the concentrated crude product by column chromatography (MeOH: $CH_2Cl_2$=2:8) afforded the title product as a pale yellow solid (80 mg, 25%).

$^1$H NMR (300 MHz, DMSO-d6), δ (ppm): 9.62 (s, 1H), 9.45 (s, 1H), 7.19 (d, J=7.8 Hz, 1H), 7.11 (s, 1H), 6.95 (d, J=7.8 Hz, 1H), 6.81 (s, 1H), 6.25 (s, 1H), 3.12-2.90 (m, 4H), 2.82-2.62 (m, 2H), 2.24 (s, 6H), 0.96 (d, J=6.9 Hz, 6H).

ESMS calcd. for $C_{22}H_{26}N_4O_2S_1$ 410.2. Found: 411.2 $(M+1)^+$.

Example 10

4-Isopropyl-6-[5-mercapto-4-(2-pyrrolidin-1-yl-indan-5-yl)-4H-[1,2,4]triazol-3-yl]-benzene-1,3-diol (Compound 16)

Compound 16 was synthesized in a similar way to Compound 13.

ESMS calcd. for $C_{24}H_{28}N_4O_2S_1$ 436.6. Found: 437.2 $(M+1)^+$.

Example 11

4-Isopropyl-6-[5-mercapto-4-(2-morpholin-4-yl-indan-5-yl)-4H-[1,2,4]triazol-3-yl]-benzene-1,3-diol (Compound 15)

Compound 15 was synthesized in a similar way to Compound 13.

ESMS calcd. for $C_{24}H_{28}N_4O_3S_1$ 452.6. Found: 453.4 $(M+1)^+$.

Example 12

4-[4-(1',3'-Dihydro-spiro[[1,3]dioxolane-2,2'-inden]-5'-yl)-5-hydroxy-4H-[1,2,4]triazol-3-yl]-6-isopropyl-benzene-1,3-diol (Compound 19)

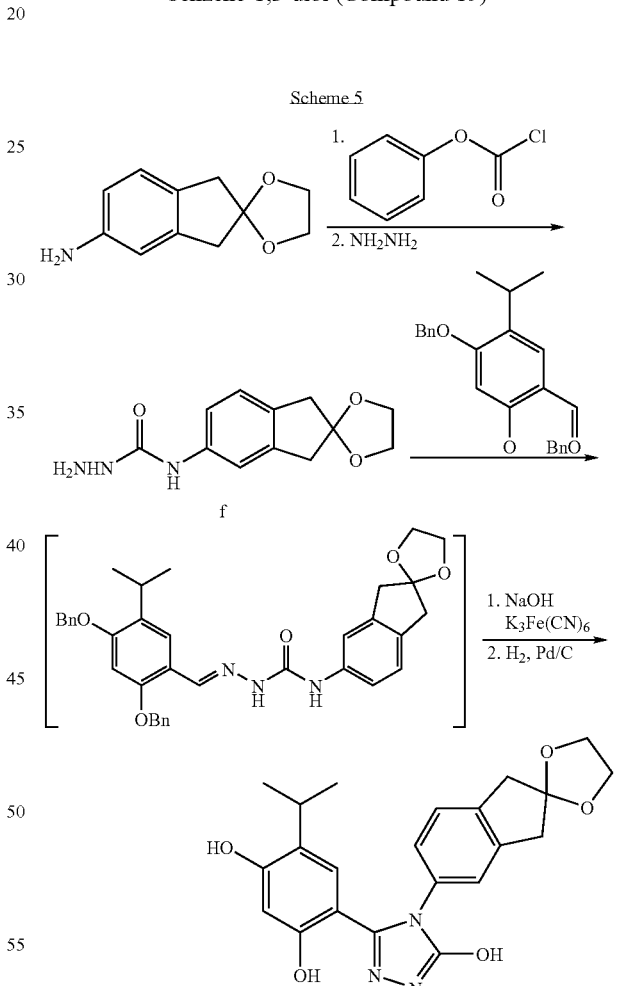

f (Scheme 5)

To a solution of 1',3'-Dihydro-spiro[[1,3]dioxolane-2,2'-inden]-5'-ylamine (1.0 g, 5.23 mmol) in $CH_2Cl_2$ (15 mL) was added phenyl chloroformate (0.66 mL, 5.23 mmol) drop wise at room temperature followed by triethylamine (1.15 mL, 8.3 mmol). The reaction mixture was stirred at r.t for 30 min and then solvent was removed under vacuum. Water was added to the resulting crude product and the precipitate was filtered and dried to give the crude (1',3'-Dihydro-spiro[[1,3]dioxolane-2,2'-inden]-5'-yl)-carbamic acid phenyl ester as a pale yellow solid (1.62 g, quantitative).

To a solution of (1',3'-Dihydro-spiro[[1,3]dioxolane-2,2'-inden]-5'-yl)-carbamic acid phenyl ester in dioxane (20 mL) was added hydrazine hydrate (1.26 mL, 26 mmol) and the reaction mixture was stirred at 100° C. for 1 h. Solvent was removed under vacuum and then water was added. Precipitated solid was filtered and dried to give the title product as an off-white solid (1.0 g, 77%).

4-[4-(1',3'-Dihydro-spiro[[1,3]dioxolane-2,2'-inden]-5'-yl)-5-hydroxy-4H-[1,2,4]triazol-3-yl]-6-isopropyl-benzene-1,3-diol (Compound 19)

f (831 mg, 3.33 mmol) and 2,4-Bis-benzyloxy-5-isopropyl-benzaldehyde (1203 mg, 3.33 mmol) were stirred in EtOH (20 mL) at 78° C. in the presence of AcOH (3 drops, cat. amount) for 2 h. White solid was precipitated as the reaction proceeded. After cooled to r.t., the white solid was filtered and dried to give the condensed intermediate (1.6 g, 81%). The intermediate (1.6 g, 2.7 mmol) and NaOH (432 mg, 10.8 mmol) were charged into a 100 mL r.b.f, and EtOH (50 mL) was added. The solution was flushed with $N_2$ and then, $K_3Fe(CN)_6$ was added to the solution. The reaction mixture was stirred at 100° C. for 20 h. After cooled to r.t., the reaction mixture was filtered and the mother liquid was concentrated. Water was added to the concentrated mother liquid and it was acidified with 1N—HCl. The precipitated yellow solid was filtered and dried. The crude product was reprecipitated in EtOAc/Hexane (1/1) to give 5-(2,4-Bis-benzyloxy-5-isopropyl-phenyl)-4-(1',3'-dihydro-spiro[[1,3]dioxolane-2,2'-inden]-5'-yl)-4H-[1,2,4]triazol-3-ol as a pale yellow solid (1.43 g, 90%).

5-(2,4-Bis-benzyloxy-5-isopropyl-phenyl)-4-(1',3'-dihydro-spiro[[1,3]dioxolane-2,2'-inden]-5'-yl)-4H-[1,2,4]triazol-3-ol (550 mg, 0.93 mmol) was subsequently hydrodebensylated using Pd/C (10%, dry, 100 mg) and $H_2$ in THF/MeOH (1/1, mL) at 1 atm at r.t. for 2 h. The reaction mixture was filtered through a pad of celite and the mother liquid was concentrated. It was again filtered through a pad of silica gel and the filtrate was concentrated to give the title compound as a white solid (370 mg, 97%).

$^1$H NMR (300 MHz, DMSO-d6), δ (ppm): 11.90 (s, 1H), 9.59 (s, 1H), 9.42 (s, 1H), 7.15 (d, J=8.1 Hz, 1H), 7.10 (s, 1H), 6.89 (dd, J=8.1, 1.8 Hz, 1H), 6.85 (s, 1H), 6.25 (s, 1H), 3.92 (s, 4H), 3.03 (d, J=6 Hz, 4H), 3.08-2.92 (m, 1H), 0.99 (d, J=6.9 Hz, 6H). ESMS calcd. for $C_{22}H_{23}N_3O_5$ 409.2. Found: 410.1 $(M+1)^+$.

Example 13

4-[5-Hydroxy-4-(2-methoxy-indan-5-yl)-4H-[1,2,4]triazol-3-yl]-6-isopropyl-benzene-1,3-diol (Compound 17)

Compound 17 was synthesized in a similar way to Compound 19.
ESMS calcd. for $C_{21}H_{23}N_3O_4$ 381.2. Found: 382.2 $(M+1)^+$.

Example 14

4-[5-Hydroxy-4-(2-methoxymethoxy-indan-5-yl)-4H-[1,2,4]triazol-3-yl]-6-isopropyl-benzene-1,3-diol (Compound 21)

Compound 21 was synthesized in a similar way to Compound 19.

ESMS calcd. for $C_{22}H_{25}N_3O_5$ 411.5. Found: 412.1 $(M+1)^+$.

Example 15

4-[4-(2-Ethoxymethoxy-indan-5-yl)-5-hydroxy-4H-[1,2,4]triazol-3-yl]-6-isopropyl-benzene-1,3-diol (Compound 22)

Compound 22 was synthesized in a similar way to Compound 19.
ESMS calcd. for $C_{23}H_{27}N_3O_5$ 425.2. Found: 426.2 $(M+1)^+$.

Example 16

4-[4-(2-Dimethylamino-indan-5-yl)-5-hydroxy-4H-[1,2,4]triazol-3-yl]-6-isopropyl-benzene-1,3-diol (Compound 24)

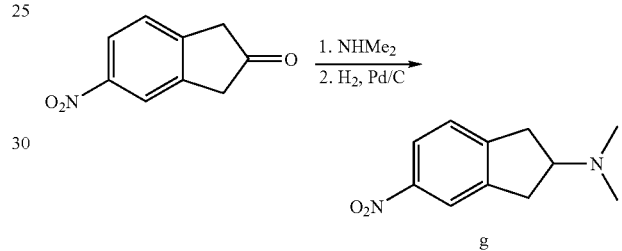

Scheme 6

Dimethyl-(5-nitro-indan-2-yl)-amine (g, Scheme 6)

To a solution of 5-nitro-2-indanone (885 mg, 5 mmol) in THF (15 mL) was added dimethylamine (2N in THF, 5 mL, 10 mmol) dropwise. The reaction mixture was stirred at r.t. for 5 h. Water was added and the reaction mixture was extracted with EtOAc. Combined organic layers were washed with water and brine and dried over $Na_2SO_4$. The concentrated crude product was filtered through a short pad of silica gel (EtOAc:hexane=1:1) and the filtrate was concentrated to give dimethyl-(5-nitro-1H-inden-2-yl)-amine as a dark red solid (1.0 g, 98%). Dimethyl-(5-nitro-1H-inden-2-yl)-amine (1.0 g, 4.9 mmol) was hydrogenated using Pd/C (10% dry, ca. 300 mg) and $H_2$ in MeOH:THF (1:1, 30 mL) at 1 atm at r.t. for 5 h. The reaction mixture was filtered through a pad of celite and the filtrate was concentrated. The concentrated filtrate was further purified via short silica gel column chromatography (EtOAc: MeOH=6:4) to give the title compound as a yellow solid (830 mg, 82%).

4-[4-(2-Dimethylamino-indan-5-yl)-5-hydroxy-4H-[1,2,4]triazol-3-yl]-6-isopropyl-benzene-1,3-diol (Compound 24)

Dimethyl-(5-nitro-indan-2-yl)-amine was further utilized in the synthesis of Compound 24 in a similar way to that of Compound 19.

$^1$H NMR (300 MHz, DMSO-d6), δ (ppm): 11.91 (s, 1H), 9.61 (s, 1H), 9.44 (s, 1H), 7.17 (d, J=7.8 Hz, 1H), 7.07 (s, 1H), 6.90 (dd, J=7.8, 1.8 Hz, 1H), 6.78 (s, 1H), 6.26 (s, 1H), 3.20-2.90 (m, 4H), 2.80-2.65 (m, 2H), 2.22 (s, 6H), 0.95 (d, J=6.9 Hz, 6H). ESMS calcd. for $C_{22}H_{26}N_4O_3$ 394.2. Found: 395.3 (M+1)$^+$.

Example 17

4-[5-Hydroxy-4-(2-pyrrolidin-1-yl-indan-5-yl)-4H-[1,2,4]triazol-3-yl]-6-isopropyl-benzene-1,3-diol (Compound 27)

Compound 27 was synthesized in a similar way to Compound 24.

ESMS calcd. for $C_{24}H_{28}N_4O_3$ 420.2. Found: 421.4 (M+1)$^+$.

Example 18

4-(5-Hydroxy-4-{2-[(2-methoxy-ethyl)-methyl-amino]-indan-5-yl}-4H-[1,2,4]triazol-3-yl)-6-isopropyl-benzene-1,3-diol (Compound 29)

Compound 29 was synthesized in a similar way to Compound 24.

ESMS calcd. for $C_{24}H_{30}N_4O_4$ 438.2. Found: 439.4 (M+1)$^+$.

Example 19

4-Ethyl-6-[5-mercapto-4-(7-methoxy-2-methyl-benzofuran-4-yl)-4H-[1,2,4]triazol-3-yl]-benzene-1,3-diol

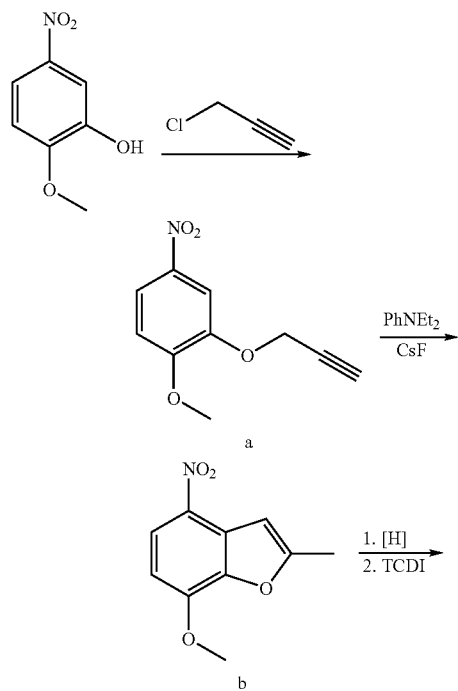

Scheme 7

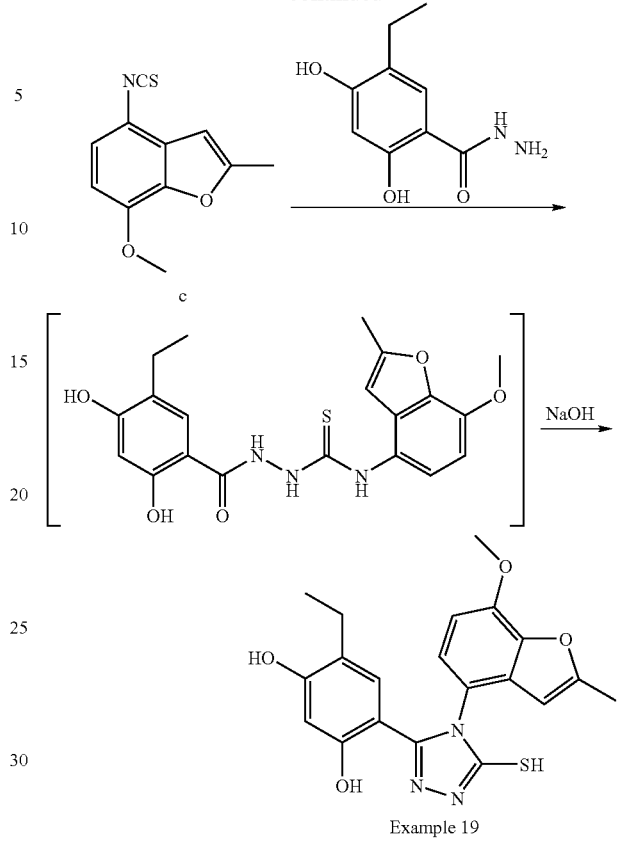

Example 19

1-Methoxy-4-nitro-2-prop-2-ynyloxy-benzene (a, Scheme 7)

2-methoxy-5-nitrophenol (6.0 g, 35 mmol) and $K_2CO_3$ (6.5 g, 43 mmol) were stirred in acetone (200 mL) for 30 min and then propargyl chloride (6 mL, excess) was added to the suspension and heated at 65° C. overnight. After cooled to room temperature, water was added and the reaction mixture was extracted with EtOAc (100 mL×3). The combined organic layers were washed with water and brine and dried over $Na_2SO_4$. Recrystallization of the crude product in MeOH/EtOAc gave the title product as a white solid (6.4 g, 88%).

7-Methoxy-2-methyl-4-nitro-benzofuran (b, Scheme 7)

1-Methoxy-4-nitro-2-prop-2-ynyloxy-benzene (6.2 g, 30 mmol) and CsF (3.0 g, 20 mmol) were charged into a schlenk flask and the reaction flask was flushed with $N_2$. PhNEt$_2$ (18 mL) was added and the reaction mixture was heated at 210° C. for 3 h. After cooled to room temperature, water was added and the reaction mixture was extracted with EtOAc (100 mL×3). The combined organic layers were washed with 1N—HCl and brine and dried over $Na_2SO_4$. Purification of the concentrated crude product by column chromatography (EtOAc:Hexane=2:8) afforded the title product as a yellow solid (2.4 g, 39%).

4-Isothiocyanato-7-methoxy-2-methyl-benzofuran (c, Scheme 7)

7-Methoxy-2-methyl-4-nitro-benzofuran (1.24 g, 6.0 mmol) was hydrogenated using Pd/C (10%, dry, 700 mg) and H₂ balloon in EtOH (30 mL) at r.t. for 2 h. The reaction mixture was filtered. Purification of the concentrated filtrate by column chromatography (EtOAc:Hexane=2.5:7.5) afforded 7-methoxy-2-methyl-benzofuran-4-ylamine as a brown oil (620 mg, 58%). 7-Methoxy-2-methyl-benzofuran-4-ylamine (620 mg, 3.5 mmol) was dissolved in CH₂Cl₂ (10 mL). TCDI (thiocarbodiimidazole, 686 mg, 3.9 mmol) was added to the solution and the reaction mixture was stirred at r.t. for 30 min. Silica gel was added to the reaction mixture and the solvent was removed under vacuum. Purification of the silica gel coated crude product by flash column chromatography (EtOAc:Hexane=2:8) afforded the title product as a pale yellow oil (630 mg, 82%).

4-Ethyl-6-[5-mercapto-4-(7-methoxy-2-methyl-benzofuran-4-yl)-4H-[1,2,4]triazol-3-yl]-benzene-1,3-diol 4-Isothiocyanato-7-methoxy-2-methyl-benzofuran (263 mg, 1.2 mmol) and 5-ethyl-2,4-dihydroxy-benzoic acid hydrazide (235 mg, 1,2 mmol) was dissolved in EtOH (8 mL) and the reaction mixture was heated at 70° C. for 30 min. After cooled to r. t., the precipitate was filtered and dried to give the intermediate as a white solid (490 mg, 98%). The intermediate (475 mg, 1.1 mmol) was charged into a resealable test tube and flushed with N₂. 2N—NaOH (degassed, 0.86 mL, 1.7 mmol) was added and the reaction mixture was heated at 110° C. for 1.5 h. After cooled to r. t., water was added and it was acidified with 1N—HCl. The precipitated solid was filtered. Purification of the crude product by flash column chromatography (MeOH: CH₂Cl₂=0.5:9.5) afforded the title product as a white solid (225 mg, 52%).
$^1$H NMR (300 MHz, DMSO-d6), δ (ppm): 9.50 (s, 1H), 9.31 (s, 1H), 6.90 (d, J=8.4 Hz, 1H), 6.83 (s, 1H), 6.79 (d, J=8.4 Hz, 1H), 6.30 (d, J=1.2 Hz, 1H), 6.15 (s, 1H), 3.88 (s, 3H), 2.36 (s, 3H), 2.26 (q, J=7.5 Hz, 2H), 0.89 (t, J=7.5 Hz, 3H). ESMS calcd. for $C_{20}H_{19}N_3O_4S_1$ 397.1. Found: 398.1 (M+1)⁺.

Example 20

4-(4-Benzothiazol-5-yl-5-mercapto-4H-[1,2,4]triazol-3-yl)-6-ethyl-benzene-1,3-diol (Compound 30)

Compound 30 was synthesized in a similar way to Example 19 from 6-aminobenzothiazole. ESMS calcd. for $C_{17}H_{14}N_4O_2S_2$ 370.1. Found: 371.1 (M+1)⁺.

Example 21

4-(4-Benzothiazol-6-yl-5-mercapto-4H-[1,2,4]triazol-3-yl)-6-ethyl-benzene-1,3-diol (Compound 31)

Compound 31 was synthesized in a similar way to Example 19 from 5-benzothiazoleamine. ESMS calcd. for $C_{17}H_{14}N_4O_2S_2$ 370.1. Found: 371.1 (M+1)⁺.

Example 22

4-Ethyl-6-(5-mercapto-4-quinolin-6-yl-4H-[1,2,4]triazol-3-yl)-benzene-1,3-diol (Compound 37)

Compound 37 was synthesized in a similar way to Example 19 from 6-aminoquinoline. ESMS calcd. for $C_{19}H_{16}N_4O_2S_1$ 364.1. Found: 365.1 (M+1)⁺.

Example 23

4-Isopropyl-6-[5-mercapto-4-(3-methyl-3H-benzoimidazol-5-yl)-4H-[1,2,4]triazol-3-yl]-benzene-1,3-diol (Compound 32)

Compound 32 was synthesized in a similar way to Example 19 from 3-methyl-3H-benzoimidazol-5-ylamine. ESMS calcd. for $C_{19}H_{19}N_5O_2S_1$ 381.1. Found: 382.1 (M+1)⁺.

Example 24

4-Isopropyl-6-[5-mercapto-4-(1-methyl-1H-benzoimidazol-5-yl)-4H-[1,2,4]triazol-3-yl]-benzene-1,3-diol (Compound 33)

Compound 33 was synthesized in a similar way to Example 19 from 1-methyl-1H-benzoimidazol-5-ylamine. ESMS calcd. for $C_{19}H_{19}N_5O_2S_1$ 381.1. Found: 382.1 (M+1)⁺.

Example 25

4-[4-(3H-Benzotriazol-5-yl)-5-mercapto-4H-[1,2,4]triazol-3-yl]-6-ethyl-benzene-1,3-diol (Compound 35)

Compound 35 was synthesized in a similar way to Example 19 from 3H-benzotriazol-5-ylamine. ESMS calcd. for $C_{16}H_{14}N_6O_2S_1$: 354.1. Found: 355.1 (M+1)⁺.

Example 26

4-Ethyl-6-[5-mercapto-4-(2-methyl-1H-benzoimidazol-5-yl)-4H-[1,2,4]triazol-3-yl]-benzene-1,3-diol (Compound 34)

Compound 34 was synthesized in a similar way to Example 19 from 2-methyl-1H-benzoimidazol-5-ylamine. ESMS calcd. for $C_{18}H_{17}N_5O_2S_1$: 367.1. Found: 368.1 (M+1)⁺.

Example 27

4-[4-(2,2-dioxo-2,3-dihydro-1H-2λ$^6$-benzo[c]thiophen-5-yl)-5-mercapto-4H-[1,2,4]triazol-3-yl]-6-ethyl-benzene-1,3-diol (Compound 1)

Compound 1 was synthesized in a similar way to Compound 4. ESMS calcd. for $C_{18}H_{17}N_3O_4S_2$ 403.1. Found: 404.1 (M+1)⁺.

Example 28

5-(3-(5-ethyl-2,4-dihydroxyphenyl)-5-mercapto-4H-1,2,4-triazol-4-yl)-1-methylindolin-2-one (Compound 2)

Compound 2 was synthesized in a similar way to Compound 4. ESMS calcd. for $C_{19}H_{18}N_4O_3S_1$ 382.1. Found: 383.1 (M+1)⁺.

Example 29

5-(3-(2,4-dihydroxy-5-isopropylphenyl)-5-mercapto-4H-1,2,4-triazol-4-yl)indolin-2-one (Compound 20)

Compound 20 was synthesized in a similar way to Compound 4. ESMS calcd. for $C_{18}H_{16}N_4O_3S_1$ 368.1. Found: 369.1 (M+1)⁺.

Example 30

4-isopropyl-6-(5-mercapto-4-(2-methylisoindolin-5-yl)-4H-1,2,4-triazol-3-yl)benzene-1,3-diol (Compound 7)

Compound 7 was synthesized in a similar way to Compound 4. ESMS calcd. for $C_{20}H_{22}N_4O_2S_1$ 382.2. Found: 383.2 (M+1)$^+$.

Example 31

4-(4-(2-ethylisoindolin-5-yl)-5-mercapto-4H-1,2,4-triazol-3-yl)-6-isopropylbenzene-1,3-diol (Compound 5)

Compound 5 was synthesized in a similar way to Compound 4. ESMS calcd. for $C_{21}H_{24}N_4O_2S_1$ 396.2. Found: 397.2 (M+1)$^+$.

Example 32

4-(4-(2,3-dihydro-1H-inden-4-yl)-5-mercapto-4H-1,2,4-triazol-3-yl)-6-isopropylbenzene-1,3-diol (Compound 12)

Compound 12 was synthesized in a similar way to Compound 4. ESMS calcd. for $C_{20}H_{21}N_3O_2S_1$ 367.1. Found: 368.1 (M+1)$^+$.

Example 33

4-isopropyl-6-(5-mercapto-4-(5,6,7,8-tetrahydronaphthalen-1-yl)-4H-1,2,4-triazol-3-yl)benzene-1,3-diol (Compound 3)

Compound 3 was synthesized in a similar way to Compound 4. ESMS calcd. for $C_{21}H_{23}N_3O_2Si$ 381.2. Found: 382.2 (M+1)$^+$.

Example 34

4-(5-hydroxy-4-(1-methylindolin-5-yl)-4H-1,2,4-triazol-3-yl)-6-isopropylbenzene-1,3-diol (Compound 28)

Compound 28 was synthesized in a similar way to Compound 19. ESMS calcd. for $C_{20}H_{22}N_4O_3$ 366.2. Found: 367.2 (M+1)$^+$.

Example 35

5-(3-hydroxy-5,6,7,8-tetrahydronaphthalen-2-yl)-4-(1-methylindolin-5-yl)-4H-1,2,4-triazol-3-ol (Compound 25)

Compound 25 was synthesized in a similar way to Compound 19. ESMS calcd. for $C_{21}H_{22}N_4O_2$ 362.2. Found: 363.2 (M+1)$^+$.

Example 36

1-(5-(3-(2,4-dihydroxy-5-isopropylphenyl)-5-hydroxy-4H-1,2,4-triazol-4-yl)isoindolin-2-yl)ethanone (Compound 23)

Compound 23 was synthesized in a similar way to Compound 19. ESMS calcd. for $C_{21}H_{22}N_4O_4$ 394.2. Found: 395.2 (M+1)$^+$.

Example 37

4-(5-hydroxy-4-(2-(2-methoxyethyl)isoindolin-5-yl)-4H-1,2,4-triazol-3-yl)-6-isopropylbenzene-1,3-diol (Compound 26)

Compound 26 was synthesized in a similar way to Compound 19. ESMS calcd. for $C_{22}H_{26}N_4O_4$ 410.2. Found: 411.2 (M+1)$^+$

Example 38

4-(2,3-Dihydro-1H-inden-5-yl)-3-(2,4-dihydroxy-5-isopropylphenyl)-1H-1,2,4-triazol-5(4H)-one (Compound 38)

$^1$H-NMR (400 MHz, DMSO-d$_6$) δ (ppm): 9.59 (s, 1H), 9.44 (s, 1H), 7.19 (d, J=8 Hz, 1H), 7.09 (s, 1H), 6.88 (d, J=8 Hz, 1H), 6.73 (s, 1H), 6.29 (s, 1H), 2.94 (q, J=8 Hz, 1H), 2.82 (m, 4H), 2.03 (m, 2H), 0.93 (d, J=8 Hz, 1H).
ESMS calcd for $C_{20}H_{21}N_3O_3$: 351.1. Found: 352.0 ((M+H)$^+$.

Example 39

(4-Aminocyclohexyl)(5-(3-(2,4-dihydroxy-5-isopropylphenyl)-5-hydroxy-4H-1,2,4-triazol-4-yl)indolin-1-yl)methanone hydrochloride (Compound 39)

$^1$H-NMR (300 MHz, DMSO-d$_6$) δ (ppm): 11.89 (s, 1H), 9.65 (s, 1H), 9.42 (s, 1H), 8.10-7.98 (m, 3H), 7.10 (s, 1H)), 6.91-6.85 (m, 2H), 6.28 (s, 1H), 4.17-4.10 (m, 2H), 3.32-3.12 (m, 1H), 3.10-2.97 (m, 4H), 2.78-2.67 (m, 1H), 1.9-1.63 (m, 8H), 0.99 (d, J=6.9 Hz, 6H)
ESMS calcd for $C_{26}H_{32}ClN_5O_4$: 513.21. Found: 478.4 (M+1)$^+$.

Example 40

2-(4-(Benzo[d][1,3]dioxol-5-yl)-5-mercapto-4H-1,2,4-triazol-3-yl)-4-methoxyphenol (Compound 40)

$^1$H-NMR (300 MHz, DMSO-d$_6$) δ (ppm): 9.43 (s, 1H), 6.90-6.81 (m, 4H), 6.69-6.65 (m, 2H, 6.05 (s, 2H), 3.62 (s, 3H).
ESMS calcd for $C_{16}H_{13}N_3O_4S$: 343.06. Found: 344.1 (M+H)$^+$.

Example 41

3-(5-(1-(4-fluorophenyl)propan-2-yl)-2,4-dihydroxyphenyl)-4-(2-(methoxymethoxy)-2,3-dihydro-1H-inden-5-yl)-1H-1,2,4-triazol-5(4H)-one (Compound 41)

ESMS calcd for $C_{28}H_{28}FN_3O_5$ 505.2. Found: 506.4 (M+H)$^+$.

Example 42

3-(5-(1-(4-Fluorophenyl)propan-2-yl)-2,4-dihydroxyphenyl)-4-(2-(pyrrolidin-1-yl)-2,3-dihydro-1H-inden-5-yl)-1H-1,2,4-triazol-5(4H)-one (Compound 42)

ESMS calcd for $C_{30}H_{31}FN_4O_3$ 514.2. Found: 515.5 (M+H)$^+$.

Example 43

3-(5-(4-fluorophenethyl)-2,4-dihydroxyphenyl)-4-(2-methoxy-2,3-dihydro-1H-inden-5-yl)-1H-1,2,4-triazole-5(4H)-thione (Compound 43)

ESMS calcd for $C_{27}H_{26}FN_3O_4$ 477.1. Found: 478.3 $(M+H)^+$.

Example 44

3-(2,4-Dihydroxy-5-isopropylphenyl)-4-(1-(methylsulfonyl)indolin-5-yl)-1H-1,2,4-triazol-5(4H)-one (Compound 44)

$^1$H-NMR (300 MHz, DMSO-$d_6$) δ (ppm): 11.90 (s, 1H), 9.60 (s, 1H), 9.42 (s, 1H), 7.14-7.18 (m, 2H), 6.95 (d, J=8.7 Hz, 1H), 6.81 (s, 1H), 6.24 (s, 1H), 3.93 (t, J=8.1 Hz, 2H), 3.31 (s, 3H), 2.95-3.07 (m, 4H), 0.96 (d, J=6.9 Hz, 1H).
ESMS calcd for $C_{20}H_{22}N_4O_5S$: 430.1. Found: 431.1 $(M+H)^+$.

Example 45

3-(2,4-Dihydroxy-5-isopropylphenyl)-4-(2-morpholino-2,3-dihydro-1H-inden-5-yl)-1H-1,2,4-triazol-5(4H)-one (Compound 45)

$^1$H-NMR (300 MHz, DMSO-$d_6$) δ (ppm): 11.89 (s, 1H), 9.59 (s, 1H), 9.42 (s, 1H), 7.16 (d, J=8.1 Hz, 1H), 7.06 (s, 1H), 6.88 (d, J=7.2 Hz, 1H), 6.77 (s, 1H), 6.23 (s, 1H), 3.59 (bs, 4H), 2.96-2.99 (m, 4H), 2.41-2.48 (m, 6H), 0.94 (d, J=6.6 Hz, 1H).
ESMS calcd for $C_{24}H_{28}N_4O_4$: 436.2. Found: 437.2 $(M+H)^+$.

Example 46

4-[2-(3,4-Dimethoxy-phenyl)-ethyl]-6-[5-hydroxy-4-(1-methyl-1H-indol-5-yl)-4H-[1,2,4]triazol-3-yl]-benzene-1,3-diol (Compound 1a)

$^1$H-NMR ($d_6$-DMSO): 11.80 (br, 1H); 9.58 (s, 1H); 9.39 (s, 1H); 7.40-7.34 (m, 3H); 6.88-6.83 (m, 2H); 6.81 (dd, 1H); 6.71 (m, 1H); 6.56 (dm, 1H); 6.41 (m, 1H); 6.20 (m, 1H); 3.77 (s, 3H); 3.64 (s, 6H); 2.63-2.46 (m, 4H); MS: expected ion=487.2; observed ion=487.1.

4-[2-(3,4-Dimethoxy-phenyl)-ethyl]-6-[5-hydroxy-4-(1-methyl-1H-indol-5-yl)-4H-[1,2,4]triazol-3-yl]-benzene-1,3-diol: A flask was charged with 5-{2,4-bis-benzyloxy-5-[2-(3,4-dimethoxy-phenyl)-vinyl]-phenyl}-4-(1-methyl-1H-indol-5-yl)-4H-[1,2,4]triazol-3-ol (164 mg; 0.25 mmol), 10% palladium on carbon (50 mg); methanol (20 mL), and place under an atmosphere of hydrogen. The reaction was stirred overnight, and then filtered through celite. The solvent was removed to give 4-[2-(3,4-Dimethoxy-phenyl)-ethyl]-6-[5-hydroxy-4-(1-methyl-1H-indol-5-yl)-4H-[1,2,4]triazol-3-yl]-benzene-1,3-diol (109 mg; 0.22 mmol).

5-{2,4-Bis-benzyloxy-5-[2-(3,4-dimethoxy-phenyl)-vinyl]-phenyl}-4-(1-methyl-1H-indol-5-yl)-4H-[1,2,4]triazol-3-ol: A flask was charged with 5-(2,4-Bis-benzyloxy-5-bromo-phenyl)-4-(1-methyl-1H-indol-5-yl)-4H-[1,2,4]triazol-3-ol (290 mg; 0.50 mmol), 3,4-dimethoxystyrene (98 mg; 0.60 mmol), tris(dibenzylideneacetone)dipalladium(0) (11 mg; 0.025 eq.), tris-tert-butylphosphine (10 mg; 0.10 eq.), diisopropylethylamine (77 mg; 0.60 mmol), and dimethylformamide (2 mL). The reaction was heated at 135° C. overnight, and then cooled. The solution was diluted with ethyl acetate (40 mL) and washed with water (3×40 mL). The organic layer was dried with sodium sulfate, evaporated, and purified by column chromatography to give 5-{2,4-bis-benzyloxy-5-[2-(3,4-dimethoxy-phenyl)-vinyl]-phenyl}-4-(1-methyl-1H-indol-5-yl)-4H-[1,2,4]triazol-3-ol (220 mg; 0.33 mmol).

5-(2,4-Bis-benzyloxy-5-bromo-phenyl)-4-(1-methyl-1H-indol-5-yl)-4H-[1,2,4]triazol-3-ol: A flask was charged with crude N-(1-methyl-1H-indol-5-yl)-N"-(2,4-bis-benzyloxy-5-bromo-benzylidene)-semicarbazide (<19 mmol), sodium hydroxide (3.8 g; >5 eq.); ethanol (300 mL) and potassium ferricyanide (18.8 g; >3 eq.). The reaction was heated at reflux overnight, and then cooled. To the reaction was added water (1 liter) and the precipitate was collected and washed with water (2×100 mL). After drying under vacuum, 5-(2,4-Bis-benzyloxy-5-bromo-phenyl)-4-(1-methyl-1H-indol-5-yl)-4H-[1,2,4]triazol-3-ol (9.5 g; 16.35 mmol) was collected.

N-(1-Methyl-1H-indol-5-yl)-N"-(2,4-bis-benzyloxy-5-bromo-benzylidene)-semicarbazide: A flask was charged with N-(1-methyl-1H-indol-5-yl)-semicarbazide (3.83 g; 18.77 mmol), 2,4-bis-benzyloxy-5-bromobenzaldehyde (7.46 g; 18.77 mmol) and ethanol (100 mL). The reaction was stirred at reflux for one hour, cooled, filtered, washed with ethanol (2×20 mL), and dried under vacuum to give N-(1-methyl-1H-indol-5-yl)-N"-(2,4-bis-benzyloxy-5-bromo-benzylidene)-semicarbazide, which was used crude in the next step.

2,4-bis-Benzyloxy-5-bromobenzaldehyde: A flask was charged with 2,4-bis-benzyloxy-5-bromobenzyl alcohol (10.5 g; 26 mmol), manganese dioxide (45 g; 0.520 mol), and dichloromethane (250 mL). The reaction was stirred at reflux for three days. The slurry was then filtered through celite, and evaporated to give 2,4-bis-benzyloxy-5-bromobenzaldehyde (7.46 g; 18.77 mmol).

2,4-bis-Benzyloxy-5-bromobenzyl alcohol: A flask was charged with 2,4-bis-benzyloxy-5-bromobenzoic acid (12.4 g; 30 mmol) and tetrahydrofuran (200 mL) and stirred under nitrogen until the solution was homogeneous. Lithium aluminum hydride (1.425 g; 1.25 eq.) was slowly added and the reaction was stirred until TLC indicated that the starting material had been consumed. The reaction was slowly quenched with a saturated solution of sodium sulfate (20 mL) and then filtered through celite. The solid was washed with an additional charge of tetrahydrofuran (100 mL), and the organic layers were evaporated to give 2,4-bis-benzyloxy-5-bromobenzyl alcohol (10.5 g; 26 mmol).

2,4-bis-Benzyloxy-5-bromobenzoic acid: A flask was charged with benzyl-2,4-bis-benzyloxy-5-bromobenzoate (25 g; 50 mmol); 5N aqueous sodium hydroxide (80 mL), and methanol (200 mL). The reaction was heated at reflux overnight, cooled, and acidified to pH=2 with concentrated hydrochloric acid. The solvent was reduced by half using evaporation, and the solid was filtered, washed with water (100 mL), dissolved in dichloromethane, dried with sodium sulfate, and evaporated to give 2,4-bis-benzyloxy-5-bromobenzoic acid (15.5 g; 37.5 mmol).

benzyl-2,4-bis-benzyloxy-5-bromobenzoate: A flask was charged with 5-bromo-2,4-dihydroxy-benzoic acid (7.5 g; 30 mmol), benzyl bromide (25.6 g; 150 mmol), potassium carbonate (21 g; 150 mmol), and dimethylformamide (100 mL). The reaction was heated at 70° C. overnight. The reaction was cooled, diluted with ethyl acetate (500 mL), washed with a one normal sodium chloride solution (3×500 mL), dried over sodium sulfate, and evaporated to give benzyl-2,4-bis-benzyloxy-5-bromobenzoate (11.0 g; 21.8 mmol).

Example 47

4-[5-hydroxy-4-(1-methyl-1H-indol-5-yl)-4H-[1,2,4]triazol-3-yl]-6-phenethyl-benzene-1,3-diol (Compound 2a)

$^1$H-NMR (d$_6$-DMSO): 11.81 (br, 1H); 9.60 (s, 1H); 9.40 (s, 1H); 7.43-7.36 (m, 3H); 7.35-7.03 (m, 5H); 6.88 (d, 1H); 6.80 (s, 1H); 6.42 (d, 1H); 6.22 (s, 1H); 3.80 (s, 3H); 3.64 (s, 6H); 2.62-2.47 (m, 4H); MS: expected ion=427.2; observed ion=427.1.

Compound 2a was synthesized in an analogous fashion to Compound 1a.

Example 48

4-[2-(2,6-Difluoro-phenyl)-ethyl]-6-[5-hydroxy-4-(1-methyl-1H-indol-5-yl)-4H-[1,2,4]triazol-3-yl]-benzene-1,3-diol (Compound 3a)

$^1$H-NMR (d$_6$-DMSO): 11.81 (br, 1H); 9.61 (s, 1H); 9.39 (s, 1H); 7.40-7.22 (m, 4H); 7.04-6.97 (m, 2H); 6.83 (dd, 1H); 6.70 (s, 1H); 6.41 (d, 1H); 6.18 (s, 1H); 3.78 (s, 3H); 2.69 (t, 2H); 2.55 (t, 2H); MS: expected ion=463.2; observed ion=463.1.

Compound 3a was synthesized in an analogous fashion to Compound 1a.

Example 49

4-(2-{2,4-Dihydroxy-5-[5-hydroxy-4-(1-methyl-1H-indol-5-yl)-4H-[1,2,4]triazol-3-yl]-phenyl}-ethyl)-benzonitrile (Compound 4a)

$^1$H-NMR (d$_6$-DMSO): 11.81 (br, 1H); 9.60 (s, 1H); 9.40 (s, 1H); 7.68 (d, 2H); 7.41-7.36 (m, 3H); 7.24 (d, 2H); 6.86-6.81 (m, 2H); 6.42 (d, 1H); 6.19 (s, 1H); 3.79 (s, 3H); 2.64 (t, 2H); 2.57 (t, 2H); MS: expected ion=452.2; observed ion=452.1.

Compound 4a was synthesized in an analogous fashion to Compound 1a.

Example 50

4-[5-Hydroxy-4-(1-methyl-1H-indol-5-yl)-4H-[1,2,4]triazol-3-yl]-6-[2-(3,4,5-trimethoxy-phenyl)-ethyl]-benzene-1,3-diol (Compound 5a)

$^1$H-NMR (MeOD): 7.58 (d, 2H); 7.41 (d, 1H); 7.14 (d, 1H); 7.09 (dd, 1H); 6.56 (d, 1H); 6.40 s, 1H); 6.08 (s, 2H); 3.88-3.77 (m, 12H); 2.35 (m, 2H); 2.09 (m, 2H); MS: expected ion=517.2; observed ion=517.2.

Compound 5a was synthesized in an analogous fashion to Compound 1a.

Example 51

4-[5-Hydroxy-4-(1-methyl-1H-indol-5-yl)-4H-[1,2,4]triazol-3-yl]-6-(2-pentafluorophenyl-ethyl)-benzene-1,3-diol (Compound 6a)

$^1$H-NMR (MeOD): 7.48 (d, 1H); 7.41 (d, 1H); 7.09 (d, 1H); 7.04 (dd, 1H); 6.44 (d, 1H); 6.32 (s, 1H); 6.18 (s, 1H); 3.80 (s, 3H); 2.29 (m, 2H); 2.19 (dd, 2H); MS: expected ion=517.2; observed ion=517.1.

Compound 6a was synthesized in an analogous fashion to Compound 1a.

Example 52

4-(2-Benzo[1,3]dioxol-5-yl-1-methyl-ethyl)-6-[5-hydroxy-4-(1-methyl-1H-indol-5-yl)-4H-[1,2,4]triazol-3-yl]-benzene-1,3-diol (Compound 7a)

$^1$H-NMR (MeOD): 7.53 (m, 1H); 7.41 (d, 1H); 7.14 (d, 1H); 7.08 (dd, 1H); 6.57 (d, 1H); 6.49 (d, 1H); 6.30 (d, 2H); 6.18 (m, 1H); 5.69 (s, 1H); 5.31 (s, 1H); 4.67 (s, 1H); 3.79 (s, 3H); 2.83 (m, 1H); 2.19 (dd, 1H); 1.56 (dd, 1H); 0.34 (d, 3H); MS: expected ion=485.2; observed ion=485.2.

Compound 7a was synthesized in an analogous fashion to Compound 1a.

Example 53

4-[5-Hydroxy-4-(1-methyl-1H-indol-5-yl)-4H-[1,2,4]triazol-3-yl]-6-[2-(4-methoxy-phenyl)-ethyl]-benzene-1,3-diol (Compound 8a)

$^1$H-NMR (MeOD): 7.50-7.44 (m, 2H); 7.23 (d, 1H); 7.01 (dd, 1H); 6.73 (s, 4H); 6.53 (d, 1H); 6.43 (s, 1H); 6.25 (s, 1H); 3.77 (s, 1H); 3.73 (s, 1H); 2.36 (m, 2H); 2.18 (m, 2H); MS: expected ion=457.2; observed ion=457.1.

Compound 8a was synthesized in an analogous fashion to Compound 1a.

Example 54

4-[5-Hydroxy-4-(1-methyl-1H-indol-5-yl)-4H-[1,2,4]triazol-3-yl]-6-[2-(3-methoxy-phenyl)-ethyl]-benzene-1,3-diol (Compound 9a)

$^1$H-NMR (MeOD): 7.51-7.43 (m, 2H); 7.22 (m, 1H); 7.12-6.98 (m, 3H); 6.66 (m, 1H); 6.43-6.37 (m, 3H); 6.28 (s, 1H); 3.77 (s, 1H); 3.72 (s, 1H); 2.37 (m, 2H); 2.20 (m, 2H); MS: expected ion=457.2; observed ion=457.1.

Compound 9a was synthesized in an analogous fashion to Compound 1a.

Example 55

4-[5-Hydroxy-4-(1-methyl-1H-indol-5-yl)-4H-[1,2,4]triazol-3-yl]-6-(1-methyl-2-phenyl-ethyl)-benzene-1,3-diol (Compound 10a)

$^1$H-NMR (MeOD): 7.59 (d, 1H); 7.46 (d, 1H); 7.22-6.96 (m, 5H); 6.77 (dd, 1H); 6.56 (d, 1H); 6.38-6.34 (m, 2H); 3.79 (s, 3H); 3.00 (m, 1H); 2.43 (dd, 1H); 1.67 (dd, 1H); 0.40 (d, 3H); MS: expected ion=441.2; observed ion=441.1.

Compound 10a was synthesized in an analogous fashion to Compound 1a.

Example 56

4-(4-chlorophenethyl)-6-(5-hydroxy-4-(1-methyl-1H-indol-5-yl)-4H-1,2,4-triazol-3-yl)benzene-1,3-diol (Compound 38a)

Compound 38a was synthesized in an analogous fashion to Compound 1a. MS: expected ion=461.2; observed ion=461.2.

Example 57

4-(4-fluorophenethyl)-6-(5-hydroxy-4-(1-methyl-1H-indol-5-yl)-4H-1,2,4-triazol-3-yl)benzene-1,3-diol (Compound 39a)

Compound 39a was synthesized in an analogous fashion to Compound 1a. MS: expected ion=459.2; observed ion=459.3.

Example 58

4-(2,4-difluorophenethyl)-6-(5-hydroxy-4-(1-methyl-1H-indol-5-yl)-4H-1,2,4-triazol-3-yl)benzene-1,3-diol (Compound 40a)

Compound 40a was synthesized in an analogous fashion to Compound 1a. MS: expected ion=463.2; observed ion=463.3.

Example 59

4-(2,5-difluorophenethyl)-6-(5-hydroxy-4-(1-methyl-1H-indol-5-yl)-4H-1,2,4-triazol-3-yl)benzene-1,3-diol (Compound 41a)

Compound 41a was synthesized in an analogous fashion to Compound 1a. MS: expected ion=463.2; observed ion=463.3.

Example 60

4-(3,5-difluorophenethyl)-6-(5-hydroxy-4-(1-methyl-1H-indol-5-yl)-4H-1,2,4-triazol-3-yl)benzene-1,3-diol (Compound 42a)

Compound 42a was synthesized in an analogous fashion to Compound 1a. MS: expected ion=463.2; observed ion=463.3.

Example 61

5-(5-Mercapto-4-naphthalen-1-yl-4H-[1,2,4]triazol-3-yl)-biphenyl-2,4-diol (Compound 35a)

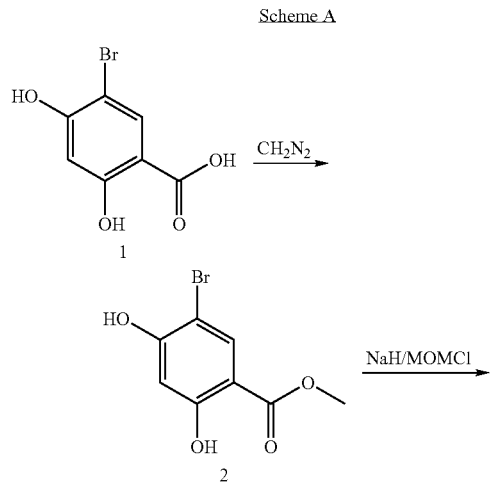

Scheme A

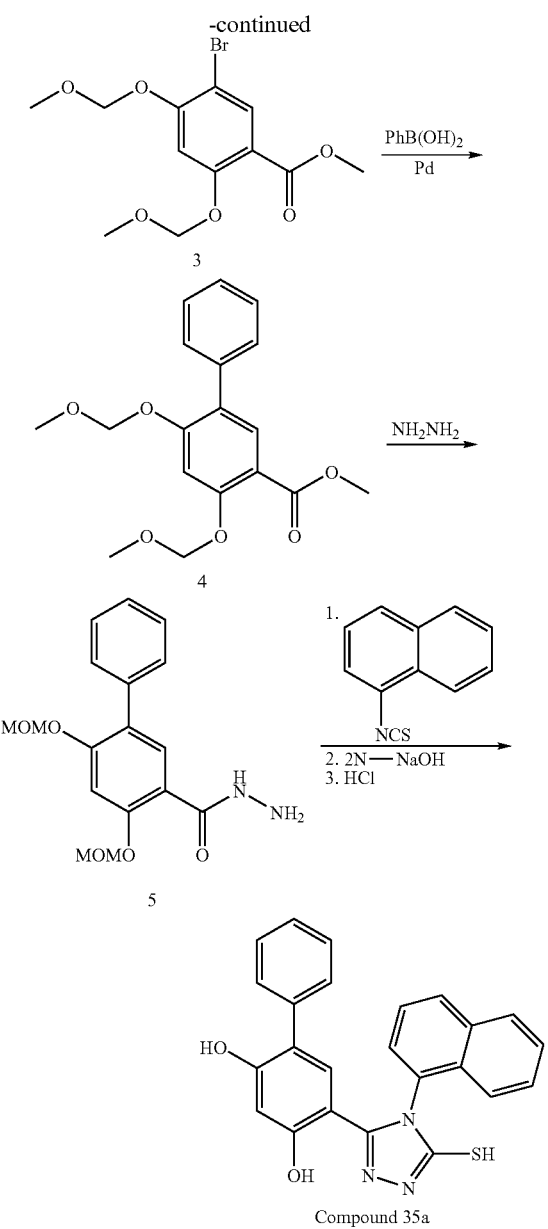

5-Bromo-2,4-dihydroxy-benzoic acid methyl ester (2)

5-Bromo-2,4-dihydroxy-benzoic acid monohydrate (1) (20.0 g, 80 mmol) was charged into a 1000 ml round bottom flask and dissolved in THF (200 ml). The solution was cooled down to 0° C. in an ice-water bath. At the same time, KOH (30.0 g, excess)/water (200 mL) solution was prepared in a 500 ml r.b.f in an ice-water bath. Ether (200 mL) was added to the KOH/water solution followed by N-nitroso-N-methyl urea (71%, 13.0 g, 128 mmol) while stirring vigorously. The generated yellow ether layer was slowly transferred into the THF solution of 1. Additional ether (100 mL) was added to the KOH/water solution and the yellow ether layer was transferred into THF solution of 1. (It was repeated two more times). The reaction was monitored by TLC analysis. (If 1 still remains in the reaction mixture, additional N-nitroso-N-methyl urea can be used). The reaction was quenched by adding acetic acid (ca.1 mL). The reaction mixture was washed with water (150 mL×2) and brine (150 mL), dried over MgSO$_4$, filtered and concentrated. Recrystallization of the concentrated crude product from hot EtOAc/hexane afforded the product as a pale yellow solid (10.5 g, 53%). Recrystallization of the concentrated mother liquid gave additional product (5.5 g, 28%). The products were combined to give 16.0 g (81% total yield) of the title product.

5-Bromo-2,4-bis-methoxymethoxy-benzoic acid methyl ester (3)

To a suspension of NaH (60% suspension in mineral oil, 6 g, 150 mmol) in DMF (60 mL) was added 5-bromo-2,4-dihydroxy-benzoic acid methyl ester (2) (12.4 g, 50 mmol) in DMF (100 mL) slowly at 0° C. It was stirred at 0° C. for 10 min and then at room temperature for 30 min. MOMCI (11.4 mL, 150 mmol) was slowly added to the reaction mixture at 0° C., and the reaction mixture was stirred at 0° C. for 30 min and then stirred at room temperature overnight. After poured into ice-water in an ice-water bath, the reaction mixture was extracted with EtOAc (100 mL×3). The combined organic layers were washed with water, and brine, and dried over $MgSO_4$. Purification of the concentrated crude product by column chromatography (EtOAc:Hexane=2:8) afforded the title product as a pale yellow oil (15.8 g, 94%), which became a solid once stored in fridge (Solid is easy to handle).

4,6-Bis-methoxymethoxy-biphenyl-3-carboxylic acid methyl ester (4)

A Schlenk tube was charged with 5-bromo-2,4-bis-methoxymethoxy-benzoic acid methyl ester (3) (503 mg, 1.5 mmol), phenylboronic acid (272 mg, 2.3 mmol), $Pd(OAc)_2$ (22 mg, 0.1 mmol), and 2-dicyclohexylphosphino-2',6'-dimethoxybiphenyl (82 mg, 0.2 mmol), $K_3PO_4 \cdot H_2O$ (4.70 g, 34.0 mmol). The reaction tube was evacuated and backfilled with $N_2$ (×3). Toluene (10 mL, anhydrous and sure seal bottle from Aldrich) was added. The reaction was stirred at room temperature for 10 min and heated at 105° C. (preheated oil bath) for 24 h. The reaction mixture was allowed to cool to room temperature and diluted with EtOAc (50 mL) and water (70 mL). The aqueous phase was extracted with EtOAc (40 mL×3) and the combined organic layers were washed with water and brine and dried over $MgSO_4$. The purification of the concentrated crude product by column chromatography (25% EtOAc in Hexane) afforded the title product as colorless oil (460 mg, 93%).

4,6-Bis-methoxymethoxy-biphenyl-3-carboxylic acid hydrazide (5)

2,4-Dihydroxy-5-isopropyl-benzoic acid methyl ester (4, 460 mg, 1.35 mmol) was dissolved in dioxane. Hydrazine (excess) was added and the reaction mixture was heated at 100° C. until all compound 5 was consumed. After the reaction mixture was allowed to cool to room temperature, solvent and excess $NH_2NH_2$ were removed under vacuum (and then high vacuum while heating in water bath). The crude product was dissolved in hot EtOH and dried under high vacuum in hot water bath. This was repeated until all hydrazine was removed from the crude product 7 (hydrazine is detectable on the bottom line on TLC once stained in PMA). Recrystallization of the crude product gave 5.

5-(5-Mercapto-4-naphthalen-1-yl-4H-[1,2,4]triazol-3-yl)-biphenyl-2,4-diol (Compound 35a)

5 (301 mg, 1.0 mmol) and 1-isothiocyanato-naphthalene (200 mg, 1.0 mmol) was stirred in EtOH (10 mL) at 70° C. for 30 min and the reaction mixture was cooled to room temperature. Precipitated solid was filtered and dried to give the intermediate (412 mg, 80%)

To the intermediate (400 mg, 0.77 mmol) was added degassed 2N—NaOH (0.7 mL, 0.35 mmol) and the reaction mixture was stirred at 110° C. for 2 h. After cooled down to room temperature, the reaction mixture was acidified with 1N—HCl. The white precipitate was filtered and dried to give 5-(4,6-Bis-methoxymethoxy-biphenyl-3-yl)-4-naphthalen-1-yl-4H-[1,2,4]triazole-3-thiol as a white solid (250 mg, 65%). 5-(4,6-Bis-methoxymethoxy-biphenyl-3-yl)-4-naphthalen-1-yl-4H-[1,2,4]triazole-3-thiol (190 mg, 0.38 mmol) was dissolved in MeOH (7 mL) and 6N—HCl (0.5 mL) was added to the solution. The reaction mixture was heated at 50° C. for 2 h. After MeOH was removed under vacuum, the reaction mixture was extracted with EtOAc (20 mL×3). The combined organic layers were washed with water and brine and dried over $MgSO_4$. The purification of the concentrated crude product by column chromatography (MeOH 10% in $CH_2Cl_2$) afforded the title product as white solid (120 mg, 77%).

ESMS calcd. for $C_{24}H_{17}N_3O_2S_1$ 411.1. Found: 412.1 $(M+1)^+$.

Example 62

4-(furan-2-yl)-6-(5-mercapto-4-(naphthalen-1-yl)-4H-1,2,4-triazol-3-yl)benzene-1,3-diol (Compound 36a)

Compound 36a was synthesized in a similar way to Compound 35a. ESMS calcd. for $C_{22}H_{15}N_3O_3S_1$ 401.1. Found: 402.1 $(M+1)^+$.

Example 63

4-(5-hydroxy-4-(1-methyl-1H-indol-5-yl)-4H-1,2,4-triazol-3-yl)-6-(1H-pyrazol-1-yl)benzene-1,3-diol (Compound 37a)

Compound 37a was synthesized in a similar way to Compound 1a. ESMS calcd. for $C_{20}H_{16}N_6O_3$ 388.1. Found: 389.1 $(M+1)^+$.

Example 64

3-(4-(2-Aminoethoxy)-2-hydroxyphenyl)-4-(1-methyl-1H-indol-5-yl)-1H-1,2,4-triazol-5(4H)-one (Compound 1b)

Scheme 8

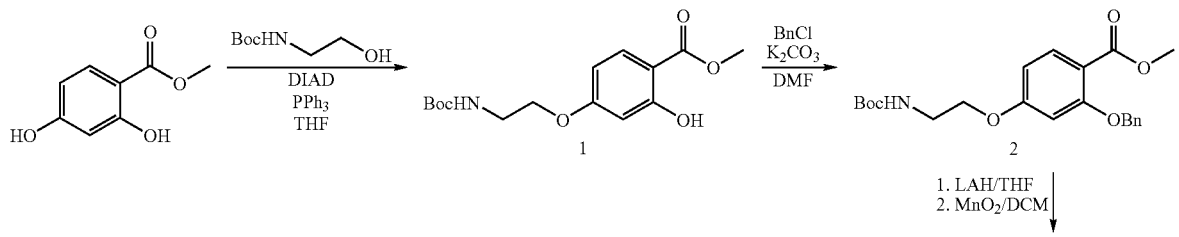

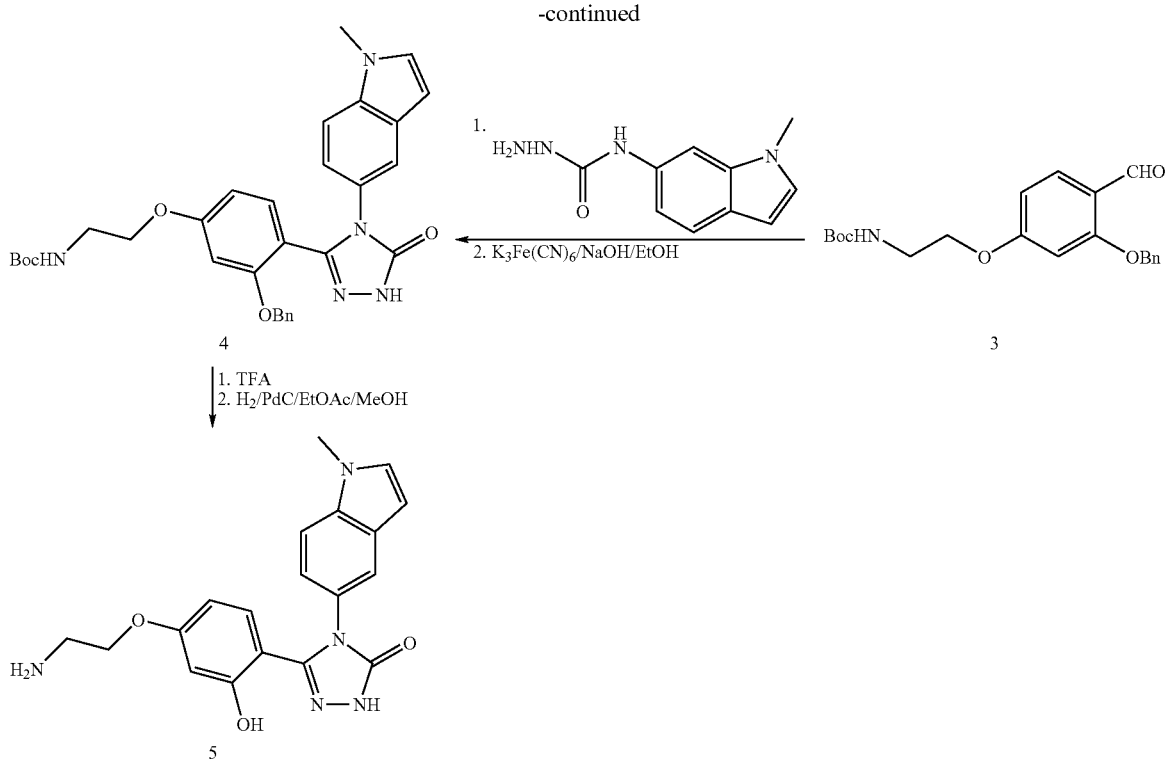

Methyl 4-(2-(tert-butoxycarbonylamino)ethoxy)-2-hydroxybenzoate (1)

Commercially available starting materials 2,4-dihydroxybenzoate (1.04 g, 6.21 mmol), tert-butyl 2-hydroxyethylcarbamate (1.10 g, 6.82 mmol) and triphenylphosphine (1.8 g, 6.86 mmol) were dissolved in anhydrous THF (50 mL). To this solution was added diisopropyl azodicarboxylate (1.3 mL, 6.82 mmol) and the reaction was stirred for 18 h at room temperature. Water (200 mL) and ethyl acetate (200 mL) were added; the organic layer was separated, washed with water (2×200 mL), dried over MgSO₄, filtered and evaporated to dryness. The crude product was purified by silcagel column chromatography eluting with a gradient from 10%-50% ethyl acetate in hexane. Fractions containing the pure desired product were combined and solvent was removed under reduced pressure to produce a white solid (1.09 g, 56%).

Methyl 2-(benzyloxy)-4-(2-(tert-butoxycarbonylamino)ethoxy)benzoate (2)

To a solution of (1) (1.07 g, 3.44 mmol) and benzyl chloride (0.43 mL, 3.78 mmol) in THF (100 mL) was added potassium carbonate (1.57 g, 11 mmol), then the reaction was heated to 90° C. for 18 h. After cooling to room temperature, water (200 mL) and ethyl acetate (200 mL) were added; the organic layer was separated and washed with water (2×200 mL), dried over MgSO₄, filtered and evaporated to dryness under reduced pressure. The crude product was purified by silcagel column chromatography eluting with a gradient from 10%-50% ethyl acetate in hexane. Fractions containing the pure desired product were combined and solvent was removed under reduced pressure to produce a colorless oil (890 mg, 64%).

Tert-Butyl 2-(3-(benzyloxy)-4-formylphenoxy)ethylcarbamate (3)

A solution of (2) (900 mg, 2.24 mmol) in THF (50 mL) was cooled to 5° C. in an ice bath. A solution of LAH (3.4 mL of a 2M solution in THF, 6.72 mmol) was added then the reaction was allowed to warm to room temperature and stirred for a total duration of 18 h. After cooling to room temperature, water (100 mL) and ethyl acetate (100 mL) were added; the organic layer was separated and washed with water (2×100 mL), dried over MgSO₄, filtered and evaporated to dryness under reduced pressure to produce the crude product which was used without further purification in the next step.

The crude product from above was immediately redissolved in dichloromethane (50 mL) and MnO₂ (900 mg) was added. After stirring for 5 h, excess MnO₂ was removed by filtration through a silcagel plug and solvent was removed under reduced pressure. The crude product was purified by silcagel column chromatography, eluting with a gradient from 10%-50% ethyl acetate in hexane. Fractions containing the pure desired product were combined and solvent was removed under reduced pressure to produce a colorless oil (490 mg, 59% over two steps).

tert-Butyl 2-(3-(benzyloxy)-4-(4-(1-methyl-1H-indol-5-yl)-5-oxo-4,5-dihydro-1H-1,2,4-triazol-3-yl)phenoxy)ethylcarbamate (4)

A combination of N-(1-methyl-1H-indol-6-yl)hydrazinecarboxamide (270 mg, 1.35 mmol) and (3) (500 mg, 1.35 mmol) in ethanol (20 mL) was heated to 80° C. for 1 h. Then excess solvent was removed under reduced pressure and the crude product was used in the next step without further purification.

The crude product from above was suspended in ethanol (20 mL) and solid NaOH (170 mg, 4.25 mmol) and potassium ferrocyanide powder (900 mg, 2.73 mmol) were added. The entire mixture was heated to reflux for 18 h. After cooling to room temperature, water (100 mL) and ethyl acetate (100 mL) were added; the organic layer was separated and washed with water (2×100 mL), dried over MgSO$_4$, filtered and evaporated to dryness under reduced pressure to produce the crude product. Further purification by silcagel column chromatography, eluting with a gradient from 10%-50% ethyl acetate in hexane produced the desired product as a white solid (380 mg, 77%).

3-(4-(2-Aminoethoxy)-2-hydroxyphenyl)-4-(1-methyl-H-indol-5-yl)-1H-1,2,4-triazol-5(4H)-one (5)

The BOC-protected amine (4) (100 mg, 1.8 mmol) was dissolved in TFA (5 mL) and dichloromethane (5 mL) and stirred at room temperature for 18 h. Solvents were removed under reduced pressure to produce a white solid which was used directly in the next step.

The crude product from above was dissolved in EtOAc (5 ml) and MeOH (5 mL). To this solution was added palladium (50 mg, 10% on activated carbon) and the reaction was stirred under a hydrogen atmosphere (balloon) for 18 h. Excess palladium was removed by filtration through a silcagel plug and removal of the solvent under reduced pressure produced the desired product as a white solid (20 mg, 30%).

$^1$H NMR (300 MHz, DMSO-d6), δ (ppm): 11.89 (s, 1H), 9.94 (s, 1H), 9.54 (bs, 1H), 7.33-7.36 (m, 3H), 7.13 (d, J=8.7 Hz, 1H), 6.88 (d, J=8.7 Hz, 1H), 6.29-6.37 (m, 3H), 4.01 (m, 2H), 3.73 (s, 3H), 3.13 (m, 2H).

ESMS calcd. for C$_{19}$H$_{19}$N$_5$O$_3$ 365.15. Found: 366.1 (M+1)$^+$.

Example 65

3-(2-hydroxy-4-(2-hydroxyethyl)phenyl)-4-(1-methyl-1H-indol-5-yl)-1H-1,2,4-triazol-5(4H)-one (Compound 8b)

3-(2-(tert-Butyldimethylsilyloxy)ethyl)phenol (1)

A solution of 3-(2-hydroxyethyl)phenol (7.55 g, 0.0546 mol), TBSCI (8.22 g, 0.0546 mol) and imidazole (3.71 g, 0.0546 mol) in DMF was stirred for 18 h at room temperature. Water (200 mL) and ethyl acetate (200 mL) were added; the organic layer was separated and washed with water (2×100 mL), dried over MgSO$_4$, filtered and evaporated to dryness under reduced pressure to produce the desired product as a clear oil which was used without further purification.

4-(2-(tert-butyldimethylsilyloxy)ethyl)-2-hydroxybenzaldehyde (2)

To a solution of (1) (538 mg, 2.13 mmol) in THF (20 ml) and triethylamine (3 ml) cooled in an ice bath was added ethyl magnesium bromide (2.13 mL of a 1M solution, 2.13 mmol). The reaction was allowed to warm to room temperature and stirred for a total duration of 1 h. Solvent was removed under reduced pressure then toluene (50 ml) was added which was subsequently removed under reduced pressure. This procedure was repeated two times. After the third addition of toluene, paraformaldehyde (160 mg, 5.32 mmol) was added and the reaction was heated to reflux for 18 h. After cooling to room temperature, water (100 mL) and ethyl acetate (100 mL) were added; the organic layer was separated and washed with water (2×100 mL), dried over MgSO$_4$, filtered and evaporated to dryness under reduced pressure to produce the crude product as a yellow oil. This crude product was purified by silcagel column chromatography, eluting with a gradient from 10%-50% ethyl acetate in hexane producing the final product as a yellow oil (100 mg, 17%).

2-(benzyloxy)-4-(2-(tert-butyldimethylsilyloxy) ethyl)benzaldehyde (3)

A combination of (2) (14 g, 0.050 mol), benzyl chloride (6.3 mL, 0.055 mol) and potassium carbonate (20.7 g, 0.15 mol) was heated to 100° C. for 3 h. After cooling to room temperature, water (200 mL) and ethyl acetate (400 mL) were added; the organic layer was separated and washed with water (5×200 mL), dried over MgSO$_4$, filtered and evaporated to

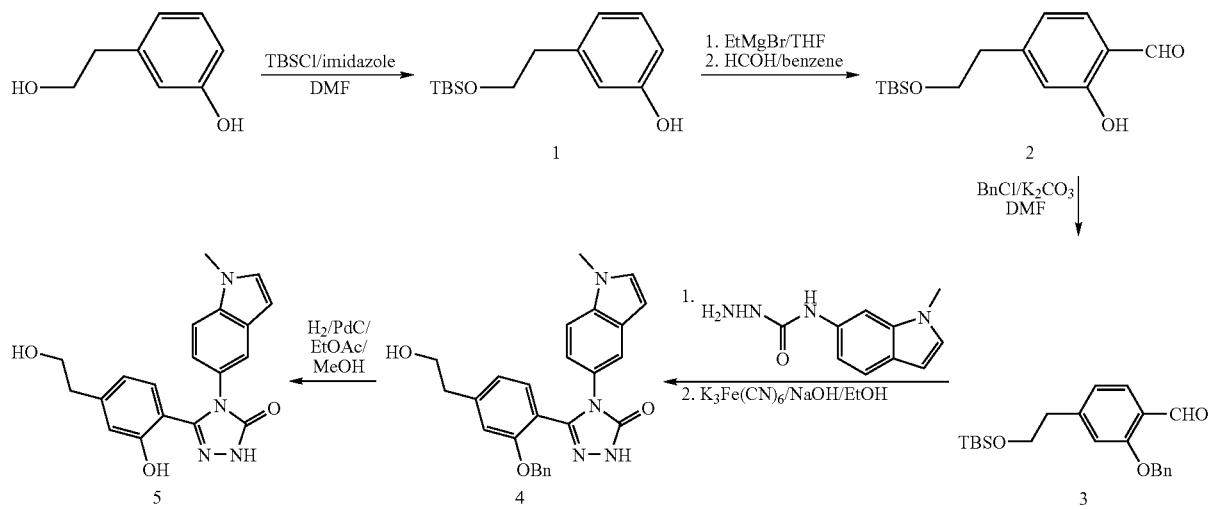

Scheme 9 dryness under reduced pressure to produce the crude product as a yellow oil. This was used without further purification in the next step.

3-(2-(Benzyloxy)-4-(2-hydroxyethyl)phenyl)-4-(1-methyl-1H-indol-5-yl)-1H-1,2,4-triazol-5(4H)-one (4)

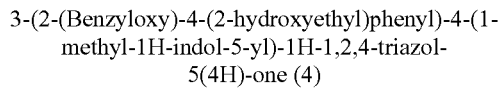

The aldehyde (3) (1.1 g, 2.57 mmol) and N-(1-methyl-1H-indol-6-yl)hydrazinecarboxamide (0.61 g, 2.57 mmol) were suspended in ethanol. Heating to 80° C. produced a clear solution which was maintained at this temperature for 1 h. Solvent was removed under reduced pressure and the crude product was purified by silcagel column chromatography, eluting with a gradient from 50%-100% ethyl acetate in hexane. The pure desired product was obtained as a white solid (690 mg, 48%).

The product from the previous step (690 mg, 1.23 mmol) was combined with NaOH (150 mg, 3.75 mmol) and potassium ferrocyanide powder (810 mg, 2.46 mmol) in ethanol. This combination was heated to 80° C. for 18 h. After cooling to room temperature, water (100 mL) and ethyl acetate (200 mL) were added. The organic layer was separated, washed with water (3×100 mL), dried over $MgSO_4$, filtered and evaporated to dryness under reduced pressure to produce the crude product as a brown solid. This crude product was purified by silcagel column chromatography, eluting with a gradient from 50%-100% ethyl acetate in hexane then 10% MeOH in dichloromethane. Fractions containing the pure desired product were combined to produce a white solid (200 mg, 37%).

3-(2-hydroxy-4-(2-hydroxyethyl)phenyl)-4-(1-methyl-1H-indol-5-yl)-1H-1,2,4-triazol-5(4H)-one (5)

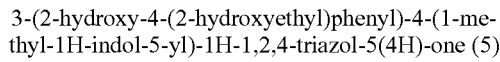

The protected triazolone (4) (150 mg, 0.34 mmol) was dissolved in EtOAc (2 ml) and MeOH (2 mL) then palladium (100 mg, 10% on activated carbon) was added. The reaction was stirred under an atmosphere of hydrogen (balloon) at room temperature for 18 h. Filtration through a silcagel plug followed by removal of solvent under reduced pressure produced the desired product as a white solid (100 mg, 83%).

$^1$H NMR (300 MHz, DMSO-d6), δ (ppm): 11.90 (s, 1H), 9.60 (s, 1H), 7.33-7.36 (m, 3H), 7.08 (d, J=8.4 Hz, 1H), 6.90 (d, J=8.7 Hz, 1H), 6.54-6.60 (m, 2H), 6.37-6.38 (m, 1H), 4.59-4.61 (m, 1H), 3.74 (s, 3H), 3.48-3.55 (m, 2H), 2.56 (t, J=6 Hz, 2H).

ESMS calcd. for $C_{19}H_{18}N_4O_3$ 350.14. Found: 351.1 $(M+1)^+$.

Example A

Inhibition of Hsp90

Hsp90 protein is obtained from Stressgen (Cat#SPP-770). Assay buffer: 100 mM Tris-HCl, Ph7.4, 20 mM KCl, 6 mM $MgCl_2$. Malachite green (0.0812% w/v) (M9636) and polyvinyl alcohol USP (2.32% w/v) (P1097) are obtained from Sigma. A Malachite Green Assay (see Methods Mol Med, 2003, 85:149 for method details) is used for examination of ATPase activity of Hsp90 protein. Briefly, Hsp90 protein in assay buffer (100 mM Tris-HCl, Ph7.4, 20 mM KCl, 6 mM $MgCl_2$) is mixed with ATP alone (negative control) or in the presence of Geldanamycin (a positive control) or a compound of the invention in a 96-well plate. Malachite green reagent is added to the reaction. The mixtures are incubated at 37° C. for 4 hours and sodium citrate buffer (34% w/v sodium citrate) is added to the reaction. The plate is read by an ELISA reader with an absorbance at 620 nm.

Example B

Degradation of Hsp90 Client Proteins via Inhibition of Hsp90 Activity

A. Cells and Cell Culture

Human high-Her2 breast carcinoma BT474 (HTB-20), SK-BR-3 (HTB-30) and MCF-7 breast carcinoma (HTB-22) from American Type Culture Collection, VA, USA were grown in Dulbecco's modified Eagle's medium with 4 mM L-glutamine and antibiotics (100 IU/ml penicillin and 100 ug/ml streptomycine; GibcoBRL). To obtain exponential cell growth, cells were trypsinized, counted and seeded at a cell density of $0.5 \times 10^6$ cells/ml regularly, every 3 days. All experiments were performed on day 1 after cell passage.

B. Degradation of Her2 in Cells After Treatment with a Compound of the Invention 1. Method 1

BT-474 cells are treated with 0.5 µM, 2 µM, or 5 µM of 17AAG (a positive control) or 0.5 µM, 2 µM, or 5 µM of a compound of the invention overnight in DMEM medium. After treatment, each cytoplasmic sample is prepared from $1 \times 10^6$ cells by incubation of cell lysis buffer (#9803, cell Signaling Technology) on ice for 10 minutes. The resulting supernatant used as the cytosol fractions is dissolved with sample buffer for SDS-PAGE and run on a SDS-PAGE gel, blotted onto a nitrocellulose membrane by using semi-dry transfer. Non-specific binding to nitrocellulose is blocked with 5% skim milk in TBS with 0.5% Tween at room temperature for 1 hour, then probed with anti-Her2/ErB2 mAb (rabbit IgG, #2242, Cell Signaling) and anti-Tubulin (T9026, Sigma) as housekeeping control protein. HRP-conjugated goat anti-rabbit IgG (H+L) and HRP-conjugated horse anti-mouse IgG (H+L) are used as secondary Ab (#7074, #7076, Cell Signaling) and LumiGLO reagent, 20× Peroxide (#7003, Cell Signaling) is used for visualization.

Her2, an Hsp90 client protein, is expected to be degraded when cells are treated with compounds of the invention. 0.5 µM of 17AAG, a known Hsp90 inhibitor which is used as a positive control, causes partial degradation of Her2.

2. Method 2

MV-4-11 cells (20,000 cells/well) were cultured in 96-well plates and maintained at 37° C. for several hours. The cells were treated with a compound of the invention or 17AAG (a positive control) at various concentrations and incubated at 37° C. for 72 hours. Cell survival was measured with Cell Counting Kit-8 (Dojindo Laboratories, Cat. # CK04).

The $IC_{50}$ range for Her2 degradation by compounds of the invention are lised below in Table 4.

Tables 4-6: $IC_{50}$ range of compounds of the invention for inhibition of Hsp90

TABLE 4

| $IC_{50}$ | Compound Number |
|---|---|
| <30 nM | 17, 19, 21 |
| <75 nM | 6, 8, 9, 10, 18, 22, 24, 26, 27, 29, 38, 45 |
| <300 nM | 3, 4, 5, 7, 13, 15, 16, 33, 41, 42, 44 |
| <500 nM | 23 |
| <1 µM | 39 |
| >1 µM | 1, 2, 30, 31, 32, 34, 35, 43 |

TABLE 5

| IC$_{50}$ (nM) | Compound Number |
|---|---|
| <175 | 3a, 7a, 10a, 11a, 38a, 39a, |
| <500 | 1a, 4a, 41a, |
| <775 | 2a, 6a, 40a, 42a, |
| >1000 | 5a, 8a, 9a, |

TABLE 6

| IC$_{50}$ (μM) | Compound Number |
|---|---|
| >10 | 1b, 8b, 9b |

C.5 Fluorescent Staining of Her2 on the Surface of Cells Treated with a Compound of the Invention After treatment with a compound of the invention, cells are washed twice with 1×PBS/1% FBS, and then stained with anti-Her2-FITC (#340553, BD) for 30 min at 4° C. Cells are then washed three times in FACS buffer before the fixation in 0.5 ml 1% paraformadehyrede. Data is acquired on a FACSCalibur system. Isotype-matched controls are used to establish the non-specific staining of samples and to set the fluorescent markers. A total 10,000 events were recorded from each sample. Data are analysed by using CellQuest software (BD Biosciences).

D. Apoptosis Analysis

After treatment with the compounds of the invention, cells are washed once with 1×PBS/1% FBS, and then stained in binding buffer with FITC-conjugated Annexin V and Propidium iodide (PI) (all obtained from BD Biosciences) for 30 min at 4° C. Flow cytometric analysis is performed with FACSCalibur (BD Biosciences) and a total 10,000 events are recorded from each sample. Data is analyzed by using CellQuest software (BD Biosciences). The relative fluorescence is calculated after subtraction of the fluorescence of control.

E. Degradation of c-Kit in Cells after Treatment with a Compound of the Invention Two leukemia cell lines, HEL92.1.7 and Kasumi-1, are used for testing c-kit degradation induced by Hsp90 inhibitors of the invention. The cells ($3×10^5$ per well) are treated with 17AAG (0.5 μM), or a compound of the invention for about 18 h. The cells are collected and centrifuged (SORVALL RT 6000D) at 1200 rpm for 5 min. The supernatants are discarded, and the cells are washed one time with 1×PBS. After centrifugation the cells are stained with FITC conjugated c-kit antibody (MBL International, Cat# K0105-4) in 100 ml 1×PBS at 4° C. for 1 h. The samples are read and analyzed with FACSCalibur flow cytometer (Becton Dicknson).

c-Kit, a tyrosine kinase receptor and one of the Hsp90 client proteins, is selected and used in a FACS-based degradation assay. Compounds of the invention are expected to induce c-kit degradation in a dose-dependent manner. Compounds of the invention are expected to be effective in the treatment of c-kit associated tumors, such as leukemias, mast cell tumors, small cell lung cancer, testicular cancer, some cancers of the gastrointestinal tract (including GIST), and some central nervous system.

The results of the FACS analysis can be confirmed with Western blot analysis.

F. Degradation of c-Met in Cells After Treatment with a Compound of the Invention The ability of the Hsp90 inhibitors of the invention to induce the degradation of c-Met, an Hsp90 client protein that is expressed at high levels in several types of non-small cell lung cancer can be examined. NCI-H1993 (ATCC, cat# CRL-5909) are seeded in 6-well plates at $5×10^5$ cells/well. The cells are treated with 17AAG (100 nM or 400 nM) or a compound of the invention (100 nM or 400 nM), and cell lysis is prepared 24 h after treatment. Equal amount of proteins are used for Western blot analysis. The compounds of the invention are expected to potently induce degradation of c-Met in this cell line due to inhibition of Hsp90.

Example C

Anti-Tumor Activity Against the Human Tumor Cell Line MDA-MB435S in a nude Mouse Xenograft Model The human tumor cell line, MDA-MB-435S (ATCC #HTB-129; G. Ellison, et al., *Mol. Pathol.* 55:294-299, 2002), is obtained from the American Type Culture Collection (Manassus, Va., USA). The cell line is cultured in growth media prepared from 50% Dulbecco's Modified Eagle Medium (high glucose), 50% RPMI Media 1640, 10% fetal bovine serum (FBS), 1% 100× L-glutamine, 1% 100× Penicillin-Streptomycin, 1% 100× sodium pyruvate and 1% 100× MEM non-essential amino acids. FBS is obtained from Sigma-Aldrich Corp. (St. Louis, Mo., USA), and all other reagents are obtained from Invitrogen Corp. (Carlsbad, Calif., USA). Approximately $4-5×10(6)$ cells that have been cryopreserved in liquid nitrogen are rapidly thawed at 37° C., and transferred to a 175 cm$^2$ tissue culture flask containing 50 ml of growth media and then incubated at 37° C. in a 5% $CO_2$ incubator. The growth media is replaced every 2-3 days until the flask becomes 90% confluent, typically in 5-7 days. To passage and expand the cell line, a 90% confluent flask is washed with 10 ml of room temperature phosphate buffered saline (PBS) and the cells are disassociated by adding 5 ml 1× Trypsin-EDTA (Invitrogen) and incubating at 37° C. until the cells detach from the surface of the flask. To inactivate the trypsin, 5 ml of growth media is added and then the contents of the flask are centrifuged to pellet the cells. The supernatant is aspirated and the cell pellet is resuspended in 10 ml of growth media and the cell number determined using a hemocytometer. Approximately $1-3×10(6)$ cells per flask are seeded into 175 cm$^2$ flasks containing 50 ml of growth media and incubated at 37° C. in a 5% $CO_2$ incubator. When the flasks reach 90% confluence, the above passaging process is repeated until sufficient cells have been obtained for implantation into mice.

Six to eight week old, female Crl:CD-1-nuBR (nude) mice are obtained from Charles River Laboratories (Wilmington, Mass., USA). Animals are housed 4-5/cage in micro-isolators, with a 12 hr/12 hr light/dark cycle, acclimated for at least 1 week prior to use and fed normal laboratory chow ad libitum. Studies are conducted on animals between 7 and 12 weeks of age at implantation. To implant tumor cells into nude mice, the cells are trypsinized as above, washed in PBS and resuspended at a concentration of $50×10(6)$ cells/ml in PBS. Using a 27 gauge needle and 1 cc syringe, 0.1 ml of the cell suspension is injected into the corpus adiposum of nude mice. The corpus adiposum is a fat body located in the ventral abdominal vicera in the right quadrant of the abdomen at the juncture of the os coxae (pelvic bone) and the os femoris (femur). Tumors are then permitted to develop in vivo until they reach approximately 150 mm$^3$ in volume, which typically requires 2-3 weeks following implantation. Tumor volumes (V) are calculated by caliper measurement of the width (W), length (L) and thickness (T) of tumors using the following formula: $V=0.5326×(L×W×T)$. Animals are randomized into treatment groups so that the average tumor volumes of each group are similar at the start of dosing.

Sock solutions of test compounds are prepared by dissolving the appropriate amounts of each compound in dimethyl sulfoxide (DMSO) by sonication in an ultrasonic water bath. Stock solutions are prepared at the start of the study, stored at −20° C., and diluted fresh each day for dosing. A solution of 20% Cremophore RH40 (polyoxyl 40 hydrogenated castor oil; BASF Corp., Aktiengesellschaft, Ludwigshafen, Germany) in 80% D5W (5% dextrose in water; Abbott Laboratories, North Chicago, Ill., USA) is also prepared by first heating 100% Cremophore RH40 at 50-60° C. until liquefied and clear, diluting 1:5 with 100% D5W, reheating again until clear and then mixing well. This solution is stored at room temperature for up to 3 months prior to use. To prepare formulations for daily dosing, DMSO stock solutions are diluted 1:10 with 20% Cremophore RH40. The final formulation for dosing contains 10% DMSO, 18% Cremophore RH40, 3.6% dextrose and 68.4% water and the appropriate amount of test article. Animals are intraperitoneal (IP) injected with this solution at 10 ml per kg body weight on a schedule of 5 days per week (Monday thru Friday, with no dosing on Saturday and Sunday) for 3 weeks. Compounds of the invention are expected to result in decreased the growth rate of MDA-MB-435S cells in nude mice to a greater extent than a dose of 100 mg/kg body weight of the Hsp90 inhibitor 17-AAG.

Example D

Anti-Tumor Activity Against Human

Tumor Cells in a Nude Mouse Xenograft Model

The human squamous non-small cell lung cancer cell line, RERF-LC-AI (RCB0444; S. Kyoizumi, et al., *Cancer. Res.* 45:3274-3281, 1985), is obtained from the Riken Cell Bank (Tsukuba, Ibaraki, Japan). The cell line is cultured in growth media prepared from 50% Dulbecco's Modified Eagle Medium (high glucose), 50% RPMI Media 1640, 10% fetal bovine serum (FBS), 1% 100×L-glutamine, 1% 100× penicillin-streptomycin, 1% 100× sodium pyruvate and 1% 100× MEM non-essential amino acids. FBS is obtained from American Type Culture Collection (Manassas, Va., USA) and all other reagents are obtained from Invitrogen Corp. (Carlsbad, Calif., USA). Approximately 4-5×10(6) cells that have been cryopreserved in liquid nitrogen are rapidly thawed at 37° C., and transferred to a 175 cm$^2$ tissue culture flask containing 50 ml of growth media and then incubated at 37° C. in a 5% $CO_2$ incubator.

The growth media is replaced every 2-3 days until the flask becomes 90% confluent, typically in 5-7 days. To passage and expand the cell line, a 90% confluent flask is washed with 10 ml of room temperature phosphate buffered saline (PBS) and the cells are disassociated by adding 5 ml 1× trypsin-EDTA (Invitrogen) and incubating at 37° C. until the cells detach from the surface of the flask. To inactivate the trypsin, 5 ml of growth media is added and then the contents of the flask are centrifuged to pellet the cells. The supernatant is aspirated and the cell pellet is resuspended in 10 ml of growth media and the cell number determined using a hemocytometer. Approximately 1-3×10(6) cells per flask are seeded into 175 cm$^2$ flasks containing 50 ml of growth media and incubated at 37° C. in a 5% $CO_2$ incubator. When the flasks reach 90% confluence, the above passaging process is repeated until sufficient cells have been obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 8 and 12 weeks of age at implantation. To implant RERF-LC-AI tumor cells into nude mice, the cells are trypsinized as above, washed in PBS and resuspended at a concentration of 50×10(6) cells/ml in 50% non-supplemented RPMI Media 1640 and 50% Matrigel Basement Membrane Matrix (#354234; BD Biosciences; Bedford, Mass., USA). Using a 27 gauge needle and 1 cc syringe, 0.1 ml of the cell suspension is injected subcutaneously into the flank of each nude mouse. Tumor volumes (V) are calculated by caliper measurement of the width (W), length (L) and thickness (T) of tumors using the following formula: $V=0.5236\times(L\times W\times T)$.

In vivo passaged RERF-LC-AI tumor cells (RERF-LC-AI$^{IVP}$) are isolated to improve the rate of tumor implantation relative to the parental cell line in nude mice. RERF-LC-AI tumors are permitted to develop in vivo until they reach approximately 250 mm$^3$ in volume, which requires approximately 3 weeks following implantation. Mice are euthanized via $CO_2$ asphyxiation and their exteriors sterilized with 70% ethanol in a laminar flow hood. Using sterile technique, tumors are excised and diced in 50 ml PBS using a scalpel blade. A single cell suspension is prepared using a 55 ml Wheaton Safe-Grind tissue grinder (catalog #62400-358; VWR International, West Chester, Pa., USA) by plunging the pestle up and down 4-5 times without twisting. The suspension is strained through a 70 μM nylon cell strainer and then centrifuged to pellet the cells. The resulting pellet is resuspended in 0.1 M $NH_4Cl$ to lyse contaminating red blood cells and then immediately centrifuged to pellet the cells. The cell pellet is resuspended in growth media and seeded into 175 cm$^2$ flasks containing 50 ml of growth media at 1-3 tumors/flask or approximately 10×10(6) cells/flask. After overnight incubation at 37° C. in a 5% $CO_2$ incubator, non-adherent cells are removed by rinsing two times with PBS and then the cultures are fed with fresh growth media. When the flasks reach 90% confluence, the above passaging process is repeated until sufficient cells have been obtained for implantation into mice.

RERF-LC-AI$^{IVP}$ cells are then implanted as above and tumors are permitted to develop in vivo until the majority reached an average of 100-200 mm$^3$ in tumor volume, which typically requires 2-3 weeks following implantation. Animals with oblong or very small or large tumors are discarded, and only animals carrying tumors that display consistent growth rates are selected for studies. Animals are randomized into treatment groups so that the average tumor volumes of each group are similar at the start of dosing.

The HSP90 inhibitor, 17-allylamino-17-demethoxygeldanamycin (17-AAG), can be employed as a positive control (Albany Molecular Research, Albany, N.Y., USA). Stock solutions of test articles are prepared by dissolving the appropriate amounts of each compound in dimethyl sulfoxide (DMSO) by sonication in an ultrasonic water bath. Stock solutions are prepared weekly, stored at −20° C., and diluted fresh each day for dosing. A solution of 20% Cremophore RH40 (polyoxyl 40 hydrogenated castor oil; BASF Corp., Aktiengesellschaft, Ludwigshafen, Germany) in 80% D5W (5% dextrose in water; Abbott Laboratories, North Chicago, Ill., USA) is also prepared by first heating 100% Cremophore RH40 at 50-60° C. until liquefied and clear, diluting 1:5 with 100% D5W, reheating again until clear and then mixing well. This solution is stored at room temperature for up to 3 months prior to use. To prepare formulations for daily dosing, DMSO stock solutions are diluted 1:10 with 20% Cremophore RH40. The final formulation for dosing contains 10% DMSO, 18% Cremophore RH40, 3.6% dextrose, 68.4% water and the appropriate amount of test article. Animals are intraperitoneally (i.p.) injected with this solution at 10 ml per kg body weight on a schedule of 5 days per week (Monday, Tuesday, Wednesday, Thursday and Friday, with no dosing on Saturday and Sunday) for a total of 15 doses.

Treatment with compounds of the invention is expected to result in the decreased growth rate of RERF-LC-AI$^{IVP}$ human lung tumor cells in nude mice.

Example E

Necrosis in a Nude Mouse Tumor Model

The mouse mammary carcinoma cell line, EMT6 (ATCC #CRL-2755), is obtained from the American Type Culture Collection (ATCC; Manassas, Va., USA). The cell line is cultured in growth media prepared from 50% Dulbecco's Modified Eagle Medium (high glucose), 50% RPMI Media 1640, 10% fetal bovine serum (FBS), 1% 100× L-glutamine, 1% 100× Penicillin-Streptomycin, 1% 100× sodium pyruvate and 1% 100× MEM non-essential amino acids. FBS is obtained from ATCC and all other reagents are obtained from Invitrogen Corp. (Carlsbad, Calif., USA). Approximately 4–5×10(6) cells that have been cryopreserved in liquid nitrogen are rapidly thawed at 37° C., and transferred to a 175 cm$^2$ tissue culture flask containing 50 ml of growth media and then incubated at 37° C. in a 5% $CO_2$ incubator. The growth media is replaced every 2-3 days until the flask became 90% confluent, typically in 5-7 days. To passage and expand the cell line, a 90% confluent flask is washed with 10 ml of room temperature phosphate buffered saline (PBS) and the cells are disassociated by adding 5 ml 1× Trypsin-EDTA (Invitrogen) and incubating at 37° C. until the cells detach from the surface of the flask. To inactivate the trypsin, 5 ml of growth media is added and then the contents of the flask are centrifuged to pellet the cells. The supernatant is aspirated and the cell pellet is resuspended in 10 ml of growth media and the cell number determined using a hemocytometer. Approximately 1–3×10 (6) cells per flask are seeded into 175 cm$^2$ flasks containing 50 ml of growth media and incubated at 37° C. in a 5% $CO_2$ incubator. When the flasks reach 90% confluence, the above passaging process is repeated until sufficient cells have been obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 8 and 10 weeks of age at implantation. To implant EMT6 tumor cells into nude mice, the cells are trypsinized as above, washed in PBS and resuspended at a concentration of 10×10(6) cells/ml in PBS. Using a 27 gauge needle and 1 cc syringe, 0.1 ml of the cell suspension is injected subcutaneously into the flank of each nude mouse.

Tumors are then permitted to develop in vivo until the majority reached 75-125 mm$^3$ in tumor volume, which typically requires 1 week following implantation. Animals with oblong, very small or large tumors are discarded, and only animals carrying tumors that display consistent growth rates are selected for studies. Tumor volumes (V) are calculated by caliper measurement of the width (W), length (L) and thickness (T) of tumors using the following formula: V=0.5236× (L×W×T). Animals are randomized into treatment groups so that each group had median tumor volumes of ~100 mm$^3$ at the start of dosing.

To formulate a compound of the invention in DRD, a stock solution of the test article is prepared by dissolving an appropriate amount of the compound in dimethyl sulfoxide (DMSO) by sonication in an ultrasonic water bath. A solution of 20% Cremophore RH40 (polyoxyl 40 hydrogenated castor oil; BASF Corp., Aktiengesellschaft, Ludwigshafen, Germany) in 5% dextrose in water (Abbott Laboratories, North Chicago, Ill., USA) is also prepared by first heating 100% Cremophore RH40 at 50-60° C. until liquefied and clear, diluting 1:5 with 100% D5W, reheating again until clear and then mixing well. This solution is stored at room temperature for up to 3 months prior to use. To prepare a DRD formulation for dosing, the DMSO stock solution is diluted 1:10 with 20% Cremophore RH40. The final DRD formulation for dosing contains 10% DMSO, 18% Cremophore RH40, 3.6% dextrose, 68.4% water and the appropriate amount of test article.

Tumor-bearing animals are given a single intravenous (i.v.) bolus injections of either DRD vehicle or a compound of the invention formulated in DRD, both at 10 mL per kg body weight. Then, 4-24 hr after drug treatment, tumors are excised, cut in half and fixed overnight in 10% neutral-buffered formalin. Each tumor is embedded in paraffin with the cut surfaces placed downwards in the block, and rough cut until a complete section is obtained. From each tumor, 5 μM serial sections are prepared and stained with hematoxylin and eosin. Slides are evaluated manually using light microscopy with a 10×10 square gridded reticle. The percentage of necrosis in a tumor is quantified at 200× magnification by scoring the total number of grid squares containing necrosis and the total number of grid squares containing viable tumor cells.

It is expected that compounds of the invention will result in an increase in necrotic tissue in the center of EMT6 tumors relative to the baseline necrosis observed in vehicle treated tumors. As would be expected for a vascular targeting mechanism of action, rapid onset of necrosis is consistent with there being a loss of blood flow to tumors resulting in hypoxia and tumor cell death.

Example F

Vascular Disrupting Activities in a Nude Mouse Tumor Model

The mouse mammary carcinoma cell line, EMT6 (ATCC #CRL-2755), is obtained from the American Type Culture Collection (ATCC; Manassas, Va., USA). The cell line is cultured in growth media prepared from 50% Dulbecco's Modified Eagle Medium (high glucose), 50% RPMI Media 1640, 10% fetal bovine serum (FBS), 1% 100× L-glutamine, 1% 100× Penicillin-Streptomycin, 1% 100× sodium pyruvate and 1% 100× MEM non-essential amino acids. FBS is obtained from ATCC and all other reagents are obtained from Invitrogen Corp. (Carlsbad, Calif., USA). Approximately 4-5×10$^6$ cells that have been cryopreserved in liquid nitrogen are rapidly thawed at 37° C., and transferred to a 175 cm$^2$ tissue culture flask containing 50 mL of growth media and then incubated at 37° C. in a 5% $CO_2$ incubator. The growth media is replaced every 2-3 days until the flask became 90% confluent, typically in 5-7 days. To passage and expand the cell line, a 90% confluent flask is washed with 10 mL of room temperature phosphate buffered saline (PBS) and the cells are disassociated by adding 5 mL 1× Trypsin-EDTA (Invitrogen) and incubating at 37° C. until the cells detach from the surface of the flask. To inactivate the trypsin, 5 mL of growth media is added and then the contents of the flask are centrifuged to pellet the cells. The supernatant is aspirated and the cell pellet is resuspended in 10 mL of growth media and the cell number determined using a hemocytometer. Approximately 1-3×10$^6$ cells per flask are seeded into 175 cm$^2$ flasks containing 50 mL of growth media and incubated at 37° C. in a 5% $CO_2$ incubator. When the flasks reach 90% confluence, the above passaging process is repeated until sufficient cells have been obtained for implantation into mice.

Seven to eight week old, female Crl:CD-1-nuBR (nude) mice are obtained from Charles River Laboratories (Wilmington, Mass., USA). Animals are housed 4-5/cage in microisolators, with a 12 hr/12 hr light/dark cycle, acclimated for at least 1 week prior to use and fed normal laboratory chow ad libitum. Studies are conducted on animals between 8 and 10 weeks of age at implantation. To implant EMT6 tumor cells into nude mice, the cells are trypsinized as above, washed in PBS and resuspended at a concentration of $10 \times 10^6$ cells/mL in PBS. Using a 27 gauge needle and 1 cc syringe, 0.1 mL of the cell suspension is injected subcutaneously into the flank of each nude mouse.

For the Evans Blue dye assay, tumors are permitted to develop in vivo until the majority reach 40-90 $mm^3$ in tumor volume (to minimize the extent of tumor necrosis), which typically require 4-6 days following implantation. Animals with visibly necrotic, oblong, very small or very large tumors are discarded and only animals carrying tumors that display consistent growth rates are selected for use. Tumor volumes (V) are calculated by caliper measurement of the width (W), length (L) and thickness (T) of tumors using the following formula: $V=0.5236 \times (L \times W \times T)$. Animals are randomized into treatment groups so that at the start of dosing each group have median tumor volumes of ~125 $mm^3$ or ~55 $mm^3$ for the Evans Blue dye assay.

To formulate compounds of the invention for dosing, the appropriate amount of compound is dissolved in 5% dextrose in water (D5W; Abbott Laboratories, North Chicago, Ill., USA). Vehicle-treated animals are dosed with D5W.

To conduct the Evans Blue dye assay, tumor-bearing animals are dosed with vehicle or test article at 0 hr, and then i.v. injected with 100 µL of a 1% (w/v) Evan's Blue dye (Sigma #E-2129; St. Louis, Mo., USA) solution in 0.9% NaCl at +1 hr. Tumors are excised at +4 hr, weighed and the tissue disassociated by incubation in 50 µL 1 N KOH at 60° C. for 16 hr. To extract the dye, 125 µL of a 0.6 N phosphoric acid and 325 µL acetone are added, and the samples vigorously vortexed and then microcentrifuged at 3000 RPM for 15 min to pellet cell debris. The optical absorbance of 200 µL of supernatant is then measured at 620 nM in a Triad spectrophotometer (Dynex Technologies, Chantilly, Va., USA). Background $OD_{620}$ values from similarly sized groups of vehicle or test article-treated animals that have not been injected with dye are subtracted as background. $OD_{620}$ values are then normalized for tumor weight and dye uptake is calculated relative to vehicle-treated tumors.

To examine the vascular disrupting activity of a compound of the invention, the Evans Blue dye assay is employed as a measurement of tumor blood volume (Graff et al., Eur J Cancer 36:1433-1440, 2000). Evans Blue dye makes a complex with serum albumin by electrostatic interaction between the sulphonic acid group of the dye and the terminal cationic nitrogens of the lysine residues in albumin. The dye leaves the circulation very slowly, principally by diffusion into extravascular tissues while still bound to albumin. Albumin-dye complex taken up by tumors is located in the extracellular space of non-necrotic tissue, and intracellular uptake and uptake in necrotic regions is negligible. The amount of dye present in a tumor is a measurement of the tumor blood volume and microvessel permeability. Compounds of the invention are expected to result in substantially decreased tumor dye uptake relative to vehicle-treated animals. Such a decrease in dye penetration into the tumor is consistent with there being a loss of blood flow to tumors due to blockage of tumor vasculature, consistent with a vascular disrupting mechanism of action.

Example G

Inhibition of the Production of Inflammatory Cytokines in Human PBMCs

Human PBMC are isolated using Ficoll 400 and diatrizoate sodium (density 1.077 g/ml) solution and purified with RosetteSep (StemCell Technologies). The PBMCs are primed with human IFN-γ (800 U/ml, Pierce Biotechnology #R-IFNG-50), seeded at $0.5 \times 10^6/100$ µL/well in 96-well U-bottom plate with culture medium (RPMI 1640, 10% FBS, 1% Pen/Strep), and incubated in 37° C. for overnight. The cells are then stimulated with 1 µg/ml of LPS (Lipopolysaccharide, Sigma#L2654-1 MG) or 0.025% of SAC (*Staphylococcus Aureus* Cowan, Calbiochem-Novabiochem Corp. #507858), and treated with a test compound at different concentrations with final DMSO concentration less than 0.5% for 16-18 hrs. About 180 µl/well of supernatant is collected and measured using ELISA kit or Bio-plex (Bio-Rad) to determine the levels of cytokine production. The cell survival is determined using Cell Counting Kit-8 (Dojindo Molecular Technologies, Inc.). Compounds of the invention are expected to broadly inhibit the production of proinflammatory cytokines.

Example H

Suppression of Glucocorticoid Receptor Levels in Rat and Human PBMCs

Cell Preparation:

Whole blood samples from healthy human volunteers and male SD rats are collected and the PBMCs are isolated immediately as follows. 5 ml of whole blood is diluted with an equal volume of sterile 1×PBS. The diluted blood is overlayed carefully into a sterile centrifuge tube without disturbing the bottom layer that containing 5 ml of Ficoll-paque plus density gradient solution. The layered blood is centrifuged at 1500×g for 30 minutes at room temperature. The middle thin layer containing PBMCs is carefully removed, transferred to another sterile centrifuge tube, and washed twice with PBS to remove Percoll. Isolated rat and human PBMCs are cultured in 10% fetal bovine serum/DMEM.

Treatment:

The rat and human PBMCs are treated with DMSO (control), compounds of the invention, or 17-DMAG at concentrations of 0, 1, 5, 25, or 100 nM (in DMSO) for 16 hours. The cells are then collected and rinsed in ice-cold PBS and stored in liquid nitrogen until further analysis.

Immunoblot

PBMC are prepared in Western lysis buffer (10 mmol/L HEPES, 42 mmol/L KCl, 5 mmol/L $MgCl_2$, 0.1 mmol/L EDTA, 0.1 mmol/L EGTA, 1 mmol/L DTT, 1% Triton X-100, freshly supplemented with 1× protease inhibitor cocktail from Pierce, Rockford, Ill.). Lysate protein concentrations are quantified by bicinchoninic acid assay (Pierce) and normalized. Equal amounts of protein are loaded onto 10% NuPAGE Bis-Tris Gels (Invitrogen) and subsequently transferred onto polyvinylidene difluoride membranes. The membranes are blocked in 5% milk in TBST. Primary antibody of glucocorticod receptor from Santa Cruz Biotechnology, Inc. is added and incubated at room temperature for 1 hour with shaking. The blots are washed extensively in TBST before secondary antibodies are added for overnight incubation at 4° C. with gentle shaking. The blots are again washed extensively and developed with SuperSignal West Femto substrate (Pierce). The immunoblot analysis is performed to measure the level of total GRs by Quantity One software from Bio-Rad.

Example I

Suppression of Glucocorticoid Receptor Levels in Human PBMCs and Renal Cells, as Well as in Several Human Cancer Cell Lines Cell Preparation:
Normal human renal proximal tubule epithelial cells and tumor cell lines of MV-4-11, Kasumi-1, and Hela are obtained from Cambrex Bioproducts and American Type Culture Collection, respectively. Cells are cultured with 10% fetal bovine serum/DMEM.

The whole blood samples from healthy human volunteers are collected and the PBMCs are isolated immediately as described in Example H. Isolated human PBMCs are cultured in 10% fetal bovine serum/DMEM.

Treatment:
Human PBMCs, kasumi-1, Mv-4-11, Hela, and human renal proximal tubule epithelial cells are treated with DMSO (control), compounds of the invention, 17-DMAG at concentrations of 0, 5, 25, or 100 nM (in DMSO) for 16 hours. The cells are then collected and rinsed in ice-cold PBS and stored in liquid nitrogen until further analysis.

Immunoblot
PBMC, renal and tumor cell pellets are prepared in Western lysis buffer (10 mmol/L HEPES, 42 mmol/L KCl, 5 mmol/L $MgCl_2$, 0.1 mmol/L EDTA, 0.1 mmol/L EGTA, 1 mmol/L DTT, 1% Triton X-100, freshly supplemented with 1× protease inhibitor cocktail from Pierce, Rockford, Ill.). Lysate protein concentrations are quantified by bicinchoninic acid assay (Pierce) and normalized. Equal amounts of protein are loaded onto 10% NuPAGE Bis-Tris Gels (Invitrogen) and subsequently transferred onto polyvinylidene difluoride membranes. The membranes are blocked in 5% milk in TBST. Primary antibody of glucocorticod receptor from Santa Cruz Biotechnology, Inc. is added and incubated at room temperature for 1 hour with shaking. The blots are washed extensively in TBST before secondary antibodies are added for overnight incubation at 4° C. with gentle shaking. The blots are again washed extensively and developed with SuperSignal West Femto substrate (Pierce). Compounds of the invention are expected to suppress the expression of glucocorticoid receptors in cancer cells as well as in normal PBMCs and renal cells.

Example J

Suppression of Glucocorticoid Receptor Levels In Vivo

Male adult Sprague-Dawley (SD) rats, five per group, are randomly assigned into five testing groups which receive treatments as shown in Table 7:

TABLE 7

| Treatment group | Treatment |
|---|---|
| G1 | 5 mL/kg of vehicle (5% DMSO/13.5% Cr-RH40/D5W) |
| G2 | 6 mg/kg of 17-DMAG |
| G3 | 5 mg/kg of Paclitaxel |
| G4 | 80 mg/kg of Compound of the invention |
| G5 | 50 mg/kg of Compound of the invention |

The test compounds are administered daily intravenously via tail vein for four days. All rats are sacrificed at the study day 5. About 1-2 mL of blood samples are collected per animal. The blood samples are then pulled together as a group for PBMC isolation. PBMCs are isolated and an immunoblot using an antibody that recognizes the glucocorticoid receptor is prepared, as described in Examples H and I.

Example K

Inhibition of Topoisomerase II

The ability of compounds of the invention to inhibit the activity of topoisomerase II is examined with a kDNA decatenation assay (TopoGEN, Inc. Port Orange, Fla.). Substrate kDNA is mixed with compounds (10, 100, or 500 µM) and incubated at 37° C. for 30 min. The reaction is stop by adding ⅕ volume of stop buffer. 20 µl of the reaction is loaded on 1% agarose gel. Image of decatenation of kDNA by compounds is taken by Kodak Image Station 440.

All publications, patent applications, patents, and other documents cited herein are incorporated by reference in their entirety. In case of conflict, the present specification, including definitions, will control. In addition, the materials, methods, and examples are illustrative only and not intended to be limiting. While this invention has been particularly shown and described with references to preferred embodiments thereof, it will be understood by those skilled in the art that various changes in form and details may be made therein without departing from the scope of the invention encompassed by the appended claims.

What is claimed is:
1. A compound represented by the following structural formula:

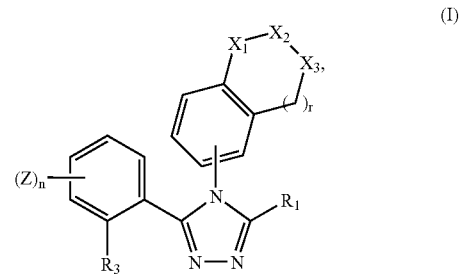

(I)

or a tautomer, or a pharmaceutically acceptable salt thereof, wherein:

$R_1$ and $R_3$ are, independently, —OH, —SH, —$NHR_7$, —$OR_{26}$, —$SR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)/NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pR_7$, —$SS(O)_pR_7$, —$NR_7S(O)_pR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$;

R$_7$ and R$_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{10}$ and R$_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{10}$ and R$_{11}$, taken together with the nitrogen to which they are attached, form an optionally substituted heterocyclyl or an optionally substituted heteroaryl;

R$_{26}$ is a lower alkyl;

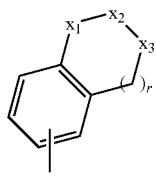

is selected from one of the following structural formulas:

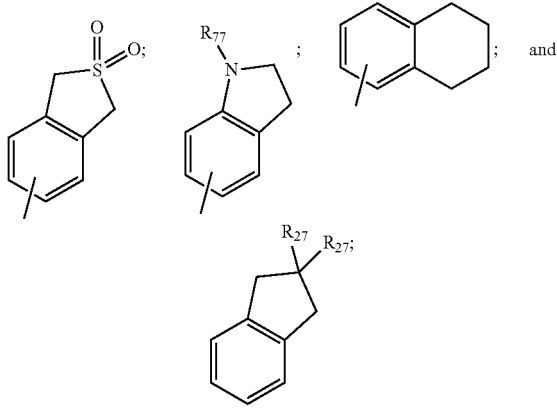

R$_{27}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$, —S(O)$_p$OR$_7$, —OP(O)(OR$_7$)$_2$, —SP(O)(OR$_7$)$_2$, —S(O)$_p$OR$_7$, —OP(O)(OR$_7$)$_2$, or —SP(O)(OR$_7$)$_2$;

or two R$_{27}$ groups taken together with the carbon atom to which they are attached form an optionally substituted cycloalkyl or optionally substituted heterocyclyl ring;

R$_{77}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, guanadino, a hydroxyalkyl, alkoxyalkyl, haloalkyl, a heteroalkyl, —OR$_7$, —C(O)R$_7$, —C(O)OR$_7$, —OC(O)R$_7$, —C(O)NR$_{10}$R$_{11}$, —SR$_7$, —S(O)$_p$R$_7$, —OS(O)$_p$R$_7$, —S(O)$_p$OR$_7$, —S(O)$_p$NR$_{10}$R$_{11}$, —S(O)$_p$OR$_7$, —OP(O)(OR$_7$)$_2$, —SP(O)(OR$_7$)$_2$, —S(O)$_p$OR$_7$, —OP(O)(OR$_7$)$_2$, —SP(O)(OR$_7$)$_2$;

Z is a substituent;
p, for each occurrence, is independently, 1 or 2;
m, for each occurrence, is independently, 1, 2, 3 or 4;
n is 0, 1, 2, or 3;
and
with the proviso that the compound is not
3-(2,4-Dihydroxyphenyl)-4-(1,2,3,4-tetrahydronaphtalen-5-yl)-5-mercapto-[1,2,4]triazole;
4-ethyl-6-(5-mercapto-4-(1-methylindolin-5-yl)-4H-1,2,4-triazol-3-yl)benzene-1,3-diol; or
4-(4-(2,3-dihydro-1H-inden-5-yl)-5-mercapto-4H-1,2,4-triazol-3-yl)-6-isopropylbenzene-1,3-diol.

2. The compound of claim 1, wherein Z is —OH, —SH, or —NHR$_7$, and R$_1$ and R$_3$ are each, independently, —OH, —SH, or —NHR$_7$.

3. The compound of claim 1, wherein the compound is selected from the group consisting of:

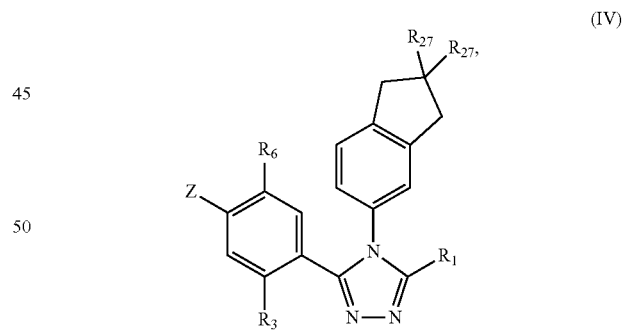

(IV)

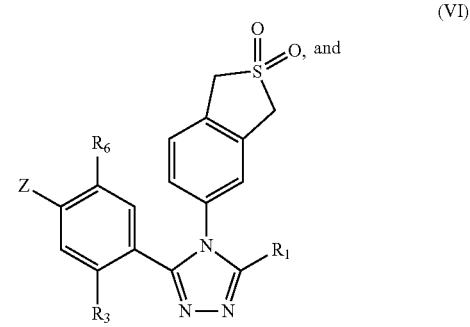

(VI)

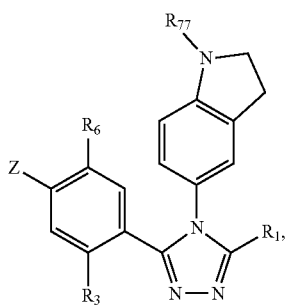

(IX)

or a tautomer or a pharmaceutically acceptable salt thereof, wherein $R_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)R_7$.

4. The compound of claim 3, wherein
Z and $R_3$ are each —OH;
$R_1$ is —OH, —SH, or —$NHR_7$; and
$R_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl.

5. The compound of claim 1, wherein the compound is represented by the following structure:

(X)

or a tautomer or a pharmaceutically acceptable salt thereof, wherein
$R_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, $NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC$ $(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$;
each of $X_1$, $X_2$, and $X_3$ is $CH_2$; and
r is 1.

6. The compound of claim 5, wherein Z is —OH, —SH, or —$NHR_7$; $R_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl; and $R_1$ and $R_3$ are each, independently, —OH, —SH, or —$NHR_7$.

7. A compound represented by the following structural formula:

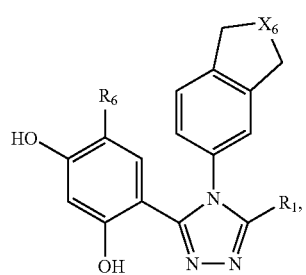

(XI)

or a tautomer, or a pharmaceutically acceptable salt thereof, wherein:
$R_1$ is —OH, —SH, —$NHR_7$, —$OR_{26}$, —$SR_{26}$, —O$(CH_2)_mOH$, —O$(CH_2)_mSH$, —O$(CH_2)_mNR_7H$, —S$(CH_2)_mOH$, —S$(CH_2)_mSH$, —S$(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC (NR₈)OR₇, —NR₇C(NR₈)OR₇, —OC(NR₈)NR₁₀R₁₁, —SC(NR₈)NR₁₀R₁₁, —NR₇C(NR₈)NR₁₀R₁₁, —OP(O)(OR₇)₂, or —SP(O)(OR₇)₂;

R₆ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR₇, —SR₇, —NR₁₀R₁₁, —OC(O)NR₁₀R₁₁, —SC(O)NR₁₀R₁₁, —NR₇C(O)NR₁₀R₁₁, —OC(O)R₇, —SC(O)R₇, —NR₇C(O)R₇, —OC(O)OR₇, —SC(O)OR₇, —NR₇C(O)OR₇, —OCH₂C(O)R₇, —SCH₂C(O)R₇, —NR₇CH₂C(O)R₇, —OCH₂C(O)OR₇, —SCH₂C(O)OR₇, —NR₇CH₂C(O)OR₇, —OCH₂C(O)NR₁₀R₁₁, —SCH₂C(O)NR₁₀R₁₁, —NR₇CH₂C(O)NR₁₀R₁₁, —OS(O)ₚR₇, —SS(O)ₚR₇, —NR₇S(O)ₚR₇, —OS(O)ₚNR₁₀R₁₁, —SS(O)ₚNR₁₀R₁₁, —NR₇S(O)ₚNR₁₀R₁₁, —OS(O)ₚOR₇, —SS(O)ₚOR₇, —NR₇S(O)ₚOR₇, —OC(S)R₇, —SC(S)R₇, —NR₇C(S)R₇, —OC(S)OR₇, —SC(S)OR₇, —NR₇C(S)OR₇, —OC(S)NR₁₀R₁₁, —SC(S)NR₁₀R₁₁, —NR₇C(S)NR₁₀R₁₁, —OC(NR₈)R₇, —SC(NR₈)R₇, —NR₇C(NR₈)R₇, —OC(NR₈)OR₇, —SC(NR₈)OR₇, —NR₇C(NR₈)OR₇, —OC(NR₈)NR₁₀R₁₁, —SC(NR₈)NR₁₀R₁₁, —NR₇C(NR₈)NR₁₀R₁₁, —C(O)R₇, —C(O)OR₇, —C(O)NR₁₀R₁₁, —C(O)SR₇, —C(S)R₇, —C(S)OR₇, —C(S)NR₁₀R₁₁, —C(S)SR₇, —C(NR₈)OR₇, —C(NR₈)R₇, —C(NR₈)NR₁₀R₁₁, —C(NR₈)SR₇, —S(O)ₚOR₇, —S(O)ₚNR₁₀R₁₁, or —S(O)ₚR₇;

R₇ and R₈, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R₁₀ and R₁₁, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R₁₀ and R₁₁, taken together with the nitrogen to which they are attached, form an optionally substituted heterocyclyl or an optionally substituted heteroaryl;

R₂₆ is a lower alkyl;

R₂₈, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —NR₁₀R₁₁, —OR₇, —C(O)R₇, —C(O)OR₇, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁, —S(O)ₚOR₇, —OP(O)(OR₇)₂, or —SP(O)(OR₇)₂, —S(O)ₚOR₇, —OP(O)(OR₇)₂, or —SP(O)(OR₇)₂;

X₆ is CHR₂₈;

p, for each occurrence, is independently, 1 or 2;

m, for each occurrence, is independently, 1, 2, 3 or 4; and n is 0, 1, 2, or 3.

8. The compound of claim 7, wherein R₆ is a C1-C6 alkyl, a C1-C6 haloalkyl, a C1-C6 alkoxy, a C1-C6 haloalkoxy, a C1-C6 alkyl sulfanyl or a C3-C6 cycloalkyl; R₁ is —OH, —SH, or —NHR₇; and R₂₈ is selected from the group consisting of —OR₇ or —NR₁₀R₁₁.

9. A compound represented by the following structural formula:

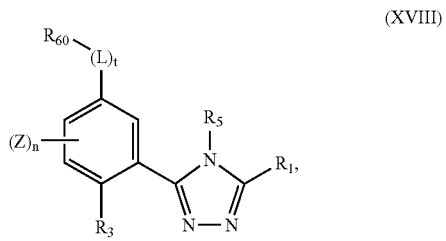

(XVIII)

or a tautomer, or a pharmaceutically acceptable salt thereof, wherein:

R₁ and R₃ are, independently, —OH, —SH, —NHR₇, —OR₂₆, —SR₂₆, —O(CH₂)ₘOH, —O(CH₂)ₘSH, —O(CH₂)NR₇H, —S(CH₂)ₘOH, —S(CH₂)ₘSH, —S(CH₂)ₘNR₇H, —OC(O)NR₁₀R₁₁, —SC(O)NR₁₀R₁₁, —NR₇C(O)NR₁₀R₁₁, —OC(O)R₇, —SC(O)R₇, —NR₇C(O)R₇, —OC(O)OR₇, —SC(O)OR₇, —NR₇C(O)OR₇, —OCH₂C(O)R₇, —SCH₂C(O)R₇, —NR₇CH₂C(O)R₇, —OCH₂C(O)OR₇, —SCH₂C(O)OR₇, —NR₇CH₂C(O)OR₇, —OCH₂C(O)NR₁₀R₁₁, —SCH₂C(O)NR₁₀R₁₁, —NR₇CH₂C(O)NR₁₀R₁₁, —OS(O)ₚR₇, —SS(O)ₚR₇, —S(O)ₚOR₇, —NR₇S(O)ₚR₇, —OS(O)ₚNR₁₀R₁₁, —SS(O)ₚNR₁₀R₁₁, —NR₇S(O)ₚNR₁₀R₁₁, —OS(O)ₚOR₇, —SS(O)ₚOR₇, —NR₇S(O)ₚOR₇, —OC(S)R₇, —SC(S)R₇, —NR₇C(S)R₇, —OC(S)OR₇, —SC(S)OR₇, —NR₇C(S)OR₇, —OC(S)NR₁₀R₁₁, —SC(S)NR₁₀R₁₁, —NR₇C(S)NR₁₀R₁₁, —OC(NR₈)R₇, —SC(NR₈)R₇, —NR₇C(NR₈)R₇, —OC(NR₈)OR₇, —SC(NR₈)OR₇, —NR₇C(NR₈)OR₇, —OC(NR₈)NR₁₀R₁₁, —SC(NR₈)NR₁₀R₁₁, —NR₇C(NR₈)NR₁₀R₁₁, —OP(O)(OR₇)₂, or —SP(O)(OR₇)₂;

R₆₀ is an optionally substituted heteroaryl or an optionally substituted aryl;

R₅ is represented by one of the following structural formulas:

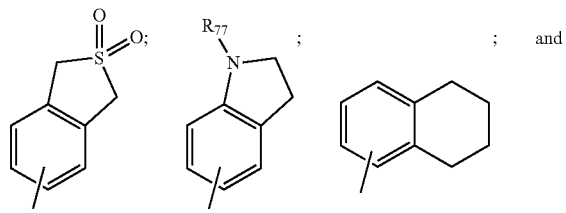

-continued

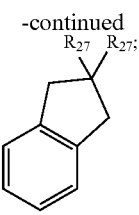

R₂₇, for each occurrence is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —NR₁₀R₁₁, —OR₇, —C(O)R₇, —C(O)OR₇, —OC(O)R₇, —C(O)NR₁₀R₁₁, —NR₈C(O)R₇, —SR₇, —S(O)ₚR₇, —OS(O)ₚR₇, —S(O)ₚOR₇, —NR₈S(O)ₚR₇, or —S(O)ₚNR₁₀R₁₁, —S(O)ₚOR₇, —OP(O)(OR₇)₂, —SP(O)(OR₇)₂, —S(O)ₚOR₇, —OP(O)(OR₇)₂, or —SP(O)(OR₇)₂;

or two R₂₇ groups taken together with the carbon atom to which they are attached form an optionally substituted cycloalkyl or optionally substituted heterocyclyl ring;

R₇₇, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, guanadino, a hydroxyalkyl, alkoxyalkyl, haloalkyl, a heteroalkyl, —OR₇, —C(O)R₇, —C(O)OR₇, —OC(O)R₇, —C(O)NR₁₀R₁₁, —SR₇, —S(O)ₚR₇, —OS(O)ₚR₇, —S(O)ₚOR₇, —S(O)ₚNR₁₀R₁₁, —S(O)ₚOR₇, —OP(O)(OR₇)₂, —SP(O)(OR₇)₂, —S(O)ₚOR₇, —OP(O)(OR₇)₂, or —SP(O)(OR₇)₂, R₇ and R₈, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R₁₀ and R₁₁, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R₁₀ and R₁₁, taken together with the nitrogen to which they are attached, form an optionally substituted heterocyclyl or an optionally substituted heteroaryl;

R₂₆ is a lower alkyl;

L is an optionally substituted 1 to 6 atom linker, wherein each linker atom is independently selected from the group consisting of C, O, S or N, provided that L is not —N=N—;

Z is a substituent;
p, for each occurrence, is independently, 1 or 2;
m, for each occurrence, is independently, 1, 2, 3 or 4;
n is 0, 1, 2, or 3; and
t is 0 or 1.

10. The compound of claim 9, wherein
R₆₀ is substituted with 1 to 4 substituents independently selected from the group consisting of halo, lower alkoxy, cyano, amino, dialkyl amino, alkyl amino, —C(O)N(Rᵧ)₂, —C(O)Rₓ, or —C(OH)Rₓ; and
Rₓ is lower alkyl; and
each Rᵧ is independently —H or lower alkyl.

11. The compound of claim 9, wherein R₆₀ is unsubstituted phenyl.

12. The compound of claim 9, wherein R₁ and R₃ are each, independently, —OH, —SH, or —NHR₇; and L is a C₁-C₆ alkylene.

13. The compound of claim 9, wherein the compound is represented by the following structure:

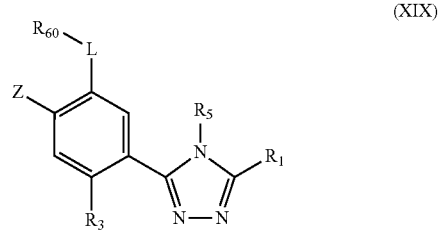

(XIX)

or a tautomer or a pharmaceutically acceptable salt thereof.

14. The compound of claim 13, wherein R₆₀ is an optionally substituted phenyl, an optionally substituted furanyl, an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, an optionally substituted pyrimidinyl, an optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo(b)thienyl.

15. The compound of claim 13, wherein
$R_{60}$ is an optionally substituted phenyl;
$R_1$, $R_3$, and Z are each, independently, —OH, —SH, or —NHR$_7$; and
L is a $C_1$-$C_6$ alkylene.

16. The compound of claim 9, wherein the compound is represented by the following formula:

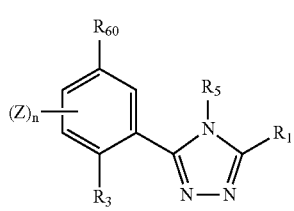

(XXIII)

or a tautomer or a pharmaceutically acceptable salt thereof.

17. The compound of claim 16, wherein
$R_{60}$ is substituted with 1 to 4 substituents independently selected from the group consisting of halo, lower alkoxy, cyano, amino, dialkyl amino, alkyl amino, —C(O)N(R$_y$)$_2$, —C(O)R$_x$, or —C(OH)R$_x$; and
$R_x$ is lower alkyl; and
each $R_y$ is independently —H or lower alkyl.

18. The compound of claim 16, wherein $R_1$ and $R_3$ are each, independently, —OH, —SH, or —NHR$_7$.

19. The compound of claim 16, wherein the compound is represented by the following structure:

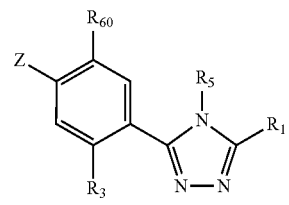

(XXIV)

or a tautomer or a pharmaceutically acceptable salt thereof.

20. The compound of claim 19, wherein Z is —OH, —SH, —NHR$_7$, —OC(O)NR$_{10}$R$_{11}$, —SC(O)NR$_{10}$R$_{11}$, —OC(O)R$_7$, —SC(O)R$_7$, —OC(O)OR$_7$, —SC(O)OR$_7$, —OS(O)$_p$R$_7$, —S(O)$_p$OR$_7$, —SS(O)$_p$R$_7$, —OS(O)$_p$OR$_7$, —SS(O)$_p$OR$_7$, —OC(S)R$_7$, —SC(S)R$_7$, —OC(S)OR$_7$, —SC(S)OR$_7$, —OC(S)NR$_{10}$R$_{11}$, —SC(S)NR$_{10}$R$_{11}$, —OC(NR$_8$)R$_7$, —SC(NR$_8$)R$_7$, —OC(NR$_8$)OR$_7$, —SC(NR$_8$)OR$_7$, —OP(O)(OR$_7$)$_2$ or —SP(O)(OR$_7$)$_2$.

21. The compound of claim 19, wherein $R_{60}$ is an optionally substituted phenyl, an optionally substituted furanyl, an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, an optionally substituted pyrimidinyl, an optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo(b)thienyl.

22. The compound of claim 21, wherein $R_{60}$ is an optionally substituted furanyl.

23. The compound of claim 19, wherein
$R_{60}$ is an optionally substituted phenyl; and
$R_1$, $R_3$, and Z are each, independently, —OH, —SH, or —NHR$_7$.

24. The compound of claim 19, wherein
$R_{60}$ is an optionally substituted furanyl; and
$R_1$, $R_3$, and Z are each, independently, —OH, —SH, or —NHR$_7$.

25. A compound represented by the following structural formula:

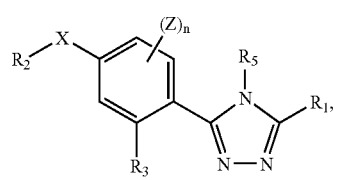

(XXVIII)

or a tautomer, or a pharmaceutically acceptable salt thereof, wherein:
$R_1$ and $R_3$ are, independently, —OH, —SH, —NHR$_7$, —OR$_{26}$, —SR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C (NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$;

R$_2$ is —OH, —SH, —NHR$_7$;

R$_5$ is represented by one of the following structural formulas:

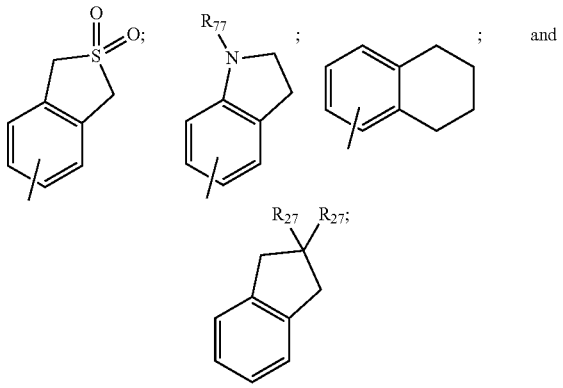

R$_{27}$, for each occurrence, is independently a substituent selected from the group consisting of —H, an optionally substituted alkyl, an optionally substituted alkenyl, an optionally substituted alkenyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$, —S(O)$_p$OR$_7$, —OP(O)(OR$_7$)$_2$, —SP(O)(OR$_7$)$_2$, —S(O)$_p$OR$_7$, —OP(O)(OR$_7$)$_2$, or —SP(O)(OR$_7$)$_2$;

or two R$_{27}$ groups taken together with the carbon atom to which they are attached form an optionally substituted cycloalkyl or optionally substituted heterocyclyl ring;

R$_{77}$, for each occurrence is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, guanadino, a hydroxyalkyl, alkoxyalkyl, haloalkyl, a heteroalkyl, —OR$_7$, —C(O)R$_7$, —C(O)OR$_7$, —OC(O)R$_2$, —C(O)NR$_{10}$R$_{11}$, —SR$_7$, —S(O)$_p$R$_7$, —OS(O)$_p$R$_7$, —S(O)$_p$OR$_7$, —S(O)$_p$NR$_{10}$R$_{11}$, —S(O)$_p$OR$_7$, —OP(O)(OR$_7$)$_2$, —SP(O)(OR$_7$)$_2$, —S(O)$_p$OR$_7$, —OP(O)(OR$_7$)$_2$, or —SP(O)(OR$_7$)$_2$ R$_7$ and R$_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{10}$ and R$_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{10}$ and R$_{11}$, taken together with the nitrogen to which they are attached, form an optionally substituted heterocyclyl or an optionally substituted heteroaryl;

R$_{26}$ is a lower alkyl;

X is an optionally substituted 1 to 6 atom linker, wherein each linker atom is independently selected from the group consisting of C, O, P, N, or S;

Z is a substituent;

p, for each occurrence, is independently, 1 or 2;

m, for each occurrence, is independently, 1, 2, 3 or 4;

n is 0, 1, or 2; and with the proviso that the compound is not.

26. The compound of claim 25, wherein R$_1$ and R$_3$ are each, independently, —OH, —SH, or —NHR$_7$.

27. The compound of claim 26, wherein R$_1$ and R$_3$ are each, independently, —OH or —SH.

28. The compound of claim 25, wherein X is an optionally substituted 1 to 4 atom linker, wherein each linker atom is independently selected from the group consisting of C or O.

29. The compound of claim 28, wherein

X is —(CH$_2$)$_s$—, —(CH$_2$)$_t$C(O)—, —O(CH$_2$)$_t$—, or —OC(O)—;

s is 1, 2, or 3; and t is 0, 1, or 2.

30. The compound of claim 25, wherein Z, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$R$_7$, —OS(O)$_p$NR$_{10}$R$_{11}$, —S(O)$_p$R$_7$, —NR$_8$S(O)$_p$R$_7$, —NR$_7$S(O)$_p$NR$_{10}$R$_{11}$, —NR$_7$S(O)$_p$R$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, or —SP(O)(OR$_7$)$_2$.

31. The compound of claim 25, wherein n is 0.

32. The compound of claim 25, wherein the compound is represented by the following structure:

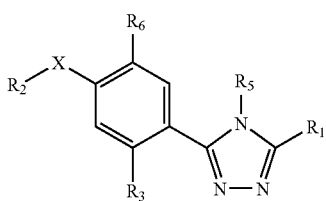

(XXIX)

or a tautomer or a pharmaceutically acceptable salt thereof, wherein $R_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally, substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$.

33. The compound of claim 32, wherein
$R_1$ and $R_3$ are each, independently, —OH or —SH;
$R_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl;
X is —$(CH_2)_s$—, —$(CH_2)_tC(O)$—, —$O(CH_2)_t$—, or —$OC(O)$—;
s is 1, 2, or 3; and
t is 0, 1, or 2.

34. The compound of claim 33, wherein $R_2$ is —$NH_2$.

35. A method of treating non-small cell lung cancer or breast cancer in a mammal, comprising administering to the mammal an effective amount of a compound represented by the following structural formula:

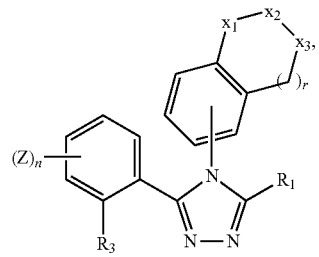

(I)

or a tautomer, or a pharmaceutically acceptable salt thereof, wherein:
$R_1$ and $R_3$ are, independently, —OH, —SH, —$NHR_7$, —$OR_{26}$, —$SR_{26}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$S(O)_pOR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pR_7$, —$SS(O)_pR_7$, —$NR_7S(O)_pR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$OP(O)(OR_7)_2$, —$SP(O)(OR_7)_2$;

$R_7$ and $R_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{26}$ is a lower alkyl;

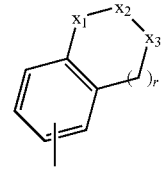

is selected from one of the following structural formulas:

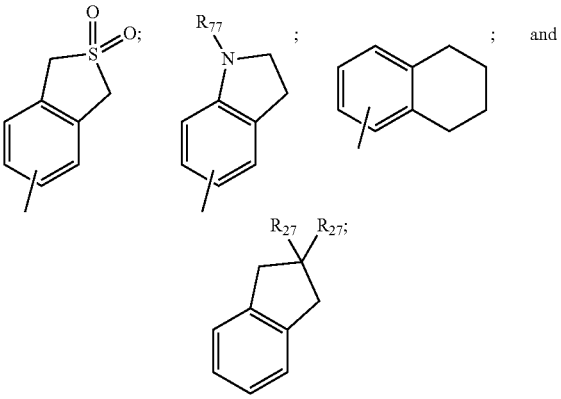

$R_{27}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$, —S(O)$_p$OR$_7$, —OP(O)(OR$_7$)$_2$, —SP(O)(OR$_7$)$_2$, —S(O)$_p$OR$_7$, —OP(O)(OR$_7$)$_2$, or —SP(O)(OR$_7$)$_2$;

or two R$_{27}$ groups taken together with the carbon atom to which they are attached form an optionally substituted cycloalkyl or optionally substituted heterocyclyl ring;

R$_{77}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, guanadino, a hydroxyalkyl, alkoxyalkyl, haloalkyl, a heteroalkyl, —OR$_7$, —C(O)R$_7$, —C(O)OR$_7$, —OC(O)R$_7$, —C(O)NR$_{10}$R$_{11}$, —SR$_7$, —S(O)$_p$R$_7$, —OS(O)$_p$R$_7$, —S(O)$_p$OR$_7$, —S(O)$_p$NR$_{10}$R$_{11}$, —S(O)$_p$OR$_7$, —OP(O)(OR$_7$)$_2$, —SP(O)(OR$_7$)$_2$, —S(O)$_p$OR$_7$, —OP(O)(OR$_7$)$_2$, or —SP(O)(OR$_7$)$_2$;

Z is a substituent;

p, for each occurrence, is independently, 1 or 2;

m, for each occurrence, is independently, 1, 2, 3 or 4;

n is 0, 1, 2, or 3;

t is 0 or 1; and with the proviso that the compound is not
3-(2,4-Dihydroxyphenyl)-4-(1,2,3,4-tetrahydronaphthalen-5-yl)-5-mercapto-[1,2,4]triazole;
4-ethyl-6-(5-mercapto-4-(1-methylindolin-5-yl)-4H-1,2,4-triazol-3-yl)benzene-1,3-diol; or
4-(4-(2,3-dihydro-1H-inden-5-yl)-5-mercapto-4H-1,2,4-triazol-3-yl)-6-isopropylbenzene-1,3-diol.

36. A pharmaceutical composition, comprising a pharmaceutically acceptable carrier and a compound selected from the group consisting of

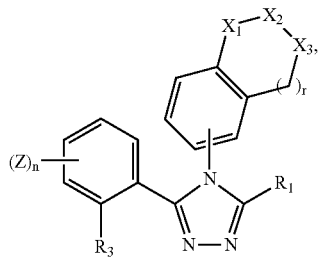

(I)

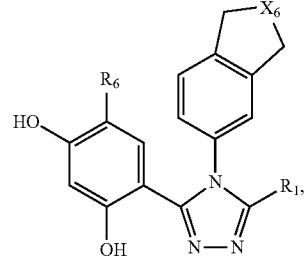

(XI)

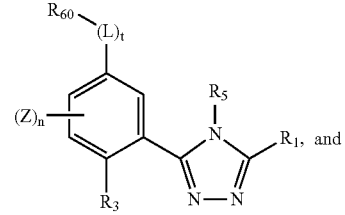

(XVIII)

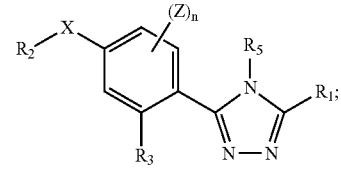

(XXVIII)

or a tautomer, or a pharmaceutically acceptable salt thereof, wherein:

R$_1$ and R$_3$ are, independently, —OH, —SH, —NHR$_7$, —OR$_{26}$, —SR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$R$_7$, —SS(O)$_p$R$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$;

R$_7$ and R$_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{10}$ and R$_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{26}$ is a lower alkyl;

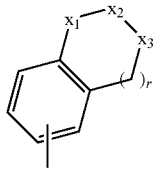

is selected from one of the following structural formulas:

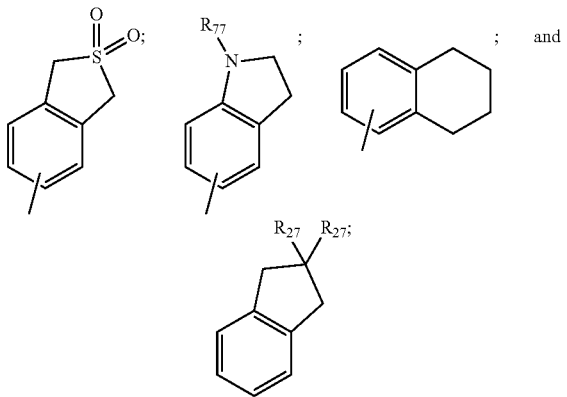

$R_{27}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pR_7$, —$OS(O)_pR_7$, —$S(O)_pOR_7$, —$NR_8S(O)_pR_7$, or —$S(O)_pNR_{10}R_{11}$, —$S(O)_pOR_7$, —$OP(O)(OR_7)_2$, —$SP(O)(OR_7)_2$, —$S(O)_pOR_7$, —$OP(O)(OR_7)_2$, or —$SP(O)(OR_7)_2$;

or two $R_{27}$ groups taken together with the carbon atom to which they are attached form an optionally substituted cycloalkyl or optionally substituted heterocyclyl ring;

$R_{77}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, guanadino, a hydroxyalkyl, alkoxyalkyl, haloalkyl, a heteroalkyl, —$OR_7$, —$C(O)R_7$, —$C(O)OR_7$, —$OC(O)R_7$, —$C(O)NR_{10}R_{11}$, —$SR_7$, —$S(O)_pR_7$, —$OS(O)_pR_7$, —$S(O)_pOR_7$, —$S(O)_pNR_{10}R_{11}$, —$S(O)_pOR_7$, —$OP(O)(OR_7)_2$, —$SP(O)(OR_7)_2$, —$S(O)_pOR_7$, —$OP(O)(OR_7)_2$, —$SP(O)(OR_7)_2$;

Z is a substituent;

p, for each occurrence, is independently, 1 or 2;

m, for each occurrence, is independently, 1, 2, 3 or 4;

n is 0, 1, 2, or 3;

t is 0 or 1;

$R_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —$SR_7$, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pR_7$, —$SS(O)_pR_7$, —$NR_7S(O)_pR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pR_7$, —$S(O)_pNR_{10}R_{11}$, or —$S(O)_pR_7$;

$R_{28}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —$NR_{10}R_{11}$, —$OR_7$, —$C(O)R_7$, —$C(O)OR_7$, —$OC(O)R_7$, —$C(O)NR_{10}R_{11}$, —$NR_8C(O)R_7$, —$SR_7$, —$S(O)_pOR_7$, —$OS(O)_pR_7$, —$S(O)_pOR_7$, —$NR_8S(O)_pR_7$, or —$S(O)_pNR_{10}R_{11}$, —$S(O)_pOR_7$, —$OP(O)(OR_7)_2$, —$SP(O)(OR_7)_2$, —$S(O)_pOR_7$, —$OP(O)(OR_7)_2$, or —$SP(O)(OR_7)_2$;

$X_6$ is $CHR_{28}$;

Ring A is an optionally substituted heteroaromatic ring, selected from the group consisting of furanyl, oxazolyl, thiazolyl, indazolyl, thiophenyl, triazolyl, or pyridyl;

Ring D is an optionally substituted aryl or an optionally substituted heteroaryl;

$R_{60}$ is an optionally substituted heteroaryl or an optionally substituted aryl;

$R_5$ is selected from one of the following structural formulas:

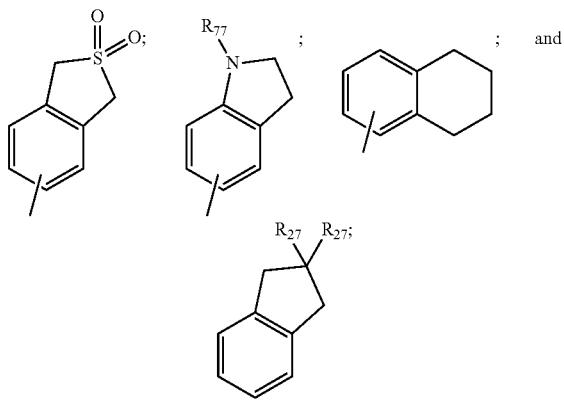

L is an optionally substituted 1 to 6 atom linker, wherein each linker atom is independently selected from the group consisting of C, O, S or N, provided that L is not —N=N—;

$R_2$ is —OH, —SH, —$NHR_7$;

X is an optionally substituted 1 to 6 atom linker, wherein each linker atom is independently selected from the group consisting of C, O, P, N, or S; and with the proviso that the compound is not 3-(2,4-Dihydroxyphenyl)-4-(1,2,3,4-tetrahydronaphthalen-5-yl)-5-mercapto-[1,2,4]triazole;

4-ethyl-6-(5-mercapto-4-(1-methylindolin-5-yl)-4H-1,2,4-triazol-3-yl)benzene-1,3-diol; or 4-(4-(2,3-dihydro-1H-inden-5-yl)-5-mercapto-4H-1,2,4-triazol-3-yl)-6-isopropylbenzene-1,3-diol.

37. The method of claim 35, wherein Z is —OH, —SH, or —$NHR_7$, and $R_1$ and $R_3$ are each, independently, —OH, —SH, or —$NHR_7$.

38. The method of claim 35, wherein the compound is selected from the group consisting of:

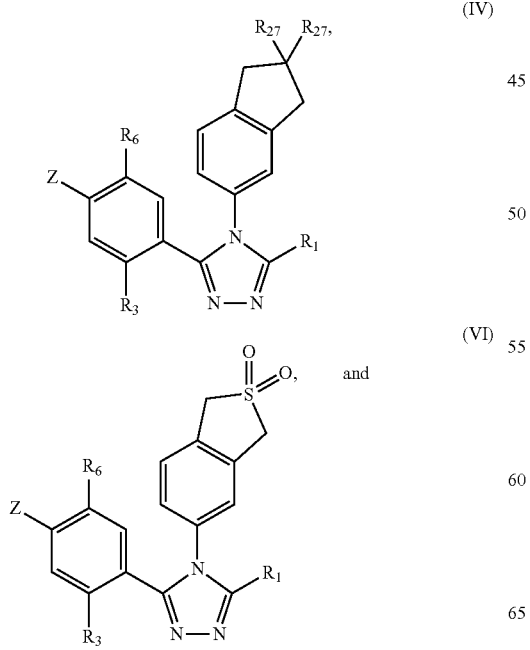

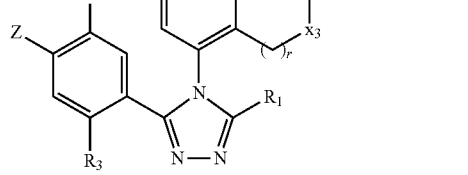

or a tautomer or a pharmaceutically acceptable salt thereof, wherein each of $X_4$ and $X_5$ is, independently, $C(R_7)_2$, $NR_7$, or S.

39. The method of claim 38, wherein
Z and $R_3$ are each —OH;
$R_1$ is —OH, —SH, or —$NHR_7$; and
$R_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl.

40. The method of claim 35, wherein the compound is represented by the following structure:

(X)

or a tautomer or a pharmaceutically acceptable salt thereof, wherein $R_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —$OR_7$, —SR, —$NR_{10}R_{11}$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pR_7$, —$SS(O)_pR_7$, —$NR_7S(O)_pR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, —$NR_7C(NR_8)NR_{10}R_{11}$, —$C(O)R_7$, —$C(O)OR_7$, —$C(O)NR_{10}R_{11}$, —$C(O)SR_7$, —$C(S)R_7$, —$C(S)OR_7$, —$C(S)NR_{10}R_{11}$, —$C(S)SR_7$, —$C(NR_8)OR_7$, —$C(NR_8)R_7$, —$C(NR_8)NR_{10}R_{11}$, —$C(NR_8)SR_7$, —$S(O)_pOR_7$, —$S(O)_pNR_{10}R_{11}$, or —$S(O)_pR_7$;

each of $X_1$, $X_2$, and $X_3$ is $CH_2$; and r is 1.

41. The method of claim 40, wherein Z is —OH, —SH, or —NHR$_7$; R$_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl; and R$_1$ and R$_3$ are each, independently, —OH, —SH, or —NHR$_7$.

42. A method of treating non-small cell lung cancer or breast cancer in a mammal, comprising administering to the mammal an effective amount of a compound represented by the following structural formula:

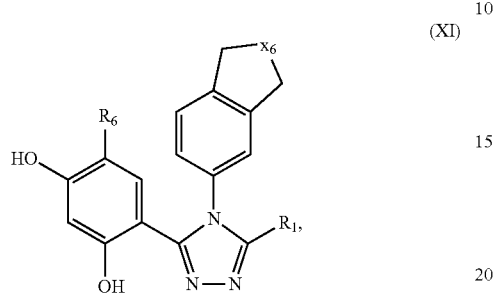

(XI)

or a tautomer, or a pharmaceutically acceptable salt thereof, wherein:

R$_1$ is —OH, —SH, —NHR$_7$, —OR$_{26}$, —SR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$R$_7$, —SS(O)$_p$R$_7$, —NR$_7$S(O)$_p$R$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$;

R$_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR$_7$, —SR$_7$, —NR$_{10}$R$_{11}$, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$R$_7$, —SS(O)$_p$R$_7$, —NR$_7$S(O)$_p$R$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$, R$_7$ and R$_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{10}$ and R$_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{10}$ and R$_{11}$, taken together with the nitrogen to which they are attached, form an optionally substituted heterocyclyl or an optionally substituted heteroaryl;

R$_{26}$ is a lower alkyl;

R$_{28}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —NR$_{10}$R$_{11}$, —OR$_7$, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$, —S(O)$_p$OR$_7$, —OP(O)(OR$_7$)$_2$, or —SP(O)(OR$_7$)$_2$, —S(O)$_p$OR$_7$, —OP(O)(OR$_7$)$_2$, or —SP(O)(OR$_7$)$_2$;

X$_6$ is CHR$_{28}$;

p, for each occurrence, is independently, 1 or 2;

m, for each occurrence, is independently, 1, 2, 3 or 4; and n is 0, 1, 2, or 3.

43. The method of claim 42, wherein R$_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl; R$_1$ is —OH, —SH, or —NHR$_7$; and R$_{28}$ is selected from the group consisting of —OR$_7$, or —NR$_{10}$R$_{11}$.

44. A method of treating non-small cell lung cancer or breast cancer in a mammal, comprising administering to the mammal an effective amount of a compound represented by the following structural formula:

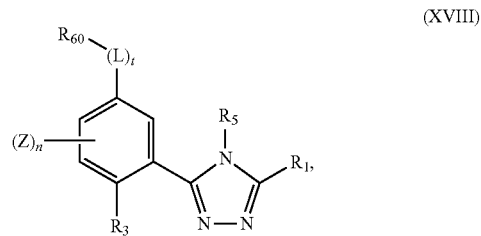

(XVIII)

or a tautomer, or a pharmaceutically acceptable salt thereof, wherein:

R$_1$ and R$_3$ are, independently, —OH, —SH, —NHR$_7$, —OR$_{26}$, —SR$_{26}$, —O(CH$_2$)$_m$OH, —O(CH$_2$)$_m$SH, —O(CH$_2$)$_m$NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O) NR$_{10}$R$_{11}$, —NR$_7$C(O)NR$_{10}$R$_{11}$, —OC(O)R$_7$, —SC(O) R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O) OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$R$_7$, —NR$_7$S(O)$_p$ R$_7$, —OS(O)$_p$NR$_{10}$R$_{11}$, —SS(O)$_p$NR$_{10}$R$_{11}$, —NR$_7$S (O)$_p$NR$_{10}$R$_{11}$, —OS(O)$_p$R$_7$, —SS(O)$_p$R$_7$, —NR$_7$S (O)$_p$R$_7$, —OC(S)R$_7$, —SC(S)R$_7$, —NR$_7$C(S)R$_7$, —OC (S)OR$_7$, —SC(S)OR$_7$, —NR$_7$C(S)OR$_7$, —OC(S) NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C (NR$_8$)NR$_{10}$R$_{11}$, —OP(O)(OR$_7$)$_2$, or —SP(O)(OR$_7$)$_2$;

R$_{60}$ is an optionally substituted heteroaryl or an optionally substituted aryl;

R$_5$ is represented by one of the following structural formulas:

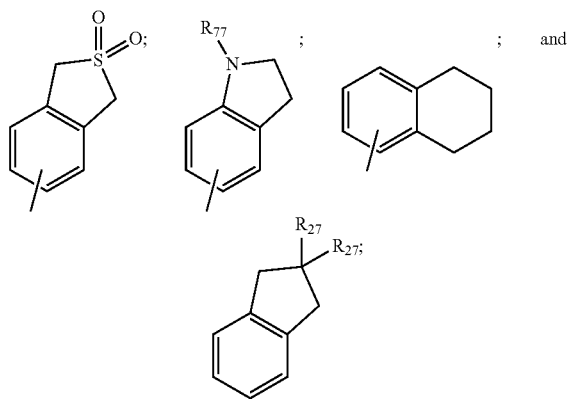

R$_{27}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —NR$_{10}$R$_{11}$, —OR$_7$, —C(O)R$_7$, —C(O)OR$_7$, —OC(O)R$_7$, —C(O) NR$_{10}$R$_{11}$, —NR$_8$C(O)R$_7$, —SR$_7$, —S(O)$_p$R$_7$, —OS (O)$_p$R$_7$; —S(O)$_p$OR$_7$, —NR$_8$S(O)$_p$R$_7$, or —S(O)$_p$ NR$_{10}$R$_{11}$, —S(O)$_p$OR$_7$, —OP(O)(OR$_7$)$_2$, —SP(O) (OR$_7$)$_2$, —S(O)$_p$OR$_7$, —OP(O)(OR$_7$)$_2$, or —SP(O) (OR$_7$)$_2$;

or two R$_{27}$ groups taken together with the carbon atom to which they are attached form an optionally substituted cycloalkyl or optionally substituted heterocyclyl ring;

R$_{77}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, guanadino, a hydroxyalkyl, alkoxyalkyl, haloalkyl, a heteroalkyl, —OR$_7$, —C(O)R$_7$, —C(O)OR$_7$, —OC(O)R$_7$, —C(O)NR$_{10}$R$_{11}$, —SR$_7$, —S(O)$_p$R$_7$, —OS(O)$_p$R$_7$, —S(O)$_p$OR$_7$, —S(O)$_p$ NR$_{10}$R$_{11}$, —S(O)OR$_7$, —OP(O)(OR$_7$)$_2$, —SP(O) (OR$_7$)$_2$, —S(O)$_p$OR$_7$, —OP(O)(OR$_7$)$_2$, or —SP(O) (OR$_7$)$_2$;

R$_7$ and R$_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{10}$ and R$_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{10}$ and R$_{11}$, taken together with the nitrogen to which they are attached, form an optionally substituted heterocyclyl or an optionally substituted heteroaryl;

R$_{26}$ is a lower alkyl;

L is an optionally substituted 1 to 6 atom linker, wherein each linker atom is independently selected from the group consisting of C, O, S or N, provided that L is not —N=N—;

Z is a substituent;

p, for each occurrence, is independently, 1 or 2;

m, for each occurrence, is independently, 1, 2, 3 or 4;

n is 0, 1, 2, or 3; and t is 0 or 1.

45. The method of claim 44, wherein

R$_{60}$ is substituted with 1 to 4 substituents independently selected from the group consisting of halo, lower alkoxy, cyano, amino, dialkyl amino, alkyl amino, —C(O)N(R$_y$)$_2$, —C(O)R$_x$, or —C(OH)R$_x$; and R$_x$ is lower alkyl; and each R$_y$ is independently —H or lower alkyl.

46. The method of claim 44, wherein R$_{60}$ is unsubstituted phenyl.

47. The method of claim 44, wherein R$_1$ and R$_3$ are each, independently, —OH, —SH, or —NHR$_7$; and L is a C$_1$-C$_6$ alkylene.

48. The method of claim 44, wherein the compound is represented by the following structure:

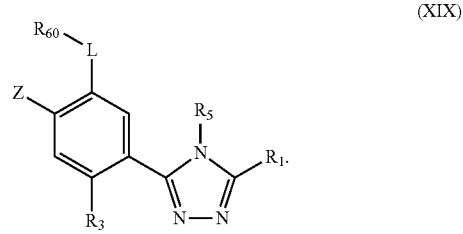

(XIX)

or a tautomer or a pharmaceutically acceptable salt thereof.

49. The method of claim 48, wherein R$_{60}$ is an optionally substituted phenyl, an optionally substituted furanyl, an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, an optionally substituted pyrimidinyl, an optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo(b)thienyl.

50. The method of claim 48, wherein
$R_{60}$ is an optionally substituted phenyl;
$R_1$, $R_3$, and Z are each, independently, —OH, —SH, or —NHR$_7$; and
L is a $C_1$-$C_6$ alkylene.

51. The method of claim 44, wherein the compound is represented by the following formula:

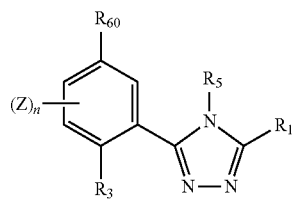

(XXIII)

or a tautomer or a pharmaceutically acceptable salt thereof.

52. The method of claim 51, wherein
$R_{60}$ is substituted with 1 to 4 substituents independently selected from the group consisting of halo, lower alkoxy, cyano, amino, dialkyl amino, alkyl amino, —C(O)N($R_y$)$_2$, —C(O)$R_x$, or —C(OH)$R_x$; and
$R_x$ is lower alkyl; and
each $R_y$ is independently —H or lower alkyl.

53. The method of claim 51, wherein $R_1$ and $R_3$ are each, independently, —OH, —SH, or —NHR$_7$.

54. The method of claim 51, wherein the compound is represented by the following structure:

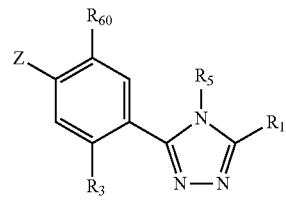

(XXIV)

or a tautomer or a pharmaceutically acceptable salt thereof.

55. The method of claim 54, wherein $R_{60}$ is an optionally substituted phenyl, an optionally substituted furanyl, an optionally substituted indolyl, an optionally substituted benzoimidazolyl, an optionally substituted indazolyl, an optionally substituted 3H-indazolyl, an optionally substituted indolizinyl, an optionally substituted quinolinyl, an optionally substituted isoquinolinyl, an optionally substituted benzoxazolyl, an optionally substituted benzo[1,3]dioxolyl, an optionally substituted benzofuryl, an optionally substituted benzothiazolyl, an optionally substituted benzo[d]isoxazolyl, an optionally substituted benzo[d]isothiazolyl, an optionally substituted thiazolo[4,5-c]pyridinyl, an optionally substituted thiazolo[5,4-c]pyridinyl, an optionally substituted thiazolo[4,5-b]pyridinyl, an optionally substituted thiazolo[5,4-b]pyridinyl, an optionally substituted oxazolo[4,5-c]pyridinyl, an optionally substituted oxazolo[5,4-c]pyridinyl, an optionally substituted oxazolo[4,5-b]pyridinyl, an optionally substituted oxazolo[5,4-b]pyridinyl, an optionally substituted imidazopyridinyl, an optionally substituted benzothiadiazolyl, benzoxadiazolyl, an optionally substituted benzotriazolyl, an optionally substituted tetrahydroindolyl, an optionally substituted azaindolyl, an optionally substituted quinazolinyl, an optionally substituted purinyl, an optionally substituted imidazo[4,5-a]pyridinyl, an optionally substituted imidazo[1,2-a]pyridinyl, an optionally substituted 3H-imidazo[4,5-b]pyridinyl, an optionally substituted 1H-imidazo[4,5-b]pyridinyl, an optionally substituted 1H-imidazo[4,5-c]pyridinyl, an optionally substituted 3H-imidazo[4,5-c]pyridinyl, an optionally substituted pyridopyrdazinyl, an optionally substituted pyrimidinyl, an optionally substituted pyridopyrimidinyl, an optionally substituted pyrrolo[2,3]pyrimidyl, an optionally substituted pyrazolo[3,4]pyrimidyl an optionally substituted cyclopentaimidazolyl, an optionally substituted cyclopentatriazolyl, an optionally substituted pyrrolopyrazolyl, an optionally substituted pyrroloimidazolyl, an optionally substituted pyrrolotriazolyl, or an optionally substituted benzo(b)thienyl.

56. The method of claim 55, wherein $R_{60}$ is an optionally substituted furanyl.

57. The method of claim 54, wherein
$R_{60}$ is an optionally substituted phenyl; and
$R_1$, $R_3$, and Z are each, independently, —OH, —SH, or —NHR$_7$.

58. The method of claim 54, wherein
$R_{60}$ is an optionally substituted furanyl; and
$R_1$, $R_3$, and Z are each, independently, —OH, —SH, or —NHR$_7$.

59. A method of treating non-small cell lung cancer or breast cancer in a mammal, comprising administering to the mammal an effective amount of a compound represented by the following structural formula:

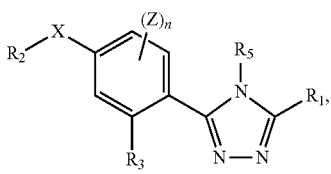

(XXVIII)

or a tautomer, or a pharmaceutically acceptable salt thereof, wherein:

$R_1$ and $R_3$ are, independently, —OH, —SH, —NHR$_7$, —OR$_{26}$, —SR$_{26}$, —O(CH$_2$)$_m$OH, —O(CH$_2$)$_m$SH, —O(CH$_2$)NR$_7$H, —S(CH$_2$)$_m$OH, —S(CH$_2$)$_m$SH, —S(CH$_2$)$_m$NR$_7$H, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$R$_{11}$, —SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —S(O)$_p$OR$_7$, —NR S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$R$_7$, —SS(O)$_p$R$_7$, —NR$_7$S(O)$_p$R$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —OP(O)(OR$_7$)$_2$, or —SP(O)(OR$_7$)$_2$;

$R_2$ is —OH, —SH, —NHR$_7$;

$R_5$ is represented by one of the following structural formulas:

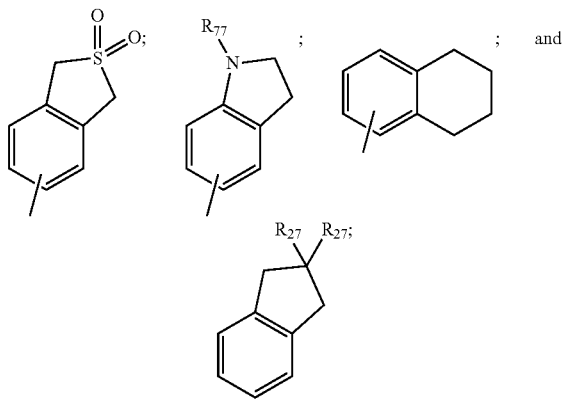

$R_{27}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanadino, a hydroxyalkyl, alkoxyalkyl, haloalkyl, a heteroalkyl, —NR$_{10}$R$_{11}$, —OR$_7$, —C(O)R$_{11}$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, or —S(O)$_p$NR$_{10}$R$_{11}$, —S(O)$_p$OR$_7$, —OP(O)(OR$_7$)$_2$, —SP(O)(OR$_7$)$_2$, —S(O)$_p$OR$_7$, —OP(O)(OR$_7$)$_2$, or —SP(O)(OR$_7$)$_2$;

or two $R_{27}$ groups taken together with the carbon atom to which they are attached form an optionally substituted cycloalkyl or optionally substituted heterocyclyl ring;

$R_{77}$, for each occurrence, is independently a substituent selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, guanadino, a hydroxyalkyl, alkoxyalkyl, haloalkyl, a heteroalkyl, —OR$_7$, —C(O)R$_7$, —C(O)OR$_7$, —OC(O)R$_7$, —C(O)NR$_{10}$R$_{11}$, —SR$_7$, —S(O)$_p$R$_7$, —OS(O)$_p$R$_7$, —S(O)$_p$OR$_7$, —S(O)$_p$NR$_{10}$R$_{11}$, —S(O)$_p$OR$_7$, —OP(O)(OR$_7$)$_2$, —SP(O)(OR$_7$)$_2$, —S(O)$_p$OR$_7$, —OP(O)(OR$_7$)$_2$, —SP(O)(OR$_7$)$_2$;

$R_7$ and $R_8$, for each occurrence, is independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

$R_{10}$ and $R_{11}$, for each occurrence, is independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_{10}$ and $R_{11}$, taken together with the nitrogen to which they are attached, form an optionally substituted heterocyclyl or an optionally substituted heteroaryl;

$R_{26}$ is a lower alkyl;

X is an optionally substituted 1 to 6 atom linker, wherein each linker atom is independently selected from the group consisting of C, O, P, N, or S;

Z is a substituent;

p, for each occurrence, is independently, 1 or 2;

m, for each occurrence, is independently, 1, 2, 3 or 4;

n is 0, 1, or 2; and with the proviso that the compound is not.

60. The method of claim 59, wherein $R_1$ and $R_3$ are each, independently, —OH, —SH, or —NHR$_7$.

61. The method of claim 60, wherein $R_1$ and $R_3$ are each, independently, —OH or —SH.

62. The method of claim 59, wherein X is an optionally substituted 1 to 4 atom linker, wherein each linker atom is independently selected from the group consisting of C or O.

63. The method of claim 62, wherein
X is —(CH$_2$)$_s$—, —(CH$_2$)$_t$C(O)—, —O(CH$_2$)$_t$—, or —OC(O)—;

s is 1, 2, or 3; and t is 0, 1, or 2.

64. The method of claim 59, wherein Z, for each occurrence, is independently an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteroaralkyl, halo, cyano, nitro, guanadino, a haloalkyl, a heteroalkyl, alkoxy, haloalkoxy, —NR$_{10}$R$_{11}$, —OR$_7$, —C(O)R$_7$, —C(O)OR$_7$, —C(S)R$_7$, —C(O)SR$_7$, —C(S)SR$_7$, —C(S)OR$_7$, —C(S)NR$_{10}$R$_{11}$, —C(NR$_8$)OR$_7$, —C(NR$_8$)R$_7$, —C(NR$_8$)NR$_{10}$R$_{11}$, —C(NR$_8$)SR$_7$, —OC(O)R$_7$, —OC(O)OR$_7$, —OC(S)OR$_7$, —OC(NR$_8$)OR$_7$, —SC(O)R$_7$, —SC(O)OR$_7$, —SC(NR$_8$)OR$_7$, —OC(S)R$_7$, —SC(S)R$_7$, —SC(S)OR$_7$, —OC(O)NR$_{10}$R$_{11}$, —OC(S)NR$_{10}$R$_{11}$, —OC(NR$_8$)NR$_{10}$R$_{11}$, —SC(O)NR$_{10}$R$_{11}$, —SC(NR$_8$)NR$_{10}$R$_{11}$, —SC(S)NR$_{10}$R$_{11}$, —OC(NR$_8$)R$_7$, —SC(NR$_8$)R$_7$, —C(O)NR$_{10}$R$_{11}$, —NR$_8$C(O)R$_7$, —NR$_7$C(S)R$_7$, —NR$_7$C(S)OR$_7$, —NR$_7$C(NR$_8$)R$_7$, —NR$_7$C(O)OR$_7$, —NR$_7$C(NR$_8$)OR$_7$, —NR$_7$C(O)NR$_{10}$R$_{11}$, —NR$_7$C(S)NR$_{10}$R$_{11}$, —NR$_7$C(NR$_8$)NR$_{10}$R$_{11}$, —SR$_7$, —S(O)$_p$R$_7$, —OS(O)$_p$R$_7$, —OS(O)$_p$OR$_7$, —OS(O)$_p$NR$_{10}$R$_{11}$, —S(O)$_p$OR$_7$, —NR$_8$S(O)$_p$R$_7$, —NR$_7$S(O)$_p$NR$_{10}$R$_{11}$, —NR$_7$S(O)$_p$R$_7$, —S(O)$_p$NR$_{10}$R$_{11}$, —SS(O)$_p$R$_7$, —SS(O)$_p$OR$_7$, —SS(O)$_p$NR$_{10}$R$_{11}$, —OP(O)(OR$_7$)$_2$, —SP(O)(OR$_7$)$_2$.

65. The method of claim 59, wherein n is 0.

66. The method of claim 59, wherein the compound is represented by the following structure:

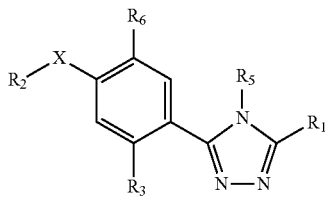

(XXIX)

or a tautomer or a pharmaceutically acceptable salt thereof, wherein

R$_6$ is an optionally substituted alkyl, an optionally substituted alkenyl, an optionally substituted alkynyl, cyano, halo, nitro, an optionally substituted cycloalkyl, haloalkyl, an optionally substituted heterocyclyl, an optionally substituted aryl, an optionally substituted heteroaryl, an optionally substituted aralkyl, an optionally substituted heteroaralkyl, —OR$_7$, —SR$_7$, —NR$_{10}$R$_{11}$, —OC(O)NR$_{10}$R$_{11}$, —SC(O)NR$_{10}$R$_{11}$, —NR$_7$C(O)NR$_{10}$R$_{11}$, —OC(O)R$_7$, —SC(O)R$_7$, —NR$_7$C(O)R$_7$, —OC(O)OR$_7$, —SC(O)OR$_7$, —NR$_7$C(O)OR$_7$, —OCH$_2$C(O)R$_7$, —SCH$_2$C(O)R$_7$, —NR$_7$CH$_2$C(O)R$_7$, —OCH$_2$C(O)OR$_7$, —SCH$_2$C(O)OR$_7$, —NR$_7$CH$_2$C(O)OR$_7$, —OCH$_2$C(O)NR$_{10}$—SCH$_2$C(O)NR$_{10}$R$_{11}$, —NR$_7$CH$_2$C(O)NR$_{10}$R$_{11}$, —OS(O)$_p$R$_7$, —SS(O)$_p$R$_7$, —NR$_7$S(O)$_p$R$_7$, —OS(O)$_p$NR$_{10}$R$_{11}$, —SS(O)$_p$NR$_{10}$R$_{11}$, —NR$_7$S(O)$_p$NR$_{10}$R$_{11}$, —OS(O)$_p$OR$_7$, —SS(O)$_p$OR$_7$, —NR$_7$S(O)$_p$OR$_7$, —OC(S)R$_7$, —SC(S)R$_7$, —NR$_7$C(S)R$_7$, —OC(S)OR$_7$, —SC(S)OR$_7$, —NR$_7$C(S)OR$_7$, —OC(S)NR$_{10}$R$_{11}$, —SC(S)NR$_{10}$R$_{11}$, —NR$_7$C(S)NR$_{10}$R$_{11}$, —OC(NR$_8$)R$_7$, —SC(NR$_8$)R$_7$, —NR$_7$C(NR$_8$)R$_7$, —OC(NR$_8$)OR$_7$, —SC(NR$_8$)OR$_7$, —NR$_7$C(NR$_8$)OR$_7$, —OC(NR$_8$)NR$_{10}$R$_{11}$, —SC(NR$_8$)NR$_{10}$R$_{11}$, —NR$_7$C(NR$_8$)NR$_{10}$R$_{11}$, —C(O)R$_7$, —C(O)OR$_7$, —C(O)NR$_{10}$R$_{11}$, —C(O)SR$_7$, —C(S)R$_7$, —C(S)OR$_7$, —C(S)NR$_{10}$R$_{11}$, —C(S)SR$_7$, —C(NR$_8$)OR$_7$, —C(NR$_8$)R$_7$, —C(NR$_8$)NR$_{10}$R$_{11}$, —C(NR$_8$)SR$_7$, —S(O)$_p$OR$_7$, —S(O)$_p$NR$_{10}$R$_{11}$, or —S(O)$_p$R$_7$.

67. The method of claim 66, wherein

R$_1$ and R$_3$ are each, independently, —OH or —SH;

R$_6$ is a C1-C6 alkyl, a C1-C6 haloalkyl, a C1-C6 alkoxy, a C1-C6 haloalkoxy, a C1-C6 alkyl sulfanyl or a C3-C6 cycloalkyl;

X is —(CH$_2$)$_s$—, —(CH$_2$)$_t$C(O), —O(CH$_2$)$_t$, or —OC(O)—;

s is 1, 2, or 3; and t is 0, 1, or 2.

68. The method of claim 67, wherein R$_2$ is —NH$_2$.

* * * * *